United States Patent
Parren et al.

(10) Patent No.: US 12,049,512 B2
(45) Date of Patent: Jul. 30, 2024

(54) ANTIBODY VARIANTS AND USES THEREOF

(71) Applicant: GENMAB B.V., Utrecht (NL)

(72) Inventors: Paul Parren, Odijk (NL); Frank Beurskens, Utrecht (NL); Rob N. De Jong, Utrecht (NL); Aran Frank Labrijn, Nigtevecht (NL); Janine Schuurman, Diemen (NL)

(73) Assignee: GENMAB B.V., Utrecht (NL)

( * ) Notice: Subject to any disclaimer, the term of this patent is extended or adjusted under 35 U.S.C. 154(b) by 547 days.

(21) Appl. No.: 16/921,154

(22) Filed: Jul. 6, 2020

(65) Prior Publication Data

US 2021/0163619 A1 Jun. 3, 2021

Related U.S. Application Data

(62) Division of application No. 14/130,543, filed as application No. PCT/EP2012/063339 on Jul. 6, 2012, now Pat. No. 10,759,867.

(60) Provisional application No. 61/504,994, filed on Jul. 6, 2011.

(30) Foreign Application Priority Data

Jul. 6, 2011 (DK) .............................. PA201100519
May 30, 2012 (DK) .............................. PA201200371

(51) Int. Cl.
| | | |
|---|---|---|
| C07K 16/00 | (2006.01) | |
| C07K 16/28 | (2006.01) | |
| C07K 16/36 | (2006.01) | |
| C12P 21/08 | (2006.01) | |
| A61K 39/00 | (2006.01) | |
| C07K 1/00 | (2006.01) | |

(52) U.S. Cl.
CPC .......... *C07K 16/2896* (2013.01); *C07K 16/00* (2013.01); *C07K 16/2863* (2013.01); *C07K 16/2887* (2013.01); *C07K 16/36* (2013.01); A61K 2039/505 (2013.01); C07K 2317/31 (2013.01); C07K 2317/34 (2013.01); C07K 2317/524 (2013.01); C07K 2317/526 (2013.01); C07K 2317/732 (2013.01); C07K 2317/734 (2013.01); C07K 2317/77 (2013.01); C07K 2317/90 (2013.01); C07K 2317/92 (2013.01)

(58) Field of Classification Search
None
See application file for complete search history.

(56) References Cited

U.S. PATENT DOCUMENTS

| | | | |
|---|---|---|---|
| 5,843,708 A * | 12/1998 | Hardman | ........... C07K 16/3007 |
| | | | 435/69.6 |
| 6,737,056 B1 | 5/2004 | Presta | |
| 7,612,181 B2 | 11/2009 | Wu et al. | |
| 10,759,867 B2 | 9/2020 | Parren et al. | |
| 10,882,913 B2 | 1/2021 | Overdijk et al. | |
| 11,180,572 B2 | 11/2021 | De Jong et al. | |
| 11,512,137 B2 * | 11/2022 | Oostindie | .............. A61K 49/00 |
| 2004/0110226 A1 * | 6/2004 | Lazar | ..................... C07K 16/32 |
| | | | 435/7.1 |
| 2008/0089892 A1 | 4/2008 | Allan et al. | |
| 2010/0015133 A1 | 1/2010 | Igawa et al. | |
| 2010/0105873 A1 * | 4/2010 | Allan | ..................... C07K 16/00 |
| | | | 506/9 |
| 2010/0184959 A1 | 7/2010 | Guler-Gane et al. | |
| 2011/0123440 A1 | 5/2011 | Hansen et al. | |
| 2014/0242075 A1 | 8/2014 | Parren et al. | |
| 2015/0175707 A1 | 6/2015 | De Jong et al. | |
| 2015/0353636 A1 | 12/2015 | Parren et al. | |
| 2019/0144554 A1 | 5/2019 | Overdijk et al. | |
| 2019/0202926 A1 | 7/2019 | Beurskens et al. | |
| 2019/0276549 A1 | 9/2019 | De Jong et al. | |
| 2019/0315877 A1 | 10/2019 | Overdijk et al. | |
| 2020/0181277 A1 | 6/2020 | Beurskens et al. | |
| 2021/0230301 A1 | 7/2021 | De Jong et al. | |
| 2021/0324096 A1 | 10/2021 | Overdijk et al. | |
| 2022/0411522 A1 | 12/2022 | Beurskens et al. | |
| 2023/0107363 A1 | 4/2023 | De Jong et al. | |

FOREIGN PATENT DOCUMENTS

| | | |
|---|---|---|
| WO | 2005/047327 A2 | 5/2005 |
| WO | 05/070963 A1 | 8/2005 |
| WO | 06/020114 A2 | 2/2006 |
| WO | 2006/053301 A2 | 5/2006 |
| WO | 2006/104989 A2 | 10/2006 |
| WO | 2006/105062 A2 | 10/2006 |
| WO | 2007/005612 A2 | 1/2007 |
| WO | 2007/039818 A2 | 4/2007 |
| WO | 2008/090958 A1 | 7/2008 |

(Continued)

OTHER PUBLICATIONS

U.S. Appl. No. 17/896,916, filed Aug. 26, 2022, Paul Parren.
U.S. Appl. No. 17/108,373, filed Dec. 1, 2020, Marije Overdijk, US 20210324096.
U.S. Appl. No. 17/684,238, filed Mar. 1, 2022, Frank Beurskens, US 20220411522.
U.S. Appl. No. 17/745,667, filed May 16, 2022, Rob De Jong, US 20230107363.

(Continued)

*Primary Examiner* — Chun W Dahle
(74) *Attorney, Agent, or Firm* — Nelson Mullins Riley & Scarborough LLP; Jane E. Remillard, Esq.; Christopher L. Frank

(57) ABSTRACT

Described herein are polypeptides and related antibodies comprising a variant Fc domain. The variant Fc domain provide for stabilized Fc:Fc interactions when the polypeptide(s), antibody or antibodies are bound to its target, antigen or antigens on the surface of a cell, thus providing for improved effector functions, such as CDC-response.

17 Claims, 32 Drawing Sheets

Specification includes a Sequence Listing.

(56) References Cited

FOREIGN PATENT DOCUMENTS

| WO | 2008/114011 A2 | 9/2008 |
|---|---|---|
| WO | 2009/006520 A1 | 1/2009 |
| WO | 2010/045193 A1 | 4/2010 |
| WO | 2010/106180 A2 | 9/2010 |
| WO | 2011/091078 A2 | 7/2011 |
| WO | 2011/131746 A2 | 10/2011 |
| WO | 2012/058768 A1 | 5/2012 |
| WO | 2012/125850 A1 | 9/2012 |
| WO | 2013/004842 A2 | 1/2013 |
| WO | 2014/006217 A1 | 1/2014 |
| WO | 2014/108198 A1 | 7/2014 |

OTHER PUBLICATIONS

U.S. Appl. No. 14/130,543, filed May 5, 2014, Paul Parren.
U.S. Appl. No. 17/012,102, filed Sep. 4, 2020, Rob N. De Jong.
U.S. Appl. No. 14/413,178, filed Mar. 17, 2015, Rob N. De Jong.
U.S. Appl. No. 14/760,135, filed Jul. 9, 2015, Paul Parren.
U.S. Appl. No. 17/108,373, filed Dec. 1, 2020, Marije Overdijk.
U.S. Appl. No. 16/451,714, filed Jun. 25, 2019, Marije Overdijk.
U.S. Appl. No. 15/780,268, filed May 31, 2018, Marije Overdijk.
U.S. Appl. No. 15/780,285, filed May 31, 2018, Frank Beurskens.
U.S. Appl. No. 16/345,044, filed Apr. 25, 2019, Rob De Jong.
U.S. Appl. No. 16/482,747, filed Aug. 1, 2019, Frank Beurskens.
U.S. Appl. No. 14/130,543, Apr. 7, 2020, C. Dahle.
U.S. Appl. No. 14/130,543, Aug. 23, 2019, C. Dahle.
U.S. Appl. No. 14/130,543, Jan. 11, 2019, C. Dahle.
U.S. Appl. No. 14/130,543, May 23, 2018, C. Dahle.
U.S. Appl. No. 14/130,543, Dec. 6, 2017, C. Dahle.
U.S. Appl. No. 14/130,543, Jun. 23, 2017, C. Dahle.
U.S. Appl. No. 14/130,543, Mar. 9, 2017, C. Dahle.
U.S. Appl. No. 14/130,543, Nov. 18, 2016, C. Dahle.
U.S. Appl. No. 14/130,543, Jul. 29, 2016, C. Dahle.
U.S. Appl. No. 14/413,178, Mar. 11, 2021, P. Huynh.
U.S. Appl. No. 14/413,178, Jun. 8, 2020, P. Huynh.
U.S. Appl. No. 14/413,178, Apr. 24, 2019, P. Huynh.
U.S. Appl. No. 14/413,178, Aug. 15, 2018, P. Huynh.
U.S. Appl. No. 14/413,178, Sep. 28, 2017, P. Huynh.
U.S. Appl. No. 14/413,178, Mar. 24, 2017, P. Huynh.
U.S. Appl. No. 14/413,178, Oct. 11, 2016, P. Huynh.
U.S. Appl. No. 14/760,135, Dec. 24, 2020, C. Dahle.
U.S. Appl. No. 14/760,135, Jul. 10, 2019, C. Dahle.
U.S. Appl. No. 14/760,135, Sep. 13, 2018, C. Dahle.
U.S. Appl. No. 14/760,135, Jan. 24, 2018, C. Dahle.
U.S. Appl. No. 14/760,135, Oct. 5, 2017, C. Dahle.
U.S. Appl. No. 15/780,285, Oct. 1, 2020, C. Dahle.
U.S. Appl. No. 15/780,285, Feb. 21, 2020, C. Dahle.
U.S. Appl. No. 16/451,714, Sep. 16, 2020, C. Kaufman.
U.S. Appl. No. 16/451,714, Sep. 2, 2020, C. Kaufman.
U.S. Appl. No. 16/451,714, May 5, 2020, C. Kaufman.
U.S. Appl. No. 16/451,714, Nov. 27, 2019, C. Kaufman.
U.S. Appl. No. 16/451,714, Aug. 9, 2019, C. Kaufman.
U.S. Appl. No. 15/780,268, Apr. 9, 2020, C. Kaufman.
U.S. Appl. No. 15/780,268, Aug. 8, 2019, C. Kaufman.
U.S. Appl. No. 18/475,055, filed Sep. 26, 2023, Paul Parren.
Burton, D.R., "Antibody: the flexible adaptor molecule," Trends Biochem Sci., vol. 15(2): 64-69. (1990).
Burton, D.R., "Immunoglobulin G: functional sites," Mol Immunol., vol. 22(3): 161-206 (1985).
Dall'Acqua, W.F., et al., "Modulation of the effector functions of a human IgG1 through engineering of its hinge region," J Immunol., vol. 177(2):1129-1138. (2006).
Desjarlais, J.R. et al., "Modulation of antibody effector function," Exp Cell Res, vol. 317(9): 1278-1285 (2011).
Fannale, M. et al., "Monoclonal antibodies in the treatment of non-Hodgkin's lymphoma," Drugs, vol. 67(3):333-350 (2007).
Feinstein, A., et al., "Immunoglobulin flexibility in complement activation," Immunology Today, vol. 7(6): 169-174 (1986).
Hornick J L et al., "Single Amino Acid Substitution in the Fc Region of Chimeric TNT-3 Antibody Accelerates Clearance and improves Immunoscintigraphy of solid tumors," Journal of Nuclear Medicine, Society of Nuclear Medicine, Reston VA: US, vol. 41(2), Feb. 1, 2000.
Hornick J L et al., "Single Amino Acid Substitution in the Fc Region of Chimeric TNT-3 Antibody Accelerates Clearance and improves Immunoscintigraphy of solid tumors," Journal of Nuclear Medicine, vol. 41(2): 355-362 (2000).
Hughes-Jones, N.C. et al., "Reaction between the isolated globular sub-units of the complement component C1q and IgG-complexes," Mol Immunol., vol. 16(9): 697-701 (1979).
Idusogie, E.E., et al., "Engineered Antibodies with Increased Activity to Recruit Complement," J Immunol., vol. 166(4):2571-25755 (2001).
Idusogie, E.E., et al., "Mapping of the C1q binding Site on Rituxan, a Chimeric Antibody with a Human IgG1 Fc," J Immunol., vol. 164(8):4178-4184. (2000).
International Preliminary Report on Patentability and Written Opinion for Application No. PCT/EP2012/063339, 16 pages, dated Jan. 7, 2014.
International Search Report for Application No. PCT/EP2012/063339, 7 pages, dated Jan. 25, 2013.
Kaneko, E. et al., "Optimizing Therapeutic Antibody Function: Progress with Fc domain Engineering," BioDrugs, vol. 25(1):1-11 (2011).
Kubota, T., et al., "Engineered therapeutic antibodies with improved effector functions," Cancer Sci., vol. 100(9):1566-1572. (2009).
Kuznetsov, Y., "Chimeric Human-Simian Anti-CD4 Antibodies Form Crystalline High Symmetry Particles," Journal of Structural Biology, vol. 131(2): p. 108-115 (2000).
Lazar, G.A., et al., "Engineered antibody Fc variants with enhanced effector function," PNAS, vol. 103(11): 4005-4010 (2006).
Michaelsen, T.E., et al., "Structural Difference in the Complement Activation Site of Human IgG1 and IgG3," Scandinavian Journal of Immunology, vol. 70(6): 553-564 (2009).
Moller, N.P. et al., "Fc-mediated immune precipitation. II. Analysis of precipitating immune complexes by rate-zonal ultracentrifugation," Immunology, vol. 38(3): 641-648. (1979).
Moore, G.L., et al., "Engineered Fc variant antibodies with enhanced ability to recruit complement and mediate effector functions," MAbs, vol. 2(2): 181-189. (2010).
Natsume, A. et al., "Improving effector functions of antibodies for cancer treatment: Enhancing ADCC and CDC," Drug Des Devel Ther., vol. 3: 7-16 (2009).
Natsume, A., et al., Engineered Antibodies of IgG1/IgG3 Mixed Isotype with Enhanced Cytotoxic Activities, Cancer Res, vol. 68(10): 3863-3872 (2008).
Natsume, A., et al., Engineered anti-CD20 Antibodies with Enhanced Complement-activating Capacity Mediate Potent Anti-lymphoma Activity, Cancer Sci., vol. 100(12):2411-2418 (2009).
Parren, P. et al., "Fc-Fc Interactions and Complement Activation," FASEB Summer Research Conference, Snowmass, Co., Jul. 5-10, 2010, 39 pages.
Perkins, S.J., "Molecular modelling of human complement subcomponent C1q and its complex with C1r2C1s2 derived from neutron-scattering curves and hydrodynamic properties," Biochem J., vol. 228(1):13-26 (1985).
Pinteric, L., et al., "Ultrastructure of the Fc fragment of human immunoglobulin G," Immunochemistry, vol. 8(11):1041-1045 (1971).
Poon, P.H., et al., "Conformation and restricted segmental flexibility of C1, the first component of human complement," J Mol Biol., vol. 8(3):563-577 (1983).
Reid, K.B., "Proteins involved in the activation and control of the two pathways of human complement," Biochem Soc Trans., vol. 11(1):1-12. (1983).
Reidler et al., 1986 I Handbook of Experimental Immunology 4th edit. (Weir, D. M. ed.), pp. 17.1-17.5. Blackwell, Edinburgh.
Saphire, E.O., et al., "Crystal structure of a neutralizing human IgG against HIV-1: A template for vaccine design," Science, vol. 293(5532):1155-1159 (2011).
Sato, F., et al., "A complement-dependent cytotoxicity-enhancing anti-CD20 antibody mediating potent antitumor activity in the

(56) References Cited

OTHER PUBLICATIONS humanized NOD/Shi-scid, IL-2Rgamma(null) mouse lymphoma model," Cancer Immunol Immunother., vol. 59(12): 1791-1800. (2010).

Shields, Robert L. et al., "High Resolution Mapping of the Binding Site on Human IgG1 for FcγRI, FcγRII, FcγRIII, and FcRn and Design of IgG1 Variants with Improved Binding to the FcγR," The Journal of Biological Chemistry, vol. 276(9):6591-6604 (2001).

Sledge, C.R. et al., "Binding properties of the human complement protein C1q," J Biol Chem., vol. 248(8): 2818-2823. (1973).

Smith, R.I. et al., "Recombinant Polymeric IgG: an approach to engineering more potent antibodies," Biotechnology (N Y), ol. 12(7): 683-638(1994).

Smith, R.I., et al., "Addition of a u-tailpiece to IgG Results in Polymeric Antibodies with Enhanced Effector Functions Including Complement-mediated cytolysis by IgG4," J Immunol., vol. 154(5): 2226-2236 (1995).

Tao, M.H., et al., "Structural features of human immunoglobulin G that determine isotype-specific differences in complement activation," J Exp Med., vol. 178(2):661-667. (1993).

Thesis by Erica Ollmann Saphire, for the Scripps Research Institute, La Jolla, California. Nov. 2000 (section 5.7 and figures 5.33, 5.37, 5.38) 12 pages.

Thommesen, J.E., et al., "Lysine 322 in the human IgG3 C(H)2 domain is crucial for antibody dependent complement activation," Mol Immunol., vol. 37(16): 995-1004 (2000).

Tschopp, J., et al., "Antigen-independent binding of IgG dimers to C 1 q as studied by sedimentation equilibrium, complement fixation and electron microscopy," Eur J Immunol., vol. 10(7): 529-535. (1980).

Weiss, V., et al., "Functional model of subcomponent C1 of human complement," J Mol Biol., vol. 189(3): 573-581 (1986).

Xu, Y., et al., "Residue at position 331 in the IgG1 and IgG4 CH2 domains contributes to their differential ability to bind and activate complement," J Biol Chem., vol. 269(5): 3469-3474 (1994).

Yamaguchi, A. et al., "Current Technological Development of Antibody Therapeutics," Immun., Endoc.& Metab. Agents in Med. Chem., vol. 11:21-32. (2011).

* cited by examiner

FIG. 1A IgG molecules in hexamer formation
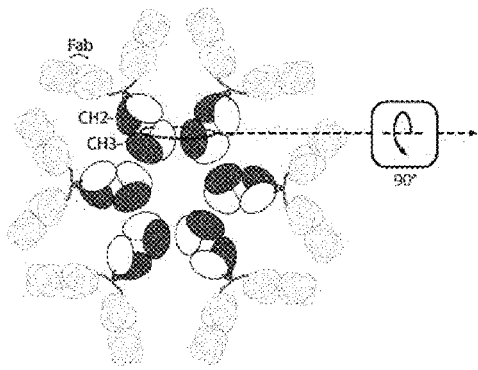
FIG. 1B Observed effect of oligomerization-enhancing mutations on CDC
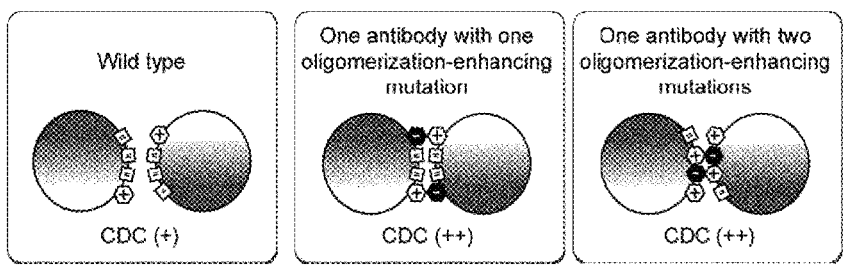
FIG. 1C Observed effect of oligomerization-inhibiting mutations on CDC
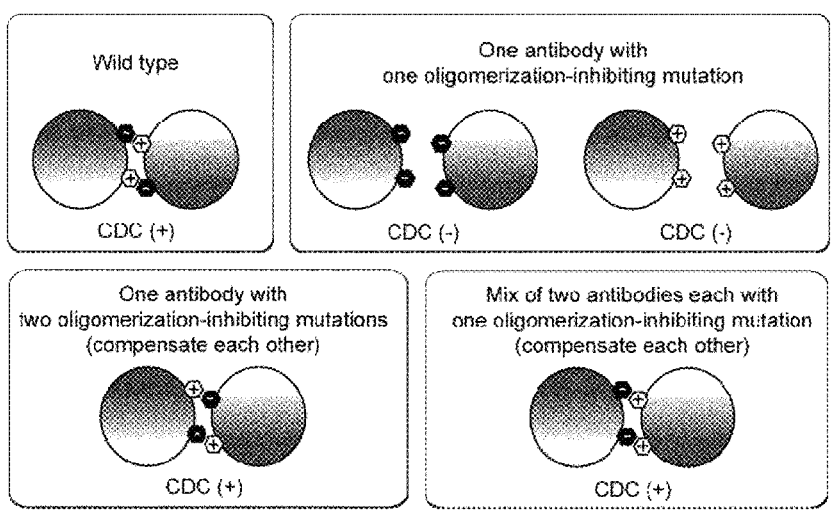

FIG. 2

```
IgG1   247 PKDTLMISRTPEVTCVVVDVSHEDPEVKFNWYVDGVEVHNAKTKPREEQYNSTYRVVSVL 306
IgG1f  247 PKDTLMISRTPEVTCVVVDVSHEDPEVKFNWYVDGVEVHNAKTKPREEQYNSTYRVVSVL 306
IgG2   247 PKDTLMISRTPEVTCVVVDVSHEDPEVQFNWYVDGVEVHNAKTKPREEQFNSTFRVVSVL 306
IgG3   247 PKDTLMISRTPEVTCVVVDVSHEDPEVQFKWYVDGVEVHNAKTKPREEQYNSTFRVVSVL 306
hgG4   247 PKDTLMISRTPEVTCVVVDVSQEDPEVQFNWYVDGVEVHNAKTKPREEQFNSTYRVVSVL 306
           ******************:*****.*:********************:***:******

IgG1   307 TVLHQDWLNGKEYKCKVSNKALPAPIEKTISKAKGQPREPQVYTLPPSRDELTKNQVSLT 366
IgG1f  307 TVLHQDWLNGKEYKCKVSNKALPAPIEKTISKAKGQPREPQVYTLPPSREEMTKNQVSLT 366
IgG2   307 TVVHQDWLNGKEYKCKVSNKGLPAPIEKTISKTKGQPREPQVYTLPPSREEMTKNQVSLT 366
IgG3   307 TVLHQDWLNGKEYKCKVSNKALPAPIEKTISKTKGQPREPQVYTLPPSREEMTKNQVSLT 366
hgG4   307 TVLHQDWLNGKEYKCKVSNKGLPSSIEKTISKAKGQPREPQVYTLPPSQEEMTKNQVSLT 366
           **:****************.**:.*******:************:*:********

IgG1   367 CLVKGFYPSDIAVEWESNGQPENNYKTTPPVLDSDGSFFLYSKLTVDKSRWQQGNVFSCS 426
IgG1f  367 CLVKGFYPSDIAVEWESNGQPENNYKTTPPVLDSDGSFFLYSKLTVDKSRWQQGNVFSCS 426
IgG2   367 CLVKGFYPSDIAVEWESNGQPENNYKTTPPMLDSDGSFFLYSKLTVDKSRWQQGNVFSCS 426
IgG3   367 CLVKGFYPSDIAVEWESSGQPENNYNTTPPMLDSDGSFFLYSKLTVDKSRWQQGNIFSCS 426
hgG4   367 CLVKGFYPSDIAVEWESNGQPENNYKTTPPVLDSDGSFFLYSRLTVDKSRWQEGNVFSCS 426
           *****************.******:****:***********:*********:**:****

IgG1   427 VMHEALHNHYTQKSLSLSPGK 447
IgG1f  427 VMHEALHNHYTQKSLSLSPGK 447
IgG2   427 VMHEALHNHYTQKSLSLSPGK 447
IgG3   427 VMHEALHNRFTQKSLSLSPGK 447
hgG4   427 VMHEALHNHYTQKSLSLSLGK 447
           ********::********.**

IgG1 = aa 130-330 of Uniprot entry P01857
IgG1f= IgG1 allotypic variant "f"
IgG2 = aa 126-326 of Uniprot entry P01859
IgG3 = aa 177-377 of Uniprot entry P01860
IgG4 = aa 127-327 of Uniprot entry P01861
```

FIG. 20A
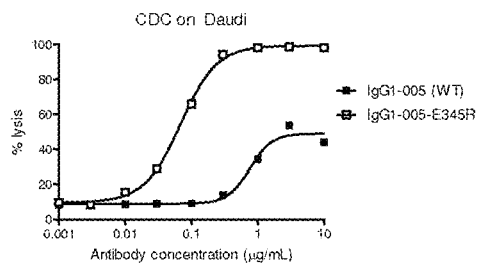
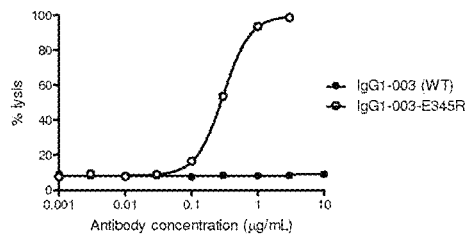
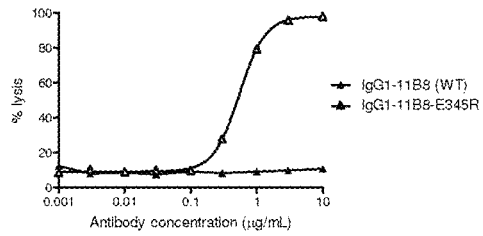
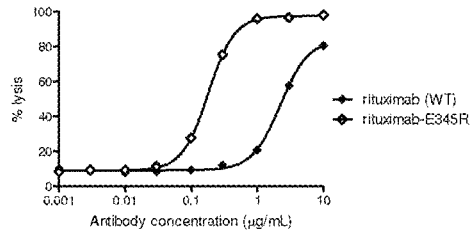
FIG. 20B
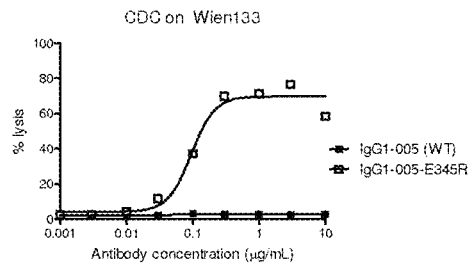
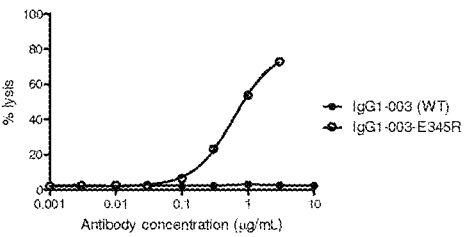
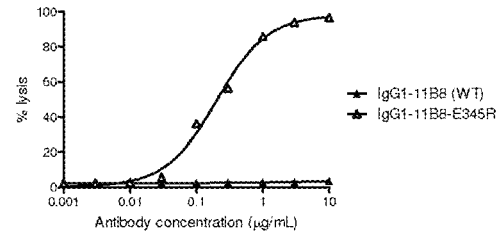
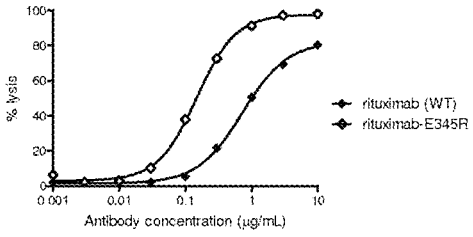

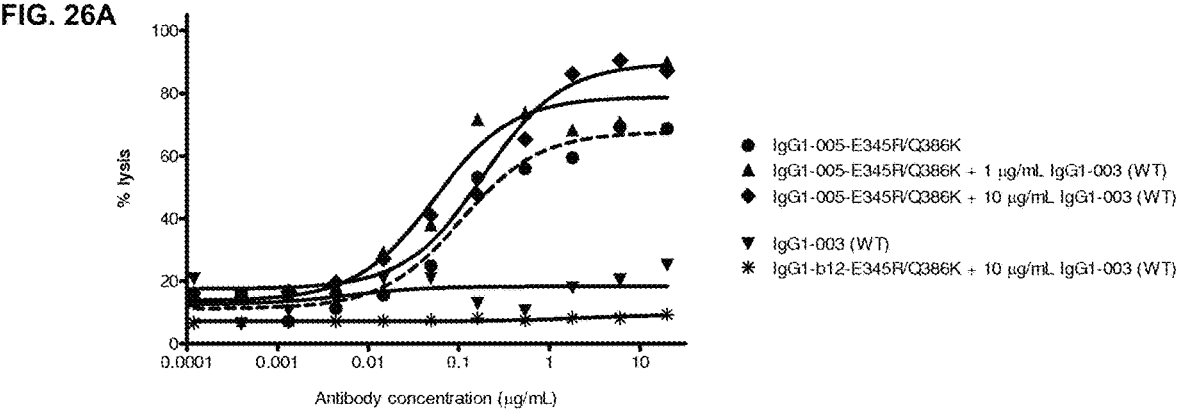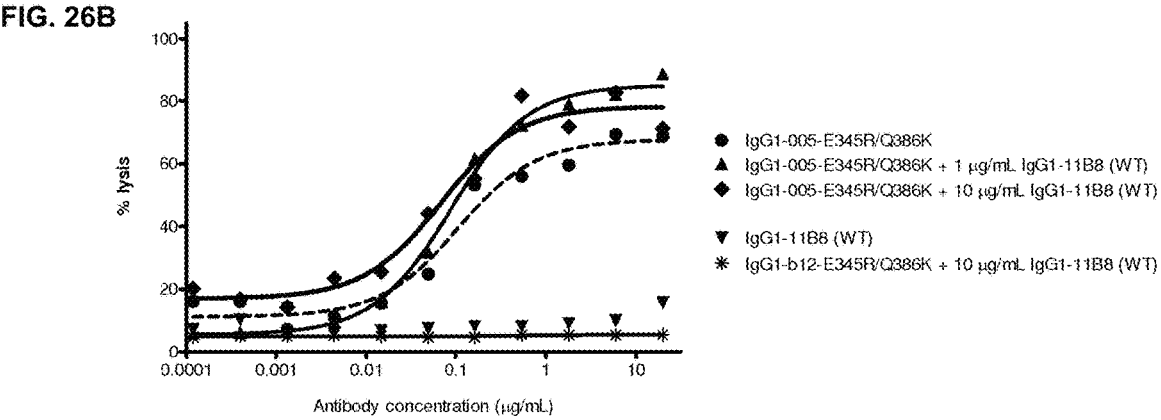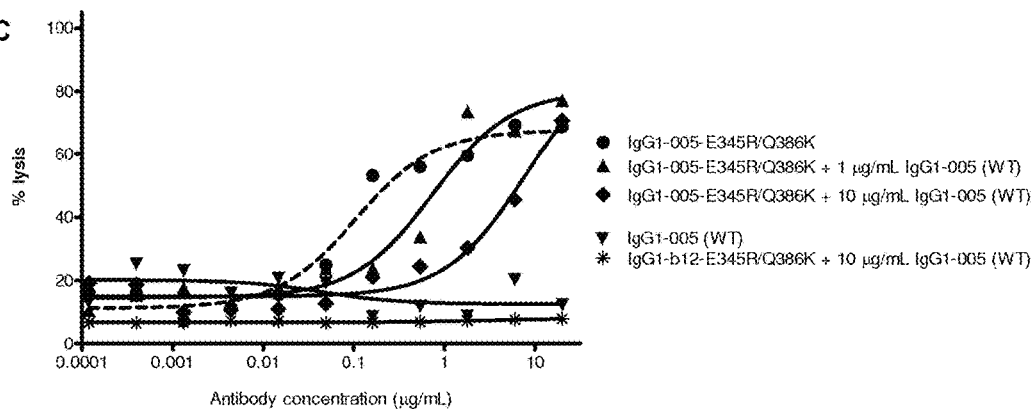

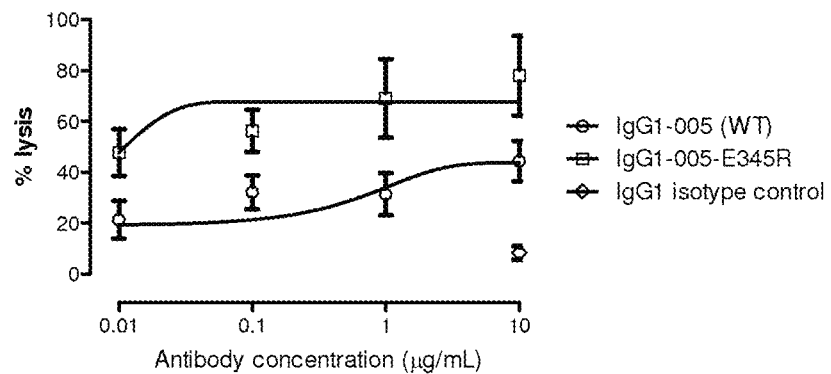
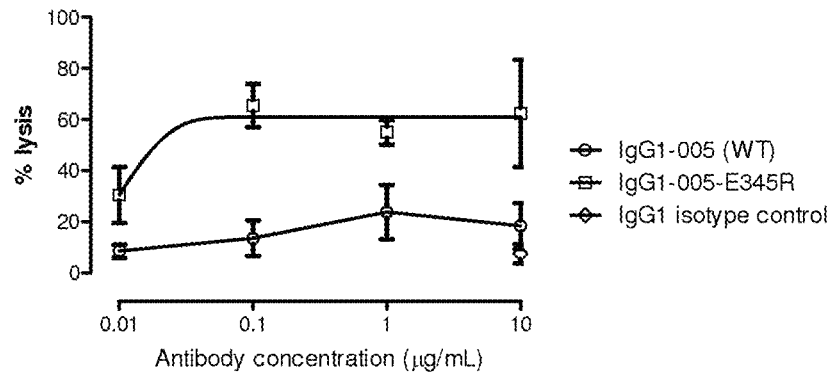

SEQUENCE LISTING

<160> NUMBER OF SEQ ID NOS: 8

<210> SEQ ID NO 1
<211> LENGTH: 330
<212> TYPE: PRT
<213> ORGANISM: homo sapiens

<400> SEQUENCE: 1

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 2
<211> LENGTH: 326
<212> TYPE: PRT
<213> ORGANISM: homo sapiens

<400> SEQUENCE: 2

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

-continued

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                 85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
            210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 3
<211> LENGTH: 377
<212> TYPE: PRT
<213> ORGANISM: homo sapiens

<400> SEQUENCE: 3

Ala Ser Thr Lys Gly Pro Ser Val Phe Pro Leu Ala Pro Cys Ser Arg
 1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

```
Tyr Thr Cys Asn Val Asn His Lys Pro Ser Asn Thr Lys Val Asp Lys
                    85                  90                  95

Arg Val Glu Leu Lys Thr Pro Leu Gly Asp Thr His Thr Cys Pro
            100                 105                 110

Arg Cys Pro Glu Pro Lys Ser Cys Asp Thr Pro Pro Cys Pro Arg
            115                 120                 125

Cys Pro Glu Pro Lys Ser Cys Asp Thr Pro Pro Cys Pro Arg Cys
    130                 135                 140

Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
                260                 265                 270

Pro Arg Glu Pro Gln Val Tyr Thr Leu Pro Pro Ser Arg Glu Glu Met
            275                 280                 285

Thr Lys Asn Gln Val Ser Leu Thr Cys Leu Val Lys Gly Phe Tyr Pro
        290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
            370                 375

<210> SEQ ID NO 4
<211> LENGTH: 327
<212> TYPE: PRT
<213> ORGANISM: homo sapiens

<400> SEQUENCE: 4

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
```

```
                65                  70                  75                  80
Tyr Thr Cys Asn Val Asp His Lys Pro Ser Asn Thr Lys Val Asp Lys
                    85                  90                  95

Arg Val Glu Ser Lys Tyr Gly Pro Pro Cys Pro Ser Cys Pro Ala Pro
                100                 105                 110

Glu Phe Leu Gly Gly Pro Ser Val Phe Leu Phe Pro Pro Lys Pro Lys
                115                 120                 125

Asp Thr Leu Met Ile Ser Arg Thr Pro Glu Val Thr Cys Val Val Val
            130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 5
<211> LENGTH: 330
<212> TYPE: PRT
<213> ORGANISM: homo sapiens

<400> SEQUENCE: 5

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                    85                  90                  95

Arg Val Glu Pro Lys Ser Cys Asp Lys Thr His Thr Cys Pro Pro Cys
                100                 105                 110
```

```
Pro Ala Pro Glu Leu Leu Gly Gly Pro Ser Val Phe Leu Phe Pro Pro
            115                 120                 125
Lys Pro Lys Asp Thr Leu Met Ile Ser Arg Thr Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 6
<211> LENGTH: 454
<212> TYPE: PRT
<213> ORGANISM: homo sapiens

<400> SEQUENCE: 6

Val Gln Leu Val Glu Ser Gly Gly Gly Val Gln Pro Gly Arg Ser
1               5                   10                  15
Leu Arg Leu Ser Cys Ala Ala Ser Gly Phe Thr Phe Ser Thr Tyr Gly
                20                  25                  30
Met His Trp Val Arg Gln Ala Pro Gly Lys Gly Leu Glu Trp Val Ala
            35                  40                  45
Val Ile Trp Asp Asp Gly Ser Tyr Lys Tyr Tyr Gly Asp Ser Val Lys
50                  55                  60
Gly Arg Phe Thr Ile Ser Arg Asp Asn Ser Lys Asn Thr Leu Tyr Leu
65                  70                  75                  80
Gln Met Asn Ser Leu Arg Ala Glu Asp Thr Ala Val Tyr Tyr Cys Ala
                85                  90                  95
Arg Asp Gly Ile Thr Met Val Arg Gly Val Met Lys Asp Tyr Phe Asp
            100                 105                 110
Tyr Trp Gly Gln Gly Thr Leu Val Thr Val Ser Ser Ala Ser Thr Lys
        115                 120                 125
Gly Pro Ser Val Phe Pro Leu Ala Pro Ser Ser Lys Ser Thr Ser Gly
    130                 135                 140
Gly Thr Ala Ala Leu Gly Cys Leu Val Lys Asp Tyr Phe Pro Glu Pro
145                 150                 155                 160
```

```
Val Thr Val Ser Trp Asn Ser Gly Ala Leu Thr Ser Gly Val His Thr
            165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
            195                 200                 205

Val Asn His Lys Pro Ser Asn Thr Lys Val Asp Lys Arg Val Glu Pro
            210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
            275                 280                 285

Val Glu Val His Asn Ala Lys Thr Lys Pro Arg Glu Glu Gln Tyr Asn
            290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
            355                 360                 365

Gln Val Ser Leu Thr Cys Leu Val Lys Gly Phe Tyr Pro Ser Asp Ile
            370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
            435                 440                 445

Ser Leu Ser Pro Gly Lys
    450

<210> SEQ ID NO 7
<211> LENGTH: 97
<212> TYPE: PRT
<213> ORGANISM: homo sapiens

<400> SEQUENCE: 7

Asn Val Asn His Lys Pro Ser Asn Thr Lys Val Asp Lys Arg Val Glu
1               5                   10                  15

Leu Lys Thr Pro Leu Gly Asp Thr Thr His Thr Cys Pro Arg Cys Pro
            20                  25                  30

Glu Pro Lys Ser Cys Asp Thr Pro Pro Cys Pro Arg Cys Pro Glu
            35                  40                  45

Pro Lys Ser Cys Asp Thr Pro Pro Cys Pro Arg Cys Pro Glu Pro
    50                  55                  60

Lys Ser Cys Asp Thr Pro Pro Cys Pro Arg Cys Pro Ala Pro Glu
```

```
                65                  70                  75                  80
Leu Leu Gly Gly Pro Ser Val Phe Leu Phe Pro Pro Lys Pro Lys Asp
                    85                  90                  95

Thr

<210> SEQ ID NO 8
<211> LENGTH: 451
<212> TYPE: PRT
<213> ORGANISM: homo sapiens

<400> SEQUENCE: 8

Val Gln Leu Val Glu Ser Gly Gly Val Val Gln Pro Gly Arg Ser
1               5                   10                  15

Leu Arg Leu Ser Cys Ala Ala Ser Gly Phe Thr Phe Ser Thr Tyr Gly
                20                  25                  30

Met His Trp Val Arg Gln Ala Pro Gly Lys Gly Leu Glu Trp Val Ala
            35                  40                  45

Val Ile Trp Asp Asp Gly Ser Tyr Lys Tyr Tyr Gly Asp Ser Val Lys
        50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Gly Ile Thr Met Val Arg Gly Val Met Lys Asp Tyr Phe Asp
            100                 105                 110

Tyr Trp Gly Gln Gly Thr Leu Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Lys Thr Tyr Thr Cys Asn
        195                 200                 205

Val Asn His Lys Pro Ser Asn Thr Lys Val Asp Lys Arg Val Glu Ser
    210                 215                 220

Lys Tyr Gly Pro Pro Cys Pro Ser Cys Pro Ala Pro Glu Phe Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser Gln
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
```

```
                340                 345                 350
Tyr Thr Leu Pro Pro Ser Gln Glu Glu Met Thr Lys Asn Gln Val Ser
        355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Glu Gly Asn Val Phe Ser Cys Ser Val Met
                420                 425                 430

His Glu Ala Leu His Asn His Tyr Thr Gln Lys Ser Leu Ser Leu Ser
        435                 440                 445

Leu Gly Lys
        450
```

ANTIBODY VARIANTS AND USES THEREOF

RELATED APPLICATIONS

This application is a divisional of U.S. patent application Ser. No. 14/130,543, filed on May 5, 2014 (now U.S. Pat. No. 10,759,867), which is a 35 U.S.C. 371 national stage filing of International Application No. PCT/EP2012/063339, filed Jul. 6, 2012, which claims priority to U.S. Provisional Application No. 61/504,994, filed Jul. 6, 2011, Danish Patent Application No. PA 2012 00371, filed May 30, 2012, and Danish Patent Application No. PA 2011 00519, filed Jul. 6, 2011. The contents of the aforementioned applications are hereby incorporated by reference.

SEQUENCE LISTING

The instant application contains a Sequence Listing which has been submitted electronically in ASCII format and is hereby incorporated by reference in its entirety. Said ASCII copy, created on Jul. 6, 2020, is named GMI_140USDV_Sequence_Listing.txt and is 23,933 bytes in size.

FIELD OF THE INVENTION

The present invention concerns polypeptides and related antibodies comprising a variant Fc domain. More particularly, the present invention concerns Fc domain-containing antibodies or polypeptides that have a modified effector function resulting from one or more amino acid modifications in the Fc-domain.

BACKGROUND OF THE INVENTION

The effector functions mediated by the Fc region of an antibody allow for the destruction of foreign entities, such as the killing of pathogens and the clearance and degradation of antigens. Antibody-dependent cell-mediated cytotoxicity (ADCC) and antibody-dependent cell-mediated phagocytosis (ADCP) is initiated by binding of the Fc region to Fc receptor (FcR)-bearing cells, whereas complement-dependent cytotoxicity (CDC) is initiated by binding of the Fc region to C1q, which initiates the classical route of complement activation.

Each IgG antibody contains two binding sites for C1q, one in each heavy chain constant (Fc) region. A single molecule of IgG in solution, however, does not activate complement as the affinity of monomeric IgG for C1q is quite weak ($K_d$~$10^{-4}$ M) (Sledge et al., 1973 J. Biol. Chem. 248, 2818-13; Hughes-Jones et al., 1979 Mol. Immunol. 16, 697-701). Antigen-driven association of IgG can lead to much tighter binding of the multivalent C1q molecule ($K_d$~$10^{-8}$ M) and complement activation (Burton et al., 1990 Mol. Immunol. 22, 161-206). In contrast, IgM exists naturally in covalently bound penta- or hexamers, and upon binding of cellular expressed or immobilized antigen IgM pentamers and hexamers can efficiently elicit CDC. Antigen-binding is a requirement to induce a conformational change in IgM to expose the C1q binding sites (Feinstein et al., 1986, Immunology Today, 169-174).

It has been suggested that also IgG can achieve complement activation by the formation of hexameric ring structures, through interaction of the CH2/CH3 domains of the Fc region (Burton et al., 1990 Trends in Biochem. Sci. 15, 64-69). Evidence supporting the existence of such hexameric IgG structures has been found in two dimensional (Reidler et al., 1986 I Handbook of Experimental Immunology $4^{th}$ edit. (Weir, D. M. ed.), pp 17.1-17.5. Blackwell, Edinburgh; Pinteric et al., 1971 Immunochem. 8, 1041-5) and three dimensional crystals, as well as for IgG1, IgG2a and IgG4 and human Fc in solution (Kuznetsov et al., 2000 J Struct. Biol. 131, 108-115). A hexameric ring formation was also observed in the crystal structure of the b12 human IgG1K antibody directed against HIV-1 gp120 (1 HZH in PDB) (Saphire et al., Science 2001 Aug. 10; 293(5532), 1155-9). In the b12 hexamer ring, six accessible C1q binding sites were presented at the hexamer surface, one from each of the six antibodies, while the other six binding sites faced downwards.

C1q resembles a bunch of tulips with six globular heads, containing the antibody combining regions, tethered to six collagenous stalks [Perkins et al., 1985 Biochem J. 228, 13-26; Poon et al., 1983 J Mol Biol. 168, 563-77; Reid et al., 1983 Biochem Soc Trans 11, 1-12; Weiss et al., 1986 J. Mol. Biol. 189, 573-81]. C1q was found to fit onto the b12 hexameric assembly of the 1 HZH crystal structure, so that each of the six globular heads were in contact with one of the six C1q binding sites (Parren, FASEB Summer Research Conference, Snowmass, Co., 5-10 Jul. 2010; "Crystal Structure of an intact human IgG: implications for HIV-1 neutralization and effector Function", Thesis by Erica Ollmann Saphire, for the Scripps Research Institute, La Jolla, California November 2000). Mutations in selected amino acids in the Fc interfaces observed between symmetry-related b12 antibodies in the crystal structure were observed to decrease the binding avidity of C1q, indicating the contribution of these amino acids to the intermolecular Fc:Fc interaction.

US 2011/0123440 describes altered antibody Fc-regions and the uses thereof. The alternated Fc-regions have one or more amino acid substitutions.

US 2008/0089892 describes polypeptide Fc-region variants and compositions comprising these Fc-region variants.

US 2010/0184959 describes methods of providing an Fc polypeptide variant with altered recognition of an Fc ligand and/or effector function.

US 2010/015133 describes methods of producing polypeptides by regulating polypeptide association.

US 2010/105873 describes integrated approach for generating multidomain protein therapeutics.

U.S. Pat. No. 6,737,056 describes polypeptide variants with a altered effector function.

Previous efforts have been made to identify antibody Fc-variants with an enhanced effector function or other modified properties. Such studies have focused on, e.g., exchanging segments between IgG isotypes to generate chimeric IgG molecules (Natsume et al., 2008 Cancer Res 68(10), 3863-72) or amino acid substitutions in the hinge region (Dall'Acqua et al., 2006 J Immunol 177, 1129-1138) or in or near the C1q-binding site in the CH2 domain, centered around residues D270, K322, P329, and P331 (Idusogie et al., 2001 J Immunol 166, 2571-2575; Michaelsen et al., 2009 Scand J Immunol 70, 553-564 and WO 99/51642). For example, Moore et al. (2010 mAbs 2(2), 181-189)) describes testing various combinations of S267E, H268F, S324T, S239D, I332E, G236A and I332E for enhanced effector function via CDC or ADCC. Other Fc mutations affecting binding to Fc-receptors (WO 2006/105062, WO 00/42072, U.S. Pat. Nos. 6,737,056 and 7,083,784) or physical properties of the antibodies (WO 2007/005612 A1) have also been suggested.

Despite these and other advances in the art, however, there remains a need for new and improved antibody-based therapeutics.

SUMMARY OF THE INVENTION

The present invention provides polypeptide and antibody variants having an enhanced effector function as compared to its parent polypeptide/antibody. Without being limited to theory, it is believed that the variants are capable of a more stable binding interaction between the Fc regions of two polypeptide/antibody molecules, thereby providing a more avid surface which leads to an enhanced effector function, such as an increased or more specific CDC response. Particular variants are also characterized by an improved ATCC response, ADCP response, and/or other enhanced effector functions. This subtle mechanism of polypeptide/antibody engineering can be applied, for instance, to increase the efficacy or specificity of antibody-based therapeutics, as described herein.

Thus in one aspect the present invention relates to a variant of a parent polypeptide comprising an Fc-domain of an immunoglobulin and a binding region, wherein the variant comprises a mutation in at least one amino acid residue selected from those corresponding to E345, E430, S440, Q386, P247, I253, S254, Q311, D/E356, T359, E382, Y436, and K447 in the Fc-region of a human IgG1 heavy chain, with the proviso that the mutation in S440 is S440Y or S440W.

The invention also provides for the use of at least one such mutation to increase the effector function mediated by the polypeptide or antibody when bound to its antigen on, for example, the surface of an antigen-expressing cell, a cell membrane or a virion.

In one aspect, herein referred to as "single-mutant", the variant has increased effector function as compared to the parent polypeptide or antibody.

In one aspect, herein referred to as "double-mutant", the variant comprises at least two mutations in said segment, and has improved effector function as compared to a variant comprising only one of the two mutations, the parent polypeptide or antibody, or both.

In one aspect, herein referred to as "mixed-mutant", the variant provides an increased effector function when used in combination with a second variant of the same or a different polypeptide or antibody comprising a mutation in a different amino acid residue in said segment, as compared to one or more of the variant, second variant, and the parent polypeptide or antibody alone.

Typically, the mutation is an amino acid substitution, such as a mutation exchanging a parent amino acid residue for one that has a different size and/or physicochemical property that promotes the formation of a new intermolecular Fc:Fc bond or increases the interaction strength of an existing pair. Exemplary amino acid residues for mutation according to the invention are shown in Tables 1 and 2A and B, along with exemplary amino acid substitutions. Non-limiting illustrations of different aspects of the invention are provided in FIG. 1.

These and other aspects of the invention, particularly various uses and therapeutic applications for the antibody variants, are described in further detail below.

BRIEF DESCRIPTION OF THE DRAWINGS

FIGS. 1A-1D: Schematic representation of IgG molecules in hexamer formation. The dotted circle illustrates two adjacent Fc:Fc interaction pairs of two neighbouring IgG molecules. The arrow in the box illustrates the direction from which the illustrations in FIGS. 1B, 1C and 1D are viewed: the two neighbouring Fc molecules are 90° rotated (in the plane of the drawing) and viewed from the Fab-arms in the direction of the CH3 domains. (FIG. 1B) Observed effect of oligomerization-enhancing mutations on CDC. Schematic representation illustrating Fc:Fc interaction pairs with increased efficacy according to the single mutant and double mutant aspects of the invention. (FIG. 1C) Observed effect of oligomerization-inhibiting mutations on CDC. Schematic representation illustrating how at least two oligomerization-inhibiting mutations that compensate each other can be, either combined into one molecule (double mutant aspect), or separated over two molecules (mixed mutant aspect), to restore or increase Fc:Fc interaction according to the double mutant and mixed mutants aspects of the invention. Mixed mutants achieve specific effector function activation dependent on binding of both antibodies, which can recognize different targets. (FIG. 1D) Theoretical effect of C1q binding-inhibiting mutations on CDC. Schematic representation of Fc:C1q interactions, illustrating that if mutations inhibit C1q-binding, they cannot be combined or mixed to restore CDC activity, because C1q cannot compensate for the defect introduced in the antibody.

FIG. 2: Sequence alignment of the human IgG1, IgG1f, IgG2, IgG3 and IgG4 Fc segments corresponding to residues P247 to K447 in the IgG1 heavy chain, using Clustal 2.1 software, as numbered by the EU index as set forth in Kabat. The sequences shown represent residues 130 to 330 of the human IgG1 heavy chain constant region (SEQ ID NO:1; UniProt accession No. P01857) and of the allotypic variant IgG1m(f); residues 126 to 326 of the IgG2 heavy chain constant region (SEQ ID NO:2; UniProt accession No. P01859); and residues 177 to 377 of the IgG3 heavy chain constant region (SEQ ID NO:2; UniProt accession No. P01860); and residues 127 to 327 of the IgG4 heavy chain constant region (SEQ ID NO:4; UniProt accession No. P01861).

FIGS. 3A and 3B: Sequence alignment of anti-EGFr antibody 2F8 in an IgG1 (SEQ ID NO:3), IgG4 (SEQ ID NO:5) and (partial) IgG3 (SEQ ID NO:6) backbone. Amino acid numbering according to Kabat and according to the EU-index are depicted (both described in Kabat et al., Sequences of Proteins of Immunological Interest, 5th Ed. Public Health Service, National Institutes of Health, Bethesda, MD (1991)).

S440K mix) on CD20-positive Daudi cells. A concentration series of 7D8 mutants were tested for their efficacy to induce CDC.

FIGS. 9A-9D: CDC mediated by mutants of CD38 antibody HuMAb 005 on CD38-positive cells. (FIG. 9A) CDC efficacy on Daudi cells by a concentration series of 005 mutants. (FIG. 9B) CDC efficacy on Raji cells by a concentration series of HuMAb 005 mutants. (FIG. 9C) CDC efficacy of E345R mutant of HuMAb 005 with either 20% or 50% NHS on Wien133 cells. (FIG. 9D) CDC efficacy of E345R mutants of HuMAb 005 and 7D8 with either 20% or 50% NHS on Raji cells. Unpurified antibody samples isolated from transient transfections were tested. As a negative control, supernatant of mock-transfected cells was used.

Figure 10A:
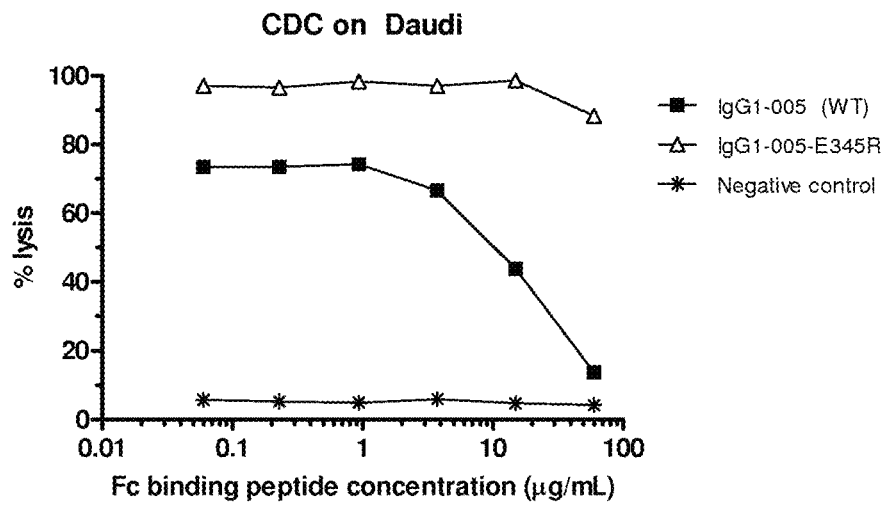
Figure 10B:
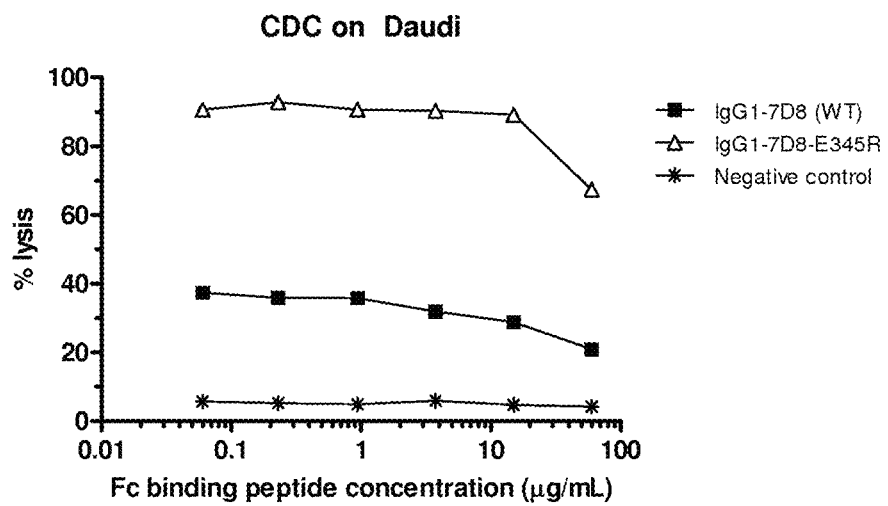

FIGS. 10A and 10B: CDC by wild type and E345R mutants of CD38 antibody HuMAb 005, (FIG. 10A) and CD20 antibody HuMAb 7D8 (FIG. 10B) in a competition experiment with an Fc-binding peptide. Cell lysis was measured after CDC on antibody-opsonized Daudi-cells incubated with a concentration series of the Fc-binding DCAWHLGELVWCT peptide (SEQ ID NO:7). Unpurified antibody samples isolated from transient transfections were used. As a negative control, supernatant of mock-transfected cells was used.

Figure 11:
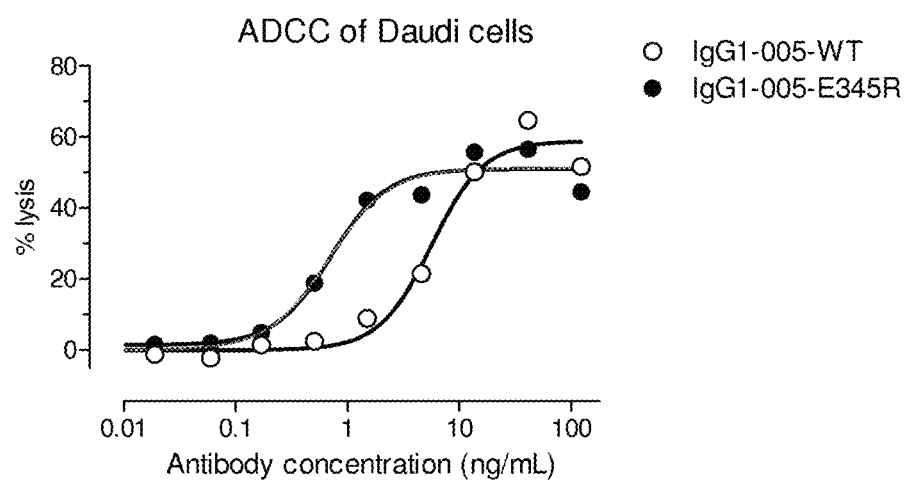

FIG. 11: ADCC of CD38 expressing Daudi cells by wild type CD38 antibody HuMAb 005 and mutant IgG1-005-E345R. ADCC of PBMC of one donor is shown, depicted as % lysis.

Figure 12A:
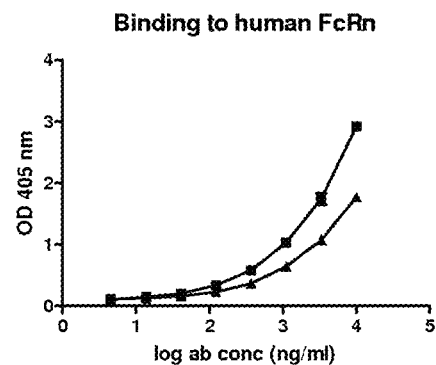
Figure 12B:
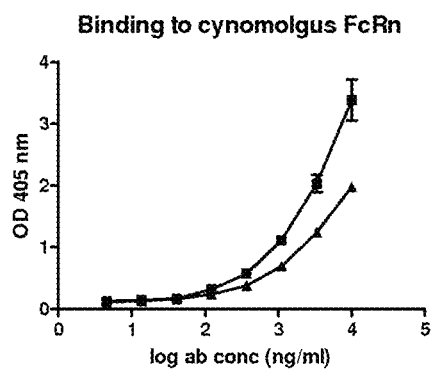
Figure 12C:
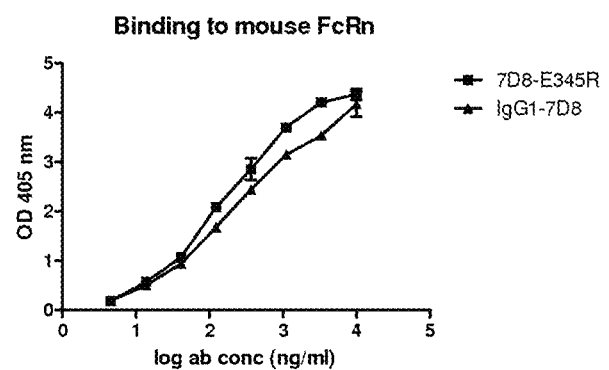

FIGS. 12A-12C: Binding of wild type IgG1-7D8 and mutant IgG1-7D8-E345R to human, cynomolgus and mouse FcRn, as determined by ELISA at pH 6.

Figure 13:
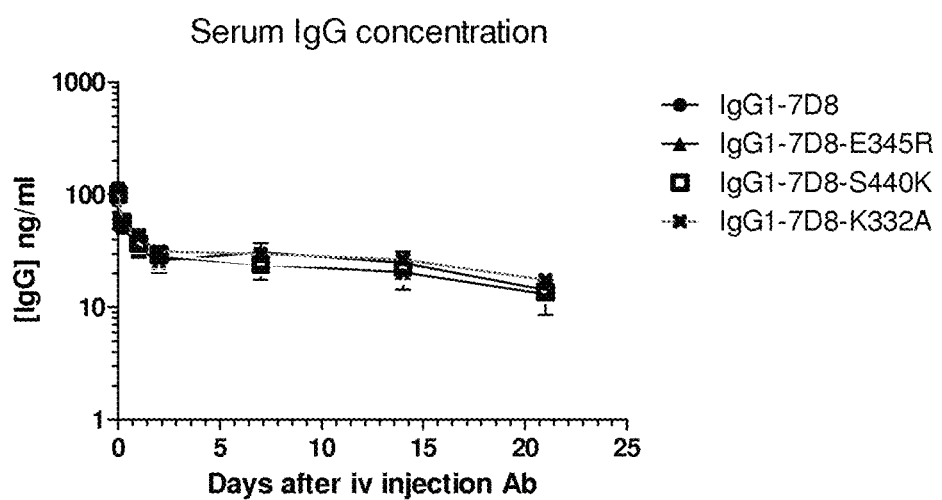
Figure 14A:
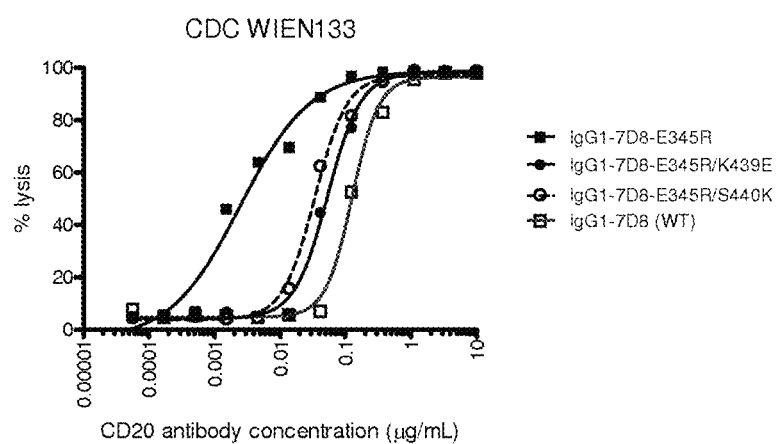
Figure 14B:
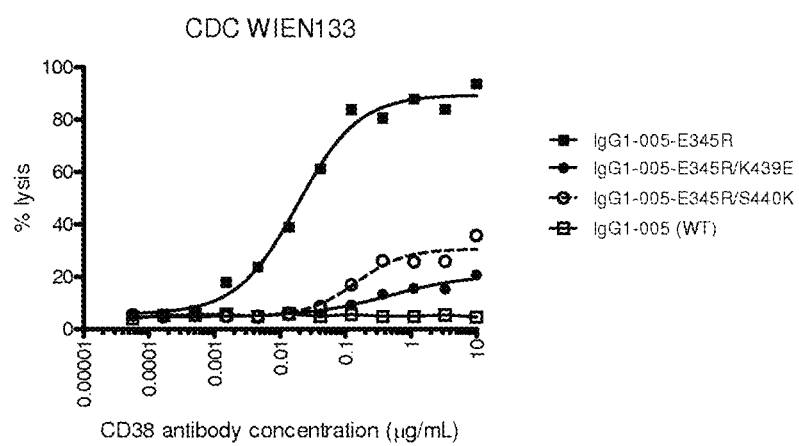
Figure 14C:
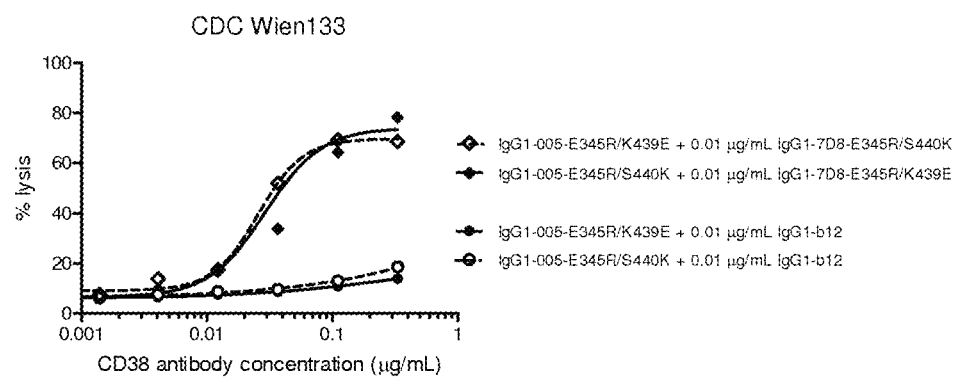
Figure 14D:
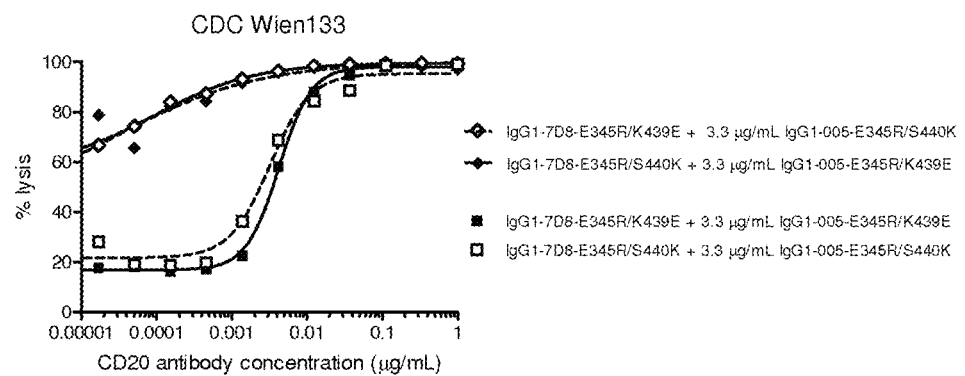

FIG. 13: Plasma concentrations of wild type IgG1-7D8 and -E354R, -S440K and K322A variants following intravenous injection in SCID mice.

FIGS. 14A-14D: CDC on CD20- and CD38-positive Wien133 cells.

Figure 15A:
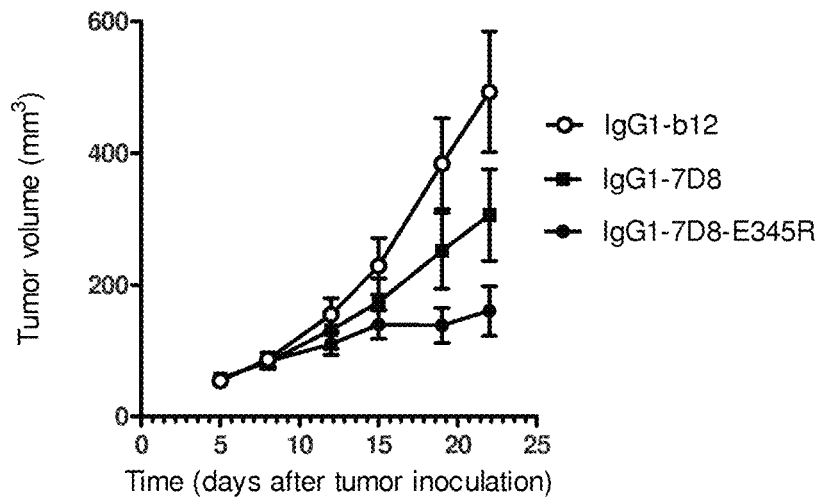
Figure 15B:
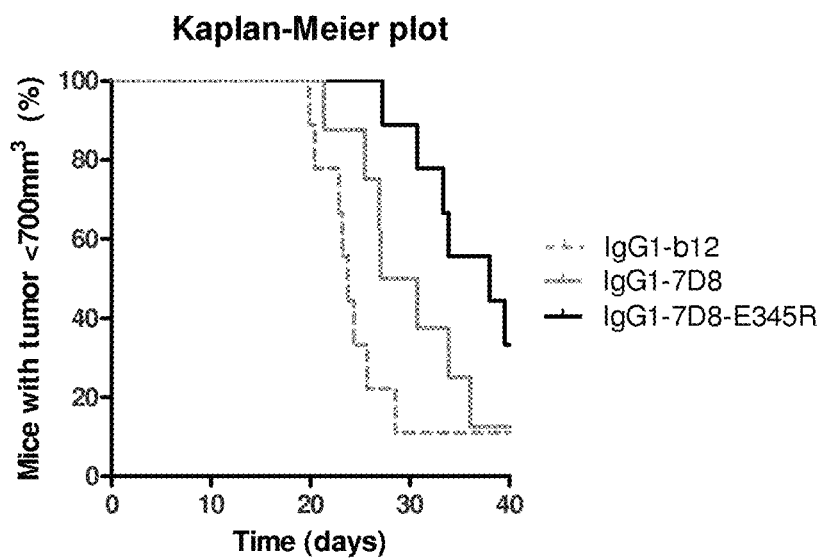

FIGS. 15A and 15B: Evaluation of the in vivo efficacy of IgG1-7D8-E345R in a subcutaneous xenograft model with Raji-luc #2D1 cells.

Figure 16A:
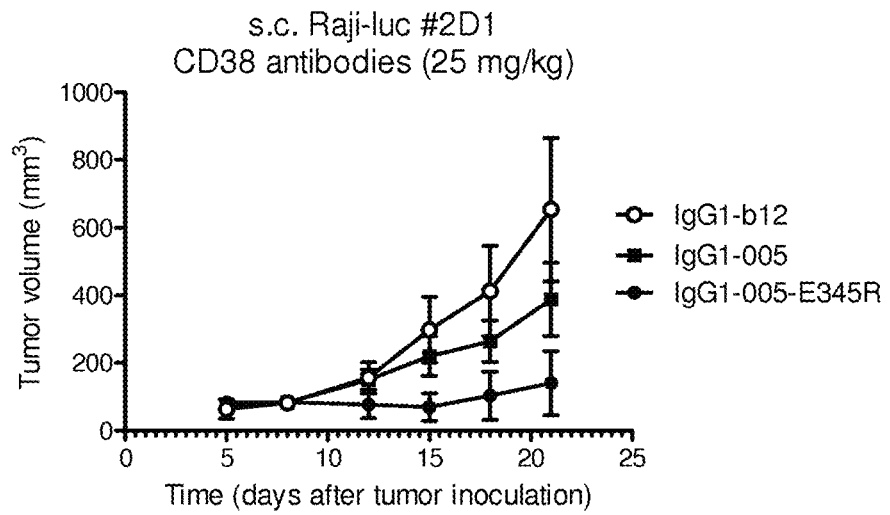
Figure 16B:
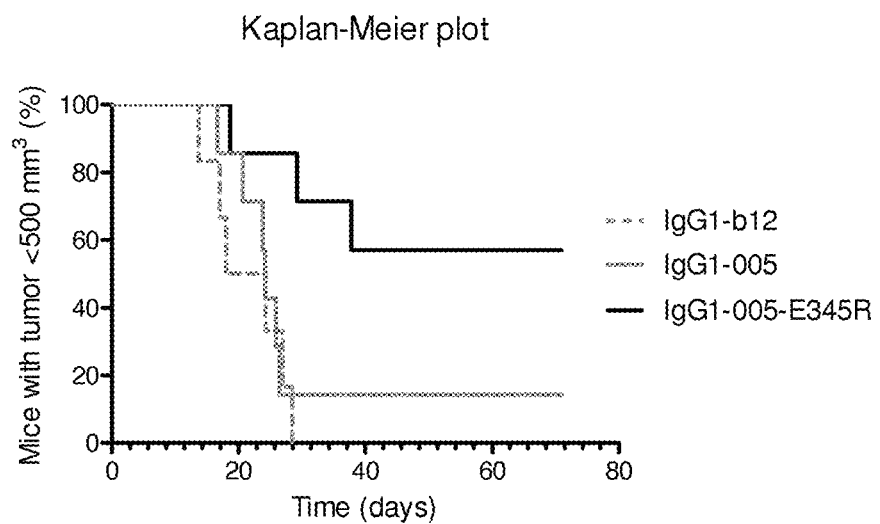

FIGS. 16A and 16B: Evaluation of the in vivo efficacy of IgG1-005-E345R in a subcutaneous xenograft model with Raji-luc #2D1 cells.

Figure 17:
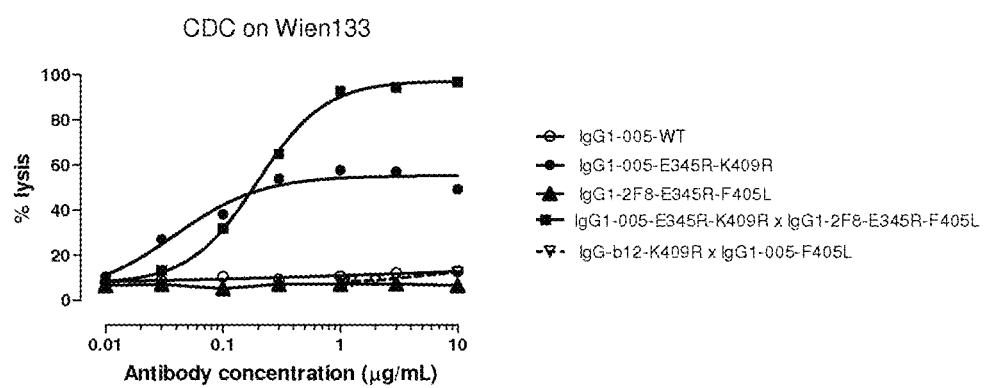

FIG. 17: CDC on CD38-positive, EGFR-negative Wien133 cells by CD38/EGFR bispecific antibody with the E345R mutation.

Figure 18A:
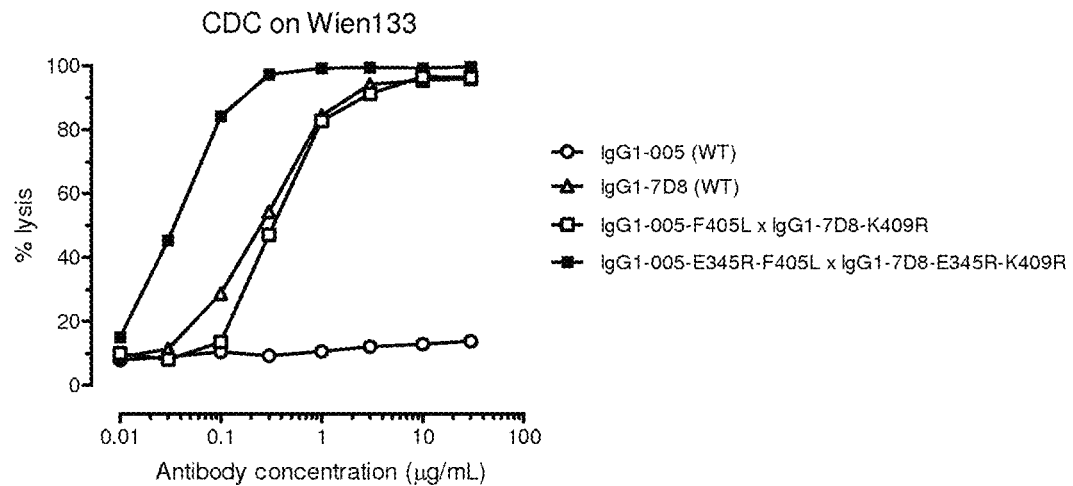
Figure 18B:
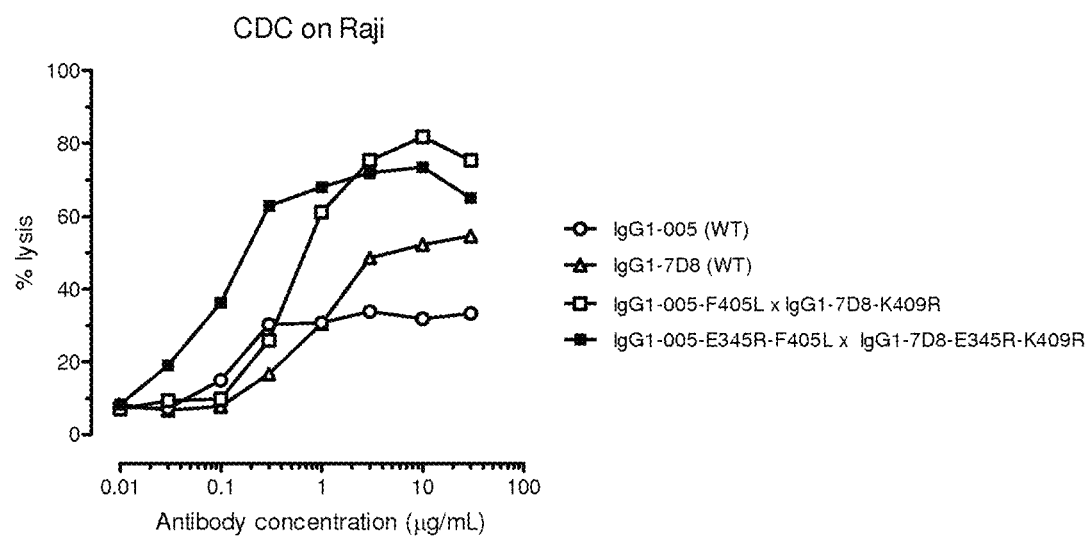

FIGS. 18A and 18B: CDC on CD20-positive, CD38-negative Wien133 cells or Raji cells by CD20/CD38 bispecific antibody with and without the E345R mutation.

Figure 19:
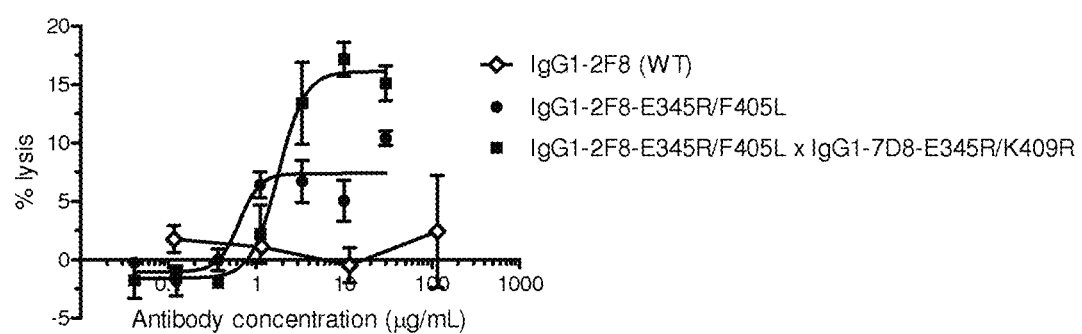

FIG. 19: CDC on EGFR-positive A431 cells by EGFR antibody 2F8 with the E345R mutation.

FIGS. 20A and 20B: CDC mediated by E345R mutant antibodies.

Figure 21:
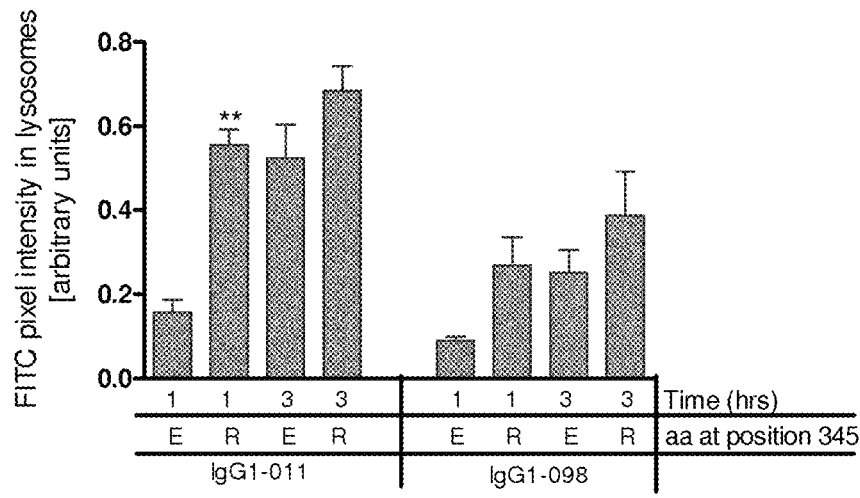

FIG. 21: Colocalization analysis of TF antibodies (FITC) with lysosomal marker LAMP1 (APC).

FIGS. 22A-22D: Introduction of E345R resulted in enhanced CDC-mediated killing compared to wild type rituximab tested on different B cell lines.

Figure 22A:
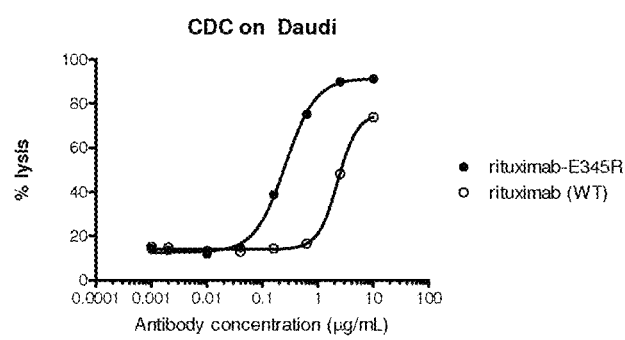
Figure 22B:
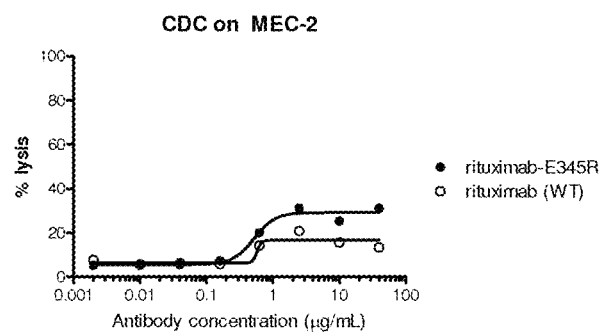
Figure 22C:
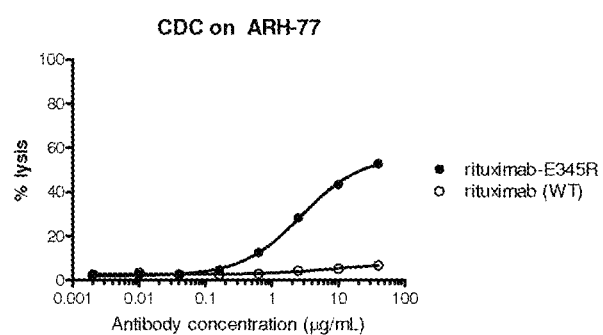
Figure 22D:
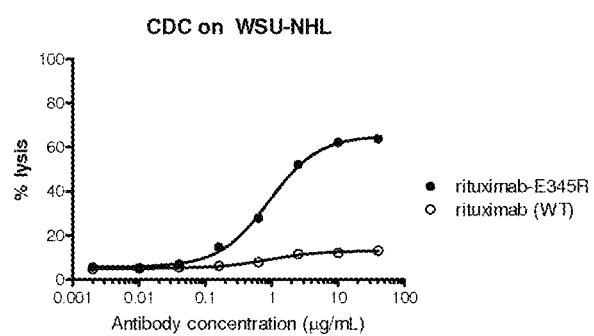
Figure 22E:
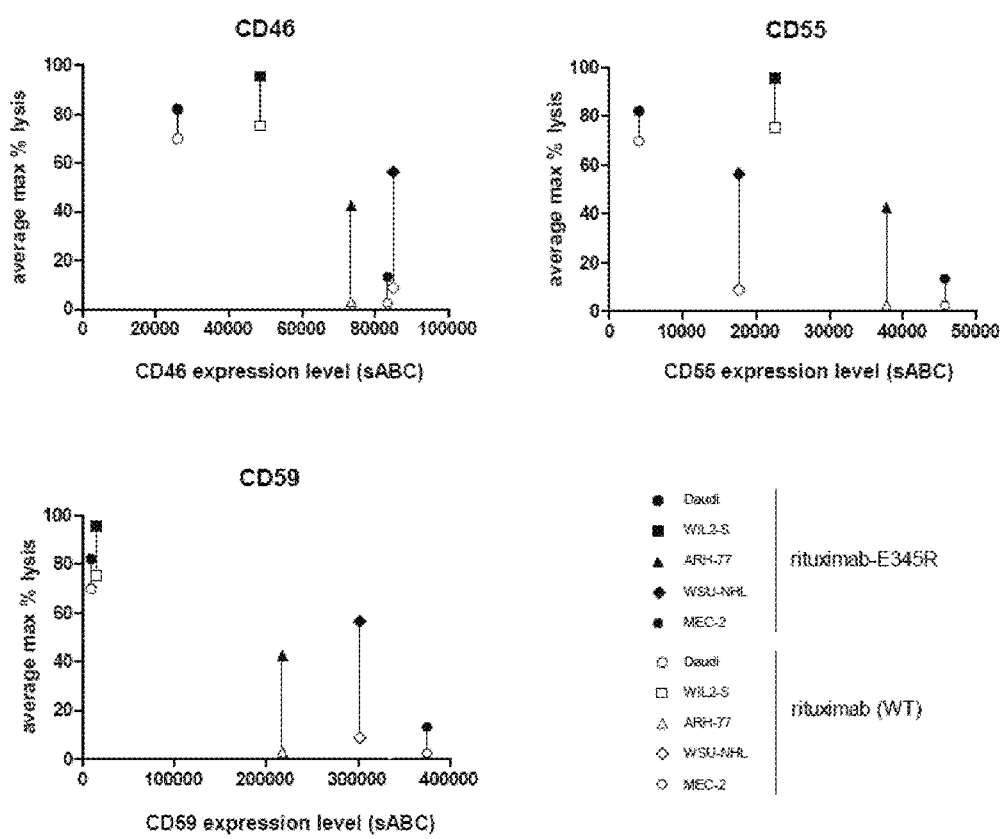

FIG. 22E: Introduction of E345R resulted in increased maximal CDC-mediated killing compared to wild type rituximab, independent of the expression levels of the complement regulatory proteins CD46 (FIG. 22A), CD55 (FIG. 22B) or CD59 (FIG. 22C) in different B cell lines with comparable CD20 expression levels.

FIGS. 23A-23D: CDC kinetics. E345R antibodies result in more rapid and more substantial target cell lysis by CDC than compared to wild type antibodies.

Figure 24:
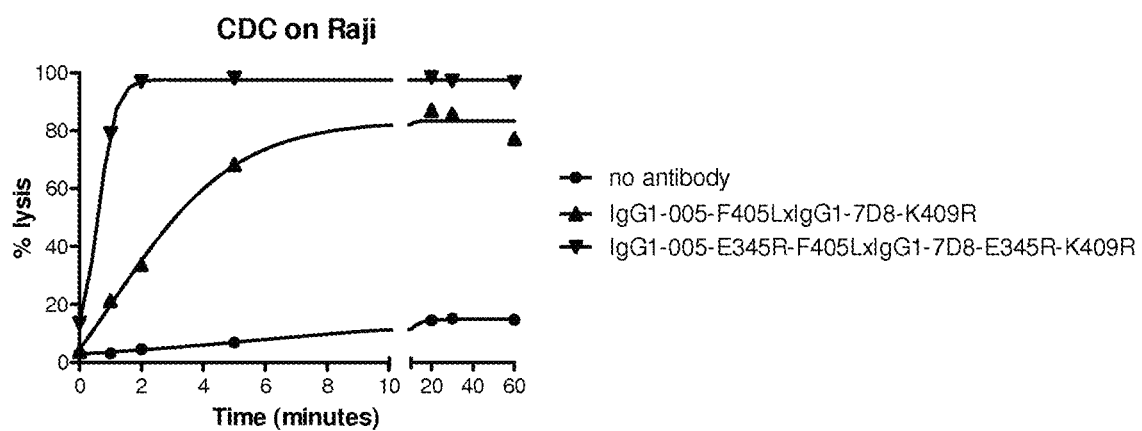

FIG. 24: CDC kinetics. Introduction of the E345R mutation in the bispecific CD38×CD20 antibody results in more rapid and more substantial CDC-mediated target cell lysis.

Figure 25:
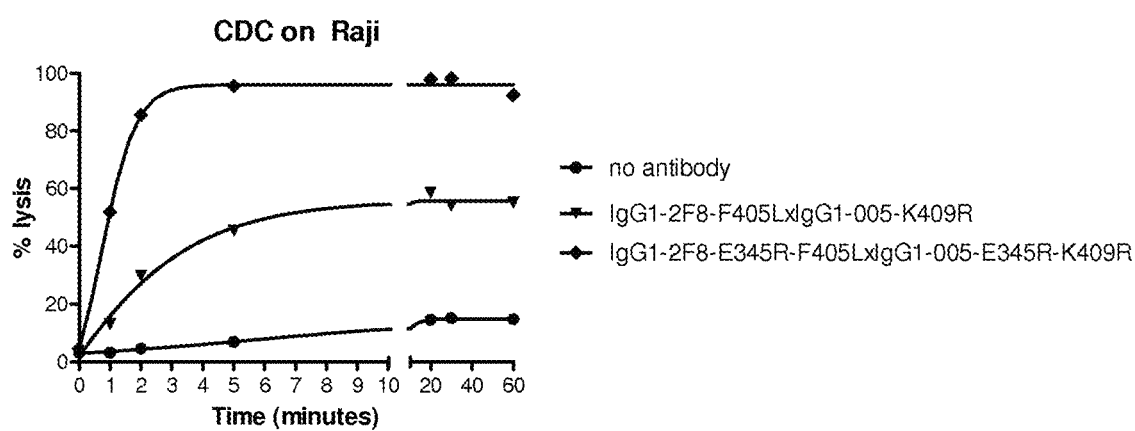

FIG. 25: CDC kinetics. Introduction of the E345R mutation in bispecific antibody CD38×EGFR that binds monovalently to the EGFR-negative Raji cells, results in more rapid and more substantial CDC-mediated target cell lysis.

FIGS. 26A-26F: CDC on Wien133 cells by a combination of a wild type antibody with a mutant antibody containing (FIGS. 26A-26C) E345R and Q386K or (FIGS. 26D-26F) E345R, E430G and Q386K. IgG1-b12 mutants do not bind Wien133 cells and were used as negative control antibodies.

Figure 27A:
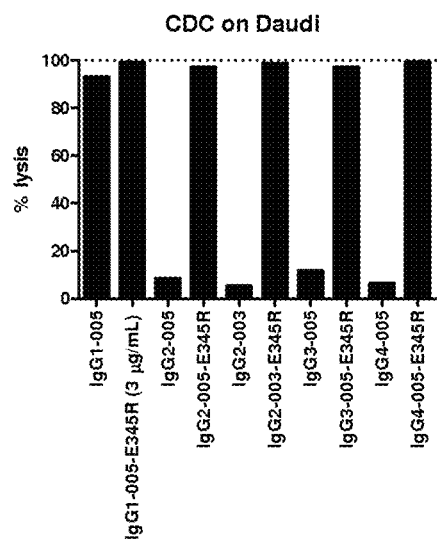
Figure 27B:
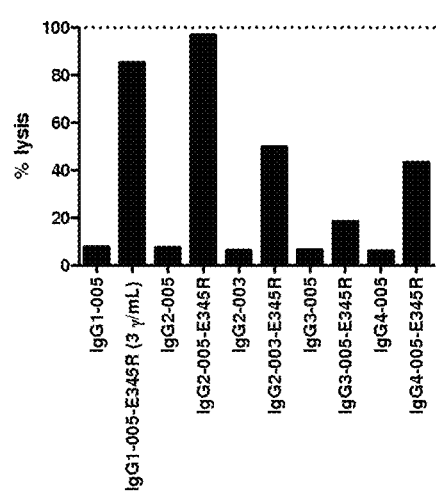

FIGS. 27A and 27B: CDC efficacy of IgG1, IgG2, IgG3 and IgG4 isotype antibodies containing the E345R mutation.

FIGS. 28A and 28B: Introduction of the Fc-Fc stabilizing E345R mutation in wild type CD38 antibody 005 results in enhanced killing of primary CLL cells in an ex vivo CDC assay (average±standard error of the mean).

DETAILED DESCRIPTION OF THE INVENTION

As described herein, surprisingly, mutations in amino acids that are not directly involved in Fc:C1q binding can nevertheless increase the CDC of an antibody, and can also improve other Fc-mediated effector functions of the antibody. This supports the hypothesis that antibody molecules such as IgG1 antibodies can form oligomeric structures which are later bound by C1q. Further, while some mutations were found to decrease CDC-induction, some combinations of such mutations in the same or different antibody molecules resulted in restored CDC-induction, and showed further specificity for oligomerization of antibodies, and thereby promoting more specific CDC-induction. Particular mutations increasing the CDC-response were also characterized by an improved ADCC response, increased avidity, increased internalization and in vivo efficacy in a mouse tumor model system as shown in the Examples. These discoveries allow for novel antibody-based therapeutics with enhanced CDC-induction capability, more selective CDC-induction, and/or other improved effector functions.

Figure 1D:
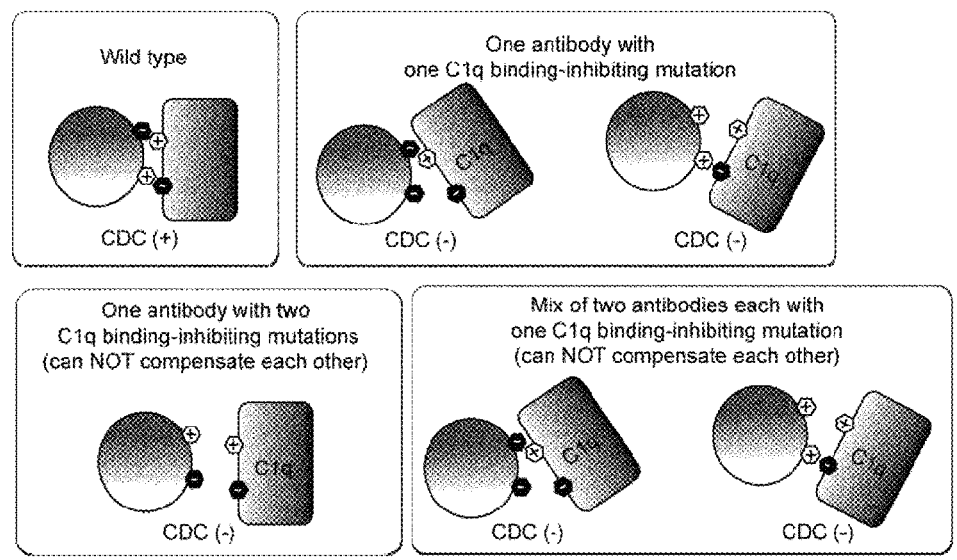

The antibody variants of the invention all comprise an antigen-binding region and a full-length or partial Fc region comprising at least one mutation in the segment corresponding to amino acid residues P247 to K447 in IgG1. Without being limited to theory, it is believed that the identified mutations result in a more effective and/or more specific CDC-induction based on three different principles, schematically represented in FIG. 1, and herein referred to as "single mutant", "double mutant" and "mixed mutants".

The improved C1q and/or CDC effects from the variants of the invention are primarily only detectable in assays allowing antibody oligomers to form, such as in cell-based assays where the antigen is not fixed but present in a fluid membrane. Further, that these effects result from a more stable antibody oligomer and not from a modification of a direct binding site of C1q can be verified according to the principles shown in FIG. 1C.

Definitions

The term "single-mutant", is to be understood as a variant of the present invention which has increased effector function as compared to the parent polypeptide or antibody.

The term "double-mutant", is to be understood as a variant comprising at least two mutations in said segment, and has improved effector function as compared to a variant comprising only one of the two mutations, the parent polypeptide or antibody, or both.

The term "mixed-mutant", is to be understood as a variant providing an increased effector function when used in combination with a second variant of the same or a different polypeptide or antibody comprising a mutation in a different amino acid residue in said segment, as compared to one or more of the variant, second variant, and the parent polypeptide or antibody alone.

The term "polypeptide comprising an Fc-domain of an immunoglobulin and a binding region" refers in the context of the present invention to a polypeptide which comprises an Fc-domain of an immunoglobulin and a binding region which is a capable of binding to any molecule, such as a polypeptide, e.g. present on a cell, bacterium, or virion. The Fc-domain of an immunoglobulin is defined as the fragment of an antibody which would be typically generated after digestion of an antibody with papain (which is known for someone skilled in the art) which includes the two CH2-CH3 regions of an immungloubulin and a connecting region, e.g. a hinge region. The constant domain of an antibody heavy chain defines the antibody isotype, e.g. IgG1, IgG2, IgG3, IgG4, IgA1, IgA2, IgE. The Fc-domain mediates the effector functions of antibodies with cell surface receptors called Fc receptors and proteins of the complement system. The binding region may be a polypeptide sequence, such as a protein, protein ligand, receptor, an antigen-binding region, or a ligand-binding region capable to bind to a cell, bacterium, virion. If the binding region is e.g. a receptor the "polypeptide comprising an Fc-domain of an immunoglobulin and a binding region" may have been prepared as a fusion protein of Fc-domain of an immunoglobulin and said binding region. If the binding region is an antigen-binding region the "polypeptide comprising an Fc-domain of an immunoglobulin and a binding region" may be an antibody, like a human antibody or a heavy chain only antibody or a ScFv-Fc-fusion. The polypeptide comprising an Fc-domain of an immunoglobulin and a binding region may typically comprise a connecting region, e.g. a hinge region, and two CH2-CH3 region of the heavy chain of an immunoglobulin, thus the "polypeptide comprising a Fc-domain of an immunoglobulin and a binding region" may be a "polypeptide comprising at least an Fc-domain of an immunoglobulin and a binding region". The term "Fc-domain of an immunoglobulin" means in the context of the present invention that a connecting region, e.g. hinge depending on the subtype of antibody, and the CH2 and CH3 region of an immunoglobulin are present, e.g. a human IgG1, IgG2, IgG3, IgG4, IgD, IgA1, IgGA2 or IgE.

The term "CH2 region" or "CH2 domain" as used herein is intended to refer the CH2 region of an immunoglobulin. Thus for example the CH2 region of a human IgG1 antibody corresponds to amino acids 228-340 according to the EU numbering system. However, the CH2 region may also be any of the other subtypes as described herein.

The term "CH3 region" or "CH3 domain" as used herein is intended to refer the CH3 region of an immunoglobulin. Thus for example the CH3 region of a human IgG1 antibody corresponds to amino acids 341-447 according to the EU numbering system. However, the CH2 region may also be any of the other subtypes as described herein.

The term "immunoglobulin" refers to a class of structurally related glycoproteins consisting of two pairs of polypeptide chains, one pair of light (L) low molecular weight chains and one pair of heavy (H) chains, all four potentially inter-connected by disulfide bonds. The structure of immunoglobulins has been well characterized. See for instance Fundamental Immunology Ch. 7 (Paul, W., ed., 2nd ed. Raven Press, N.Y. (1989)). Briefly, each heavy chain typically is comprised of a heavy chain variable region (abbreviated herein as VH) and a heavy chain constant region. The heavy chain constant region typically is comprised of three domains, CH1, CH2, and CH3. The heavy chains are interconnected via disulfide bonds in the so-called "hinge region". Each light chain typically is comprised of a light chain variable region (abbreviated herein as VL) and a light chain constant region. The light chain constant region typically is comprised of one domain, CL. The VH and VL regions may be further subdivided into regions of hypervariability (or hypervariable regions which may be hypervariable in sequence and/or form of structurally defined loops), also termed complementarity determining regions (CDRs), interspersed with regions that are more conserved, termed framework regions (FRs). Each VH and VL is typically composed of three CDRs and four FRs, arranged from amino-terminus to carboxy-terminus in the following order: FR1, CDR1, FR2, CDR2, FR3, CDR3, FR4 (see also Chothia and Lesk J. Mol. Biol. 196, 901 917 (1987)). Unless otherwise stated or contradicted by context, the amino acids of the constant region sequences are herein numbered according to the EU-index (described in Kabat, E. A. et al., Sequences of proteins of immunological interest. 5th Edition—US Department of Health and Human Services, NIH publication No. 91-3242, pp 662, 68, 689 (1991)).

The term "antibody" (Ab) in the context of the present invention refers to an immunoglobulin molecule, a fragment of an immunoglobulin molecule, or a derivative of either thereof, which has the ability to specifically bind to an antigen under typical physiological conditions with a half life of significant periods of time, such as at least about 30 minutes, at least about 45 minutes, at least about one hour, at least about two hours, at least about four hours, at least about eight hours, at least about 12 hours, about 24 hours or more, about 48 hours or more, about three, four, five, six, seven or more days, etc., or any other relevant functionally-defined period (such as a time sufficient to induce, promote, enhance, and/or modulate a physiological response associated with antibody binding to the antigen and/or time sufficient for the antibody to recruit an effector activity). The antibody of the present invention comprises an Fc-domain of an immunoglobulin and an antigen-binding region. An antibody generally contains two CH2-CH3 regions and a connecting region, e.g. a hinge region, e.g. at least an Fc-domain. Thus the antibody of the present invention may comprise an Fc region and an antigen-binding region. The variable regions of the heavy and light chains of the immunoglobulin molecule contain a binding domain that interacts with an antigen. The constant or "Fc" regions of the antibodies may mediate the binding of the immunoglobulin to host tissues or factors, including various cells of the immune system (such as effector cells) and components of the complement system such as C1q, the first component in the classical pathway of complement activation. An antibody may also be a multispecific antibody, such as a bispecific antibody or similar molecule. The term "bispecific antibody" refers to antibody having specificities for at least two different, typically non-overlapping, epitopes. Such epitopes may be on the same or different targets. If the epitopes are on different targets, such targets may be on the same cell or different cells or cell types. As indicated above, unless otherwise stated or clearly contradicted by the context, the term antibody herein includes fragments of an antibody which comprise at least a portion of an Fc-region and which retain the ability to specifically bind to the antigen. Such fragments may be provided by any known technique, such as enzymatic cleavage, peptide synthesis and recombinant expression techniques. It has been shown that the antigen-binding function of an antibody may be performed by fragments of a full-length antibody. Examples of binding fragments encompassed within the term "Ab" or "antibody" include, without limitation, monovalent antibodies (described in WO2007059782 by Genmab); heavy-chain antibodies, consisting only of two heavy chains and naturally occurring in e.g. camelids (e.g., Hamers-Casterman (1993) Nature 363:446); ThioMabs (Roche, WO2011069104), strand-exchange engineered domain (SEED or Seed-body) which are asymmetric and bispecific antibody-like molecules (Merck, WO2007110205); Triomab (Fresenius, Lindhofer et al. (1995 J Immunol 155:219); FcAAdp (Regeneron, WO2010151792), Azymetric Scaffold (Zymeworks/Merck, WO2012/058768), mAb-Fv (Xencor, WO2011/028952), Dual variable domain immunoglobulin (Abbott, DVD-Ig, U.S. Pat. No. 7,612,181); Dual domain double head antibodies (Unilever; Sanofi Aventis, WO20100226923), Di-diabody (ImClone/Eli Lilly), Knobs-into-holes antibody formats (Genentech, WO9850431); DuoBody (Genmab, WO 2011/131746); Electrostatic steering antibody formats (Amgen, EP1870459 and WO 2009089004; Chugai, US201000155133; Oncomed, WO2010129304A2); bispecific IgG1 and IgG2 (Rinat neurosciences Corporation, WO11143545), CrossMAbs (Roche, WO2011117329), LUZ-Y (Genentech), Biclonic (Merus), Dual Targeting domain antibodies (GSK/Domantis), Two-in-one Antibodies recognizing two targets (Genentech, NovImmune), Cross-linked Mabs (Karmanos Cancer Center), CovX-body (CovX/Pfizer), IgG-like Bispecific (ImClone/Eli Lilly, Shen, J., et al. J Immunol Methods, 2007. 318(1-2): p. 65-74), and DIG-body and PIG-body (Pharmabcine), and Dual-affinity retargeting molecules (Fc-DART or Ig-DART, by Macrogenics, WO/2008/157379, WO/2010/080538), Zybodies (Zyngenia), approaches with common light chain (Crucell/Merus, U.S. Pat. No. 7,262,028) or common heavy chains OaBodies by NovImmune), as well as fusion proteins comprising a polypeptide sequence fused to an antibody fragment containing an Fc-domain like scFv-fusions, like BsAb by ZymoGenetics/BMS), HERCULES by Biogen Idec (U.S. Pat. No. 7,951,918), SCORPIONS by Emergent BioSolutions/Trubion, Ts2Ab (MedImmune/AZ (Dimasi, N., et al. J Mol Biol, 2009. 393(3): p. 672-92), scFv fusion by Novartis, scFv fusion by Changzhou Adam Biotech Inc (CN 102250246), TvAb by Roche (WO 2012025525, WO 2012025530), mAb² by f-Star (WO2008/003116), and dual scFv-fusions. It also should be understood that the term antibody, unless specified otherwise, also includes polyclonal antibodies, monoclonal antibodies (such as human monoclonal antibodies), antibody mixtures (recombinant polyclonals) for instance generated by technologies exploited by Symphogen and Merus (Oligoclonics), and antibody-like polypeptides, such as chimeric antibodies and humanized antibodies. An antibody as generated can potentially possess any isotype.

The term "full-length antibody" when used herein, refers to an antibody (e.g., a parent or variant antibody) which contains all heavy and light chain constant and variable domains corresponding to those that are normally found in a wild-type antibody of that isotype.

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations, insertions or deletions introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The terms "monoclonal antibody", "monoclonal Ab", "monoclonal antibody composition", "mAb", or the like, as used herein refer to a preparation of Ab molecules of single molecular composition. A monoclonal antibody composition displays a single binding specificity and affinity for a particular epitope. Accordingly, the term "human monoclonal antibody" refers to Abs displaying a single binding specificity which have variable and constant regions derived from human germline immunoglobulin sequences. The human mAbs may be generated by a hybridoma which includes a B cell obtained from a transgenic or transchromosomal non-human animal, such as a transgenic mouse, having a genome comprising a human heavy chain transgene repertoire and a light chain transgene repertoire, rearranged to produce a functional human antibody and fused to an immortalized cell.

As used herein, "isotype" refers to the immunoglobulin class (for instance IgG1, IgG2, IgG3, IgG4, IgD, IgA1, IgA2, IgE, or IgM or any allotypes thereof such as IgG1m(za) and IgG1m(f)) that is encoded by heavy chain constant region genes. Further, each heavy chain isotype can be combined with either a kappa (κ) or lambda (λ) light chain.

The term "monovalent antibody" means in the context of the present invention that an antibody molecule is capable of binding with only one of the binding domains of the antibody to an antigen, e.g. has a single antigen-antibody interaction, and thus is not able of antigen crosslinking.

As used herein, the term "target" is in the context of the present invention to be understood as a molecule to which the binding region of the polypeptide comprising an Fc domain and a binding region, when used in the context of the binding of an antibody includes any antigen towards which the raised antibody is directed. The term "antigen" and "target" may in relation to an antibody be used interchangeably and constitute the same meaning and purpose with respect to any aspect or embodiment of the present invention.

As used herein, the term "binding" in the context of the binding of an antibody to a predetermined antigen typically is a binding with an affinity corresponding to a $K_D$ of about $10^{-6}$ M or less, e.g. $10^{-7}$ M or less, such as about $10^{-8}$ M or less, such as about $10^{-9}$ M or less, about $10^{-10}$ M or less, or about $10^{-11}$ M or even less when determined by for instance surface plasmon resonance (SPR) technology in a BIAcore 3000 instrument using the antigen as the ligand and the antibody as the analyte, and binds to the predetermined antigen with an affinity corresponding to a $K_D$ that is at least ten-fold lower, such as at least 100 fold lower, for instance at least 1,000 fold lower, such as at least 10,000 fold lower, for instance at least 100,000 fold lower than its affinity for binding to a non-specific antigen (e.g., BSA, casein) other than the predetermined antigen or a closely-related antigen. The amount with which the affinity is lower is dependent on the $K_D$ of the antibody, so that when the $K_D$ of the antibody is very low (that is, the antibody is highly specific), then the amount with which the affinity for the antigen is lower than the affinity for a non-specific antigen may be at least 10,000 fold. The term "$K_D$" (M), as used herein, refers to the dissociation equilibrium constant of a particular antibody-antigen interaction.

A "variant" or "antibody variant" or "variant of a parent antibody" of the present invention is an antibody molecule or which comprises one or more mutations as compared to a "parent antibody". Similarly, a "variant" or "a variant of a polypeptide comprising an Fc-domain of an immunoglobulin and a binding region" or "a variant of a parent polypeptide comprising an Fc-domain of an immunoglobulin and a binding region" of the present invention is a "polypeptide comprising an Fc-domain of an immunoglobulin and a binding region", which comprises one or more mutations as compared to a "parent polypeptide comprising an Fc-domain of an immunoglobulin and a binding region". The different terms may be used interchangeably and constitute the same meaning and purpose with respect to any aspect or embodiment of the present invention. Exemplary parent antibody formats include, without limitation, a wild-type antibody, a full-length antibody or Fc-containing antibody fragment, a bispecific antibody, a human antibody, or any combination thereof. Exemplary mutations include amino acid deletions, insertions, and substitutions of amino acids in the parent amino acid sequence. Amino acid substitutions may exchange a native amino acid for another naturally-occurring amino acid, or for a non-naturally-occurring amino acid derivative. The amino acid substitution may be conservative or non-conservative. In the context of the present invention, conservative substitutions may be defined by substitutions within the classes of amino acids reflected in one or more of the following three tables:

| Amino acid residue classes for conservative substitutions | |
|---|---|
| Acidic Residues | Asp (D) and Glu (E) |
| Basic Residues | Lys (K), Arg (R), and His (H) |
| Hydrophilic Uncharged Residues | Ser (S), Thr (T), Asn (N), and Gln (Q) |
| Aliphatic Uncharged Residues | Gly (G), Ala (A), Val (V), Leu (L), and Ile (I) |
| Non-polar Uncharged Residues | Cys (C), Met (M), and Pro (P) |
| Aromatic Residues | Phe (F), Tyr (Y), and Trp (W) |

| Alternative conservative amino acid residue substitution classes | | | |
|---|---|---|---|
| 1 | A | S | T |
| 2 | D | E | |
| 3 | N | Q | |
| 4 | R | K | |
| 5 | I | L | M |
| 6 | F | Y | W |

| Alternative Physical and Functional Classifications of Amino Acid Residues | |
|---|---|
| Alcohol group-containing residues | S and T |
| Aliphatic residues | I, L, V, and M |
| Cycloalkenyl-associated residues | F, H, W, and Y |
| Hydrophobic residues | A, C, F, G, H, I, L, M, R, T, V, W, and Y |
| Negatively charged residues | D and E |
| Polar residues | C, D, E, H, K, N, Q, R, S, and T |
| Positively charged residues | H, K, and R |
| Small residues | A, C, D, G, N, P, S, T, and V |
| Very small residues | A, G, and S |
| Residues involved in turn formation | A, C, D, E, G, H, K, N, Q, R, S, P, and T |
| Flexible residues | Q, T, K, S, G, P, D, E, and R |

In the context of the present invention, a substitution in a variant is indicated as:

Original amino acid—position—substituted amino acid;

The three letter code, or one letter code, are used, including the codes Xaa and X to indicate amino acid residue. Accordingly, the notation "E345R" or "Glu345Arg" means, that the variant comprises a substitution of Glutamic acid with Arginine in the variant amino acid position corresponding to the amino acid in position 345 in the parent antibody, when the two are aligned as indicated below.

Where a position as such is not present in an antibody, but the variant comprises an insertion of an amino acid, for example:

Position—substituted amino acid; the notation, e.g., "448E" is used.

Such notation is particular relevant in connection with modification(s) in a series of homologous polypeptides or antibodies.

Similarly when the identity of the substitution amino acid residues(s) is immaterial:

Original amino acid—position; or "E345".

For a modification where the original amino acid(s) and/or substituted amino acid(s) may comprise more than one, but not all amino acid(s), the substitution of Glutamic acid for Arginine, Lysine or Tryptophan in position 345:

"Glu345Arg, Lys, Trp" or "E345R, K, W" or "E345R/K/W" or "E345 to R, K or W" may be used interchangeably in the context of the invention.

Furthermore, the term "a substitution" embraces a substitution into any one of the other nineteen natural amino acids, or into other amino acids, such as non-natural amino acids. For example, a substitution of amino acid E in position 345 includes each of the following substitutions: 345A, 345C, 345D, 345G, 345H, 345F, 345I, 345K, 345L, 345M, 345N, 345Q, 345R, 345S, 345T, 345V, 345W, and 345Y. This is, by the way, equivalent to the designation 345X, wherein the X designates any amino acid. These substitutions can also be designated E345A, E345C, etc, or E345A, C, ect, or E345A/C/ etc. The same applies to analogy to each and every position mentioned herein, to specifically include herein any one of such substitutions.

Figure 3A:
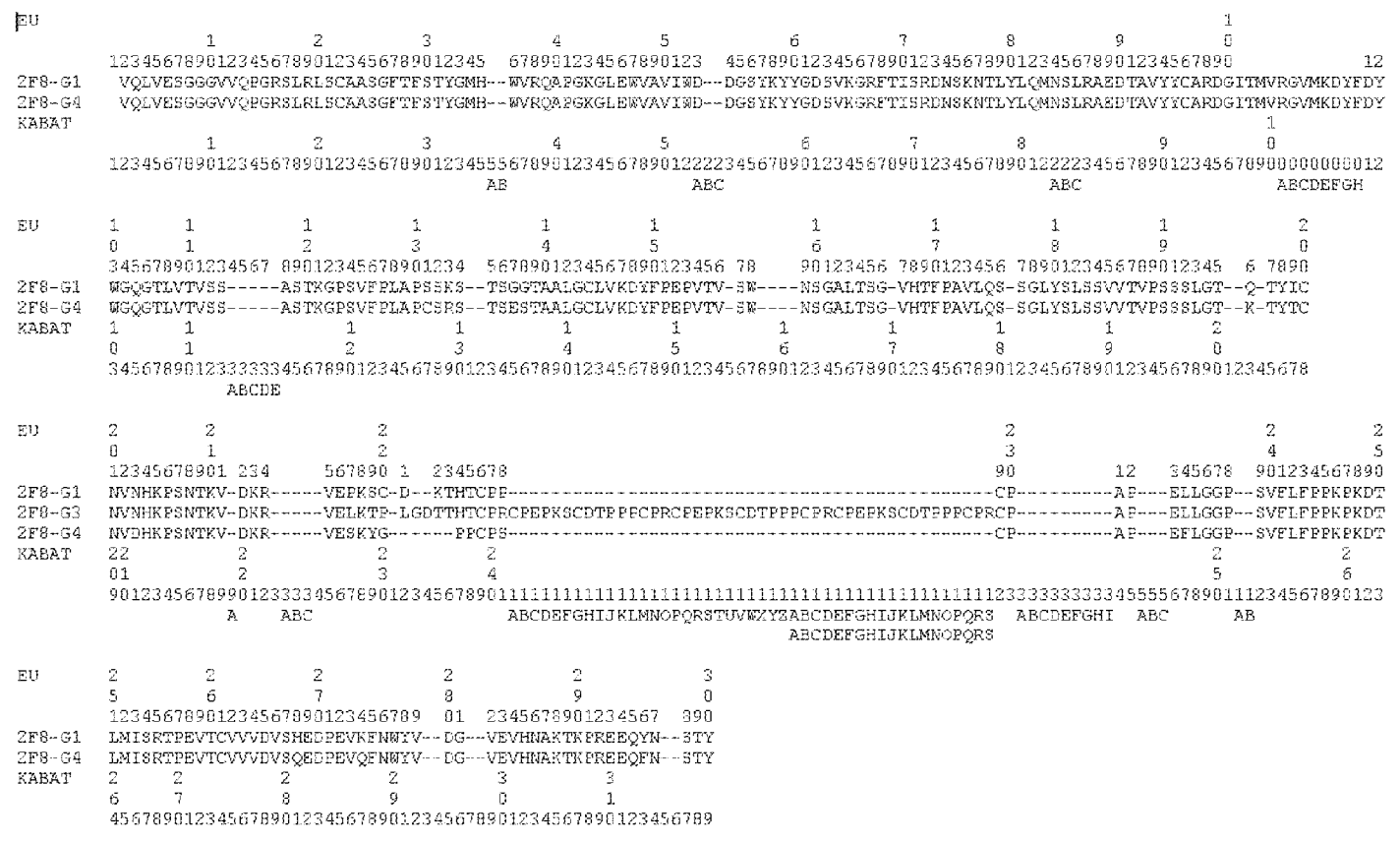
Figure 3B:
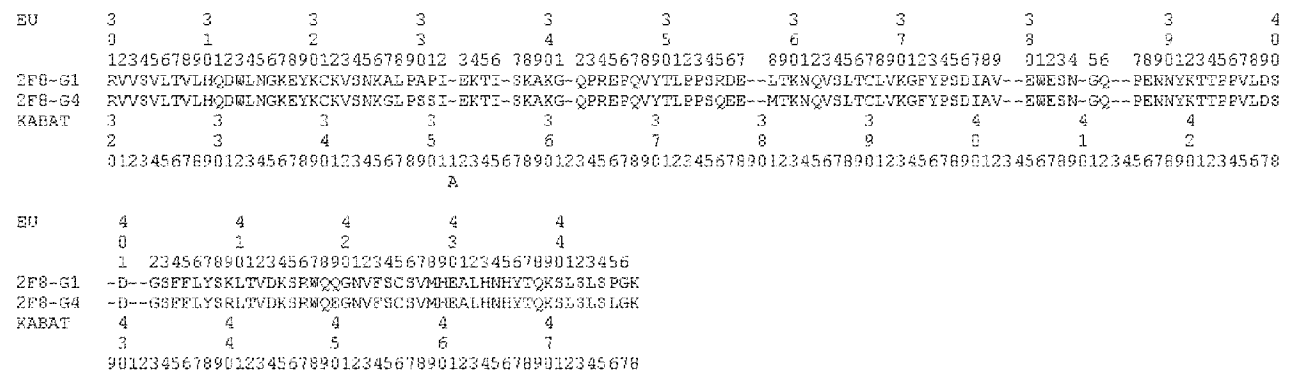

An amino acid or segment in one sequence that "corresponds to" an amino acid or segment in another sequence is one that (i) aligns with the other amino acid or segment using a standard sequence alignment program such as ALIGN, ClustalW or similar, typically at default settings and (ii) has a sequence identity to SEQ ID NO:1 of at least 50%, at least 80%, at least 90%, or at least 95%. For example, the sequence alignments shown in FIGS. 2 and 3 can be used to identify any amino acid in the IgG2, IgG3 or IgG4 Fc sequence that corresponds to a particular amino acid in the IgG1 Fc sequence.

The present invention refers to variants, viz. parent antibodies, and/or variant antibodies, having a certain degree of identity to amino acids P247 to K447 of SEQ ID Nos:1, 2, 3, 4, and 5, such parent and/or variant antibodies being hereinafter designated "homologous antibodies".

For purposes of the present invention the degree of identity between two amino acid sequences, as well as the degree of identity between two nucleotide sequences, is determined by the program "align" which is a Needleman-Wunsch alignment (i.e. a global alignment). The program is used for alignment of polypeptide, as well as nucleotide sequences. The default scoring matrix BLOSUM50 is used for polypeptide alignments, and the default identity matrix is used for nucleotide alignments, the penalty of the first residue of a gap is −12 for polypeptides and −16 for nucleotides. The penalties for further residues of a gap are −2 for polypeptides, and −4 for nucleotides.

"Align" is part of the FASTA package version v20u6 (see W. R. Pearson and D. J. Lipman (1988), "Improved Tools for Biological Sequence Analysis", PNAS 85:2444-2448, and W. R. Pearson (1990) "Rapid and Sensitive Sequence Comparison with FASTP and FASTA", Methods in Enzymology 183:63-98). FASTA protein alignments use the Smith-Waterman algorithm with no limitation on gap size (see "Smith-Waterman algorithm", T. F. Smith and M. S. Waterman (1981) J. Mol. Biolo. 147:195-197).

As used herein, the term "effector cell" refers to an immune cell which is involved in the effector phase of an immune response, as opposed to the cognitive and activation phases of an immune response. Exemplary immune cells include a cell of a myeloid or lymphoid origin, for instance lymphocytes (such as B cells and T cells including cytolytic T cells (CTLs)), killer cells, natural killer cells, macrophages, monocytes, eosinophils, polymorphonuclear cells, such as neutrophils, granulocytes, mast cells, and basophils. Some effector cells express Fc receptors (FcRs) or complement receptors and carry out specific immune functions. In some embodiments, an effector cell such as, e.g., a natural killer cell, is capable of inducing ADCC. For example, monocytes, macrophages, neutrophils, dendritic cells and Kupffer cells which express FcRs, are involved in specific killing of target cells and presenting antigens to other components of the immune system, or binding to cells that present antigens. In some embodiments the ADCC can be further enhanced by antibody driven classical complement activation resulting in the deposition of activated C3 fragments on the target cell. C3 cleavage products are ligands to complement receptors (CRs), such as CR3, expressoid on myeloid cells. The recognition of complement fragments by CRs on effector cells may promote enhanced Fc receptor-mediated ADCC. In some embodiments antibody driven classical complement activation leads to C3 fragments on the target cell. These C3 cleavage products may promote direct complement-dependent cellular cytotoxicity (CDCC). In some embodiments, an effector cell may phagocytose a target antigen, target particle or target cell. The expression of a particular FcR or complement receptor on an effector cell may be regulated by humoral factors such as cytokines. For example, expression of FcγRI has been found to be up-regulated by interferon γ (IFN γ) and/or G-CSF. This enhanced expression increases the cytotoxic activity of FcγRI-bearing cells against targets. An effector cell can phagocytose a target antigen or phagocytose or lyse a target cell. In some embodiments antibody driven classical complement activation leads to C3 fragments on the target cell. These C3 cleavage products may promote direct phagocytoses by effector cells or indirectly by enhancing antibody mediated phagocytosis.

The term "vector," as used herein, is intended to refer to a nucleic acid molecule capable of inducing transcription a nucleic acid segment ligated into the vector. One type of vector is a "plasmid", which is in the form of a circular double stranded DNA loop. Another type of vector is a viral vector, wherein the nucleic acid segment may be ligated into the viral genome. Certain vectors are capable of autonomous replication in a host cell into which they are introduced (for instance bacterial vectors having a bacterial origin of replication and episomal mammalian vectors). Other vectors (such as non-episomal mammalian vectors) may be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the present invention is intended to include such other forms of expression vectors, such as viral vectors (such as replication defective retroviruses, adenoviruses and adeno-associated viruses), which serve equivalent functions.

The term "recombinant host cell" (or simply "host cell"), as used herein, is intended to refer to a cell into which an expression vector has been introduced. It should be understood that such terms are intended to refer not only to the particular subject cell, but also to the progeny of such a cell. Because certain modifications may occur in succeeding generations due to either mutation or environmental influences, such progeny may not, in fact, be identical to the parent cell, but are still included within the scope of the term "host cell" as used herein. Recombinant host cells include, for example, transfectomas, such as CHO cells, HEK-293 cells, PER.C6, NSO cells, and lymphocytic cells, and prokaryotic cells such as E. coli and other eukaryotic hosts such as plant cells and fungi.

The term "transfectoma", as used herein, includes recombinant eukaryotic host cells expressing the Ab or a target antigen, such as CHO cells, PER.C6, NSO cells, HEK-293 cells, plant cells, or fungi, including yeast cells.

The term "preparation" refers to preparations of antibody variants and mixtures of different antibody variants which can have an increased ability to form oligomers when interacting with antigen associated with a cell (e.g., an antigen expressed on the surface of the cell), a cell membrane, a virion or other structure, thereby enabling an increased C1q binding, complement activation, CDC, ADCC, ADCP, other Fc-mediated effector function, internalization, downmodulation, apoptosis, antibody-drug-conjugate (ADC) uptake, avidity or a combination of any thereof. Exemplary assays are provided in the Examples for, e.g., C1q-binding avidity (Example 4), CDC (Examples 5, 6 and 10, 16, 19, 22, 23, 24, 25); ADCC (Example 12) and in vivo efficacy (Example 20, 21). Variants according to the aspects herein referred to as "single-mutant", "double-mutant", and "mixed-mutants", are described in further detail below, along with exemplary processes for their preparation and methods of use.

As used herein, the term "affinity" is the strength of binding of one molecule, e.g. an antibody, to another, e.g. a target or antigen, at a single site, such as the monovalent binding of an individual antigen binding site of an antibody to an antigen.

As used herein, the term "avidity" refers to the combined strength of multiple binding sites between two structures, such as between multiple antigen binding sites of antibodies simultaneously interacting with a target or e.g. between antibody and C1q. When more than one binding interactions are present, the two structures will only dissociate when all binding sites dissociate, and thus, the dissociation rate will be slower than for the individual binding sites, and thereby providing a greater effective total binding strength (avidity) compared to the strength of binding of the individual binding sites (affinity).

As used herein, the term "oligomer" refers to a molecule that consists of more than one but a limited number of monomer units (e.g. antibodies) in contrast to a polymer that, at least in principle, consists of an unlimited number of monomers. Exemplary oligomers are dimers, trimers, tetramers, pentamers and hexamers. Greek prefixes are often used to designate the number of monomer units in the oligomer, for example a tetramer being composed of four units and a hexamer of six units.

The term "oligomerization", as used herein, is intended to refer to a process that converts monomers to a finite degree of polymerization. Herein, it is observed, that the oligomerization of Fc-domains takes place after target binding by Fc-domain containing polypeptides, such as antibodies, preferably but not limited to at a cell surface. The oligomerization of antibodies can be evaluated for example using a cell surface C1q-binding assay (as described in examples 4 and 9), C1q efficacy assay (as described in example 5) and complement dependent cytotoxicity described in Example 6, 10 and 19).

The term "C1q binding", as used herein, is intended to refer to the binding of C1q in the context of the binding of C1q to an antibody bound to its antigen. The antibody bound to its antigen is to be understood as happening both in vivo and in vitro in the context described herein. C1q binding can be evaluated for example by using immobilized antibody on artificial surface (e.g. plastic in plates for ELISA, as described in example 3) or by using bound to a predetermined antigen on a cellular or virion surface (as described in examples 4 and 9). The binding of C1q to an antibody oligomer is to be understood herein as a multivalent interaction resulting in high avidity binding.

As used herein, the term "complement activation" refers to the activation of the classical complement pathway, which is triggered by the binding of complement component C1q to an antibody bound to its antigen. C1q is the first protein in the early events of the classical complement cascade that involves a series of cleavage reactions that culminate in the formation of an enzymatic activity called C3 convertase, which cleaves complement component C3 into C3b and C3a. C3b binds covalently to C5 on the membrane to form C5b that in turn triggers the late events of complement activation in which terminal complement components C5b, C6, C7, C8 and C9 assemble into the membrane attack complex (MAC). The complement cascade results in the creation of pores due to which causes cell lysis, also known as CDC. Complement activation can be evaluated by using C1q efficacy (as described in example 5), CDC kinetics (as described in examples 28, 29, and 30), CDC assays (as described in examples 6, 10, 19, 25, 27, and 33) or by the method Cellular deposition of C3b and C4b described in Beurskens et al Apr. 1, 2012 vol. 188 no. 7 3532-3541.

The term "complement-dependent cytotoxicity" ("CDC"), as used herein, is intended to refer to the process of antibody-mediated complement activation leading to lysis of the antibody bound to its target on a cell or virion as a result of pores in the membrane that are created by MAC assembly. CDC can be evaluated by in vitro assay such as a CDC assay in which normal human serum is used as a complement source, as described in example 6, 10, 19, 25, 27, and 33 or in a C1q efficacy assay, as described in example 5, in which normal human serum has been limited in C1q.

The term "antibody-dependent cell-mediated cytotoxicity" ("ADCC") as used herein, is intended to refer to a mechanism of killing of antibody-coated target cells or virions by cells expressing Fc receptors that recognize the constant region of the bound antibody. ADCC can be determined using methods such as, e.g., the ADCC assay described in example 12.

The term "antibody-dependent cellular phagocytosis" ("ADCP") as used herein is intended to refer to a mechanism of elimination of antibody-coated target cells or virions by internalization by phagocytes. The internalized antibody-coated target cells or virions is contained in a vesicle called a phagosome, which then fuses with one or more lysosomes to form a phagolysosome. ADCP may be evaluated by using an in vitro cytotoxicity assay with marcophages as effortor cells and video microscopy as described by van Bij et al. in Journal of Hepatology Volume 53, Issue 4, October 2010, Pages 677-685. Or as descriped in example 14 for e.g. *S. aureus* phagocytos by PMN.

The term "complement-dependent cellular cytotoxicity" ("CDCC") as used herein is intended to refer to a mechanism of killing of target cells or virions by cells expressing complement receptors that recognize complement 3 (C3) cleavage products that are covalently bound to the target cells or virions as a result of antibody-mediated complement activation. CDCC may be evaluated in a similar manner as described for ADCC.

The term "downmodulation", as used herein, is intended to refer a process that decreases the number of molecules, such as antigens or receptors, on a cellular surface, e.g. by binding of an antibody to a receptor.

The term "internalization", as used herein, is intended to refer to any mechanism by which an antibody or Fc-containing polypeptide is internalized into a target-expressing cell from the cell-surface and/or from surrounding medium, e.g., via endocytosis. The internalization of an antibody can be evaluated using a direct assay measuring the amount of internalized antibody (such as, e.g., the lysosomal co-localization assay described in Example 26).

The term "antibody-drug conjugate", as used herein refers to an antibody or Fc-containing polypeptide having specificity for at least one type of malignant cell, a drug, and a linker coupling the drug to e.g. the antibody. The linker is cleavable or non-cleavable in the presence of the malignant cell; wherein the antibody-drug conjugate kills the malignant cell.

The term "antibody-drug conjugate uptake", as used herein refers to the process in which antibody-drug conjugates are bound to a target on a cell followed by uptake/engulfment by the cell membrane and thereby is drawn into the cell. Antibody-drug conjugate uptake may be evaluated as "antibody-mediated internalization and cell killing by anti-TF ADC in an in vitro killing assay" as described in WO 2011/157741.

The term "apoptosis", as used herein refers to the process of programmed cell death (PCD) that may occur in a cell. Biochemical events lead to characteristic cell changes (morphology) and death. These changes include blebbing, cell shrinkage, nuclear fragmentation, chromatin condensation, and chromosomal DNA fragmentation. Binding of an antibody to a certain receptor may induce apoptosis.

Fc-receptor binding may be indirectly measured as described in Example 12.

The term "FcRn", as used herein is intended to refer to neonatal Fc receptor which is an Fc receptor. It was first discovered in rodents as a unique receptor capable of transporting IgG from mother's milk across the epithelium of newborn rodent's gut into the newborn's bloodstream. Further studies revealed a similar receptor in humans. In humans, however, it is found in the placenta to help facilitate transport of mother's IgG to the growing fetus and it has also been shown to play a role in monitoring IgG turnover. FcRn binds IgG at acidic pH of 6.0-6.5 but not at neutral or higher pH. Therefore, FcRn can bind IgG from the intestinal lumen (the inside of the gut) at a slightly acidic pH and ensure efficient unidirectional transport to the basolateral side (inside the body) where the pH is neutral to basic (pH 7.0-7.5). This receptor also plays a role in adult salvage of IgG through its occurrence in the pathway of endocytosis in endothelial cells. FcRn receptors in the acidic endosomes bind to IgG internalized through pinocytosis, recycling it to the cell surface, releasing it at the basic pH of blood, thereby preventing it from undergoing lysosomal degradation. This mechanism may provide an explanation for the greater half-life of IgG in the blood compared to other isotypes. Example 13 describes an assay showing IgG binding to FcRn at pH 6.0 in ELISA.

The term "Protein A", as used herein is intended to refer to a 56 kDa MSCRAMM surface protein originally found in the cell wall of the bacterium *Staphylococcus aureus*. It is encoded by the spa gene and its regulation is controlled by DNA topology, cellular osmolarity, and a two-component system called ArlS-ArlR. It has found use in biochemical research because of its ability to bind immunoglobulins. It is composed of five homologous Ig-binding domains that fold into a three-helix bundle. Each domain is able to bind proteins from many of mammalian species, most notably IgGs. It binds the heavy chain Fc region of most immunoglobulins (overlapping the conserved binding site of FcRn receptors) and also interacts with the Fab region of the human VH3 family. Through these interactions in serum, IgG molecules bind the bacteria via their Fc region instead of solely via their Fab regions, by which the bacteria disrupts opsonization, complement activation and phagocytosis.

The term "Protein G", as used herein is intended to refer to an immunoglobulin-binding protein expressed in group C and G Streptococcal bacteria much like Protein A but with differing specificities. It is a 65-kDa (G148 protein G) and a 58 kDa (C40 protein G) cell surface protein that has found application in purifying antibodies through its binding to the Fc region.

The term "CH2 region" or "CH2 domain" as used herein is intended to refer the CH2 region of an immunoglobulin. Thus for example the CH2 region of a human IgG1 antibody corresponds to amino acids 228-340 according to the EU numbering system.

The term "CH3 region" or "CH3 domain" as used herein is intended to refer the CH3 region of an immunoglobulin. Thus for example the CH3 region of a human IgG1 antibody corresponds to amino acids 341-447 according to the EU numbering system.

The term "allosteric mutations", as used herein, is intended to refer to modifications, eg insertions, substitutions and deletions, of amino acids P247, and E430, in Fc-domain containing polypeptides, as numbered by the EU index as set forth in Kabat.

The term "hydrophobic knob mutations", as used herein, is intended to refer to modifications, eg insertions, substitutions and deletions, of amino acids I253, and S254, and Q311, in Fc-domain containing polypeptides, as numbered by the EU index as set forth in Kabat. Hydrophobic knobs are described by Delano W L, et al., Science 287, (2000), pages 1279-1283, e.g. on page 1281.

The term "N-terminal CH3 helix mutations", as used herein, is intended to refer to modifications, eg insertions, substitutions and deletions, of amino acids R355, and D356, and E356, and E357, and M358, and L358, and T359, more specifically of D356, and E356, and T359, in Fc-domain containing polypeptides, as numbered by the EU index as set forth in Kabat.

The term "C-terminal CH3 beta strand mutations", as used herein, is intended to refer to modifications, eg insertions, substitutions and deletions, of amino acids Y436, and T437, and Q438, and K439, and S440, and L441, more specifically of Y436, and K439, and S440, in Fc-domain containing polypeptides, as numbered by the EU index as set forth in Kabat.

Methods of Affecting an Effector Function of an Antibody

It is to be understood that all embodiments described herein with reference to a parent antibody, first parent antibody or second parent antibody are also to be understood as embodiments relating to a parent, first parent or second parent polypeptide comprising an Fc-domain of an immunoglobulin and a binding region.

In one aspect the present invention relates to a method of increasing an effector function of a parent polypeptide comprising an Fc-domain of an immunoglobulin and a binding region, which method comprises introducing a mutation to the parent polypeptide in at least one amino acid residue selected from those corresponding to E345, E430, S440, Q386, P247, I253, S254, Q311, D/E356, T359, E382, Y436, and K447 in the Fc-region of a human IgG1 heavy chain, with the proviso that the mutation in S440 is S440Y or S440W.

In one embodiment the parent polypeptide may be an antibody.

Thus the present invention relates to a method of increasing an effector function of a parent antibody, comprising introducing a mutation to the parent antibody in at least one amino acid residue selected from those corresponding to E345, E430, S440, Q386, P247, I253, S254, Q311, D/E356, T359, E382, Y436, and K447 in the Fc-region of a human IgG1 heavy chain, with the proviso that the mutation in S440 is S440Y or S440W.

The reference to "D/E356" refers in the present context to allotypic variants in the sequence of human IgG1. In the IgG1m(za) allotype of human IgG1 the amino acid in position 356 is D, while in the IgG1m(f) allotype of human IgG1 the amino acid in position 356 is E.

Introducing a mutation to a parent antibody according to a method or use of the present invention results in a variant or variant antibody. Thus the method(s) of the present invention may be performed so as to obtain any variant or variant antibody as described herein.

The variant antibody obtained from a method or use of the present invention has an increased effector function compared to the parent antibody. Typically, the effect of an antibody on an effector function may be determined by the EC50 value, which is the concentration of the antibody necessary to obtain half the value of the maximal lysis.

Maximal lysis is the lysis obtained when a saturating amount of the antibody is used, in which saturating is intended to refer to the amount of antibody at which all antigens for the antibody are bound by antibody.

The term "increasing an effector function" or "improving an effector function" refers in the context of the present invention that there is a decrease in the EC50 value of the variant antibody compared to the parent antibody. The decrease in the EC50 value may e.g. be at least or about 2-fold, such as at least or about 3-fold, or at least or about 5-fold, or at least or about 10-fold. Alternatively, "increasing an effector function" or "improving an effector function" means that there is an increase in the maximal amount of cells lysed (where the total amount of cells is set at 100%) by e.g. from 10% to 100% of all cells, such as by about 10%, about 20%, about 30%, about 40%, about 50%, about 60%, about 70%, about 80%, about 90%, and about 100% under conditions where the parent antibody lyses less than 100% of all cells.

A variant could be tested for increased or improved effector function by cloning the variable domain of the IgG1-005 or IgG1-7D8 heavy chain into the variant and test its efficacy in CDC assays, such as described for Daudi (Example 6) and Wien (Example 10). Using an IgG1-7D8 HC variable domain and Daudi cells, an increase would be defined by a more than 2 fold lower EC50 than the EC50 of IgG1-7D8 under the studied condition, such as about 2-fold, about 3-fold, about 5-fold, about 10-fold or a more than 10-fold lower EC50 value, the concentration at which half-maximal lysis is observed. Using an IgG1-005 HC variable domain and Daudi cells, an increase would be defined by a more than 2 fold lower EC50 than the EC50 of IgG1-005 under the studied condition, such as about 2-fold, about 3-fold, about 5-fold, about 10-fold or a more than 10-fold lower EC50 value, the concentration at which half-maximal lysis is observed. Using an IgG1-7D8 HC variable domain and Wien133 cells, an increase would be defined by a more than 2 fold lower EC50 than the EC50 of IgG1-7D8 under the studied condition, such as about 2-fold, about 3-fold, about 5-fold, about 10-fold or a more than 10-fold lower EC50 value, the concentration at which half-maximal lysis is observed. Using an IgG1-005 HC variable domain and Wien133 cells, an increase would be defined by an increase in the maximal lysis ranging from 10% to 100% of all cells, such as by about 10%, about 20%, about 30%, about 40%, about 50%, about 60%, about 70%, about 80%, about 90%, and about 100%. An increase in CDC efficacy could also be defined by a more than 2-fold lower EC50 than the EC50 of IgG1-005 under the studied condition, such as about 2-fold, about 3-fold, about 5-fold, about 10-fold or a more than 10-fold lower EC50 value, the concentration at which half-maximal lysis is observed under conditions where lysis of Wien133 cells is detectable.

The inventors of the present invention surprisingly found that mutations in these specific positions have an improved effect on effector functions of the variant antibody, which is obtained from introducing a mutation into a parent antibody according to a method of the present invention (e.g. as shown in Example 19). Without being bound by theory, it is believed that by substituting at least one amino acid from the above-mentioned group of positions oligomerization is stimulated. The antibodies bind with higher avidity (exemplified by example 2; direct labelling of IgG-7D8-E345R resulted in increased binding to Daudi cells in comparison to IgG-7D8-WT) which causes the antibodies to bind for a longer time to the cells and thereby different effector functions are enabled, e.g. increased C1q binding, C1q efficacy CDC, ADCC, internalization, ADCP, and/or in vivo efficacy. These effects have been exemplified by example 4 (C1q binding on cells), example 5 (C1q efficacy in a CDC assay), example 6, 7, 27, 28 and 29 (CDC assay), example 12 (ADCC), example 26 (internalization) and example 21 and 22 (in vivo efficacy).

Thus the mutation of an amino acid residue selected from those corresponding to E345, E430, S440, Q386, P247, I253, S254, Q311, D/E356, T359, E382, Y436, and K447 in the Fc-region of a human IgG1 heavy chain may also be referred to as "single mutant" aspect or "effector-enhancing mutations" in the context of the present invention.

In another aspect, the present invention also provides for the use of one or more mutations in Table 1, such as a mutation in an amino acid residue selected from those corresponding to E345, E430, S440, Q386, P247, I253, S254, Q311, D/E356, T359, E382, Y436, and K447 in the Fc-region of a human IgG1 heavy chain, to increase an effector function, e.g. one or more of (i) C1q-binding, (ii) complement activation, (iii) CDC, (iv) oligomer formation, (v) oligomer stability, (vi) antibody-dependent cell-mediated cytotoxity (ADCC), (vii) FcRn-binding, (viii) Fc-gamma receptor-binding, (ix) Protein A-binding, (x) Protein G-binding, (xi) antibody-dependent cellular phagocytosis (ADCP), (xii) complement-dependent cellular cytotoxicity (CDCC), (xiii) complement-enhanced cytotoxicity, (xiv) binding to complement receptor of an opsonized antibody mediated by the antibody, (xv) internalization, (xvi) downmodulation, (xvii) induction of apoptosis, (xviii) opsonisation and (xix) a combination of any of (i) to (xviii), of an antibody when bound to its antigen on a cell, on a cell membrane, on a virion, or on another particle. In one embodiment of (iv) or (v), the oligomer is a hexamer. In one embodiment, at least one other effector function of the antibody, such as C1q-binding, complement activation, complement dependent cytotoxicity (CDC), antibody-dependent cell-mediated cytotoxity (ADCC), FcRn-binding, Fc-gamma receptor-binding, Protein A-binding, Protein G-binding, ADCP, complement-dependent cellular cytotoxicity (CDCC), complement-enhanced cytotoxicity, binding to complement receptor of an opsonized antibody mediated by the antibody, antibody mediated phagocytosis (ADCP), internalization, apoptosis, and/or binding to complement receptor of an opsonized antibody is also or alternatively increased, such as in particular FcRn binding, ADCC, Fc gamma receptor binding, Protein A binding, Protein G binding, ADCP, CDCC, complement enhanced cytotoxicity, opsonisation and any combinations thereof.

In one embodiment, the effector function of the parent antibody is increased when the parent antibody is bound to its antigen on an antigen-expressing cell, on a cell membrane, or on a virion.

The inventors of the present invention have also shown that introducing a mutation to a parent antibody in an amino acid residue corresponding to either K439 or S440 in the Fc region of a human IgG1 heavy chain decreases the effector function of the parent antibody (examples 5, 6 and 10).

In another aspect the present invention relates to a method of decreasing an effector function of a parent polypeptide comprising an Fc-domain of an immunoglobulin and a binding region, which method comprises introducing a mutation to the parent polypeptide in one amino acid residue selected from those corresponding to K439 and S440 in the Fc-region of a human IgG1 heavy chain, with the proviso that the mutation in S440 is not S440Y or S440W, such as wherein the mutation in the position corresponding to K439 in the Fc-region of human IgG1 heavy chain is K439D/E, and/or the mutation in the position corresponding to S440 in the Fc-region of human IgG1 heavy chain is S440K/H/R.

In one embodiment the parent polypeptide may be an antibody.

Hence in another aspect, the present invention relates also to a method of decreasing an effector function of a parent antibody comprising introducing a mutation to the parent antibody in one amino acid residue selected from those corresponding to K439 and S440 in the Fc-region of a human IgG1 heavy chain, with the proviso that the mutation in S440 is not S440Y or S440W, such as wherein the mutation in the position corresponding to K439 in the Fc-region of human IgG1 heavy chain is K439D/E, and/or the mutation in the position corresponding to S440 in the Fc-region of human IgG1 heavy chain is S440K/H/R.

As shown in Example 6, the amino acid substitution of position K439E or S440K as "single-mutants" decreased CDC as compared to any one of the first mutations according to the method of the present invention.

The variant antibody obtained from said method of decreasing an effector function has an decreased effector function compared to the parent antibody. Typically, the effect of an antibody on an effector function may be measured by the EC50 value, which is the concentration of the antibody necessary to obtain half the value of the maximal lysis.

Maximal lysis is the lysis obtained when a saturating amount of the antibody is used, in which saturating is intended to refer to the amount of antibody at which all antigens for the antibody are bound by antibody.

The term "decreasing an effector function" refers in the context of the present invention that there is a increase in the EC50 value of the variant antibody compared to the parent antibody. The increase in the EC50 value may e.g. be at least or about 2-fold, such as at least or about 3-fold, or at least or about 5-fold, or at least or about 10-fold. Alternatively, "decreasing an effector function" means that there is an decrease in the maximal amount of cells lysed by e.g. from 10% to 100% of all cells, such as about 10%, about 20%, about 30%, about 40%, about 50%, about 60%, about 70%, about 80%, about 90%, and about 100% under conditions where the parent antibody lyses less than 100% of all cells.

A variant could be tested for decreased effector function by cloning the variable domain of the IgG1-005 or IgG1-7D8 heavy chain into the variant and test its efficacy in CDC assays, such as described for Daudi (Example 6) and Wien (Example 10). Using an IgG1-7D8 HC variable domain and Daudi cells, an decrease would be defined by a more than 2 fold lower EC50 than the EC50 of IgG1-7D8 under the studied condition, such as about 2-fold, about 3-fold, about 5-fold, about 10-fold or a more than 10-fold lower EC50 value, the concentration at which half-maximal lysis is observed. Using an IgG1-005 HC variable domain and Daudi cells, an decrease would be defined by a more than 2 fold lower EC50 than the EC50 of IgG1-005 under the studied condition, such as about 2-fold, about 3-fold, about 5-fold, about 10-fold or a more than 10-fold lower EC50 value, the concentration at which half-maximal lysis is observed. Using an IgG1-7D8 HC variable domain and Wien133 cells, an decrease would be defined by a more than 2 fold lower EC50 than the EC50 of IgG1-7D8 under the studied condition, such as about 2-fold, about 3-fold, about 5-fold, about 10-fold or a more than 10-fold lower EC50 value, the concentration at which half-maximal lysis is observed. Using an IgG1-005 HC variable domain and Wien133 cells, an decrease would be defined by an decrease in the maximal lysis ranging from 10% to 100% of all cells, such as by about 10%, about 20%, about 30%, about 40%, about 50%, about 60%, about 70%, about 80%, about 90%, and about 100%. An decrease in CDC efficacy could also be defined by a more than 2-fold lower EC50 than the EC50 of IgG1-005 under the studied condition, such as about 2-fold, about 3-fold, about 5-fold, about 10-fold or a more than 10-fold lower EC50 value, the concentration at which half-maximal lysis is observed under conditions where lysis of Wien133 cells is detectable.

In one embodiment, the effector function is decreased, when the parent antibody is bound to its antigen on an antigen-expressing cell, on a cell membrane, or on a virion.

Thus in another aspect, the invention relates to use of at least a further mutation in an antibody variant comprising a mutation in one amino acid residue selected from those corresponding to K439 and S440 in the Fc-region of a human IgG1 heavy chain, with the proviso that the mutation in S440 is not S440Y or S440W, to restore an effector function of the antibody variant when bound to its antigen on an antigen-expressing cell, on a cell membrane, or on a virion, wherein
the first mutation is in an amino acid residue corresponding to K439 in the Fc-region of a human IgG1 heavy chain and the second mutation is in an amino acid residue corresponding to S440 in the Fc-region of a human IgG1 heavy chain, or
the first mutation is in an amino acid residue corresponding to S440 in the Fc-region of a human IgG1 heavy chain and the second mutation is in an amino acid residue corresponding to K439 in the Fc-region of a human IgG1 heavy chain.

In one embodiment, the parent antibody is a monospecific, bispecific, or multispecific antibody.

If the parent antibody is a monospecific antibody comprising two CH2-CH3 regions, a mutation according to the present invention may in principle only be present in one of the CH2-CH3 regions, although for most practical purpose a mutation increasing or decreasing an effector function according to the present invention is present in both CH2-CH3 regions.

If the parent antibody is a bispecific antibody comprising two CH2-CH3 regions, a mutation according to the present invention may in principle only be present in one of the CH2-CH3 regions; i.e. in either the first or second CH2-CH3 region, although for most practical purpose a mutation increasing or decreasing an effector function according to the present invention is present in both the first and second CH2-CH3 regions of the bispecific antibody.

Suitable examples of monospecific, bispecific, or multispecific antibodies include any of those described herein.

In a particular embodiment the parent or first and/or second antibody may be bispecific antibody such as the heterodimeric protein described in WO 11/131746, which is hereby incorporated herein by reference.

In one embodiment, the parent antibody is a bispecific antibody which comprises a first polypeptide comprising a first CH2-CH3 region of an immunoglobulin and a first antigen-binding region, and a second polypeptide comprising a second CH2-CH3 region of an immunoglobulin and a second antigen-binding region, wherein the first and second antigen-binding regions bind different epitopes on the same antigen or on different antigens.

In a further embodiment said first CH2-CH3 region comprises a further amino acid substitution at a position selected from those corresponding to K409, T366, L368, K370, D399, F405, and Y407 in the Fc-region of a human IgG1 heavy chain; and wherein said second CH2-CH3 region comprises a further amino acid substitution at a position selected from those corresponding to F405, T366, L368, K370, D399, Y407, and K409 in the Fc-region of a human IgG1 heavy chain, and wherein said further amino acid substitution in the first CH2-CH3 region is different from the said further amino acid substitution in the second CH2-CH3 region.

In a further embodiment said first CH2-CH3 region comprises an amino acid substitution at a position corresponding to K409 in the Fc-region of a human IgG1 heavy chain; and said second CH2-CH3 region comprises an amino acid substitution at a position corresponding to F405 in the Fc-region of a human IgG1 heavy chain.

In one embodiment said method comprises introducing to each of the first and second CH2-CH3 regions a mutation in at least one amino acid residue selected from those corresponding to E345, E430, S440, Q386, P247, I253, S254, Q311, D/E356, T359, E382, Y436, and K447 in the Fc-region of a human IgG1 heavy chain, with the proviso that the mutation in S440 is S440Y or S440W.

In a further embodiment the mutation introduced in the first and second CH2-CH3 region in at least one amino acid residue selected from those corresponding to E345, E430, S440, Q386, P247, I253, S254, Q311, D/E356, T359, E382, Y436, and K447 in the Fc-region of a human IgG1 heavy chain, with the proviso that the mutation in S440 is S440Y or S440W, may be in the same amino acid residue position or a different position. In a further embodiment it may be the same or a different mutation in the same amino acid residue position.

In another embodiment said method comprises introducing in the first or second CH2-CH3 region a mutation in at least one amino acid residue selected from those corresponding to E345, E430, S440, Q386, P247, I253, S254, Q311, D/E356, T359, E382, Y436, and K447 in the Fc-region of a human IgG1 heavy chain, with the proviso that the mutation in S440 is S440Y or S440W.

Any of the mutations listed in Table 1 may be introduced to the bispecific antibody. Example 24, shows that introducing the E345R mutation to a bispecific CD20×EGFR antibody enhances the CDC efficacy. Examples 23, 29 and 30 also describe some of the different of bispecific antibodies comprising a mutation according to the present invention.

In one embodiment said method comprises introducing the mutation in one or more positions other than S440 and K447, and further introducing a mutation
(i) in each of the amino acid residues corresponding to K439 and S440 in the Fc-region of a human IgG1 heavy chain, with the proviso that the mutation in S440 is not S440Y or S440W,
(ii) in each of the amino acid residues corresponding to K447 and 448 in the Fc-region of a human IgG1 heavy chain, such as K447K/R/H and 448E/D in the Fc-region of a human IgG1 heavy chain, preferably K447K and 448E in the Fc-region of a human IgG1 heavy chain, or
(iii) in each of the amino acid residues corresponding to K447, 448 and 449 in the Fc-region of a human IgG1 heavy chain, such as K447D/E, 448K/R/H and 449P in the Fc-region of a human IgG1 heavy chain, preferably K447E, 448K and 449P in the Fc-region of a human IgG1 heavy chain.

In one embodiment, said method comprises introducing the mutation in one or more positions other than S440, and further introducing a mutation in each of the amino acid residues corresponding to K439 and S440 in the Fc-region of a human IgG1 heavy chain, with the proviso that the further mutation in S440 is not S440Y or S440W.

Introduction of mutations in both amino acid residues corresponding to K439 and S440 in the Fc region of a human IgG1 heavy chain in a parent antibody, with the proviso that the mutation in S440 is not S440Y or S440W is also referred herein to as the "double mutant" aspect. The S440Y and S440W mutations have as described elsewhere been found to increase an effector function when introduced into a parent antibody.

As also described elsewhere the inventors of the present invention have found that introducing an identified mutations in an amino acid residue corresponding to either K439 or S440 in the Fc region of a human IgG1 heavy chain results in a decrease in an effector function (examples 5, 6, 10). However, when inhibiting mutations in both of the amino acid residues corresponding to K439 and S440 in the Fc region of a human IgG1 heavy chain are introduced the decrease in effector function is restored, thereby making it similar to the effector function of the parent antibody without a mutation at the K439 and S440 mutations. However, the presence of the K439 and S440 mutations is, without being bound by any theory, believed to restrict the induction of effector functions to oligomeric complexes exclusively consisting of exclusively antibodies comprising both the K439 and the S440 mutations. Thus if the K439 and S440 mutations are included in a therapeutic antibody, it is believed, without being bound by any theory, that when such therapeutic antibodies are administered to a patient the induction of effector functions is limited to oligomeric antibody complexes containing the therapeutic antibodies comprising the K439/S440 mutations but not containing the patients own antibodies, which do not comprise the K439 and S440 mutations, thereby limiting any potential side-effects caused by interaction of a therapeutic antibody with the patients own antibodies.

When combining the mutations of position K439 and/or S440 with the first mutation, enhancement of CDC is obtained and the specificity of CDC is increased.

Thus in another aspect the present invention relates to a method of increasing the specificity of a combination of at least a first and a second parent polypeptide comprising an Fc-domain of an immunoglobulin and a binding region, comprising
A)
(i) introducing to the first parent polypeptide a mutation in an amino acid residue in the position corresponding to K439 in the Fc region of a human IgG1 heavy chain; and
(ii) introducing to the second parent polypeptide a mutation in an amino acid residue in the position corresponding to S440 in the Fc-region of a human IgG1 heavy chain, with the proviso that the mutation in S440 is not S440Y or S440W,
B)
(i) introducing to the first parent polypeptide a mutation in an amino acid residue in the position corresponding to K447D/E in the Fc region of a human IgG1 heavy chain; and
(ii) introducing to the second parent polypeptide a mutation in an amino acid residue in the position corresponding to K447K/R/H and 448P in the Fc-region of a human IgG1 heavy chain; or
C)
(i) introducing to the first parent polypeptide a mutation in an amino acid residue in the position corresponding to K447D/E in the Fc region of a human IgG1 heavy chain; and
(ii) introducing to the second parent polypeptide a mutation in an amino acid residue in the position corresponding to K447K/R/H, 448K/R/H and 449P in the Fc-region of a human IgG1 heavy chain.

In one embodiment the parent polypeptide, first parent polypeptide and second parent polypeptide may each be an antibody.

Thus in further aspect the present invention also relates to a method of increasing the specificity of a combination of at least a first and a second parent antibody, comprising
(i) introducing to the first parent antibody a mutation in an amino acid residue in the position corresponding to K439 in the Fc region of a human IgG1 heavy chain; and
(ii) introducing to the second parent antibody a mutation in an amino acid residue in the position corresponding to S440 in the Fc-region of a human IgG1 heavy chain, with the proviso that the mutation in S440 is not S440Y or S440W.

The first and second variant antibodies will have preference for oligomerization with one another compared to any wildtype or naturally occurring antibody as shown in Example 10.

The increase in specificity is with respect to "induction of an effector function". Thus said method is in one embodiment a method of increasing the specificity of induction of an effector function by a combination of at least a first and a second parent antibody.

By performing the method of increasing the specificity, or specificity of induction of an effector function, by a combination of at least a first and a second parent antibody, a combination of a first variant and a second variant antibody is obtained.

By introducing a mutation in either K439 or S440 of a parent antibody, the variant antibody thereby obtained has a decreased effector function compared to the parent antibody. However, as also described elsewhere herein, the mutation in K439 and S440 are able to complement each other or restore the effector function of an antibody comprising both mutations. This ability of the mutations in K439 and S440 to complement each other may similarly be utilized in two antibodies. Thus, when a mutation in K439 is introduced into a first parent antibody and a mutation in S440 is introduced into a second parent antibody, or vice versa, the decrease in effector function is no longer seen as the first and second variant antibody are used in combination. The term "increasing specificity" or "improving specificity" refers in this context to that an effector response induced by a combination of a first variant antibody comprising a mutation in K439 and a second variant antibody comprising a mutation in S440 is higher than the effector response induced by either the first variant antibody comprising a mutation in K439 or the second variant antibody comprising a mutation in S440.

By the introduction of both an amino acid substitution in a K439 and S440 the specificity of oligomerization is increased.

When combining the mutations of position K439 and/or S440 with the first mutation, enhancement of CDC is obtained and the specificity of CDC is increased.

In one embodiment the at least first and second parent antibodies bind to same epitope.

In one embodiment the at least first and second parent antibodies bind to different epitopes on the same antigen.

In one embodiment the at least first and second parent antibodies bind to different epitopes on different targets.

In one embodiment the first and second parent antibody have the same or different VL and VH sequences.

In one embodiment the combination of at least a first and a second parent antibody comprises one first parent antibody and one second antibody.

In one embodiment, the specificity is increased, when a combination of the first and second parent antibody is bound to its antigen on an antigen-expressing cell, on a cell membrane, or on a virion.

Hence in another aspect the present invention also relates to use of mutation in two or more amino acid residues of an antibody to increase the specificity of, e.g. the effector function induced by, the antibody when bound to its antigen on an antigen-expressing cell, on a cell membrane, or on a virion, wherein
a first mutation is in an amino acid residue corresponding to K439 in the Fc-region of a human IgG1 heavy chain;
a second mutation is in an amino acid residue corresponding to S440 in the Fc-region of a human IgG1 heavy chain.

In a further aspect the present invention relates to a method of increasing an effector function of a combination of at least a first and a second parent polypeptide, wherein the at least first and second parent polypeptide each comprises an Fc-domain of an immunoglobulin and a binding region, wherein said method comprises
(i) introducing to the at least first and/or second parent polypeptide a mutation in one or more amino acid residues selected from the group consisting of:
(a) an amino acid residue within the CH2-CH3 region providing allosteric mutations,
(b) an amino acid residue within the hydrophobic knobs of the CH2-CH3 region,
(c) an amino acid residue within the N-terminal CH3 helix,
(d) an amino acid residue within the C-terminal CH3 beta-strand, with the proviso that in case of a mutation corresponding to S440 in the Fc-region of a human IgG1 heavy chain the mutation is S440Y or S440W, and
(e) an amino acid residue corresponding to E345, E382 or Q386 in the Fc-region of a human IgG1 heavy chain.

In one embodiment the first and/or second parent polypeptide may each be an antibody.

Thus in one embodiment the present invention relates to a method of increasing an effector function of a combination of at least a first and a second parent antibody, wherein the at least first and second parent antibody each comprises a Fc-domain of an immunoglobulin and an antigen-binding region, wherein said method comprises
(i) introducing to the at least first and/or second parent antibody a mutation in one or more amino acid residues selected from the group consisting of:
(a) an amino acid residue within the CH2-CH3 region providing allosteric mutations,
(b) an amino acid residue within the hydrophobic knobs of the CH2-CH3 region,
(c) an amino acid residue within the N-terminal CH3 helix,
(d) an amino acid residue within the C-terminal CH3 beta-strand, with the proviso that in case of a mutation corresponding to S440 in the Fc-region of a human IgG1 heavy chain the mutation is S440Y or S440W, and
(e) an amino acid residue corresponding to E345, E382 or Q386 in the Fc-region of a human IgG1 heavy chain.

By performing this method a combination of at least a first and second variant antibody is obtained. The at least of first and second variant antibody obtained by this method have when combined an increased effector function compared to a combination of the first and second parent antibody.

The term "increased effector function" is to be understood as described herein.

The first and/or second parent antibody may be any parent antibody as described herein.

The methods of increasing an effector function of a combination of a first and second antibody may in particular be performed so as to obtain a first and/or second variant antibody which has any of the features of a variant antibody as described herein. The inventors of the present invention have found that introducing a mutation into an amino acid residue selected from (a), (b), (c), (d) and/or (e) results in a combination of a first and second variant antibody with an increased effector function compared to a combination of the first and second parent antibody.

In one embodiment the at least first and second parent antibodies bind to the same epitope.

In one embodiment the at least first and second parent antibodies bind to different epitopes on the same antigen.

In one embodiment the at least first and second parent antibodies bind to different epitopes on different targets.

In one embodiment the first and second parent antibody have the same or different VL and VH sequences.

In one embodiment the combination of at least a first and a second parent antibody comprises one first parent antibody and one second antibody.

In one embodiment the combination of at least a first and a second parent antibody comprises further parent antibodies, such as a third, fourth or fifth parent antibody.

In one embodiment (a) an amino acid residue within the CH2-CH3 region providing allosteric mutations is an amino acid residue selected from those corresponding to P247 or E430 in the Fc-region of a human IgG1 heavy chain.

In one embodiment (b) an amino acid residue within the hydrophobic knobs of the CH2-CH3 region is an amino acid residue selected from those corresponding to I253, S254 and Q311 in the Fc-region of a human IgG1 heavy chain.

In one embodiment (c) an amino acid residue within the N-terminal CH3 helix is an amino acid residue selected from those corresponding to D/E356 and T359 in the Fc-region of a human IgG1 heavy chain.

In one embodiment (d) an amino acid residue within the C-terminal CH3 beta-strand is an amino acid residue selected from those corresponding to Y436 and S440.

The amino acid residues in (b), (c), (d) and (e) are amino acid residues which are located at the Fc:Fc interface of two antibodies, thus the Fc part of one antibody which can interact with the Fc part of another antibody the two antibodies are in proximity with each other.

Thus in a further embodiment the mutation in the at least first and/or second parent antibody is in at least one amino acid residue selected from those corresponding to E345, E430, S440, Q386, P247, I253, S254, Q311, D/E356, T359, E382, Y436, and K447 in the Fc-region of a human IgG1 heavy chain, with the proviso that the mutation in S440 is S440Y or S440W.

In one embodiment (i) comprises introducing a mutation in both the first and second parent antibodies.

In another embodiment said method comprises:
(i) introducing a mutation to the first parent antibody in at least one amino acid residue selected from those corresponding to E345, E430, S440, Q386, P247, I253, S254, Q311, D/E356, T359, E382, Y436, and K447 in the Fc-region of a human IgG1 heavy chain, with the proviso that the mutation in S440 is S440Y or S440W,
(ii) providing the second parent antibody which does not comprise a mutation in an amino acid residue selected from those corresponding to E345, E430, S440, Q386, P247, I253, S254, Q311, D/E356, T359, E382, Y436, and K447 in the Fc-region of a human IgG1 heavy chain.

In one embodiment said method comprises introducing the mutation in at least one amino residue other than S440, wherein said method further comprises the steps of introducing the mutation in one or more positions other than S440, and wherein said method further comprises the steps of
(i) introducing to the first parent antibody a second mutation in the amino acid residue corresponding to position K439 in the Fc-region of a human IgG1 heavy chain; and
(ii) introducing to the second parent antibody a second mutation in the amino acid residue corresponding to position S440 in the Fc-region of a human IgG1 heavy chain, with the proviso that the mutation in S440 is not S440Y or S440W; wherein steps (ii) and (iii) may alternatively be
(i) introducing to the first parent antibody a second mutation in the amino acid residue corresponding to position S440 in the Fc-region of a human IgG1 heavy chain, with the proviso that the mutation in S440 is not S440Y or S440W; and
(ii) introducing to the second parent antibody a second mutation in the amino acid residue corresponding to position K439 in the Fc-region of a human IgG1 heavy chain.

For those embodiments of the present invention wherein the second parent does not comprise a mutation in an amino acid residue selected from those corresponding to E345, E430, S440, Q386, P247, I253, S254, Q311, D/E356, T359, E382, Y436, and K447 in the Fc-region of a human IgG1 heavy chain, the term "second mutation" in step (ii) may be a first mutation, e.g. the second parent antibody may comprise no other mutations than the mutation introduced in step (ii). The term "second mutation" in steps (i) and (ii) are also not intended to limit the number of mutations that may be introduced into the first and/or second parent antibody.

In one embodiment the parent antibody, the first parent antibody and the second parent antibody may each be selected from the group consisting of but not limited to monospecific, bispecific and multispecific antibodies. The bispecific may e.g. be a heterodimeric protein.

In one embodiment the first and second parent antibodies are monospecific antibodies, which may e.g. bind to the same or different epitopes. If the first and second parent antibody bind to different epitopes it may on the same or different antigen.

In another embodiment the first parent antibody is a monospecific antibody and the second parent antibody is bispecific or multispecific antibody, or vice versa.

In another embodiment the first and second parent antibodies are bispecific or multispecific antibodies. In one embodiment the first and second bispecific or multispecific parent antibodies are the same or different antibodies. In one embodiment the first and second bispecific or multispecific parent antibodies bind to different epitopes on the same or different antigen. Thus in one embodiment said at least first and second parent antibodies are bispecific or multispecific antibodies which bind different epitopes on the same antigen or on different antigens.

In another embodiment the first parent antibody is a monospecific antibody and the second parent antibody is a bispecific antibody, or vice versa. The monospecific may bind the same epitope as the bispecific (one part of the bispecific) or the monospecific and the bispecific antibody may bind different epitopes on the same or different antigens. The bispecific antibody may bind to different epitopes on the same or different antigens.

In one embodiment said at least first and second parent antibodies are each a bispecific antibody which comprises a first polypeptide comprising a first CH2-CH3 region of an immunoglobulin and a first antigen-binding region, and a second polypeptide comprising a second CH2-CH3 region of an immunoglobulin and a second antigen-binding region, wherein the first and second antigen-binding regions bind different epitopes on the same antigen or on different antigens, and wherein said first CH2-CH3 region comprises a further amino acid substitution at a position selected from those corresponding to K409, T366, L368, K370, D399, F405, and Y407 in the Fc-region of a human IgG1 heavy chain; and wherein said second CH2-CH3 region comprises a further amino acid substitution at a position selected from those corresponding to F405, T366, L368, K370, D399, Y407, and K409 in the Fc-region of a human IgG1 heavy chain, and wherein said further amino acid substitution in the first CH2-CH3 region is different from the said further amino acid substitution in the second CH2-CH3 region.

In a further embodiment said first CH2-CH3 region comprises an amino acid substitution at a position corresponding to K409 in the Fc-region of a human IgG1 heavy chain; and said second CH2-CH3 region comprises an amino acid substitution at a position corresponding to F405 in the Fc-region of a human IgG1 heavy chain.

In one embodiment of the methods and/or uses of the present invention the parent antibody, whether it is a parent antibody, a first parent antibody or a second parent antibody, may contain other mutations than those of the present invention which have been found to affect an effector function. Such other mutations may be introduced at the same time as the mutations of the present invention which affect an effector function or they may introduced sequentially, the methods or uses of the present invention are not limited to either simultaneous or sequential introduction of mutations. The bispecific antibody may be any bispecific antibody and the methods and uses of the present invention are not limited to any particular bispecific format as it is foreseen that different formats may be used.

The method of combining a first antibody which comprises one of said mutations capable of increasing an effector function with a second antibody which does not comprise such a mutation may as shown in Example 31 increase the effector function of the combination. Thus, without being bound by theory, it is believed that e.g. this method may be used to combine a therapeutic antibody, as a second antibody, which have been proven to be safe but not efficient enough with a first antibody comprising a mutation, and thereby resulting in a combination which is efficacious.

Thus in one embodiment the second parent antibody which does not comprise a mutation in an amino acid residue selected from those corresponding to E345, E430, S440, Q386, P247, I253, S254, Q311, D/E356, T359, E382, Y436, and K447 in the Fc-region of a human IgG1 heavy chain, is a therapeutic antibody. In a particular embodiment it is therapeutic antibody which has suitable safety profile. In one embodiment it may be a therapeutic antibody which has a suitable safety profile but which is not sufficiently efficacious.

Examples of suitable second antibodies which does not comprise a mutation in an amino acid residue selected from those corresponding to E345, E430, S440, Q386, P247, I253, S254, Q311, D/E356, T359, E382, Y436, and K447 in the Fc-region of a human IgG1 heavy chain, include but are not limited to any of the following; (90Y) clivatuzumab tetraxetan; (90Y) tacatuzumab tetraxetan; (99mTc) fanolesomab; (99mTc) nofetumomab Merpentan; (99mTc) pintumomab; 3F8; 8H9; abagovomab; abatacept; abciximab; Actoxumab; adalimumab; adecatumumab; afelimomab; aflibercept; Afutuzumab; alacizumab pegol; albiglutide; ALD518; alefacept; alemtuzumab; Alirocumab; altumomab; Altumomab pentetate; alvircept sudotox; amatuximab; AMG714/HuMax-IL15; anatumomab mafenatox; Anrukinzumab (=IMA-638); apolizumab; arcitumomab; aselizumab; atacicept; atinumab; Atlizumab (=tocilizumab); atorolimumab; baminercept; Bapineuzumab; basiliximab; bavituximab; bectumomab; belatacept; belimumab; benralizumab; bertilimumab; besilesomab; bevacizumab; Bezlotoxumab; biciromab; bifarcept; bivatuzumab; Bivatuzumab mertansine; blinatumomab; blosozumab; brentuximab vedotin; briakinumab; briobacept; brodalumab; canakinumab; cantuzumab mertansine; cantuzumab ravtansine; caplacizumab; capromab; Capromab pendetide; carlumab; catumaxomab; CC49; cedelizumab; certolizumab pegol; cetuximab; Ch.14.18; citatuzumab bogatox; cixutumumab; Clazakizumab; clenoliximab; Clivatuzumab tetraxetan; conatumumab; conbercept; CR6261; crenezumab; dacetuzumab; daclizumab; dalantercept; dalotuzumab; daratumumab; Demcizumab; denosumab; Detumomab; Dorlimomab aritox; drozitumab; dulaglutide; ecromeximab; eculizumab; edobacomab; edrecolomab; efalizumab; efungumab; elotuzumab; elsilimomab; enavatuzumab; enlimomab; enlimomab pegol; enokizumab; ensituximab; epitumomab; epitumomab cituxetan; epratuzumab; erlizumab; ertumaxomab; etanercept; etaracizumab; etrolizumab; exbivirumab; Fanolesomab; faralimomab; farletuzumab; Fasinumab; FBTA05; felvizumab; Fezakinumab; ficlatuzumab; figitumumab; flanvolumab; fontolizumab; foralumab; foravirumab; fresolimumab; fulranumab; galiximab; ganitumab; gantenerumab; gavilimomab; gemtuzumab; Gemtuzumab ozogamicin; gevokizumab; girentuximab; glembatumumab; Glembatumumab vedotin; golimumab; Gomiliximab; GS6624; anti-CD74 antibodies; anti-cMet antibodies as disclosed in WO 2011/110642; anti-Her2 antibodies as disclosed WO 2011/147986 or WO 2011/147982; anti-IL8 antibodies as disclosed in WO 2004/058797; anti-TAC antibodies as disclosed in WO 2004/045512; anti-tissue factor (TF) antibodies as disclosed in WO 2010/066803 or WO 2011/157741; ibalizumab; ibritumomab tiuxetan; icrucumab; igovomab; Imciromab; inclacumab; indatuximab ravtansine; infliximab; inolimomab; inotuzumab ozogamicin; intetumumab; iodine (124I) girentuximab; ipilimumab; iratumumab; itolizumab; ixekizumab; keliximab; labetuzumab; lebrikizumab; lemalesomab; lenercept; lerdelimumab; lexatumumab; libivirumab; lintuzumab; lorvotuzumab mertansine; lucatumumab; lumiliximab; mapatumumab; maslimomab; matuzumab; mavrilimumab; mepolizumab; metelimumab; milatuzumab; minretumomab; mirococept; mitumomab; mogamulizumab; morolimumab; motavizumab; moxetumomab; pasudotox; muromonab-CD3; nacolomab tafenatox; namilumab; naptumomab estafenatox; narnatumab; natalizumab; nebacumab; necitumumab; nerelimomab; nimotuzumab; Nivolumab; Nofetumomab; merpentan; obinutuzumab; Ocaratuzumab; ocrelizumab; odulimomab; ofatumumab; olaratumab; olokizumab; omalizumab; onartuzumab; onercept; oportuzumab monatox; oregovomab; otelixizumab; oxelumab; ozoralizumab; pagibaximab; palivizumab; panitumumab; panobacumab; pascolizumab; pateclizumab; patritumab; pegsunercept; Pemtumomab; pertuzumab; pexelizumab; Pintumomab; Placulumab; ponezumab; priliximab; pritumumab; PRO 140; quilizumab; racotumomab; radretumab; rafivirumab; ramucirumab; ranibizumab; raxibacumab; regavirumab; reslizumab; RG1507/HuMax-IGF1R; RG1512/HuMax-pSelectin; rilonacept; rilotumumab; rituximab; robatumumab; roledumab; romosozumab; rontalizumab; rovelizumab; ruplizumab; samalizumab; sarilumab; satumomab; Satumomab pendetide; secukinumab; sevirumab; sibrotuzumab; sifalimumab; siltuximab; siplizumab; sirukumab; solanezumab; solitomab; Sonepcizumab; sontuzumab; sotatercept; stamulumab; sulesomab; suvizumab; tabalumab; Tacatuzumab tetraxetan; tadocizumab; talizumab; tanezumab; taplitumomab paptox; tefibazumab; telimomab aritox; tenatumomab; teneliximab; teplizumab; teprotumumab; TGN1412; Ticilimumab (=tremelimumab); tigatuzumab; TNX-650; Tocilizumab (=atlizumab); toralizumab; torapsel; tositumomab; tralokinumab; trastuzumab; trastuzumab emtansine; TRBS07; trebananib; tregalizumab; tremelimumab; tucotuzumab celmoleukin; tuvirumab; ubituximab; urelumab; urtoxazumab; ustekinumab; vapaliximab; vatelizumab; vedolizumab; veltuzumab; vepalimomab; vesencumab; visilizumab; volociximab; Vorsetuzumab mafodotin; votumumab; zalutumumab; zanolimumab; ziralimumab; and zolimomab aritox.

In one embodiment of the methods and uses of the present invention the mutation in at least one amino acid residue, or in one or more amino acids residues, corresponding to E345, E430, S440, Q386, P247, I253, S254, Q311, D/E356, T359, E382, Y436, and K447 in the Fc-region of a human IgG1 heavy chain, with the proviso that the mutation in S440 is S440Y or S440W, may be in any of the exemplary and preferred amino acid positions listed in Table 1. Hence each of the amino acid positions listed in Table 1 is a separate and non-limiting embodiment of a mutation in the at least one amino acid.

Any of the mutations or combinations thereof described herein may be introduced according to a method of the present invention.

Mutations selected from the exemplary or preferred amino acid substitutions can be tested in appropriate assays allowing for oligomer formation of antigen-bound antibodies and detecting enhanced C1q-binding, complement activation, CDC, ADCC and/or internalization, such as those described in the Examples. For example, C1q-binding avidity can be determined according to an assay similar to the one described in Example 4, using cells expressing the antigen for the antibody variant. Exemplary CDC assays are provided in Examples 5, 6, 10, 16, 19, 22, 23, 24, or 25. An exemplary ADCC assay is provided in Example 12. An exemplary internalization assay is provided in Example 26. Finally, to discriminate between mutations in amino acid residues directly involved in C1q-binding from mutations affecting oligomer formation, C1q-binding in an ELISA assay according to, e.g., Example 3 can be compared to C1q-binding in a cell-based assay according to, e.g., Example 4.

In a further embodiment said mutation is selected from those corresponding to E345, E430, S440 and Q386 in the Fc-region of a human IgG1 heavy chain, with the proviso that the mutation in S440 is S440Y or S440W.

In an alternative embodiment the mutation in at least one amino acid residue, or one or more amino acid residues, is in an amino acid residue corresponding to E382 and H433 in the Fc region of a human IgG1 heavy chain.

In a particular embodiment one mutation is in the amino acid residue corresponding to E345 in the Fc region of a human IgG1 heavy chain.

In a particular embodiment one mutation is in the amino acid residue corresponding to E430 in the Fc region of a human IgG1 heavy chain.

In a particular embodiment one mutation is in the amino acid residue corresponding to S440 in the Fc region of a human IgG1 heavy chain, with the proviso that the mutation is S440Y or S440W.

In a particular embodiment one mutation is in the amino acid residue corresponding to Q386 in the Fc region of a human IgG1 heavy chain.

In an alternative embodiment one mutation is in the amino acid residue corresponding to E382 or H433 in the Fc region of a human IgG1 heavy chain.

In one embodiment the mutation in at least one amino acid residue may be an amino acid substitution, an amino acid deletion or an amino acid insertion.

In one embodiment the mutation in at least one amino acid residue is an amino acid deletion.

In one embodiment the mutation in at least one amino acid residue is an amino acid insertion.

In a particular embodiment mutation in at least one amino acid residue is an amino acid substitution.

In one embodiment the mutation in at least one amino acid residue may be selected from any of the amino acid substitutions, amino acid deletions listed in Table 1. Further, each preferred amino acid substitution in each specific amino acid residue listed in Table 1 is a separate and specific non-limiting embodiment for this use. Exemplary amino acid substitutions include exchanging an E residue for an R residue, and exchanging an H residue for an R residue.

In a further embodiment the mutation in at least one amino acid residue is an amino acid substitution selected from those corresponding to E345X, E430X, S440Y or W, and Q386K in the Fc-region of a human IgG1 heavy chain, wherein X refers to any amino acid, e.g. any natural amino acid or non-natural occurring amino acid. X may in particular refer to any of the 20 naturally occuring amino acids.

Thus in one embodiment the mutation is in at least one amino acid residue selected from those corresponding to E345, E430, S440 to Y or W, and Q386 in the Fc-region of a human IgG1 heavy chain, preferably wherein the mutation is at least one amino acid substitution of the following: E345 to R, Q, N, or K, E430 to T, S, or G, S440 to Y or W, or Q386 to K.

Thus in one embodiment E345X may be E345R, Q, N, K, Y, A, C, D, F, G, H, I, L, M, P, S, T, V, W, or Y; in particular E345A, D, G, H, K, N, Q, R, S, T, Y or W, or more particularly E345D, K, N, Q, R, or W; or even more particular E345R, Q, N, K, or Y. In another further embodiment E430X may be E430T, S, G, F, H, A, C, D, I, K, L, M, N, P, Q, R, V, W, or Y; in particular E430T, S, G, F, or H. In a preferred embodiment the amino acid substitution is selected from the group comprising E345R, E345Q, E345N, E345K, E345Y, E430T, E430S, E430G, E430F, E430H, S440W and S440Y. In a further embodiment the mutation in at least one amino acid residue is selected from E345R and E430G. In a further embodiment the mutation in at least one amino acid residue is E345R. In a further embodiment the mutation in at least one amino acid residue is E430G.

In an alternative embodiment the mutation in at least one amino acid residue is selected from those corresponding to I253, H310, Q311, E382, G385, H433, N434, Y436, and Q438 in the Fc-region of a human IgG1 heavy chain, such as E382 or H433. In a further alternative embodiment the mutation in at least one amino acid residue may an amino acid substitution selected from those corresponding to I253E, N, Q, S or T, e.g. I253N or Q; H310N, Q, W or Y, e.g.

H310Q; Q311E or R, E382D, H, K, R, N, Q, S, T, W or Y, e.g. E382D, Q, K, or R; G385E, H, K, N, Q, R, S, T, W or Y, e.g. G385D, E, K or R; H433R; N434D, E, H, K, Q, R, S, T, W or Y, e.g. N434H, K, Q or R; Y436A, E, F, H, I, K, L, M, N, Q, R, S, T or V, e.g. Y436N, Q, S or T; Q438A, E, G, H, K, N, Q, R, S, T, W or Y, or e.g. Q438 N, S or T.

Thus in an even further alternative embodiment the mutation in at least one amino acid residue may be an amino acid substition selected from those corresponding to P247G, I253V, S254L/V, Q311L/W, D/E356G/R, I359R, E382L/V, and Y436I in the Fc-region of a human IgG1 heavy chain, e.g. in particular E382L, V, D, Q, K, or R or H433R. In a further alternative embodiment the mutation in at least one amino acid residue is selected from E382R and H433R. In an alternative embodiment, the mutation is E382R. In another alternative embodiment, the mutation is H433R.

In another embodiment, the mutation is not in an amino acid residue directly involved in C1q-binding, optionally as determined by comparing C1q-binding in an ELISA assay according to Example 3 with C1q-binding in a cell-based assay according to Example 4.

In one embodiment, the mutation is not in an amino acid residue corresponding to I253, N434, or Q311, and optionally not in an amino acid residue corresponding to H433, or the amino acid substitution is not H433A.

In one embodiment, the at least one mutation is one mutation, i.e. no more than one mutation is introduced to the parent antibody.

In another embodiment, the method or use according to the present invention comprises introducing a mutation in at least two, such as two, three, four, five, or more of the amino acids residues in Table 1.

Any of the combinations of mutations described herein may be introduced according to a method of the present invention.

In one embodiment the method or uses according to the present invention comprises introducing to the parent antibody a mutation in at least two amino acid residues selected from those corresponding to E345, E430, S440, Q386, P247, I253, S254, Q311, D/E356, T359, E382, Y436, and K447 in the Fc region of a human IgG1 heavy chain, with the proviso that the mutation in S440 is S440Y or S440W.

In one embodiment the method or uses according to the present invention comprises introducing to the parent antibody a mutation in at least two amino acid residues selected from those corresponding to E345, E430, Q386, and S440 in the Fc-region of a human IgG1 heavy chain, with the proviso that the mutation in S440 is S440Y or S440W, such as wherein the mutation in the at least two amino acids are selected from the following: E345 to R, Q, N, or K, E430 to T, S, or G, S440 to Y or W, or Q386 to K.

In an alternative embodiment the positions of the first mutation may be selected from the group consisting of positions I253, H310, Q311, E345, E382, G385, H433, N434, Y436, and Q438.

In one embodiment, the method further comprises introducing to the antibody a further/third mutation in an amino acid residue corresponding to E345, E430, P247, I253, S254, Q311, D/E356, T359, E382, Q386, Y436, or K447 in both the first and/or the second Fc-regions.

For example more than one, such as two, three, four, or five, in particular two or three mutations are introduced to the parent antibody in amino acid residues selected from those corresponding to E345, E430, S440, Q386, P247, I253, S254, Q311, D/E356, T359, E382, Y436, and K447 in the Fc-region of a human IgG1 heavy chain. For example, at least one of the amino acid residues corresponding to E345, E430 and S440 in the Fc region of a human IgG1 heavy chain, may be mutated, such as two or all of E345, E430 and S440, optionally in combination with a mutation in one or more other amino acids listed in Table 1. The at least two mutations may be any amino acid residue substitution of position E345 in combination with any amino acid residue substitution of position E430 or S440, or may be any amino acid substitution of position E430 in combination with any amino acid residue of position S440.

In a further embodiment the two or three mutations are introduced to the parent antibody in amino acid residues selected from those corresponding to E345, E430, S440 and Q386 in the Fc-region of a human IgG1 heavy chain.

In one embodiment the more than one mutation may in particular be amino acid substitions.

Thus according to the present invention, the method or use, comprises introducing to the antibody at least one, such as one, two, three, four, five, or six, amino acid substitution selected from the following group consisting of P247G, I253V, S254L, Q311L/W, E345X, D/E356G/R, T359R, E382L/V, Q386K, E430X, Y436I, and S440Y/W. In the preferred embodiments, the amino acid substitution is selected from the group consisting of E345X, E430X, S440Y/W, and Q386K.

In an alternative embodiment, the at least two mutations, such as two, three, four or five mutations, are in amino acid residues selected from those corresponding to H310, G385, H433, N434, and Q438 in the Fc-region of a human IgG1 heavy chain.

In another alternative embodiment, the at least one mutation, optionally two or three mutations, are selected from the group consisting of E345R, E382R, and H433R. In another alternative embodiment, at least one of the amino acid residues corresponding to E382 and H433 in the Fc region of a human IgG1 heavy chain may be mutated, such as both, optionally in combination with a mutation in one or more other amino acids listed in Table 1.

In some embodiments of the methods and/or uses of the present invention a mutation in an amino acid residue corresponding to K439 and/or S440 is introduced in an antibody selected from the group consisting of a parent antibody, a first parent antibody, a second parent antibody and combinations thereof. As described above introducing a mutation in the amino acid residues corresponding to K439 and S440 in the Fc region of a human IgG1 heavy chain, is shown to limit the intermolecular interactions between antibodies to those comprising such mutations (Examples 4, 5, 6, 10). Depending on whether the K439 and S440 are introduced to the same parent antibody or in a first and second parent antibody, respectively, these aspects are also referred to as "double mutant" and "mixed mutant" aspect.

In one embodiment of the present invention, the mutation in an amino acid residue corresponding to K439 in the Fc region of a human IgG1 heavy chain is an amino acid substitution.

In one embodiment of the present invention, the mutation in an amino acid residue corresponding to S440 in the Fc region of a human IgG1 heavy chain is an amino acid substitution.

In all embodiments of the present invention wherein a mutation in a position corresponding to K439 and S440 in the Fc region of a human IgG1 heavy chain, whether in the same polypeptide or antibody, or in first and second polypeptide or antibody may be replaced by a mutation in:
(i) in each of the amino acid residues corresponding to K447 and 448 in the Fc-region of a human IgG1 heavy chain, such as K447K/R/H and 448E/D in the Fc-region of a human IgG1 heavy chain, preferably K447K and 448E in the Fc-region of a human IgG1 heavy chain, or (ii) in each of the amino acid residues corresponding to K447, 448 and 449 in the Fc-region of a human IgG1 heavy chain, such as K447D/E, 448K/R/H and 449P in the Fc-region of a human IgG1 heavy chain, preferably K447E, 448K and 449P in the Fc-region of a human IgG1 heavy chain.

Thus combinations of such mutations include any of those described in Table 2A and 2B.

In one embodiment of the present invention, the mutations in an amino acid residue corresponding to K439 and S440 in the Fc region of a human IgG1 heavy chain are both an amino acid substitution.

In one embodiment, the mutation in an amino acid residue corresponding to K439 in the Fc region of a human IgG1 heavy chain is an amino acid substitution into an amino acid selected from E and D.

In another embodiment, the mutation is K439E.

In one embodiment, the mutation in an amino acid residue corresponding to S440 in the Fc region of a human IgG1 heavy chain is an amino acid substitution into an amino acid selected from K, R and H.

In another embodiment, the mutation is S440K.

Thus in a further embodiment the mutations introduced to the parent antibody in the amino acid residues corresponding K439 and S440 in the Fc region of a human IgG1 heavy chain are amino acid substitutions selected from K439E and D and S440K, R and H.

Thus in a further embodiment the mutations introduced to the parent antibody in the amino acid residues corresponding K439 and S440 in the Fc region of a human IgG1 heavy chain are the amino acid substitutions K439E and S440K.

Some methods and uses of the present invention comprise a first and a second parent antibody.

Thus in a further embodiment the mutation introduced to the first parent antibody in an amino acid residue corresponding K439 is an amino acid substitution selected from K439E and D, e.g. K439E and the mutation introduced to the second parent antibody in an amino acid residue corresponding S440 is an amino acid substitution selected from S440K, R and H, e.g. S440K. The mutations in the first and second parent antibody may be introduced vice versa, i.e. it may also be that the mutation in an amino acid residue corresponding to S440 is introduced in the first parent antibody, while the mutation in in an amino acid residue corresponding to K439 is introduced in the second parent antibody wherein the mutations may be the preferred amino acid substitutions as described above.

In one embodiment of the methods or uses according to the present invention, the effector function is increased when the antibody is bound to its antigen.

In a further embodiment the effector function is increased when the antibody is bound to its antigen, wherein the antigen is on an antigen-expressing cell, cell membrane, or virion. In one embodiment, the Fc-region of an IgG1 heavy chain comprises the sequence of residues 130 to 330 of SEQ ID NO:1.

The parent antibody may be any parent antibody as described herein. The parent antibody in this context is intended to be also first parent and second parent antibodies.

In one embodiment, the parent antibody is a human IgG1, IgG2, IgG3 or IgG4, IgA1, IgA2, IgD or IgE antibody.

In one embodiment the parent antibody is human full-length antibody, such as a human full-length IgG1 antibody.

In one embodiment, the parent antibody, first parent antibody and second parent antibody is a human IgG1 antibody, e.g. the IgG1m(za) or IgG1m(f) allotype, optionally comprising an Fc-region comprising SEQ ID NO:1 or 5.

In one embodiment, the parent antibody is a human IgG2 antibody, optionally comprising an Fc-region comprising SEQ ID NO:2.

In one embodiment, the parent antibody is a human IgG3 antibody, optionally comprising an Fc-region comprising SEQ ID NO:3.

In one embodiment, the parent antibody is a human IgG4 antibody, optionally comprising an Fc-region comprising SEQ ID NO:4.

In one embodiment, the parent antibody is a bispecific antibody.

In one embodiment, the parent antibody is any antibody as described herein, e.g. an antibody fragment comprising at least part of an Fc-region, monovalent antibodies (described in WO2007059782 by Genmab); heavy-chain antibodies, consisting only of two heavy chains and naturally occurring in e.g. camelids (e.g., Hamers-Casterman (1993) Nature 363:446); ThioMabs (Roche, WO2011069104), strand-exchange engineered domain (SEED or Seed-body) which are asymmetric and bispecific antibody-like molecules (Merck, WO2007110205); Triomab (Fresenius, Lindhofer et al. (1995 J Immunol 155:219); FcAAdp (Regeneron, WO2010151792), Azymetric Scaffold (Zymeworks/Merck, WO2012/058768), mAb-Fv (Xencor, WO2011/028952), Dual variable domain immunoglobulin (Abbott, DVD-Ig, U.S. Pat. No. 7,612,181); Dual domain double head antibodies (Unilever; Sanofi Aventis, WO20100226923), Di-diabody (ImClone/Eli Lilly), Knobs-into-holes antibody formats (Genentech, WO9850431); DuoBody (Genmab, WO 2011/131746); Electrostatic steering antibody formats (Amgen, EP1870459 and WO 2009089004; Chugai, U5201000155133; Oncomed, WO2010129304A2); bispecific IgG1 and IgG2 (Rinat neurosciences Corporation, WO11143545), CrossMAbs (Roche, WO2011117329), LUZ-Y (Genentech), Biclonic (Merus), Dual Targeting domain antibodies (GSK/Domantis), Two-in-one Antibodies recognizing two targets (Genentech, NovImmune), Cross-linked Mabs (Karmanos Cancer Center), CovX-body (CovX/Pfizer), IgG-like Bispecific (ImClone/Eli Lilly, Shen, J., et al. J Immunol Methods, 2007. 318(1-2): p. 65-74), and DIG-body and PIG-body (Pharmabcine), and Dual-affinity retargeting molecules (Fc-DART or Ig-DART, by Macrogenics, WO/2008/157379, WO/2010/080538), Zybodies (Zyngenia), approaches with common light chain (Crucell/Merus, U57262028) or common heavy chains OaBodies by NovImmune), as well as fusion proteins comprising a polypeptide sequence fused to an antibody fragment containing an Fc-domain like scFv-fusions, like BsAb by ZymoGenetics/BMS), HERCULES by Biogen Idec (U.S. Pat. No. 7,951,918), SCORPIONS by Emergent BioSolutions/Trubion, Ts2Ab (MedImmune/AZ (Dimasi, N., et al. J Mol Biol, 2009. 393(3): p. 672-92), scFv fusion by Novartis, scFv fusion by Changzhou Adam Biotech Inc (CN 102250246), TvAb by Roche (WO 2012025525, WO 2012025530), mAb$^2$ by f-Star (WO2008/003116), and dual scFv-fusions. It also should be understood that the term antibody, unless specified otherwise, also includes polyclonal antibodies, monoclonal antibodies (such as human monoclonal antibodies), antibody mixtures (recombinant polyclonals) for instance generated by technologies exploited by Symphogen and Merus (Oligoclonics), and antibody-like polypeptides, such as chimeric antibodies and humanized antibodies. An antibody as generated can potentially possess any isotype.

optionally selected from the group consisting of a monovalent antibody, a heavy-chain antibody, a strand-exchange engineered domain (SEED), a triomab, a dual variable domain immunoglobulin (DVD-Ig), a knob-into-holes antibody, a mini-antibody, a dual-affinity retargeting molecule (Fc-DART or Ig-DART); a LUZ-Y antibody, a Biclonic antibody, a Dual Targeting (DT)-Ig antibody, a Two-in-one Antibody, a cross-linked Mab, a mAb$^2$, a CovX-body, an IgG-like Bispecific antibody, a Ts2Ab, a BsAb, a HERCULES antibody, a TvAb, an ScFv/Fc Fusion antibody, a SCORPION, an scFv fragment fused to an Fc domain, and a dual scFv fragment fused to an Fc domain.

In another embodiment, the antigen is expressed on the surface of a cell.

In another embodiment, the cell is a human tumor cell.

In a further embodiment, the antigen is selected from the group consisting of erbB1 (EGFR), erbB2 (HER2), erbB3, erbB4, MUC-1, CD4, CD19, CD20, CD38, CD138, CXCRS, c-Met, HERV-envelop protein, periostin, Bigh3, SPARC, BCR, CD79, CD37, EGFrvIII, IGFr, L1-CAM, AXL, Tissue Factor (TF), CD74, EpCAM and MRP3.

In another embodiment, the antigen is associated with a cell membrane.

In another embodiment, the antigen is associated with a virion, optionally wherein the antigen is comprised in the protein coat or a lipid envelope of the virion.

In another embodiment, the antibody is a human antibody, optionally binding at least one antigen selected from CD20 and CD38.

In another embodiment, the antibody binds to the same epitope as at least one of 7D8 and 005, optionally comprising a variable heavy and/or variable light chain region of at least one of 7D8 and 005.

In any use according to the disclosed invention the antibody without any mutations of the present invention may be any parent antibody. Thus, the uses herein provides for any variants of such parent antibodies.

In a further embodiment of the present invention, the effector function is an Fc-mediated effector function selected from C1q-binding, complement activation, complement dependent cytotoxicity (CDC), antibody-dependent cell-mediated cytotoxicity (ADCC), FcRn-binding, Fc-receptor binding including Fc-gamma receptor-binding, Protein A-binding, Protein G-binding, antibody-dependent cellular phagocytosis (ADCP), complement-dependent cellular cytotoxicity (CDCC), complement-enhanced cytotoxicity, opsonisation, Fc-containing polypeptide internalization, target downmodulation, ADC uptake, induction of apoptosis, cell death, cell cycle arrest, and any combination thereof.

In a particular embodiment the effector function is C1q-binding, complement activation (C1q efficacy)complement dependent cytotoxicity (CDC), antibody-dependent cell-mediated cytotoxicity (ADCC), Fc-receptor binding, e.g. Fc-gamma receptor-binding, Fc-containing polypeptide internalization or any combination thereof.

In one embodiment the effector function is C1q-binding.

In one embodiment the effector function is complement activation (C1q efficacy).

In one embodiment the effector function is complement dependent cytotoxicity (CDC).

In one embodiment the effector function is antibody-dependent cell-mediated cytotoxicity (ADCC).

In one embodiment the effector function is Fc-receptor binding, e.g. including Fc-gamma receptor-binding.

In one embodiment the effector function is Fc-containing polypeptide internalization.

In one embodiment the effector function is a combination of complement dependent cytotoxicity (CDC) and antibody-dependent cell-mediated cytotoxicity (ADCC).

In another embodiment, the one or more mutations increase a further effector function selected from FcRn-binding, ADCC, Fc-gamma receptor-binding, Protein A-binding, Protein G-binding, ADCP, complement-dependent cellular cytotoxicity (CDCC), complement-enhanced cytotoxicity, binding to complement receptor of an opsonized antibody mediated by the antibody, and any combination thereof.

In another aspect, the invention relates to a method of increasing the avidity of a preparation of a parent antibody for C1q, comprising the step of mutating at least one amino acid in the Fc-region of the antibody, wherein the at least one amino acid is selected from the group consisting of E345, E430, S440, P247, I253, S254, Q311, D/E356, T359, E382, Q386, Y436, and K447.

As used herein, the term "C1q-binding", when used in the context of a variant or antibody of a parent antibody includes any mechanism of the first component on the classical pathway of complement activation mediated by binding of the variant or antibody to host tissues or factors, including various cells of the immune system (such as effector cells). C1q-binding of an antibody can be evaluated using an ELISA (such as e.g. C1q-binding ELISA used in Examples 3 and 4), or the C1q efficacy can be evaluated by a CDC assay (such as e.g. the CDC assay used in Example 5). In a further embodiment, the C1q-binding avidity of the antibody is determined according to the assay described in Example 4.

In all the methods according to the disclosed invention the antibody without any mutations of the present invention may be any parent antibody. Thus, the methods herein provides for any variants of such parent antibodies.

The parent antibody, the first parent antibody, the second parent antibody, or the variants thereof obtained by the methods and/or uses of the present invention may bind to any target as described herein.

Examples of antigens or targets that the invention may be directed against are; 5T4; ADAM-10; ADAM-12; ADAM17; AFP; AXL; ANGPT2 anthrax antigen; BSG; CAIX; CAXII; CA 72-4; carcinoma associated antigen CTAA16.88; CCL11; CCL2; CCR4; CCR5; CCR6; CD2; CD3E; CD4; CD5; CD6; CD15; CD18; CD19; CD20; CD22; CD24; CD25; CD29; CD30; CD32B; CD33; CD37; CD38; CD40; CD40LG; CD44; CD47; CD52; CD56; CD66E; CD72; CD74; CD79a; CD79b; CD80; CD86; CD98; CD137; CD147; CD138; CD168; CD200; CD248; CD254; CD257; CDH3; CEA; CEACAM5; CEACAM6; CEACAM8; Claudin4; CS-1; CSF2RA; CSPG-4; CTLA4; Cripto; DLL4; ED-B; EFNA2; EGFR; Endothelin B receptor; ENPP3; EPCAM; ERBB2; ERBB3; FAP alpha; Fc gamma RI; FCER2; FGFR3; fibrin II beta chain; FLT1; FOLH1; FOLR1; FRP-1; GD3 ganglioside; GDF2; GLP1R; Glypican-3; GPNMB; HBV (hepatitis B virus); HCMV (human cytomegalovirus); heat shock protein 90 homolog [*Candida albicans*]; herpes simplex virus gD glycoprotein; HGF; HIV-1; HIV-1 IIIB gp120 V3 loop; HLA-DRB (HLA-DR beta); human respiratory syncytial virus, glycoprotein F; ICAM1; IFNA1; IFNA1; IFNB1 bispecific; IgE Fc; IGF1R; IGHE connecting region; IL12B; IL13; IL15; IL17A; ILIA; IL1B; IL2RA; IL4; IL5; IL5RA; IL6; IL6R; IL9; interleukin-2 receptor beta subunit; ITGA2; ITGA2B ITGB3; ITGA4 ITGB7; ITGA5; ITGAL; ITGAV_ITGB3; ITGB2; KDR; L1CAM; Lewis-y; lipid A, domain of lipopolyaccharide LPS; LTA; MET; MMP14; MMp15; MST1R; MSTN;

MUC1; MUC4; MUC16; MUCSAC; NCA-90 granulocyte cell antigen; Nectin 4; NGF; NRP; NY-ESO-1; OX40L; PLAC-1; PLGF; PDGFRA; PD1; PDL1; PSCA; phosphatidylserine; PTK-7; *Pseudomonas aeruginosa* serotype IATS 011; RSV (human respiratory syncytial virus, glycoprotein F); ROR1; RTN4; SELL; SELP; STEAP1; Shiga-like toxin II B subunit [*Escherichia coli*]; SLAM7; SLC44A4; SOST; *Staphylococcus epidermidis* lipoteichoic acid; T cell receptor alpha_beta; TF; TGFB1; TGFB2; TMEFF2; TNC; TNF; TNFRSF10A; TNFRSF10B; TNFRSF12A; TNFSF13; TNFSF14; TNFSF2; TNFSF7; TRAILR2; TROP2; TYRP1; VAP-1; and Vimentin.

Methods of Inducing an Effector Response

It is to be understood that all embodiments described herein with reference to a parent antibody, first parent antibody or second parent antibody are also to be understood as embodiments relating to a parent, first parent or second parent polypeptide comprising an Fc-domain of an immunoglobulin and a binding region.

In a further main aspect the present invention relates to a method of inducing an effector response, against a cell, cell membrane, or virion expressing a target to which a parent polypeptide comprising an Fc-domain of an immunoglobulin and a binding region binds, comprising
  (i) providing a parent polypeptide or a combination of at least a first parent polypeptide and a second parent polypeptide which has been mutated according to any one of the claims 1 to 24; and
  (ii) contacting a preparation of the mutated parent polypeptide of step (i) or the mutated combination of at least a first parent polypeptide and a second parent polypeptide of step (i) with the cell, cell membrane, or virion expressing an antigen in the presence of human complement or an effector cell.

In one embodiment any or all of the parent polypeptide, first parent polypeptide and second parent polypeptide may be an antibody.

Thus in one embodiment the present invention relates to methods of using the antibody variants described herein for inducing an effector response, e.g. complement activation, CDC or other effector response against a cell, cell membrane, virion or other particle associated with the antigen or antigens. The present invention also relates to a method of inducing an effector response, against a cell, cell membrane, or virion expressing an antigen to which a parent antibody binds, comprising
  (i) providing a parent antibody or a combination of at least a first parent antibody and a second parent antibody which has been mutated according to any of the methods described herein; and
  (ii) contacting a preparation of the mutated parent antibody of step (i) or the mutated combination of at least a first parent antibody and a second parent antibody of step (i) with the cell, cell membrane, or virion expressing an antigen in the presence of human complement or an effector cell.

The parent antibody, the first parent antibody and the second parent antibody may each be selected from any parent antibody described herein, in particular any of those described above in relation to the methods of affecting an effector function of an antibody.

In one embodiment, the antigen is expressed on the surface of a cell.

In one embodiment, the cell is a human tumor cell.

In a further embodiment, the antigen is selected from the group consisting of erbB1 (EGFR), erbB2 (HER2), erbB3, erbB4, MUC-1, CD4, CD19, CD20, CD38, CD138, CXCRS, c-Met, HERV-envelop protein, periostin, Bigh3, SPARC, BCR, CD79, CD37, EGFrvIII, IGFr, L1-CAM, AXL, Tissue Factor (TF), CD74, EpCAM and MRP3.

In another embodiment, the antigen is associated with a cell membrane.

In another embodiment, the antigen is associated with a virion, optionally wherein the antigen is comprised in the protein coat or a lipid envelope of the virion.

In another embodiment, the antibody is a human antibody, optionally binding at least one antigen selected from CD20 and CD38.

In another embodiment, the antibody binds to the same epitope as at least one of 7D8 and 005, optionally comprising a variable heavy and/or variable light chain region of at least one of 7D8 and 005.

In a further embodiment of the present invention, the induced effector response is complement dependent cytotoxicity (CDC), an Fc-mediated effector response selected from an Fc-mediated effector response selected from C1q-binding, complement activation, complement dependent cytotoxicity (CDC), antibody-dependent cell-mediated cytotoxity (ADCC), FcRn-binding, Fc-receptor binding including Fc-gamma receptor-binding, Protein A-binding, Protein G-binding, antibody-dependent cellular phagocytosis (ADCP), complement-dependent cellular cytotoxicity (CDCC), complement-enhanced cytotoxicity, opsonisation, Fc-containing polypeptide internalization, target downmodulation, ADC uptake, induction of apoptosis, cell death, cell cycle arrest, and any combination thereof.

In a particular embodiment the effector response is C1q-binding, complement activation (C1q efficacy), complement dependent cytotoxicity (CDC), antibody-dependent cell-mediated cytotoxity (ADCC), Fc-receptor binding, e.g. Fc-gamma receptor-binding, Fc-containing polypeptide internalization or any combination thereof.

In one embodiment the effector response is C1q-binding.

In one embodiment the effector response is complement activation (C1q efficacy).

In one embodiment the effector response is complement dependent cytotoxicity (CDC).

In one embodiment the effector response is antibody-dependent cell-mediated cytotoxity (ADCC).

In one embodiment the effector response is Fc-receptor binding, e.g. including Fc-gamma receptor-binding.

In one embodiment the effector response is Fc-containing polypeptide internalization.

In one embodiment the effector response is a combination of complement dependent cytotoxicity (CDC) and antibody-dependent cell-mediated cytotoxity (ADCC).

In another embodiment, the method increases a further effector response selected from FcRn-binding, ADCC, Fc-gamma receptor-binding, Protein A-binding, Protein G-binding, ADCP, complement-dependent cellular cytotoxicity (CDCC), complement-enhanced cytotoxicity, binding to complement receptor of an opsonized antibody mediated by the antibody, and any combination thereof.

In another aspect, the invention relates to a method of increasing the avidity of a preparation of a parent antibody for C1q, comprising the step of mutating at least one amino acid in the Fc-region of the antibody, wherein the at least one amino acid is selected from the group consisting of E345, E430, S440, P247, I253, S254, Q311, D/E356, T359, E382, Q386, Y436, and K447.

Examples of antigens or targets that the invention may be directed against are; 514; ADAM-10; ADAM-12; ADAM17; AFP; AXL; ANGPT2 anthrax antigen; BSG; CAIX; CAXII; CA 72-4; carcinoma associated antigen CTAA16.88; CCL11; CCL2; CCR4; CCR5; CCR6; CD2; CD3E; CD4; CD5; CD6; CD15; CD18; CD19; CD20; CD22; CD24; CD25; CD29; CD30; CD32B; CD33; CD37; CD38; CD40; CD40LG; CD44; CD47; CD52; CD56; CD66E; CD72; CD74; CD79a; CD79b; CD80; CD86; CD98; CD137; CD147; CD138; CD168; CD200; CD248; CD254; CD257; CDH3; CEA; CEACAM5; CEACAM6; CEACAM8; Claudin4; CS-1; CSF2RA; CSPG-4; CTLA4; Cripto; DLL4; ED-B; EFNA2; EGFR; Endothelin B receptor; ENPP3; EPCAM; ERBB2; ERBB3; FAP alpha; Fc gamma RI; FCER2; FGFR3; fibrin II beta chain; FLT1; FOLH1; FOLR1; FRP-1; GD3 ganglioside; GDF2; GLP1R; Glypican-3; GPNMB; HBV (hepatitis B virus); HCMV (human cytomegalovirus); heat shock protein 90 homolog [*Candida albicans*]; herpes simplex virus gD glycoprotein; HGF; HIV-1; HIV-1 IIIB gp120 V3 loop; HLA-DRB (HLA-DR beta); human respiratory syncytial virus, glycoprotein F; ICAM1; IFNA1; IFNA1; IFNB1 bispecific; IgE Fc; IGF1R; IGHE connecting region; IL12B; IL13; IL15; IL17A; ILIA; IL1B; IL2RA; IL4; IL5; IL5RA; IL6; IL6R; IL9; interleukin-2 receptor beta subunit; ITGA2; ITGA2B ITGB3; ITGA4 ITGB7; ITGA5; ITGAL; ITGAV_ITGB3; ITGB2; KDR; L1CAM; Lewis-y; lipid A, domain of lipopolysaccharide LPS; LTA; MET; MMP14; MMp15; MST1R; MSTN; MUC1; MUC4; MUC16; MUCSAC; NCA-90 granulocyte cell antigen; Nectin 4; NGF; NRP; NY-ESO-1; OX40L; PLAC-1; PLGF; PDGFRA; PD1; PDL1; PSCA; phosphatidylserine; PTK-7; *Pseudomonas aeruginosa* serotype IATS 011; RSV (human respiratory syncytial virus, glycoprotein F); ROR1; RTN4; SELL; SELP; STEAP1; Shiga-like toxin II B subunit [*Escherichia coli*]; SLAM7; SLC44A4; SOST; *Staphylococcus epidermidis* lipoteichoic acid; T cell receptor alpha_beta; Tissue Factor (TF); TGFB1; TGFB2; TMEFF2; TNC; TNF; TNFRSF10A; TNFRSF10B; TNFRSF12A; TNFSF13; TNFSF14; TNFSF2; TNFSF7; TRAILR2; TROP2; TYRP1; VAP-1; and Vimentin.

In one embodiment, the cell is a human tumor cell or a bacterial cell.

In another embodiment, the antigen is selected from the group consisting of erbB1 (EGFR), erbB2 (HER2), erbB3, erbB4, MUC-1, CD4, CD19, CD20, CD25, CD32, CD37, CD38, CD74, CD138, CXCRS, c-Met, HERV-envelop protein, periostin, Bigh3, SPARC, BCR, CD79, EGFrvIII, IGFr, L1-CAM, EpCAM and MRP3.

In a further embodiment, the antigen is CD20 or CD38.

In another embodiment, the IgG1 parent antibody is a human IgG1 antibody.

In another embodiment, the parent antibody is selected from 7D8 and 005.

In one embodiment, the cell is a human tumor cell.

In another embodiment, the first and second antigens are separately selected from the group consisting of erbB1 (EGFR), erbB2 (HER2), erbB3, erbB4, MUC-1, CD4, CD19, CD20, CD25, CD32, CD37, CD38, CD74, CD138, CXCRS, c-Met, HERV-envelop protein, periostin, Bigh3, SPARC, BCR, CD79, EGFrvIII, IGFr, L1-CAM, AXL, Tissue Factor (TF), EpCAM and MRP3.

In another embodiment, the first and second parent antibodies are fully human, optionally wherein the first and second parent antibodies bind antigens separately selected from CD20 and CD38.

In a further embodiment, the first and second parent antibodies are separately selected from 7D8 and 005.

In an even further embodiment, the cell is a bacterial cell.

In another embodiment, the bacterial cell is selected from the group consisting of *S. aureus, S. Epidermidis, S. pneumonia, Bacillus anthracis, Pseudomonas aeruginosa, Chlamydia, E. coli, Salmonella, Shigella, Yersinia, S. typhimurium, Neisseria meningitides* and *Mycobacterium tuberculosis*.

In another embodiment, the first and/or second antigen is Lipoteichoic acid (LTA), optionally wherein at least one of the first and second parent antibody is pagibaximab.

In another embodiment, the antigen is expressed on a virion.

In another embodiment, the first and second antibody binds the same antigen.

In another embodiment, the first and second antibodies comprise the same VH sequence, VL sequence, or both VH and VL sequence.

For the purposes of the present invention, the target cell that expresses or is otherwise associated with an antigen can be any prokaryotic or eukaryotic cell. Exemplary antigen-expressing cells include, but are not limited to, mammalian cells, particularly human cells, such as human cancer cells; and unicellular organisms such as bacteria, protozoa, and unicellular fungi such as yeast cells. Cell membranes comprising or otherwise associated with an antigen include partial and/or disrupted cell membranes derived from an antigen-expressing cell. An antigen associated with a virion or virus particle may be comprised in or otherwise associated with the protein coat and/or a lipid envelope of the virion.

The target cell may, for example, be a human tumor cell. Suitable tumor antigens include any target or antigen described herein, but are not limited to, erbB1 (EGFR), erbB2 (HER2), erbB3, erbB4, MUC-1, CD4, CD19, CD20, CD25, CD32, CD37, CD38, CD74, CD138, CXCRS, c-Met, HERV-envelop protein, periostin, Bigh3, SPARC, BCR, CD79, EGFrvIII, IGFR, L1-CAM, AXL, Tissue Factor (TF), EpCAM and MRP3. Preferred antigens include CD20, CD38, HER2, EGFR, IGFR, CD25, CD74 and CD32. Exemplary antibodies include anti-CD20 antibody 7D8 as disclosed in WO 2004/035607, anti-CD38 antibody 005 as disclosed in WO 06/099875, anti-CD20 antibody 11B8 as disclosed in WO 2004/035607, anti-CD38 antibody 003 as disclosed in WO 06/099875, anti-EGFr antibody 2F8 as disclosed in WO 02/100348. Examples of other particular antibodies are provided herein.

Alternatively, the target cell can be a bacterial cell, such as, e.g., *S. aureus, S. epidermidis, S. pneumonia, Bacillus anthracis, Pseudomonas aeruginosa, Chlamydia, E. coli, Salmonella, Shigella, Yersinia, S. typhimurium, Neisseria meningitides* and *Mycobacterium tuberculosis*. Exemplary antigens include Lipoteichoic acid (LTA), and exemplary antibodies include pagibaximab.

Alternatively, the target may be present on the surface of a virus, fungal cell or other particle, such as, e.g., West Nile virus, Dengue virus, hepatitis C-virus (HCV), human immunodeficiency virus (HIV), human papillomavirus, Epstein-Barr virus, Herpesviruses, poxviruses, avian influenza virus, RVS, *Aspergillus, Candida albicans, Cryptococcus,* and *Histoplasma*.

In one embodiment, the contacting step (ii) takes place in vitro.

In one embodiment, the contacting step (ii) takes place in vivo.

In another embodiment, step (ii) comprises administering the variants to a subject.

In a further embodiment, the subject suffers from cancer, a bacterial infection, or a viral infection. The contacting step (ii) of the above-mentioned embodiments may take place in vitro or in vivo. In the latter case, step (ii) may further comprise administering the preparation or preparations to a subject, optionally a subject suffering from cancer or a bacterial infection. Further details on therapeutic applications are provided below.

The first and the second antibodies comprise antigen-binding regions which may bind to the same or different epitope. Such epitopes may be on the same or different target.

In an embodiment, the first and the second antibody binds different epitopes on different targets. Such targets may be expressed on the same cell or cell type, or may be expressed on different cells or cell types. In such an embodiment, the enhancement of an effector function is directed only towards cells or cell types expressing both the targets, and thereby reducing the risks of any collateral damage of cells or cell types which are not the cause of a disease to be treated.

Without being bound by any theory, it is believed that the enhancement of CDC can be restricted to target cells that express two specific targets/antigens simultaneously provided that the first and second antibody bind epitopes found on the same cell, thereby exploiting the combined expression of targets to improve selectivity of enhaved CDC induction.

In cases where the targets are expressed on different cells or cell types, it is believed without being bound by theory, that the administration in any order of the first and second antibody will improve CDC enhancement and possibly also other effector functions by "recruitment" of a second cell or cell type expressing the second target.

In one embodiment wherein a combination of a first and second antibody are used, step (ii) may be performed by simultaneously, separately, or sequentially contacting the cell with the mutated first and second parent antibodies in the presence of human complement and/or an effector cell.

In yet another aspect, the invention relates to a method of improving the CDC-inducing capability of a preparation of a parent antibody, comprising the step of mutating at least one amino acid in the Fc-region of the antibody, wherein the at least one amino acid is selected from the group consisting of E345, E430, S440, P247, I253, S254, Q311, D/E356, T359, E382, Q386, Y436, and K447.

In an alternative aspect, the present invention relates to a method of inducing an effector response, optionally a CDC-response, against a cell, cell membrane, or virion expressing an antigen to which an IgG1 parent antibody binds, comprising (i) providing an antibody comprising a mutation in at least one amino acid residue selected from the group consisting of E345, E430, S440, P247, I253, S254, Q311, D/E356, T359, E382, Q386, Y436, and K447 in the Fc-region of an IgG1 heavy chain; and
(ii) contacting a preparation of the antibody with the cell, cell membrane, or virion in the presence of human complement or an effector cell.

In another alternative embodiment, the method further comprises administering a first antibody comprising a first mutation in at least one amino acid residue selected from those corresponding to E345, E430, S440, P247, I253, S254, Q311, D/E356, T359, E382, Q386, Y436, and K447 in the Fc-region of the first antibody;
administering a second antibody comprising a second mutation in at least one amino acid residue selected from those corresponding to E345, E430, S440, P247, I253, S254, Q311, D/E356, T359, E382, Q386, Y436, and K447 in the Fc-region of the second antibody;
wherein the first and second antibodies may be administered simultaneously, separately or sequentially. The first and second antibody may bind to the same or different epitope on the same or different target. The target(s) may be found on the same or different cell or cell types.

In another alternative aspect, the invention relates to a method of improving the CDC-inducing capability of a preparation of an IgG1 parent antibody, comprising mutating at least one amino acid in the Fc-region of the antibody, wherein the at least one amino acid is selected from the group consisting of E345, E382 and H433.

In another alternative aspect, the invention relates to a method of inducing an effector response, optionally a CDC-response, against a cell, cell membrane, or virion expressing an antigen to which an IgG1 parent antibody binds, comprising the steps of (i) providing a variant of the parent antibody comprising a mutation in at least one amino acid in the Fc-region of the antibody, the at least one amino acid selected from the group consisting of E345, E382 and H433; and
(ii) contacting a preparation of the variant with the cell in the presence of human complement or an effector cell.

In another alternative aspect, the invention relates to a method of inducing an effector response, optionally a CDC-response, against a cell expressing an antigen to which an IgG1 parent antibody binds, comprising the steps of (i) providing a variant of the parent antibody comprising K439E and a S440K mutations in the Fc-region of the antibody; and
(ii) contacting a preparation of the variant with the cell in the presence of human complement or an effector cell.

In another alternative aspect, the invention relates to a method of inducing a CDC-response against a cell, cell membrane or virion expressing a first antigen to which a first IgG1 parent antibody binds and a second antigen to which a second parent antibody binds, comprising the steps of (i) providing a first variant of the first parent antibody comprising a K439E mutation and a second variant of the second parent antibody comprising a S440K mutation; and
(ii) simultaneously, separately or sequentially contacting the cell with the first and second variants in the presence of human complement and/or an effector cell.

In another alternative aspect, the invention provides for a method of inducing a CDC- or other effector response against a target cell, cell membrane, virion or other particle associated with an antigen to which an IgG1 or IgG3 antibody binds, comprising the steps of (i) providing a variant of the antibody comprising a mutation in at least one amino acid corresponding to E345, E430 or S440 in the Fc-region of an IgG1 antibody; and (ii) contacting a preparation of the variant with the cell in the presence of human complement and/or effector cells.

In further alternative aspect, the invention provides for a method of inducing ADCC or ADCP against, or phagocytosis of, a target cell, cell membrane, virion or other particle associated with an antigen to which an IgG1 or IgG3 antibody binds, comprising the steps of (i) providing a variant of the antibody comprising a mutation in at least one amino acid corresponding to E345, E430 or S440 in the Fc-region of an IgG1 antibody; and (ii) contacting a preparation of the variant with the cell in the presence of an effector cell.

The invention also provides for a method of inducing a CDC or other effector response against a target cell, cell membrane, virion or other particle associated with an antigen to which an IgG1 or IgG3 antibody binds, comprising the steps of (i) providing a variant of the antibody comprising a mutation in K439 which is K439E and a mutation in S440 which is S440K or S440R in the Fc-region of the antibody; and (ii) contacting a preparation of the variant with the cell in the presence of human complement and/or an effector cell The invention also provides for a method of inducing a CDC or other effector response against a target cell, cell membrane or virion expressing a first antigen to which a first IgG1 antibody binds and a second antigen to which a second antibody binds, comprising the steps of (i) providing a first variant which is the first antibody comprising a K439E mutation and a second variant which is the second antibody comprising a S440K or S440R mutation; and (ii) simultaneously, separately or sequentially contacting the cell with preparations of the first and second variants in the presence of human complement or an effector cell.

In separate and specific embodiments, the first and second antibodies bind (i) different antigens; (ii) different epitopes on the same antigen, (iii) the same epitope on an antigen, and (iv) the same epitope on an antigen and comprise the same VH and/or VL sequences.

In one embodiment, the first and second antibodies further comprise a mutation in one or more of E345, E430 and S440, such as E345R. In one embodiment, the first and second antibodies further comprise a mutation in one or more of E345, E382 and H433, such as E345R.

Other Methods

In another main aspect, the invention relates to a method of identifying a mutation in an antibody which enhances the effector function of the antibody to bind C1q, comprising the steps of
  (i) preparing at least one antibody comprising a mutation in at least one amino acid selected from the group consisting of E345, E430, S440, K439, P247, I253, S254, Q311, D/E356, T359, E382, Q386, Y436, and K447;
  (ii) evaluating the C1q-activity of the antibody when bound to the surface of antigen-expressing cell as compared to the parent antibody; and
  (iii) selecting the mutation of any variant having an increased C1q-avidity.

In one embodiment, the at least one antibody comprises at least one amino acid substitution selected from the group of E345R, E345Q, E345N, E345K, E345Y, E430T, E430S, E430G, E430F, E430H, S440W and S440Y.

In yet another main aspect, the invention relates to a method of identifying a mutation in a parent antibody which increases the ability of the antibody to induce a CDC-response, comprising the steps of
  (i) preparing at least one variant of the parent antibody comprising a mutation in at least one amino acid selected from the group consisting of E345, E430, S440, K439, P247, I253, S254, Q311, D/E356, T359, E382, Q386, Y436, and K447;
  (ii) evaluating the CDC-response induced by the variant when bound to the surface of an antigen-expressing cell, in the presence of effector cells or complement, as compared to the parent antibody; and
  (iii) selecting the mutation of any variant having an increased CDC-response.

In one embodiment, the at least one amino acid is selected from E345, E382 and H433.

In one embodiment, the at least one antibody comprises at least one amino acid substitution selected from the group of E345R, E345Q, E345N, E345K, E345Y, E430T, E430S, E430G, E430F, E430H, S440W and S440Y.

In another aspect, the invention relates, to a method of increasing the avidity of a preparation of an IgG1 parent antibody for C1q, comprising mutating at least one amino acid in the Fc-region of the antibody, wherein the at least one amino acid is selected from the group consisting of E345, E382 and H433.

Antibodies of the Present Invention

Parent Antibodies

As described herein, the present invention inter alia relates to variants of parent antibodies comprising one or more mutations in the CH2 and/or CH3 region of an immunoglobulin, e.g. in the antibody the heavy chain. The "parent" antibodies, which may be wild-type antibodies, to be used as starting material of the present invention before modification may e.g. be produced by the hybridoma method first described by Kohler et al., Nature 256, 495 (1975), or may be produced by recombinant DNA methods. Monoclonal antibodies may also be isolated from phage antibody libraries using the techniques described in, for example, Clackson et al., Nature 352, 624 628 (1991) and Marks et al., J. Mol. Biol. 222, 581 597 (1991). Monoclonal antibodies may be obtained from any suitable source. Thus, for example, monoclonal antibodies may be obtained from hybridomas prepared from murine splenic B cells obtained from mice immunized with an antigen of interest, for instance in form of cells expressing the antigen on the surface, or a nucleic acid encoding an antigen of interest. Monoclonal antibodies may also be obtained from hybridomas derived from antibody-expressing cells of immunized humans or non-human mammals such as rabbits, rats, dogs, primates, etc.

The parent antibodies may be e.g. chimeric or humanized antibodies. In another embodiment, the antibody is a human antibody. Human monoclonal antibodies may be generated using transgenic or transchromosomal mice, e.g. HuMAb mice, carrying parts of the human immune system rather than the mouse system. The HuMAb mouse contains a human immunoglobulin gene minilocus that encodes unrearranged human heavy (μ and γ) and κ light chain immunoglobulin sequences, together with targeted mutations that inactivate the endogenous β and κ chain loci (Lonberg, N. et al., Nature 368, 856 859 (1994)). Accordingly, the mice exhibit reduced expression of mouse IgM or κ and in response to immunization, the introduced human heavy and light chain transgenes, undergo class switching and somatic mutation to generate high affinity human IgG,κ monoclonal antibodies (Lonberg, N. et al. (1994), supra; reviewed in Lonberg, N. Handbook of Experimental Pharmacology 113, 49 101 (1994), Lonberg, N. and Huszar, D., Intern. Rev. Immunol. Vol. 13 65 93 (1995) and Harding, F. and Lonberg, N. Ann. N.Y. Acad. Sci 764 536 546 (1995)). The preparation of HuMAb mice is described in detail in Taylor, L. et al., Nucleic Acids Research 20, 6287 6295 (1992), Chen, J. et al., International Immunology 5, 647 656 (1993), Tuaillon et al., J. Immunol. 152, 2912 2920 (1994), Taylor, L. et al., International Immunology 6, 579 591 (1994), Fishwild, D. et al., Nature Biotechnology 14, 845 851 (1996). See also U.S. Pat. Nos. 5,545,806, 5,569,825, 5,625,126, 5,633,425, 5,789,650, 5,877,397, 5,661,016, 5,814,318, 5,874,299, 5,770,429, 5,545,807, WO 98/24884, WO 94/25585, WO 93/1227, WO 92/22645, WO 92/03918 and WO 01/09187. Splenocytes from these transgenic mice may be used to generate hybridomas that secrete human monoclonal antibodies according to well known techniques.

Further, human antibodies of the present invention or antibodies of the present invention from other species may be identified through display-type technologies, including, without limitation, phage display, retroviral display, ribosomal display, mammalian display, yeast display and other techniques known in the art, and the resulting molecules may be subjected to additional maturation, such as affinity maturation, as such techniques are well known in the art. A particular strategy, described in Example 17, can be applied to any antibody to prepare and obtain a variant of the invention using phage-display.

The parent antibody is not limited to antibodies which have a natural, e.g. a human Fc domain but it may also be an antibody having other mutations than those of the present invention, such as e.g. mutations that affect glycosylation or enables the antibody to be a bispecific antibody. By the term "natural antibody" is meant any antibody which does not comprise any genetically introduced mutations. An antibody which comprises naturally occurred modifications, e.g. different allotypes, is thus to be understood as a "natural antibody" in the sense of the present invention, and can thereby be understood as a parent antibody. Such antibodies may serve as a template for the one or more mutations according to the present invention, and thereby providing the variant antibodies of the invention. An example of a parent antibody comprising other mutations than those of the present invention is the bispecific antibody as described in WO2011/131746 (Genmab), utilizing reducing conditions to promote half-molecule exchange of two antibodies comprising IgG4-like CH3 regions, thus forming bispecific antibodies without concomitant formation of aggregates. Other examples of parent antibodies include but are not limited to bispecific antibodies such as heterodimeric bispecifics: Tri-omabs (Fresenius); bispecific IgG1 and IgG2 (Rinat neurosciences Corporation); FcAAdp (Regeneron); Knobs-into-holes (Genentech); Electrostatic steering (Amgen, Chugai, Oncomed); SEEDbodies (Merck); Azymetric scaffold (Zymeworks); mAb-Fv (Xencor); and LUZ-Y (Genentch). Other exemplary parent antibody formats include, without limitation, a wild-type antibody, a full-length antibody or Fc-containing antibody fragment, a human antibody, or any combination thereof.

The parent antibody may bind any target, examples of such targets or antigens the invention may be, and is not limited to, directed against are; 5T4; ADAM-10; ADAM-12; ADAM17; AFP; AXL; ANGPT2 anthrax antigen; BSG; CAIX; CAXII; CA 72-4; carcinoma associated antigen CTAA16.88; CCL11; CCL2; CCR4; CCR5; CCR6; CD2; CD3E; CD4; CD5; CD6; CD15; CD18; CD19; CD20; CD22; CD24; CD25; CD29; CD30; CD32B; CD33; CD37; CD38; CD40; CD40LG; CD44; CD47; CD52; CD56; CD66E; CD72; CD74; CD79a; CD79b; CD80; CD86; CD98; CD137; CD147; CD138; CD168; CD200; CD248; CD254; CD257; CDH3; CEA; CEACAM5; CEACAM6; CEACAM8; Claudin4; CS-1; CSF2RA; CSPG-4; CTLA4; Cripto; DLL4; ED-B; EFNA2; EGFR; Endothelin B receptor; ENPP3; EPCAM; ERBB2; ERBB3; FAP alpha; Fc gamma RI; FCER2; FGFR3; fibrin II beta chain; FLT1; FOLH1; FOLR1; FRP-1; GD3 ganglioside; GDF2; GLP1R; Glypican-3; GPNMB; HBV (hepatitis B virus); HCMV (human cytomegalovirus); heat shock protein 90 homolog [*Candida albicans*]; herpes simplex virus gD glycoprotein; HGF; HIV-1; HIV-1 IIIB gp120 V3 loop; HLA-DRB (HLA-DR beta); human respiratory syncytial virus, glycoprotein F; ICAM1; IFNA1; IFNA1; IFNB1 bispecific; IgE Fc; IGF1R; IGHE connecting region; IL12B; IL13; IL15; IL17A; IL1A; IL1B; IL2RA; IL4; IL5; IL5RA; IL6; IL6R; IL9; interleukin-2 receptor beta subunit; ITGA2; ITGA2B ITGB3; ITGA4 ITGB7; ITGA5; ITGAL; ITGAV_ITGB3; ITGB2; KDR; L1CAM; Lewis-y; lipid A, domain of lipopolyaccha-ride LPS; LTA; MET; MMP14; MMp15; MST1R; MSTN; MUC1; MUC4; MUC16; MUCSAC; NCA-90 granulocyte cell antigen; Nectin 4; NGF; NRP; NY-ESO-1; OX40L; PLAC-1; PLGF; PDGFRA; PD1; PDL1; PSCA; phosphatidylserine; PTK-7; *Pseudomonas aeruginosa* serotype IATS 011; RSV (human respiratory syncytial virus, glycoprotein F); ROR1; RTN4; SELL; SELP; STEAP1; Shiga-like toxin II B subunit [*Escherichia coli*]; SLAM7; SLC44A4; SOST; *Staphylococcus epidermidis* lipoteichoic acid; T cell receptor alpha_beta; TF; TGFB1; TGFB2; TMEFF2; TNC; TNF; TNFRSF10A; TNFRSF10B; INFRSF12A; TNFSF13; TNFSF14; TNFSF2; TNFSF7; TRAILR2; TROP2; TYRP1; VAP-1; and Vimentin.

The parent antibody may be any human antibody of any isotype, e.g. IgG1, IgG2, IgG3, IgG4, IgA1, IgA2, IgE, and IgD, optionally a human full-length antibody, such as a human full-length IgG1 antibody. The parent antibody may comprise a sequence according to any of SEQ ID NOs: 1, 2, 3, 4, and 5.

Monoclonal antibodies, such as the parent and/or variants, for use in the present invention, may be produced, e.g., by the hybridoma method first described by Kohler et al., Nature 256, 495 (1975), or may be produced by recombinant DNA methods. Monoclonal antibodies may also be isolated from phage antibody libraries using the techniques described in, for example, Clackson et al., Nature 352, 624-628 (1991) and Marks et al., J. Mol. Biol. 222, 581-597 (1991). Monoclonal antibodies may be obtained from any suitable source. Thus, for example, monoclonal antibodies may be obtained from hybridomas prepared from murine splenic B cells obtained from mice immunized with an antigen of interest, for instance in form of cells expressing the antigen on the surface, or a nucleic acid encoding an antigen of interest. Monoclonal antibodies may also be obtained from hybridomas derived from antibody-expressing cells of immunized humans or non-human mammals such as rats, dogs, primates, etc.

In one embodiment, the antibody is a human antibody. Human monoclonal antibodies directed against any antigen may be generated using transgenic or transchromosomal mice carrying parts of the human immune system rather than the mouse system. Such transgenic and transchromosomic mice include mice referred to herein as HuMAb® mice and KM mice, respectively, and are collectively referred to herein as "transgenic mice".

The HuMAb® mouse contains a human immunoglobulin gene miniloci that encodes unrearranged human heavy (β and γ) and κ light chain immunoglobulin sequences, together with targeted mutations that inactivate the endogenous β and κ chain loci (Lonberg, N. et al., Nature 368, 856-859 (1994)). Accordingly, the mice exhibit reduced expression of mouse IgM or κ and in response to immunization, the introduced human heavy and light chain transgenes, undergo class switching and somatic mutation to generate high affinity human IgG,κ monoclonal antibodies (Lonberg, N. et al. (1994), supra; reviewed in Lonberg, N. Handbook of Experimental Pharmacology 113, 49-101 (1994), Lonberg, N. and Huszar, D., Intern. Rev. Immunol. Vol. 13 65-93 (1995) and Harding, F. and Lonberg, N. Ann. N.Y. Acad. Sci 764 536-546 (1995)). The preparation of HuMAb® mice is described in detail in Taylor, L. et al., Nucleic Acids Research 20, 6287-6295 (1992), Chen, J. et al., International Immunology 5, 647-656 (1993), Tuaillon et al., J. Immunol. 152, 2912-2920 (1994), Taylor, L. et al., International Immunology 6, 579-591 (1994), Fishwild, D. et al., Nature Biotechnology 14, 845-851 (1996). See also U.S. Pat. Nos. 5,545,806, 5,569,825, 5,625,126, 5,633,425, 5,789,650, 5,877,397, 5,661,016, 5,814,318, 5,874,299, 5,770,429, 5,545,807, WO 98/24884, WO 94/25585, WO 93/1227, WO 92/22645, WO 92/03918 and WO 01/09187.

The HCo7, HCo12, HCo17 and HCo20 mice have a JKD disruption in their endogenous light chain (kappa) genes (as described in Chen et al., EMBO J. 12, 821-830 (1993)), a CMD disruption in their endogenous heavy chain genes (as described in Example 1 of WO 01/14424), and a KCo5 human kappa light chain transgene (as described in Fishwild et al., Nature Biotechnology 14, 845-851 (1996)). Additionally, the Hco7 mice have a HCo7 human heavy chain transgene (as described in U.S. Pat. No. 5,770,429), the HCo12 mice have a HCo12 human heavy chain transgene (as described in Example 2 of WO 01/14424), the HCo17 mice have a HCo17 human heavy chain transgene (as described in Example 2 of WO 01/09187) and the HCo20 mice have a HCo20 human heavy chain transgene. The resulting mice express human immunoglobulin heavy and kappa light chain transgenes in a background homozygous for disruption of the endogenous mouse heavy and kappa light chain loci.

In the KM mouse strain, the endogenous mouse kappa light chain gene has been homozygously disrupted as described in Chen et al., EMBO J. 12, 811-820 (1993) and the endogenous mouse heavy chain gene has been homozygously disrupted as described in Example 1 of WO 01/09187. This mouse strain carries a human kappa light chain transgene, KCo5, as described in Fishwild et al., Nature Biotechnology 14, 845-851 (1996). This mouse strain also carries a human heavy chain transchromosome composed of chromosome 14 fragment hCF (SC20) as described in WO 02/43478. HCo12-Balb/C mice can be generated by crossing HCo12 to KCo5P/KliBalb) as described in WO/2009/097006. Splenocytes from these transgenic mice may be used to generate hybridomas that secrete human monoclonal antibodies according to well known techniques.

Further, any antigen-binding regions may be obtained from human antibodies or antibodies from other species identified through display-type technologies, including, without limitation, phage display, retroviral display, ribosomal display, and other techniques, using techniques well known in the art and the resulting molecules may be subjected to additional maturation, such as affinity maturation, as such techniques are well known in the art (see for instance Hoogenboom et al., J. Mol. Biol. 227, 381 (1991) (phage display), Vaughan et al., Nature Biotech 14, 309 (1996) (phage display), Hanes and Plucthau, PNAS USA 94, 4937-4942 (1997) (ribosomal display), Parmley and Smith, Gene 73, 305-318 (1988) (phage display), Scott TIBS 17, 241-245 (1992), Cwirla et al., PNAS USA 87, 6378-6382 (1990), Russel et al., Nucl. Acids Research 21, 1081-1085 (1993), Hogenboom et al., Immunol. Reviews 130, 43-68 (1992), Chiswell and McCafferty TIBTECH 10, 80-84 (1992), and U.S. Pat. No. 5,733,743). If display technologies are utilized to produce antibodies that are not human, such antibodies may be humanized.

In another aspect, the invention relates to a parent polypeptide comprising a Fc domain and a binding region. It is understood in the context of the present invention all embodiments relating to parent antibody similarly applies to a "parent polypeptide".

A mutation according to the present invention may be, but is not limited to, a deletion, insertion or substitution of one or more amino acids. Such a substitution of amino acids may be with any naturally occurring or non-naturally amino acid. "Single-Mutants"

It is to be understood that all embodiments described herein with reference to a parent antibody, first parent antibody or second parent antibody are also to be understood as embodiments relating to a parent, first parent or second parent polypeptide comprising an Fc-domain of an immunoglobulin and a binding region.

Antibody or polypeptide variants according to the "single-mutant" aspect of the present invention comprise a mutation, typically an amino acid substitution, in at least one amino acid residue shown in Table 1, which lists each amino acid residue, numbered according to the EU index in a human IgG1 antibody, along with the amino acid in the corresponding position in an IgG2, IgG3, and IgG4 parent antibody and "Exemplary" and "Preferred" amino acid substitutions. The IgG2 segment corresponding to residues P247 to K447, the IgG3 Fc-segment corresponding to residues P247 to K447 and the IgG4 segment corresponding to residues P247 to K447 in IgG1 are shown in FIG. 2.

TABLE 1

Exemplary mutation sites and amino acid substitutions for the "single-mutant" aspect

| Amino acid (IgG1) | Amino acid (IgG2) | Amino acid (IgG3) | Amino acid (IgG4) | Exemplary substitutions | Preferred substitutions |
|---|---|---|---|---|---|
| P2467 | P247 | P247 | P247 | ACDFGHIKLMNRSTVW | G |
| I253 | I253 | I253 | I253 | ADKLMNRSV, alternatively EQT | LV, alternatively QN |
| S254 | S254 | S254 | S254 | EFGHIKLPTVW | L |
| H310 | H310 | H310 | H310 | AGFKLPRTWV, alternatively NQY | PW, alternatively Q |
| Q311 | Q311 | QA311 | Q311 | ACEGHFIKLNPRSTWY | LW, alternatively ER |
| E345 | E345 | E345 | E345 | ACDGHFIKLMNPQRSTVWY | ADGHFIKLMNPQRSTVWY |
| D356/E356 | E356 | E356 | E356 | GILRTV | R |
| T359 | T359 | T359 | T359 | GNPR | R |
| E382 | E382 | E382 | E382 | FKLMPVW, alternatively DHNQSTY | LV, alternatively DQKR |

TABLE 1-continued

Exemplary mutation sites and amino acid substitutions for the "single-mutant" aspect

| Amino acid (IgG1) | Amino acid (IgG2) | Amino acid (IgG3) | Amino acid (IgG4) | Exemplary substitutions | Preferred substitutions |
|---|---|---|---|---|---|
| G385 | G385 | G385 | G385 | ADHILNPQRSTV, alternatively EKWY | NR, alternatively DEKR |
| Q386 | Q386 | Q386 | Q386 | ACDEGHFIKLNPRSTVWY | K |
| E430 | E430 | E430 | E430 | ACDFGHIKLMNPQRSTVWY | ADGHFIKLMNPQRSTVWY |
| H433 | H433 | H433 | H433 | R | R |
| N434 | N434 | N434 | N434 | DEGKRSVW, alternatively HQTY | W, alternatively QHKR |
| Y436 | Y436 | Y436 | Y436 | IKLRSTVW, alternatively AEFHMNQ | IV, alternatively NQST |
| Q438 | Q438 | Q438 | Q438 | CEIKLSTVWY, alternatively AGHNQR | CL, alternatively NST |
| K439 | K439 | K439 | K439 | ADEHLPRTY, alternatively QW | DEHR, alternatively Q |
| S440 | S440 | S440 | S440 | ACDEGHFIKLMNPQRTVWY | WY, alternatively DEQ |
| K447 | K447 | K447 | K447 | DENQ, deletion | DENQ, deletion |

As seen in Table 1, the amino acid substitutions which resulted in an increase of cell lysis of Wien133 cells in Example 19 are included as "Preferred substitutions".

In one aspect the present invention relates to a variant of a parent polypeptide comprising an Fc-domain of an immunoglobulin and a binding region, wherein the variant comprises a mutation in at least one amino acid residue selected from those corresponding to E345, E430, S440, Q386, P247, I253, S254, Q311, D/E356, T359, E382, Y436, and K447 in the Fc-region of a human IgG1 heavy chain, with the proviso that the mutation in S440 is S440Y or S440W.

In one embodiment the variant polypeptide may be a variant antibody.

Thus in another aspect, the invention relates to a variant of a parent antibody comprising an antigen-binding region and Fc-domain of an immunoglobulin, wherein the variant comprises a mutation in at least one amino acid residue selected from those corresponding to E345, E430, S440, Q386, P247, I253, S254, Q311, D/E356, T359, E382, Y436, and K447 in the Fc-region of a human IgG1 heavy chain, with the proviso that the mutation in S440 is S440Y or S440W. Alternatively, the amino acid residue is selected from those corresponding to H310, G385, H433, N434, Q438, and K439 in the Fc-region of a human IgG1 heavy chain.

Each of the amino acid residues corresponding to E345, E430, S440, Q386, P247, I253, S254, Q311, D/E356, T359, E382, Y436, and K447 in the Fc-region of a human IgG1 heavy chain may be grouped according to the following as described above:
  (a) an amino acid residue within the CH2-CH3 region providing allosteric mutations,
  (b) an amino acid residue within the hydrophobic knobs of the CH2-CH3 region,
  (c) an amino acid residue within the N-terminal CH3 helix,
  (d) an amino acid residue within the C-terminal CH3 beta-strand, with the proviso that in case of a mutation corresponding to S440 in the Fc-region of a human IgG1 heavy chain the mutation is S440Y or S440W, and
  (e) an amino acid residue corresponding to E345, E382 or Q386 in the Fc-region of a human IgG1 heavy chain.

A mutation according to the present invention may be, but is not limited to, a deletion, insertion or substitution of one or more amino acids. Such a substitution of amino acids may be with any naturally occurring or non-naturally amino acid. Thus, in one embodiment, the mutation in at least one amino acid residue is a deletion. In another embodiment, the mutation in at least one amino acid residue is an insertion. In another embodiment, the mutation in at least one amino acid residue is a substitution.

In one embodiment, the mutation in at least one amino acid residue is selected from those corresponding to E345X, E430X, S440W/Y, Q386K, P247G, I253V, S254L, Q311L/W, D/E356R, E382V, Y436I, and K447D/E/deletion in the Fc region of a human IgG1 heavy chain, wherein X is any amino acid, such as a natural occurring amino acid.

In one specific embodiment, the antibody variant comprises a mutation in at least one amino acid residue selected from E345, E430, S440, and Q386 in the Fc-region of a human IgG1 heavy chain.

In a further embodiment, the mutation in at least one amino acid residue is an amino acid substitution selected from those corresponding to E345X, E430X, S440W/Y, Q386K, in the Fc region of a human IgG1 heavy chain, wherein X is any amino acid, such as a natural occurring amino acid.

In a preferred embodiment, the mutation in at least one amino acid residue is an amino acid substitution selected from those corresponding to E345R, Q, N, K, A, C, D, F, G, H, I, L, M, P, S, T, V, W, Y; E430T, S, G, A, C, D, F, H, I, L, K, M, N, P, Q, R, V, W, Y; S440W, Y, and Q386K in the Fc region of a human IgG1 heavy chain.

In a further preferred embodiment, the mutation in at least one amino acid residue is an amino acid substitution selected from those corresponding to E345Ft/Q/N/K, E430T/S/G, S440Y/W, and Q386K in the Fc-region of a human IgG1 heavy chain.

Alternatively, the at least one amino acid residue is selected from E382 and H433. Particular alternatively amino acid substitutions include E345Y, D, W; and E430F, H. Alternatively, E382D, Q, K, R; and H433R.

In one specific embodiment, the amino acid substitution is E345R. In an alternative embodiment, the mutation is selected from the group consisting of I253 to E, N, Q, S or T; H310 to N, Q, W or Y; Q311 to E or R; E382 to D, H, K, R, N, Q, S, T, W or Y; G385 to E, H, K, N, Q, R, S, T, W or Y; H433 to R; N434 to D, E, H, K, Q, R, S, T, W or Y; Y436 to A, E, F, H, I, K, L, M, N, Q, R, S, T or V; Q438 to A, E, G, H, K, N, Q, R, S, T, W or Y; K439 to D, H, Q, R, W or Y; and S440 to D, E, H, F, N, Q, W or Y.

In another alternative embodiment, the mutation is selected from the group consisting of I253 to N or Q; H310 to Q; Q311 to E or R; E382 to D, Q, K, or R; G385 to D, E, K or R; H433 to R; N434 to H, K, Q or R; Y436 to N, Q, S or T; Q438 to N, S or T; K439 to Q; and S440 to D, E or Q.

In another alternative embodiment, the mutation is selected from the group consisting of E382 to D, Q, K, or R; and H433 to R.

In one embodiment, the variant comprises a E382R mutation.

In one embodiment, the variant comprises a H433R mutation.

As shown in the Examples, variants of CD38 antibody HuMab-005 and -003 and/or CD20 antibody HuMab-7D8 and -11B8 and rituximab and/or EGFR antibody HuMab-2F8 comprising one of these amino acid substitutions had higher C1q-binding, complement activation and/or CDC than wild-type HuMab 005 and 7D8, respectively.

It is to be understood that the variant may also only comprise one mutation of the "Exemplary substitutions" listed in Table 1. The variant may also comprise more than one mutation, such as two, three, four, five or six of any the mutations listed in Table 1.

A preferred embodiment of the present invention, thus, provides a variant comprising one mutation in an amino acid residue selected from those listed in the aspect above. Particular amino acid mutations may be an amino acid substitution corresponding to any of the group consisting of P247G, I253V, S254L, Q311L, Q311W, E345A, E345C, E345D, E345F, E345G, E345H, E345I, E345K, E345L, E345M, E345N, E345P, E345Q, E345R, E345S, E345T, E345V, E345W, E345Y, D/E356G, D/E356R, T359R, E382L, E382V, Q386K, E430A, E430C, E430D, E430F, E430G, E430H, E430I, E430K, E430L, E430M, E430N, E430P, E430Q, E430R, E430S, E430T, E430V, E430W, E430Y, Y436I, S440Y and S440W. These have an increased cell lysis (>39% on Wien133 cells) as shown in Example 19, Table 17.

In an alternative embodiment, the variant comprises a mutation in one amino acid residue selected from those corresponding to E382R, H433R, H435R, and H435A.

Besides the indicated mutations, the variant may have any of the features as described for the parent antibody. In particular, it may be a human antibody. The variant may further be, besides the mutations, of any IgG1 subtype.

When bound to its antigen on the surface of an antigen-expressing cell, on a cell membrane, on a virion, or on another particle, or the antigen is associated with a virion, optionally wherein the antigen is comprised in the protein coat or a lipid envelope of the virion, such an antibody variant can have compared to the parent antibody at least one of an increased (i) C1q-binding, (ii) complement activation mediated by the antibody, (iii) CDC mediated by the antibody, (iv) oligomer formation, (v) oligomer stability, or a combination of any of (i) to (v). In one embodiment of (iv) or (v), the oligomer is a hexamer. In one embodiment, the variant also or alternatively has a retained or improved other effector function, such as C1q-binding, complement activation, complement dependent cytotoxicity (CDC), antibody-dependent cell-mediated cytotoxity (ADCC), FcRn-binding, Fc-receptor binding including Fc-gamma receptor-binding, Protein A-binding, Protein G-binding, antibody-dependent cellular phagocytosis (ADCP), complement-dependent cellular cytotoxicity (CDCC), complement-enhanced cytotoxicity, opsonisation, Fc-containing polypeptide internalization, target downmodulation, ADC uptake, induction of apoptosis, cell death, cell cycle arrest, and any combination thereof.

Without being limited to any specific theory, the effect caused by substituting amino acids at the indicated positions, with the amino acid residues in Table 1 may, for example, cause the effect itself, be involved in contacting the Fc domain of another molecule directly, or may be mutated to interact with another Fc domain directly or indirectly affect the intermolecular Fc:Fc interaction. Thus, substitutions are believed to, without being bound by theory, directly or indirectly enhance the binding strength between the antibody molecules in the oligomeric form, enhancing the stability of the oligomer structure, such as a hexameric, pentameric, tetrameric, trimeric, or dimeric structure. For example, the amino acid substitution can be one that promotes or strengthens the formation of new intermolecular Fc:Fc bonds, such as, but not limited to, Van der Waals interactions, hydrogen bonds, charge-charge interactions, or aromatic stacking interactions, or one that promotes increased entropy upon Fc:Fc interaction by release of water molecules. With reference to Table 1, "Exemplary substitutions" may be selected based on size and physicochemical properties engaging in or promoting intermolecular Fc:Fc interactions or intramolecular interactions (allosteric mutations). "Preferred substitutions" may be selected based on size and and physicochemical properties optimal for engaging in or stimulating intermolecular Fc: Fc interactions or intramolecular interactions (allosteric mutations).

"Exemplary substitutions" of amino acids listed in Table 1, include exchanging an E residue for an R residue, and exchanging an H residue for an R residue. Each "Exemplary substitution" of amino acids in each specific amino acid residue listed in Table 1 is a separate and specific non-limiting embodiment according to the invention. Further, each "Preferred substitution" in each specific amino acid residue listed in Table 1 is a separate and specific non-limiting embodiment according to the invention.

In another aspect the present invention relates to a variant of a parent polypeptide comprising an Fc-domain of an immunoglobulin and a binding region, wherein the variant comprises a mutation in at least two amino acid residues selected from the group of
  (a) an amino acid residue within the CH2-CH3 region providing allosteric mutations,
  (b) an amino acid residue within the hydrophobic knobs of the CH2-CH3 region,
  (c) an amino acid residue within the N-terminal CH3 helix,
  (d) an amino acid residue within the C-terminal CH3 beta-strand, with the proviso that in case of a mutation corresponding to S440 in the Fc-region of a human IgG1 heavy chain the mutation is S440Y or S440W, and
  (e) an amino acid residue corresponding to E345, E382 or Q386 in the Fc-region of a human IgG1 heavy chain, wherein the at least two amino acid mutations are different.

In one embodiment the parent polypeptide and thereby also the variant thereof, may be an antibody.

Thus the present invention also relates to a variant of a parent antibody comprising an antigen-binding region and a Fc-domain, wherein the variant comprises a mutation in at least two amino acid residues selected from the group of
  (a) an amino acid residue within the CH2-CH3 region providing allosteric mutations,
  (b) an amino acid residue within the hydrophobic knobs of the CH2-CH3 region,
  (c) an amino acid residue within the N-terminal CH3 helix,
  (d) an amino acid residue within the C-terminal CH3 beta-strand, with the proviso that in case of a mutation corresponding to S440 in the Fc-region of a human IgG1 heavy chain the mutation is S440Y or S440W, and
  (e) an amino acid residue corresponding to E345, E382 or Q386 in the Fc-region of a human IgG1 heavy chain, wherein the at least two amino acid mutations are different.

Thus, a variant of the embodiment above may comprise a mutation in at least two, such as two, three, four, five, or more amino acids in Table 1.

In any embodiments where such a mutation in at least two amino acids is comprised in the variant, it may be present in each of the heavy chains of the variant, or one of the two may be comprised in one of the heavy chains and the other may be comprised in the other heavy chain, respectively, or vice versa.

In one embodiment, the variant comprises a mutation in at least two amino acid residues selected from those corresponding to E345, E430, S440, Q386, P247, I253, S254, Q311, D/E356, T359, E382, Y436, and K447 in the Fc-region of a human IgG1 heavy chain, with the proviso that the mutation in S440 is S440Y or S440W. Alternatively, the variant further comprises a mutation in at least one residue selected from the group consisting of H310, G385, H433, N434, Q438, and K439.

In one embodiment, the variant comprises a mutation in at least two amino acid residues selected from those corresponding to E345X, E430X, S440W/Y, Q386K, P247G, I253V, S254L, Q311L/W, D/E356R, E382V, and Y436I in the Fc region of a human IgG1 heavy chain, wherein X is any amino acid, such as a natural occurring amino acid.

For example, the antibody variant may comprise a mutation in at least one of E345, E430, S440, and Q386, alternatively E382 and H433, such as two or all of E345, E430, S440, and Q386, alternatively E382 and H433, optionally further comprising a mutation in one or more other amino acids listed in Table 1. Thus, in a further embodiment, the variant comprises a mutation in at least two amino acid residues selected from the group of corresponding to those of E345X, E430X, S440W/Y, and Q386K in the Fc-region of a human IgG1 heavy chain, wherein X is any amino acid, such as a natural occurring amino acid.

Exemplary combinations of a mutation in at least two amino acid residues are E345X/E430X, E345X/S440Y or W, E345X/Q386K, E430X/S440Y or W, and E430X/Q386K.

In one embodiment, the mutation in at least two amino acid residues is a deletion, insertion or substitution. Such a substitution of amino acids may be with any naturally occurring or artificially amino acids.

In a particular embodiment, the mutation in at least two amino acid residues may be an amino acid substitution corresponding to any of the group consisting of P247G, I253V, S254L, Q311L, Q311W, E345A, E345C, E345D, E345F, E345G, E345H, E345I, E345K, E345L, E345M, E345N, E345P, E345Q, E345R, E345S, E345I, E345V, E345W, E345Y, D/E356G, D/E356R, I359R, E382L, E382V, Q386K, E430A, E430C, E430D, E430F, E430G, E430H, E430I, E430K E430L, E430M, E430N, E430P, E430Q, E430R, E430S, E430T, E430V, E430W, E430Y, Y436I, S440Y and S440W.

In a preferred embodiment, the variant comprises a mutation in at least two amino acid residues are amino acid substitutions selected from those corresponding to E345R, Q, N, K, A, C, D, F, G, H, I, L, M, P, S, T, V, W, Y; E430T, S, G, A, C, D, F, H, I, L, K, M, N, P, Q, R, V, W, Y; S440W, Y; and Q386K, in the Fc region of a human IgG1 heavy chain.

Alternatively the further mutation is selected from those corresponding to I253E, N, Q, S, T; H310N, Q, W, Y; Q311E, R; E382D, H, K, R, N, Q, S, T, W, Y; G385E, H, K, N, Q, R, S, T, W, Y; H433R; N434D, E, H, K, Q, R, S, T, W, Y; Y436, A, E, F, H, I, K, L, M, N, Q, R, S, T, V; Q438A, E, G, H, K, N, Q, R, S, T, W, Y; K439D, H, Q, R, W, Y; and S440D, E, H, F, N, Q In a preferred embodiment, the mutation in at least two amino acid residues are is amino acid substitutions selected from those corresponding to E345Ft/Q/N/K, E430T/S/G, S440Y/W, and Q386K in the Fc-region of a human IgG1 heavy chain. Alternatively the further mutation is selected from those corresponding to I253N, Q; H310Q; Q311E, R; E382D, Q, K, R; G385D, E, K, R; H433R; N434H, K, Q, R; Y436N, Q, S, T; Q438N, S, T; K439Q; and S440D, E, Q.

Exemplary specific combinations of a mutation in at least two amino acid residues are E345R/E430T, E345R/S440Y, E345R/S440W, E345R/Q386K, E345R/E430G, E345Q/E430T, E345Q/S440Y, E345Q/S440W, E430T/S440Y, E430T/S440W, E430T/Q386K, and S440Y/Q386K.

In one specific embodiment, the mutation is not in an amino acid residue corresponding to I253, N434, or Q311. In one additional or alternative embodiment, the mutation is not in H433, or the amino acid substitution is not H433A.

In one embodiment, the present invention relates to a variant comprising a mutation in at least three amino acid residues selected from the group of
  (a) an amino acid residue within the CH2-CH3 region providing allosteric mutations,
  (b) an amino acid residue within the hydrophobic knobs of the CH2-CH3 region,
  (c) an amino acid residue within the N-terminal CH3 helix,
  (d) an amino acid residue within the C-terminal CH3 beta-strand, with the proviso that it does not comprise a mutation corresponding to S440 in the Fc-region of a human IgG1 heavy chain, and
  (e) an amino acid residue corresponding to E345, E382 or Q386 in the Fc-region of a human IgG1 heavy chain. wherein the at least three amino acid mutations are different.

In one particular embodiment, the variant comprises a mutation in the amino acid residues, which are amino acid substitutions corresponding to E345R, Q396K and E430G, which may be in either one or both the heavy chains of the variant.

The mutation in the at least three amino acid residues may be individually selected from the substitutions listed in Table 1. Non-limiting examples of variants comprising at least three mutations are; E345R/E430G/S440Y, E345R/E430G/S440W, E345K/E430G/S440Y, E345K/E430G/S440W, E345Q/E430G/S440Y, E345Q/E430G/S440W, E345N/

E430G/S440Y, E345N/E430G/S440W, E345R/E430T/S440Y, E345R/E430T/S440W, E345K/E430T/S440Y, E345K/E430T/S440W, E345Q/E430T/S440Y, E345Q/E430T/S440W, E345N/E430T/S440Y, E345N/E430T/S440W, E345R/E430S/S440Y, E345R/E430S/S440W, E345K/E430S/S440Y, E345K/E430S/S440W, E345Q/E430S/S440Y, E345Q/E430S/S440W, E345N/E430S/S440Y, E345N/E430S/S440W, E345R/E430F/S440Y, E345R/E430F/S440W, E345K/E430F/S440Y, E345K/E430F/S440W, E345Q/E430F/S440Y, E345Q/E430F/S440W, E345N/E430F/S440Y, and E345N/E430F/S440W.

Apart from mutations in one or more amino acids in Tables 1 or 2A and B, the IgG heavy chain may comprise additional mutations known in the art, e.g., mutations that further improve effector functions. Such additional mutations include known mutations enhancing CDC, Fc-gamma receptor binding or FcRn-binding and/or improving Fc-gamma receptor-mediated effector functions.

In one embodiment, a variant according to the invention further comprises a known CDC enhancing modification e.g., an exchange of segments between IgG isotypes to generate chimeric IgG molecules (Natsume et al., 2008 Cancer Res 68(10), 3863-72); one or more amino acid substitutions in the hinge region (Dall'Acqua et al., 2006 J Immunol 177, 1129-1138), and/or one or more amino acid substitutions in or near the C1q-binding site in the CH2 domain, centered around residues D270, K322, P329, and P331 (Idusogie et al., 2001 J Immunol 166, 2571-2575; Michaelsen et al., 2009 Scand J Immunol 70, 553-564 and WO 99/51642). For example, in one embodiment, a variant according to the invention further comprises a combination of any of the amino acid substitutions S267E, H268F, S324T, S239D, G236A and I332E, providing enhanced effector function via CDC or ADCC (Moore et al., 2010 mAbs 2(2), 181-189)). Other Fc mutations affecting binding to Fc-receptors (described in WO 2006/105062, WO 00/42072, U.S. Pat. Nos. 6,737,056 and 7,083,784) or physical properties of the antibodies (described in WO 2007/005612 A1) can also be used in the variants of the invention.

In one embodiment, a variant according to the invention further comprises modifications enhancing Fc-gamma receptor binding and/or Fc-gamma receptor-mediated effector function. Such modifications include (i) reducing the amount of fucose in the CH2 attached glycosylation (glyco-engineering) (Umana P, et al., Nat Biotechnol 1999; 17: 176-80; Niwa R, et al., Clin Cancer Res 2004; 10: 6248-55)), and (ii) site-directed mutagenesis of amino acids in the hinge or CH2 regions of antibodies (protein-engineering) (Lazar G A, et al., Proc Natl Acad Sci USA 2006; 103: 4005-10).

In one embodiment, a variant according to the invention is further engineered in the FcRn binding site, e.g., to extend the half-life (t1/2) of IgG antibodies. Such modifications include (i) N434A and T307A/E380A/N434A mutations (Petcova et al. Int Immunol. 2006 December; 18(12):1759); (ii) a substitution of one or more of Pro238, Thr256, Thr307, Gn311, Asp312, Glu380, Glu382, and Asn434 into an alanine residue improving FcRn binding (Shields R L, et al. J. Biol. Chem. 2001; 276:6591); and (iii) an amino acid substitution or combination of amino acid substitutions selected from M252Y/S254T/T256E, M252W, M252Y, M252Y/T256Q, M252F/T256D, V308T/L309P/Q311S, G385D/Q386P/N389S, G385R/Q386T/P387R/N389P, H433K/N434F/Y436H, N434F/Y436H, H433R/N434F/Y436H, M252Y/S254T/T256E-H433K/N434F/Y436H or M252Y/S254T/T256E-G385R/Q386T/P387R/N389P in IgG1, increasing the affinity for FcRn (Dall'Acqua et al., supra).

"Double-Mutant"

It is to be understood that all embodiments described herein with reference to a parent antibody, first parent antibody or second parent antibody are also to be understood as embodiments relating to a parent, first parent or second parent polypeptide comprising an Fc-domain of an immunoglobulin and a binding region.

As described above and further below, the present invention also relates to a "double-mutant" aspect, wherein two mutations individually each decrease an effector function but together restores the effector function to the level of the parent antibody. When used together the specificity of the variant is increased. Antibody variants according to the "double-mutant" aspect comprise two mutations, typically amino acid substitutions, in the specific amino acid residue interaction pair K439 and S440.

Thus in one aspect the present invention relates to a variant of a parent polypeptide comprising an Fc-domain of an immunoglobulin and a binding region, wherein the variant comprises a mutation (i) in at least one amino acid residue selected from those corresponding to K439 and S440 in the Fc-region of a human IgG1 heavy chain, with the proviso that the mutation in S440 is not S440Y or S440W, such as wherein the mutation in the position corresponding to K439 in the Fc-region of human IgG1 heavy chain is K439D/E, and/or the mutation in the position corresponding to S440 in the Fc-region of human IgG1 heavy chain is S440K/H/R;

(ii) in at least one amino acid residue corresponding to K447D/E or corresponding to K447K/R/H and 448P in the Fc region of a human IgG1 heavy chain; or (iii) in at least one amino acid residue corresponding to K447D/E or corresponding to K447K/R/H and 448K/R/H and 449P in the Fc region of a human IgG1 heavy chain.

In one embodiment the parent polypeptide, and thereby also the variant thereof, may be an antibody.

Thus, in one aspect, the present invention relates to a variant of a parent antibody comprising an antigen-binding region and Fc-domain of an immunoglobulin, wherein the variant comprises a mutation in at least one amino acid residue selected from those corresponding to K439 and S440 in the Fc-region of a human IgG1 heavy chain, with the proviso that the mutation in S440 is not S440Y or S440W, such as wherein the mutation in the position corresponding to K439 in the Fc-region of human IgG1 heavy chain is K439D/E, and/or the mutation in the position corresponding to S440 in the Fc-region of human IgG1 heavy chain is S440K/H/R. Table 2A and B shows "Exemplary" and "Preferred substitutions" for the "double-mutant" (Table A) and "mixed-mutant" (Table 2B) aspects.

TABLE 2A

Exemplary mutation sites and amino acid substitutions for "double-mutant" aspects

| Amino acid pair (IgG1, 2, 3, 4) | Exemplary substitutions | Preferred substitutions |
|---|---|---|
| K439/S440 | K439ED, alternatively R/S440KR, alternatively ED | K439E/S440K |
| K447/448/449 | K447ED/448KRH/449P | K447E/448K/449P |
| K447/448 | K447KRH/448ED | K447K/448E |

TABLE 2B

Exemplary mutation sites and amino acid substitutions for "mixed-mutants" aspect (Ab1 + Ab2)

| Amino acid pair (IgG1) | Exemplary substitutions | Preferred substitutions |
|---|---|---|
| K439 + S440 | K439DER + S440DEKR | K439E + S440K |
| K447 + K447/448 | K447DE + K447KRH/448P | K447E + K447/448P |
| K447 + | K447DE + | K447E + |
| K447/448/449 | K447KRH/448KRH/449P | K447/448K/449P |

In one embodiment the of the variant, wherein the mutation is on position(s) other than S440 and K447, and wherein the variant further comprises a mutation
(i) in at least one amino acid residue corresponding to K439 or S440 in the Fc-region of a human IgG1 heavy chain, with the proviso that the mutation in S440 is not S440W or S440Y;
(ii) in at least one amino acid residue corresponding to K447D/E or corresponding to K447K/R/H and 448P in the Fc region of a human IgG1 heavy chain; or
(iii) in at least one amino acid residue corresponding to K447D/E or corresponding to K447K/R/H and 448K/R/H and 449P in the Fc region of a human IgG1 heavy chain.

Accordingly, the invention provides a variant of an antibody comprising a first mutation in a residue in the CH2 and/or CH3 region of a human IgG1 heavy chain corresponding to K439, and a second mutation in a residue in the CH2 and/or CH3 region of a human IgG1 heavy chain corresponding to S440.

It is contemplated by the present invention that the variant may also comprise only one of the amino acid residue substitutions, such as either K439E or S440K, such as the variant comprises a mutation in K439, optionally with no mutation in S440.

In one embodiment, the invention relates to the variant, wherein the mutation in K439 is an amino acid substitution into an amino acid selected from E and D, such as K439E.

In another embodiment, the variant comprises a mutation in S440, optionally with no mutation in K439.

In one embodiment, the invention relates to the variant, wherein the mutation in S440 is an amino acid substitution into an amino acid selected from K, R and H, such as S440K.

In one embodiment, the variant comprises mutations in both K439 and S440.

In another embodiment, the mutation in K439 is selected from K439 to D, E or R, and the mutation in S440 is selected from S440 to D, E, K, H and R.

In another embodiment, the mutation in K439 is selected from K439D and K439E, and the mutation in S440 is selected from S440K, S440R, and S440H.

In another embodiment, the variant comprises K439E and S440K mutations.

Figure 4:
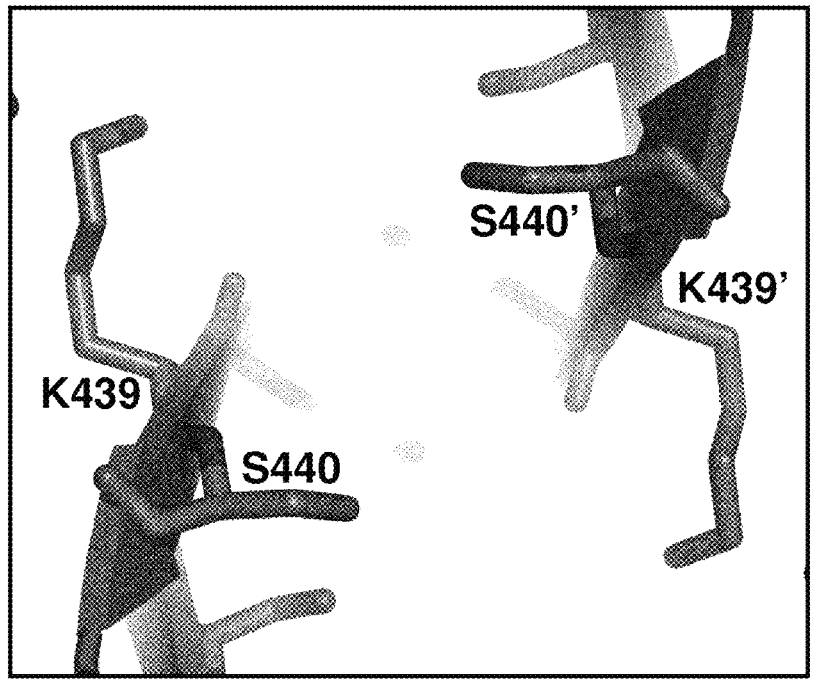
FIG. 4: Detailed view of the K439/5440 interactions between the Fc of adjacent molecules (Fc and Fc', respectively) in a multimeric (e.g., hexameric) arrangement, illustrating the interaction between wild-type, unmodified Fc and Fc' molecules.
Figure 5:
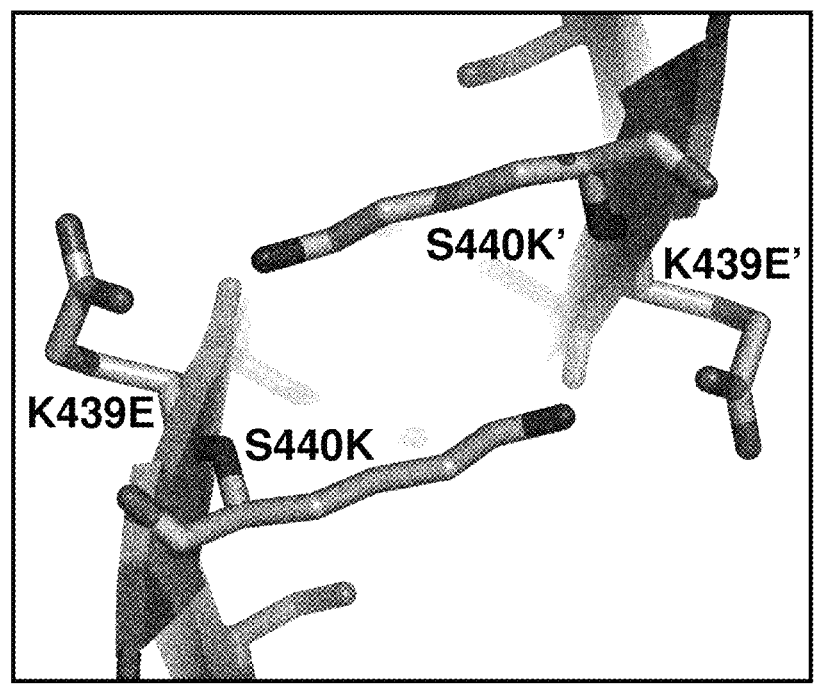
FIG. 5: Detailed view of the K439/5440 interactions between the Fc of adjacent molecules (Fc and Fc', respectively) in a multimeric (e.g., hexameric) arrangement illustrating the interaction between variant Fc and Fc' molecules comprising K439E and S440K mutations.
Figure 6:
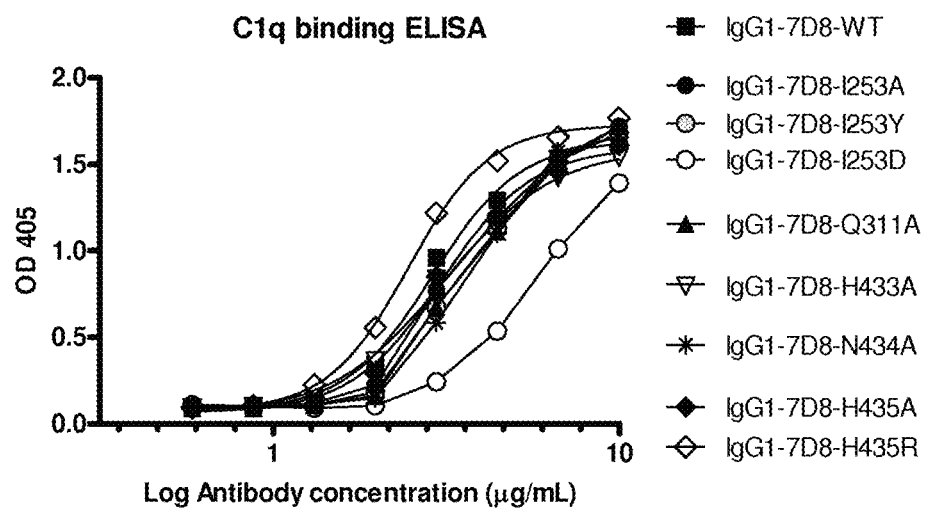
FIG. 6: C1q binding ELISA with 7D8 Fc:Fc mutants. Concentration series of the indicated antibodies were coated to the wells of a microtiter plate and incubated with a fixed concentration C1q. The efficiency to bind C1q was comparable to wild type 7D8 for all coated mutants, except I253D. A representative of at least 3 experiments is shown.

As described in the Examples 4-6, antibody variants comprising only one of the K439E and S440K mutations had a drastically increased $K_D$ for C1q, reflecting a decreased complement activation and/or CDC capability. Surprisingly, it was found that antibody variants of HuMAb 7D8 or 005 comprising both mutations had a restored or increased C1q-binding or CDC. Without being bound by any specific theory, the underlying mechanism could perhaps be explained by the respective mutations sterically compensating for each other, as illustrated in FIGS. 4 and 5.

Any "double-mutant" as described herein may also be used in combination with a mutation which by itself is capable of increasing an effector function. Thus, the "double-mutant" aspect may be combined with the "single-mutant" aspect, e.g. the variant may further comprise a mutation in any of the amino acid positions listed in Table 1 or any other embodiments described for the "single-mutant" aspect above. Thus, in one embodiment, the mutation is on position(s) other than S440, and wherein the variant further comprises a mutation in at least one amino acid residue corresponding to K439 or S440 in the Fc-region of a human IgG1 heavy chain, with the proviso that the mutation in S440 is not S440W or S440Y.

In one aspect the present invention relates to a variant of a parent polypeptide comprising an Fc-domain of an immunoglobulin and a binding region, wherein the variant comprises a mutation in at least one amino acid residues selected from the group of
 (a) an amino acid residue within the CH2-CH3 region providing allosteric mutations,
 (b) an amino acid residue within the hydrophobic knobs of the CH2-CH3 region,
 (c) an amino acid residue within the N-terminal CH3 helix,
 (d) an amino acid residue within the C-terminal CH3 beta-strand, with the proviso that it does not comprise a mutation corresponding to S440 in the Fc-region of a human IgG1 heavy chain, and
 (e) an amino acid residue corresponding to E345, E382 or Q386 in the Fc-region of a human IgG1 heavy chain, and
wherein the variant comprises a further mutation
(i) in at least one amino acid residue corresponding to K439 or S440 in the Fc-region of a human IgG1 heavy chain, with the proviso that the mutation in S440 is not S440W or S440Y;
(ii) in at least one amino acid residue corresponding to K447D/E or corresponding to K447K/R/H and 448P in the Fc region of a human IgG1 heavy chain; or
(iii) in at least one amino acid residue corresponding to K447D/E or corresponding to K447K/R/H and 448K/R/H and 449P in the Fc region of a human IgG1 heavy chain.

In one embodiment the parent polypeptide, and thereby the variant thereof, may be an antibody.

Thus in one aspect, the present invention relates to a variant of a parent antibody comprising an antigen-binding region and a Fc-domain of an immunoglobulin, wherein the variant comprises a mutation in at least one amino acid residues selected from the group of
 (a) an amino acid residue within the CH2-CH3 region providing allosteric mutations,
 (b) an amino acid residue within the hydrophobic knobs of the CH2-CH3 region,
 (c) an amino acid residue within the N-terminal CH3 helix,
 (d) an amino acid residue within the C-terminal CH3 beta-strand, with the proviso that it does not comprise a mutation corresponding to S440 in the Fc-region of a human IgG1 heavy chain, and
 (e) an amino acid residue corresponding to E345, E382 or Q386 in the Fc-region of a human IgG1 heavy chain, and
wherein the variant comprises a further mutation
(i) in at least one amino acid residue corresponding to K439 or S440 in the Fc-region of a human IgG1 heavy chain, with the proviso that the mutation in S440 is not S440W or S440Y,
(ii) in at least one amino acid residue corresponding to K447D/E or corresponding to K447K/R/H and 448P in the Fc region of a human IgG1 heavy chain; or (iii) in at least one amino acid residue corresponding to K447D/E or corresponding to K447K/R/H and 448K/R/H and 449P in the Fc region of a human IgG1 heavy chain.

In one embodiment, the variant comprises a mutation in at least an amino acid residue selected from those corresponding to E345, E430, S440, Q386, P247, I253, S254, Q311, D/E356, T359, E382, Y436, and K447 in the Fc-region of a human IgG1 heavy chain, with the proviso that the mutation in S440 is S440Y or S440W, and the variant comprises a further mutation in at least one amino acid residue corresponding to K439 or S440 in the Fc-region of a human IgG1 heavy chain, with the proviso that the mutation in S440 is not S440W or S440Y.

In a further embodiment, the variant comprises a mutation in at least one amino acid residue is an amino acid substitution selected from those corresponding to E345X, E430X, S440W/Y, Q386K, in the Fc region of a human IgG1 heavy chain, wherein X is any amino acid, such as a natural occurring amino acid, and the variant comprises a further mutation in at least one amino acid residue corresponding to K439 or S440 in the Fc-region of a human IgG1 heavy chain, with the proviso that the mutation in S440 is not S440W or S440Y.

In one embodiment, the variant comprises an amino acid mutation in both of the positions corresponding to K439 and S440 in the Fc-region of an IgG1 heavy chain, with the proviso that the mutation in S440 is not S440Y or S440W.

In a further embodiment, the mutation in the position corresponding to K439 in the Fc-region of human IgG1 heavy chain is K439D/E, and/or the mutation in the position corresponding to S440 in the Fc-region of human IgG1 heavy chain is S440K/H/R.

In a further embodiment, the first mutation is in an amino acid residues selected from those corresponding to E345, E430, Q386, and S440 in the Fc-region of a human IgG1 heavy chain, with the proviso that the mutation in S440 is S440Y or S440W; and the second and third mutation is an amino acid substitution in position K439E or S440K.

In one embodiment, the first mutation is a deletion, insertion or substitution. Such a substitution may be any naturally occurring or non-naturally amino acid.

In a further embodiment, the first mutation is selected from the group of E345R, Q, N, K, A, F, G, H, I, L, M, P, S, T, V, W, Y, C, D; E430T, S, G, A, F, H, L, P, R, V, C, D, I, K, M, N, Q, W, Y; and S440W, Y, D; and the second and third mutation is an amino acid substitution in position K439E or S440K.

In a preferred embodiment, the one mutation is selected from the group of E345R, Q, N, K, Y; E430T, S, G, F, H; S440W, Y; and Q386K.

Another example, in one embodiment of the present invention, the variant comprises E345R, K439E and S440K mutations, thus providing for both increased and more specific mediation of a CDC-response.

In one embodiment, the variant comprises a mutation in at least two amino acid residues selected from those corresponding to E345, E430, S440, Q386, P247, I253, S254, Q311, D/E356, T359, E382, Y436, and K447 in the Fc-region of a human IgG1 heavy chain, with the proviso that the mutation in S440 is S440Y or S440W, and the variant comprises a further mutation in at least one amino acid residue corresponding to K439 or S440 in the Fc-region of a human IgG1 heavy chain, with the proviso that the mutation in S440 is not S440W or S440Y.

In a further embodiment, the variant comprises a mutation in at least two amino acid residues is an amino acid substitution selected from those corresponding to E345X, E430X, S440W/Y, Q386K, in the Fc region of a human IgG1 heavy chain, wherein X is any amino acid, such as a natural occurring amino acid, and the variant comprises a further mutation in at least one amino acid residue corresponding to K439 or S440 in the Fc-region of a human IgG1 heavy chain, with the proviso that the mutation in S440 is not S440W or S440Y.

In one embodiment, the variant comprises an amino acid mutation in both of the positions corresponding to K439 and S440 in the Fc-region of an IgG1 heavy chain, with the proviso that the mutation in S440 is not S440Y or S440W.

In a further embodiment, the mutation in the position corresponding to K439 in the Fc-region of human IgG1 heavy chain is K439D/E, and/or the mutation in the position corresponding to S440 in the Fc-region of human IgG1 heavy chain is S440K/H/R.

In a further embodiment, the first and second mutation is in an amino acid residues selected from those corresponding to E345, E430, Q386, and S440 in the Fc-region of a human IgG1 heavy chain, with the proviso that the mutation in S440 is S440Y or S440W; and the third and fourth mutation is an amino acid substitution in position K439E or S440K.

In another embodiment, the variant comprising a mutation in both positions K439 and S440 as described herein has an increase in an Fc-mediated effector function selected from C1q-binding, complement activation, complement dependent cytotoxicity (CDC), antibody-dependent cell-mediated cytotoxity (ADCC), FcRn-binding, Fc-receptor binding including Fc-gamma receptor-binding, Protein A-binding, Protein G-binding, antibody-dependent cellular phagocytosis (ADCP), complement-dependent cellular cytotoxicity (CDCC), complement-enhanced cytotoxicity, opsonisation, Fc-containing polypeptide internalization, target downmodulation, ADC uptake, induction of apoptosis, cell death, cell cycle arrest, and any combination thereof, as compared to parent antibody or an antibody variant comprising a mutation in only one of K439 and S440.

The invention also provides for the use of the K439E and S440K mutations in an antibody to restore one or more of (i) C1q-binding avidity, (ii) complement activation mediated by the antibody, (iii) CDC mediated by the antibody, (iv) oligomer formation, (v) oligomer stability, or a combination of any of (i) to (v), as compared to parent antibody, which may, e.g., be a wild-type antibody or an antibody variant comprising only one of the K439E or S440K mutations. In one embodiment of (iv) or (v), the oligomer is a hexamer.

In one embodiment, the variant is selected from a monospecific antibody, bispecific antibody or multispecific antibody.

Mixed Mutants

It is to be understood that all embodiments described herein with reference to a parent antibody, first parent antibody or second parent antibody are also to be understood as embodiments relating to a parent, first parent or second parent polypeptide comprising an Fc-domain of an immunoglobulin and a binding region.

As described above, the inventors of the present invention have also found that there are mutations which by itself decreases an effector function but when used together the effector function is restored, e.g. the mutations in positions K439 and S440 of in the Fc-region of a human IgG1 heavy chain. This concept may also be used to ensure pairing of two different antibodies, thus, by introducing K439 in one antibody and S440 in the other. Thus, antibody variants according to the "mixed-mutant" aspect comprise a mutation, but one that typically leads to a reduced or much reduced Fc:Fc interaction between identical Fc-molecules.

However, as the "mixed-mutant" antibody variants of the invention are capable of pairing with each other; providing a restored or even increased C1q-binding, complement activation, CDC, oligomer formation, and/or oligomer stability for the specific antibody variant pair, as compared to, e.g., each variant alone or a mix of the parent antibody or parent antibodies. In one embodiment of the invention, the oligomer is a hexamer. In one embodiment, the antibody variant pair also or alternatively has a retained or improved other effector function, such as C1q-binding, complement activation, complement dependent cytotoxicity (CDC), antibody-dependent cell-mediated cytotoxity (ADCC), FcRn-binding, Fc-receptor binding including Fc-gamma receptor-binding, Protein A-binding, Protein G-binding, antibody-dependent cellular phagocytosis (ADCP), complement-dependent cellular cytotoxicity (CDCC), complement-enhanced cytotoxicity, opsonisation, Fc-containing polypeptide internalization, target downmodulation, ADC uptake, induction of apoptosis, cell death, cell cycle arrest, and any combination thereof. This aspect of the invention provides for a number of applications where not only the strength but also the selectivity in the C1q-binding, complement activation, CDC or other effector function can be regulated.

Exemplary mutation sites for each antibody variant in a "mixed-mutant" pair are shown in Table 2. Specifically, the invention provides a variant of an antibody comprising an antigen-binding region and an Fc-domain of an immunoglobulin, which variant comprises a mutation in a residue in the Fc-region of a human IgG1 heavy chain corresponding to one of K439 and S440. In one embodiment, the mutation is in K439, and is an amino acid substitution into an amino acid selected from E or D, such as K439E. In one embodiment, the mutation is in S440, and is an amino acid substitution into an amino acid selected from K, R or H, such as S440K.

Thus in one embodiment the present invention also relates to a variant comprising a mutation in at least one amino acid residue selected from:
(a) an amino acid residue within the CH2-CH3 region providing allosteric mutations,
(b) an amino acid residue within the hydrophobic knobs of the CH2-CH3 region,
(c) an amino acid residue within the N-terminal CH3 helix,
(d) an amino acid residue within the C-terminal CH3 beta-strand, with the proviso that in case of a mutation corresponding to S440 in the Fc-region of a human IgG1 heavy chain the mutation is S440Y or S440W, and
(e) an amino acid residue corresponding to E345, E382 or Q386 in the Fc-region of a human IgG1 heavy chain; and in an amino acid residue corresponding to K439 in the Fc region of a human IgG1 heavy chain.

In another embodiment the present invention also relates to a variant comprising a mutation in at least one amino acid residue selected from:
(a) an amino acid residue within the CH2-CH3 region providing allosteric mutations,
(b) an amino acid residue within the hydrophobic knobs of the CH2-CH3 region,
(c) an amino acid residue within the N-terminal CH3 helix,
(d) an amino acid residue within the C-terminal CH3 beta-strand, with the proviso that in case of a mutation corresponding to S440 in the Fc-region of a human IgG1 heavy chain the mutation is S440Y or S440W, and
(e) an amino acid residue corresponding to E345, E382 or Q386 in the Fc-region of a human IgG1 heavy chain; and in an amino acid residue corresponding to S440 in the Fc region of a human IgG1 heavy chain.

In one embodiment, the two above described embodiments may be combined in the "mixed-mutant" pair aspect according to the present invention.

Each variant in a "mixed-mutant" pair may further comprise a mutation in an amino acid listed in Table 1.

In one embodiment of the present invention, the "mixed-mutant" pair comprises a first variant of a parent antibody and a second variant of a parent antibody, wherein the first variant comprises a first Fc-domain of an immunoglobulin and an antigen-binding region, wherein said first variant comprises (i) a first mutation in at least one amino acid residue other than a mutation in K439 selected from the group of
(a) an amino acid residue within the CH2-CH3 region providing allosteric mutations,
(b) an amino acid residue within the hydrophobic knobs of the CH2-CH3 region,
(c) an amino acid residue within the N-terminal CH3 helix,
(d) an amino acid residue within that C-terminal CH3 beta-strand, with the proviso that in case of a mutation corresponding to S440 in the Fc-region of a human IgG1 heavy chain the mutation is S440Y or S440W, and
(e) an amino acid residue corresponding to E345, E382 or Q386 in the Fc-region of a human IgG1 heavy chain, and
(ii) a second mutation in the position corresponding to K439 in the Fc-region of a human IgG1 heavy chain; and
wherein the second variant comprises a second Fc-domain of an immunoglobulin and an antigen-binding region, wherein said second variant comprises (i) a first mutation in at least one amino acid residue other than a mutation in S440 selected from the group of
(a) an amino acid residue within the CH2-CH3 region providing allosteric mutations,
(b) an amino acid residue within the hydrophobic knobs of the CH2-CH3 region,
(c) an amino acid residue within the N-terminal CH3 helix,
(d) an amino acid residue within that C-terminal CH3 beta-strand, and
(e) an amino acid residue corresponding to E345, E382 or Q386 in the Fc-region of a human IgG1 heavy chain, and (ii) a second mutation in the position corresponding to S440 in the Fc region of an IgG1 heavy chain, with the proviso that the mutation in S440 is not S440Y or S440W.

Other exemplary "mixed-mutant" pairs may further comprise, and is not limited to, any of the following pairs; a first variant comprising the mutation K447E and a second variant comprising the mutation K447/P448; a first variant comprising the mutation K447E and a second variant comprising the mutation K447/K448/P449.

In one embodiment, the mutation is a deletion, insertion or substitution. Such a substitution of amino acids may be with any naturally occurring or non-naturally amino acids. In one embodiment, the mutation is a deletion. In another embodiment, the mutation is an insertion. In another embodiment, the mutation is a substitution of an amino acid.

In a particular embodiment, the first variant and/or second variant comprises a mutation in at least one amino acid residue selected from those corresponding to E345, E430, S440, Q386, P247, I253, S254, Q311, D/E356, T359, E382, Y436, and K447 in the Fc-region of a human IgG1 heavy chain, with the proviso that the mutation in S440 is S440Y or S440W.

In a particular embodiment, the first variant and/or the second variant comprises a mutation in at least one amino acid residues may be an amino acid substitution corresponding to any of the group consisting of P247G, I253V, S254L, Q311L, Q311W, E345A, E345C, E345D, E345F, E345G, E345H, E345I, E345K, E345L, E345M, E345N, E345P, E345Q, E345R, E345S, E345I, E345V, E345W, E345Y, D/E356G, D/E356R, T359R, E382L, E382V, Q386K, E430A, E430C, E430D, E430F, E430G, E430H, E430I, E430K, E430L, E430M, E430N, E430P, E430Q, E430R, E430S, E430T, E430V, E430W, E430Y, Y436I, S440Y and S440W, and the first variant comprises a second mutation in the position corresponding to K439 in the Fc-region of a human IgG1 heavy chain; and the second variant comprises a second mutation in the position corresponding to S440 in the Fc-region of a human IgG1 heavy chain.

For example, in one embodiment, one variant in a "mixed-mutant" pair comprises E345R and K439E mutations, while the other variant comprises E345R and S440K mutations, thus providing for both increased and more specific C1q-binding avidity, complement activation, CDC, oligomer formation, oligomer stability, and/or other effector-related function such as FcRn-binding, ADCC, Fc-gamma receptor-binding, Protein A-binding, Protein G-binding, ADCP, CDCC, complement-enhanced cytotoxicity, antibody mediated phagocytosis, internalization, apoptosis, binding to complement receptor of an opsonized antibody, and/or combinations thereof.

The "mixed-mutant" aspect, may also comprise two variants comprising each more than one mutations listed in Table 1, in the Fc-region of a human IgG1 heavy chain, such as a first variant comprising the mutations S440K/K447E, and a second variant comprising the mutation K439E/K447/P448; such as a first variant comprising the mutations K439E/K447E, and a second variant comprising the mutation S440K/K447/P448.

The variants in a "mixed-mutant" pair as described herein may derive from the same or from different parent antibodies. Further, the "mixed-mutant" aspect can also be employed in bispecific or asymmetrical antibodies. Further, the first, second and third antibody may bind different epitopes, on the same or different targets.

Further, the "mixed-mutant" aspect can provide for a CDC or other effector response that is more specifically directed to tumor cells expressing two specific tumor antigens, by utilizing a first antibody against the first antigen with a K439E mutation and a second antibody against the second antigen with a S440K or S440R mutation. By utilizing the "mixed-mutant" aspect comprising three variants, optionally being bispecific antibodies, may provide for a CDC or other effector response that is more specifically directed to tumor cells expressing at least two, such as two, three, four, five or six, specific tumor antigens.

In one embodiment of any of the "single-mutant", "double-mutant" and "mixed-mutant" aspects, the variant is selected from a monospecific antibody, bispecific antibody or multispecific antibody.

In any embodiment of the "mixed-mutant" aspect, the first, second and/or third variant may comprise the same or different mutation of any of the amino acid substitutions listed in Table 1.

Multispecific Antibodies

It is to be understood that all embodiments described herein with reference to a parent antibody, first parent antibody or second parent antibody are also to be understood as embodiments relating to a parent, first parent or second parent polypeptide comprising an Fc-domain of an immunoglobulin and a binding region.

It is to be understood that any embodiment of the "single-mutant", "double-mutant" and "mixed-mutant" aspects described herein may be used in the multispecific antibody aspect described below.

In one main aspect, the invention relates to a variant, which is a bispecific antibody comprising a first polypeptide comprising a first CH2-CH3 region of an immunoglobulin and a first antigen-binding region, and a second polypeptide comprising a second CH2-CH3 region of an immunoglobulin and a second antigen-binding region, wherein the first and second antigen-binding regions bind different epitopes on the same antigen or on different antigens, and wherein the first and second CH2-CH3 region each comprises a first mutation in at least one amino acid residue selected from those corresponding to E345, E430, S440, Q386, P247, I253, S254, Q311, D/E356, T359, E382, Y436, and K447 in the Fc-region of a human IgG1 heavy chain, with the proviso that the mutation in S440 is S440Y or S440W.

In one embodiment, the mutation is a deletion, insertion or substitution. Such a substitution of amino acids may be with any naturally occurring or non-naturally acids.

The bispecific antibody of the present invention is not limited to a particular format and it may be any of those described above and herein.

In one embodiment of the present invention, the first and second polypeptide comprises one first mutation in an amino acid residue selected from those corresponding to E345, E430, S440, Q386, P247, I253, S254, Q311, D/E356, T359, E382, Y436, and K447 in the Fc-region of a human IgG1 heavy chain.

In a particular embodiment, the mutation in at least one amino acid residues may be an amino acid substitution corresponding to any of the group consisting of P247G, I253V, S254L, Q311L, Q311W, E345A, E345C, E345D, E345F, E345G, E345H, E345I, E345K, E345L, E345M, E345N, E345P, E345Q, E345R, E345S, E345T, E345V, E345W, E345Y, D/E356G, D/E356R, T359R, E382L, E382V, Q386K, E430A, E430C, E430D, E430F, E430G, E430H, E430I, E430L, E430M, E430N, E430P, E430Q, E430R, E430S, E430T, E430V, E430W, E430Y, Y436I, S440Y and S440W.

In a particular embodiment, the bispecific antibody has the format described in WO 2011/131746. Thus, in one embodiment, the variant which is a bispecific antibody, wherein the first polypeptide comprises a further mutation in an amino acid residue selected from those corresponding to K409, T366, L368, K370, D399, F405, and Y407 in the Fc-region of a human IgG1 heavy chain; and the second polypeptide comprises a further mutation in an amino acid residue selected from those corresponding to F405, T366, L368, K370, D399, Y407 and K409 in the Fc-region of a human IgG1 heavy chain, and wherein the said further mutation in the first polypeptide is different from the said further mutation in the second polypeptide.

In a particular embodiment, the bispecific antibody has a first polypeptide comprises the further mutation in the amino acid residue corresponding to K409 in the Fc-region of a human IgG1 heavy chain, and the second polypeptide comprises the further mutation in the amino acid residue corresponding to F405 in the Fc-region of a human IgG1 heavy chain. Such bispecific antibodies according to the invention can be generated as described in Example 22. Furthermore, the effect on CDC killing by the generated heterodimeric proteins can be tested by using an assay as used in Example 23.

In a particular embodiment, the bispecific antibody comprising a first and a second polypeptide, wherein the first polypeptide comprises a mutation in the amino acid residue corresponding to K409 in the Fc-region of a human IgG1 heavy chain; the second polypeptide comprises a mutation in the amino acid residue corresponding to F405 in the Fc-region of a human IgG1 heavy chain; and the first and/or second polypeptide comprises further a mutation in the amino acid residue corresponding to the amino acid substitution E345R in the Fc-region of a human IgG1 heavy chain.

In a particular embodiment, the bispecific antibody comprising a first and a second polypeptide, wherein the first polypeptide comprises a mutation in the amino acid residue corresponding to K409 in the Fc-region of a human IgG1 heavy chain; the second polypeptide comprises a mutation in the amino acid residue corresponding to F405 in the Fc-region of a human IgG1 heavy chain; the first and/or the second polypeptide comprises each further a mutation in the amino acid residues corresponding to the amino acid substitution E345R and Q386K in the Fc-region of a human IgG1 heavy chain. Said further mutations may be both in the first and second polypeptide, or E345R may be in the first polypeptide and Q386K in the second polypeptide; or vice versa.

In a particular embodiment, the bispecific antibody comprising a first and a second polypeptide, wherein the first polypeptide comprises a mutation in the amino acid residue corresponding to K409 in the Fc-region of a human IgG1 heavy chain; the second polypeptide comprises a mutation in the amino acid residue corresponding to F405 in the Fc-region of a human IgG1 heavy chain; and the first and/or second polypeptide comprises each further a mutation in the amino acid residues corresponding to the amino acid substitution E345R, Q386K, and E430G in the Fc-region of a human IgG1 heavy chain. Said mutations may be in both the first and second polypeptide, or the first polypeptide may comprise the mutations E345R and E430G, and the second polypeptide may comprise the mutation Q386K; or vice versa.

The bispecific antibody may, for example, comprise an antigen-binding region of a CD20 antibody and an antigen-binding region of a CD38 antibody, and an amino acid substitution in one or more amino acids listed in Tables 1 and/or 2. Exemplary CD20-binding regions include those of ofatumumab (2F2), 7D8 and 11B8, described in WO2004/035607, which is hereby incorporated by reference in its entirety, and rituximab (WO 2005/103081). Exemplary CD38-binding regions include those of 003 and daratumumab (005), described in WO2006/099875, which is hereby incorporated by reference in its entirety.

In one embodiment, the bispecific antibody binds different epitopes on the same or different target.

In another embodiment, the first mutation in the first and second polypeptide may be the same or different.

In one embodiment of the "single-mutant", "double-mutant", "mixed-mutant" and multispecific antibody aspect, the variant is a human IgG1, IgG2, IgG3, IgG4, IgA1, IgA2, IgD or IgE antibody, optionally a human full-length antibody, such as a human full-length IgG1 antibody.

In any "single-mutant", "double-mutant", "mixed-mutant" aspect, and the multispecific antibody aspects the C1q-binding of the antibody is determined according to the assay described in Example 4, the CDC is determined according to the assay described in Example 5, 6 or 10, the mutation is not in an amino acid residue directly involved in C1q-binding, optionally as determined by comparing C1q-binding in an ELISA assay according to Example 3 with C1q-binding in a cell-based assay according to Example 4, and the ADCC is determined according to the assay described in Example 12.

Additionally, the invention provides for a preparation of a variant of any "single-mutant", "double-mutant", "mixed-mutant" and multispecific antibody aspect or embodiment described above. The invention also provides for a composition comprising a variant of any "double-mutant" aspect and embodiment described above, e.g., a pharmaceutical compositions. The invention also provides for the use of any such variant, preparation, or composition as a medicament.

The above "single-mutant", "double-mutant", "mixed mutant" and multispecific antibody aspects of the invention are particularly applicable to human antibody molecules having an IgG1 heavy chain comprising the relevant segment, P247 to K447, corresponding to the underlined residues 130 to 330 of the human IgG1 heavy chain constant region (UniProt accession No. P01857; SEQ ID NO:1):

```
  1 astkgpsvfp lapssktstsg gtaalgclvk dyfpepvtvs wnsgaltsgv
 51 htfpavlqss glyslssvvt vpssslgtqt yicnvnhkps ntkvdkkvep
101 kscdkthtcp pcpapellgg psvflfppkp kdtlmisrtp evtcvvvdvs
151 hedpevkfnw yvdgvevhna ktkpreeqyn styrvvsvlt vlhqdwlngk
201 eykckvsnka lpapiektis kakgqprepq vytlppsrde ltknqvsltc
251 lvkgfypsdi avewesngqp ennykttppv ldsdgsffly skltvdksrw
301 qqgnvfscsv mhealhnhyt qkslslspgk
```

The present invention can also be applied to antibody molecules having a human IgG2 heavy chain portion. Amino acid residues P247 to K447 of the IgG1 heavy chain correspond to the underlined residues 126 to 326 of the IgG2 heavy chain constant region (accession number P01859; SEQ ID NO:2)

```
  1 astkgpsvfp lapcsrstse staalgclvk dyfpepvtvs wnsgaltsgv 51 htfpavlqss glyslssvvt vpssnfgtqt ytcnvdhkps ntkvdktver 101 kccvecppcp appvagpsvf lfppkpkdtl misrtpevtc vvvdvshedp 151 evqfnwyvdg vevhnaktkp reeqfnstfr vvsvltvvhq dwlngkeykc 201 kvsnkglpap iektisktk.g qprepqvytl ppsreemtkn qvsltclvkg 251 .fypsdiavew esngqpenny kttppmldsd gsfflysklt vdksrwqqgn 301 .vfscsvmhea lhnhytqksl slspgk
```

The present invention can also be applied to antibody molecules having a human IgG3 heavy chain portion. Amino acid residues P247 to K447 of the IgG1 heavy chain correspond to residues 177 to 377 of the IgG3 heavy chain constant region (UniProt accession No. P01860, SEQ ID NO:3), underlined in the following:

```
  1 astkgpsvfp lapcsrstsg gtaalgclvk dyfpepvtvs wnsgaltsgv 51 htfpavlqss glyslssvvt vpssslgtqt ytcnvnhkps ntkvdkrvel 101 ktplgdttht cprcpepksc dtpppcprcp epkscdtppp cprcpepksc 151 dtpppcprcp apellggpsv flfppkpkdt lmisrtpevt cvvvdvshed 201 pevqfkwyvd gvevhnaktk preeqynstf rvvsvltvlh qdwlngkeyk 251 ckvsnkalpa piektisktk gqprepqvyt lppsreemtk nqvsltclvk 301 gfypsdiave wessgqpenn ynttppmlds dgsfflyskl tvdksrwqqg 351 nifscsvmhe alhnrftqks lslspgk
```

The present invention can also be applied to antibody molecules having a human IgG4 heavy chain portion. Amino acid residues P247 to K447 of the IgG1 heavy chain correspond to the underlined residues 127 to 327 of the IgG4 heavy chain constant region (accession number P01859, SEQ ID NO:4)

```
  1 astkgpsvfp lapcsrstse staalgclvk dyfpepvtvs wnsgaltsgv 51 htfpavlqss glyslssvvt vpssslgtkt ytcnvdhkps ntkvdkrves 101 kygppcpscp apeflggpsv flfppkpkdt lmisrtpevt cvvvdvsqed 151 pevqfnwyvd gvevhnaktk preeqfnsty rvvsvltvlh qdwlngkeyk 201 ckvsnkglps siektiskak gqprepqvyt lppsqeemtk nqvsltclvk 251 gfypsdiave wesngqpenn ykttppvlds dgsfflysrl tvdksrwqeg 301 nvfscsvmhe alhnhytqks lslslgk
```

The present invention can also be applied to an antibody having a human IgG1m(f) allotype heavy chain portion. The amino acid sequence of the IgG1m(f) allotype (the CH3 sequence is underlined)—SEQ ID NO:5

```
  1 astkgpsvfp lapsskstsg gtaalgclvk dyfpepvtvs wnsgaltsgv 51 htfpavlqss glyslssvvt vpssslgtqt yicnvnhkps ntkvdkrvep 101 kscdkthtcp pcpapellgg psvflfppkp kdtlmisrtp evtcvvvdvs 151 hedpevkfnw yvdgvevhna ktkpreeqyn styrvvsvlt vlhqdwlngk 201 eykckvsnka lpapiektis kakgqprepq vytlppsree mtknqvsltc 251 lvkgfypsdi avewesngqp ennykttppv ldsdgsffly skltvdksrw 301 qqgnvfscsv mhealhnhyt qkslslspgk
```

An alignment of the respective segments of the IgG1, IgG2, IgG3, IgG4, and IgG1m(f) constant regions is shown in FIG. 2. Accordingly, any mutation in an amino acid described in Table 1 or Table 2A and B can be introduced at its equivalent position in IgG2, IgG3, IgG4, and/or IgG1m (f) as defined by the alignment to obtain a variant according to the invention.

In one embodiment, the invention provides a variant of a full-length IgG1, IgG2, IgG3, or IgG4 antibody, comprising one or more amino acid substitutions according to any aspect described above.

In any "single-mutant", "double-mutant", "mixed-mutant" aspects and multispecific antibody, the Fc-region of an IgG1 heavy chain may comprise the sequence of residues 130 to 330 of SEQ ID NO:1, residues 126 to 326 of SEQ ID NO:2, residues 177 to 377 of SEQ ID NO:3, or residues 127 to 327 of SEQ ID NO:4.

In one embodiment, a parent antibody comprises a sequence selected from SEQ ID No.: 1-5, such as SEQ ID No.:1, SEQ ID No.:2, SEQ ID No.:3, SEQ ID No.:4, or SEQ ID No.:5.

In one embodiment, the Fc-region of an IgG1 heavy chain comprises the sequence of residues 130 to 330 of SEQ ID NO:1.

The parent antibody may be any parent antibody as described herein. The parent antibody in this context is intended to be also first parent and second parent antibodies.

In one embodiment, the parent antibody is a human IgG1, IgG2, IgG3 or IgG4, IgA1, IgA2, IgD or IgE antibody.

In one embodiment the parent antibody is human full-length antibody, such as a human full-length IgG1 antibody.

In one embodiment, the parent antibody, first parent antibody and second parent antibody is a human IgG1 antibody, e.g. the IgG1m(za) or IgG1m(f) allotype, optionally comprising an Fc-region comprising SEQ ID NO:1 or 5.

In one embodiment, the parent antibody is a human IgG2 antibody, optionally comprising an Fc-region comprising SEQ ID NO:2.

In one embodiment, the parent antibody is a human IgG3 antibody, optionally comprising an Fc-region comprising SEQ ID NO:3.

In one embodiment, the parent antibody is a human IgG4 antibody, optionally comprising an Fc-region comprising SEQ ID NO:4.

In particular embodiments of any of the "single-mutant", "double-mutant", "mixed-mutant" and multispecific antibody aspects, the variant comprises an amino acid sequence which has a degree of identity to amino acids P247 to K447 of SEQ ID Nos: 1, 2, 3, 4, and 5 of at least 70%, 72%, 74%, 76%, 78%, 80%, 81%, 82%, 83%, 84%, 85%, 86%, 87%, 88%, 89%, 90%, 91%, 92%, 93%, 94%, 95%, 96%, 97%, 98%, or at least about 99%, except for the mutations introduced according to the present invention.

Thus, the variant may comprise a sequence according to SEQ ID No:1, SEQ ID No:2, SEQ ID No:3, SEQ ID No: 4, or SEQ ID No:5 except for any mutation defined herein.

In any of the above "single-mutant", "double-mutant", "mixed-mutant" and multispecific aspects according to the present invention may be understood to include the following embodiments.

In one embodiment, the first and/or second parent antibody is an antibody fragment, optionally selected from the group consisting of a monovalent antibody, a heavy-chain antibody, a strand-exchange engineered domain (SEED), a triomab, a dual variable domain immunoglobulin (DVD-Ig), a knob-into-holes antibody, a mini-antibody, a dual-affinity retargeting molecule (Fc-DART or Ig-DART); a LUZ-Y antibody, a Biclonic antibody, a Dual Targeting (DT)-Ig antibody, a Two-in-one Antibody, a cross-linked Mab, a mAb², a CovX-body, an IgG-like Bispecific antibody, a Ts2Ab, a BsAb, a HERCULES antibody, a TvAb, an ScFv/Fc Fusion antibody, a SCORPION, an scFv fragment fused to an Fc domain, and a dual scFv fragment fused to an Fc domain.

In a further embodiment, both the first and the second parent antibody bind an antigen expressed on the surface of a human tumor cell.

In a further embodiment, the antigens for the first and second parent antibody are separately selected from the group consisting of erbB1 (EGFR), erbB2 (HER2), erbB3, erbB4, MUC-1, CD4, CD19, CD20, CD38, CD138, CXCRS, c-Met, HERV-envelop protein, periostin, Bigh3, SPARC, BCR, CD79, CD37, EGFrvIII, L1-CAM, AXL, Tissue Factor (TF), CD74, EpCAM and MRP3.

In a further embodiment, the first and second parent antibodies are fully human.

In a further embodiment, the antigens for the first and second parent antibody are, in any order, selected from CD20 and CD38, optionally wherein the first and second parent antibodies are, in any order, selected from 7D8 and 005.

In a further embodiment, both the first antibody and the second antibody bind antigens expressed on the surface of a bacterial cell or a virion.

In another embodiment, the bacterial cell is selected from the group consisting of *S. aureus, S. epidermidis, S. pneumonia, Bacillus anthracis, Pseudomonas aeruginosa, Chlamydia trachomatis, E. coli, Salmonella, Shigella, Yersinia, S. typhimurium, Neisseria meningitides*, and *Mycobacterium tuberculosis*.

In a further embodiment, the first and second parent antibody binds the same antigen.

In another embodiment, the first and second parent antibodies are the same antibody.

In another embodiment, the parent antibody is selected from 7D8 and 005.

Compositions

It is to be understood that all embodiments described herein with reference to a parent antibody, first parent antibody or second parent antibody are also to be understood as embodiments relating to a parent, first parent or second parent polypeptide comprising an Fc-domain of an immunoglobulin and a binding region.

The invention also relates to compositions comprising variants and parent antibodies may be any variant and parent antibody as described herein. Specific aspects and embodiments will be described below. Furthermore, such variants may be obtained according to any method described herein.

In one aspect the present invention relates to a composition comprising a first variant of a parent polypeptide and a second variant of a parent polypeptide, wherein the first variant comprises a first Fc-domain of an immunoglobulin and a binding region, wherein the second variant comprises a second Fc-domain of an immunoglobulin and a binding region, and wherein
(i) said first variant comprises a mutation in the position corresponding to K439 in the Fc-region of a human IgG1 heavy chain, and said second variant comprises a mutation in the position corresponding to S440 in the Fc-region of a human IgG1 heavy chain, with the proviso that the mutation in S440 is not S440Y or S440W,
(ii) said first variant comprises a mutation in the position corresponding to K447D/E in the Fc region of a human IgG1 heavy chain; and said second variant comprises a mutation in the position corresponding to K447K/R/H and 448P in the Fc-region of a human IgG1 heavy chain, or
(iii) said first variant comprises a mutation in the position corresponding to K447D/E in the Fc region of a human IgG1 heavy chain; and said second variant comprises a mutation in the position corresponding to K447K/R/H, 448K/R/H and 449P in the Fc-region of a human IgG1 heavy chain.

In one embodiment the first one or both of the variant of a parent polypeptide and the second variant of a parent polypeptide may be an antibody.

Thus in one an aspect, the invention relates to a composition comprising a first variant of a parent antibody and a second variant of a parent antibody, wherein the first variant comprises a first Fc-domain of an immunoglobulin and an antigen-binding region, wherein the second variant comprises a second Fc-domain of an immunoglobulin and an antigen-binding region, and wherein
(i) said first variant comprises a mutation in the position corresponding to K439 in the Fc-region of a human IgG1 heavy chain, and said second variant comprises a mutation in the position corresponding to S440 in the Fc-region of a human IgG1 heavy chain, with the proviso that the mutation in S440 is not S440Y or S440W,
(ii) said first variant comprises a mutation in the position corresponding to K447D/E in the Fc region of a human IgG1 heavy chain; and said second variant comprises a mutation in the position corresponding to K447K/R/H and 448P in the Fc-region of a human IgG1 heavy chain, or
(iii) said first variant comprises a mutation in the position corresponding to K447D/E in the Fc region of a human IgG1 heavy chain; and said second variant comprises a mutation in the position corresponding to K447K/R/H, 448K/R/H and 449P in the Fc-region of a human IgG1 heavy chain.

In one embodiment the composition comprising a first variant of a parent antibody and a second variant of a parent antibody, wherein the first variant comprises a first Fc-domain of an immunoglobulin and an antigen-binding region, wherein the second variant comprises a second Fc-domain of an immunoglobulin and an antigen-binding region, and wherein said first variant comprises a mutation in the position corresponding to K439 in the Fc-region of a human IgG1 heavy chain, and wherein the second variant comprises a mutation in the position corresponding to S440, with the proviso that the mutation in S440 is not S440Y or S440W.

In one embodiment, the composition comprising the first variant of a parent antibody and the second variant of a parent antibody, wherein the first variant comprises a first Fc-domain of an immunoglobulin and an antigen-binding region, wherein said first variant comprises (i) a first mutation in at least one amino acid residue other than a mutation in K439 selected from the group of
  (a) an amino acid residue within the CH2-CH3 region providing allosteric mutations,
  (b) an amino acid residue within the hydrophobic knobs of the CH2-CH3 region,
  (c) an amino acid residue within the N-terminal CH3 helix,
  (d) an amino acid residue within the C-terminal CH3 beta-strand, with the proviso that in case of a mutation corresponding to S440 in the Fc-region of a human IgG1 heavy chain the mutation is S440Y or S440W, and
  (e) an amino acid residue corresponding to E345, E382 or Q386 in the Fc-region of a human IgG1 heavy chain, and
  (ii) a second mutation in the position corresponding to K439 in the Fc-region of a human IgG1 heavy chain; and
wherein the second variant comprises a second Fc-domain of an immunoglobulin and an antigen-binding region, wherein said second variant comprises (i) a first mutation in at least one amino acid residue other than a mutation in S440 selected from the group of
  (a) an amino acid residue within the CH2-CH3 region providing allosteric mutations,
  (b) an amino acid residue within the hydrophobic knobs of the CH2-CH3 region,
  (c) an amino acid residue within the N-terminal CH3 helix,
  (d) an amino acid residue within the C-terminal CH3 beta-strand, and
  (e) an amino acid residue corresponding to E345, E382 or Q386 in the Fc-region of a human IgG1 heavy chain, and
  (ii) a second mutation in the position corresponding to S440 in the Fc region of an IgG1 heavy chain, with the proviso that the mutation in S440 is not S440Y or S440W.

In another embodiment, the composition comprising the first variant of an antibody and the second variant of a parent antibody, wherein the first variant comprises (i) a first mutation in at least one amino acid residue other than a mutation in K439 selected from the group of
  (a) an amino acid residue within the CH2-CH3 region providing allosteric mutations,
  (b) an amino acid residue within the hydrophobic knobs of the CH2-CH3 region,
  (c) an amino acid residue within the N-terminal CH3 helix,
  (d) an amino acid residue within the C-terminal CH3 beta-strand, with the proviso that in case of a mutation corresponding to S440 in the Fc-region of a human IgG1 heavy chain the mutation is S440Y or S440W, and (e) an amino acid residue corresponding to E345, E382 or Q386 in the Fc-region of a human IgG1 heavy chain, and (ii) a second mutation in the position corresponding to K439 in the Fc-region of a human IgG1 heavy chain, and wherein the second variant comprises a mutation in the position corresponding to S440 in the Fc-region of a human IgG1 heavy chain, which is not is not S440Y or S440W.

In another embodiment, the composition comprising the first variant of a parent antibody and the second variant of a parent antibody,
wherein the first variant comprises a mutation in the position corresponding to K439 in the Fc-region of a human IgG1 heavy chain; and
wherein the second variant comprises a second Fc-domain of an immunoglobulin and an antigen-binding region, wherein said second variant comprises (i) a first mutation in at least one amino acid residue other than a mutation in S440 selected from the group of (a) an amino acid residue within the CH2-CH3 region providing allosteric mutations,
(b) an amino acid residue within the hydrophobic knobs of the CH2-CH3 region,
(c) an amino acid residue within the N-terminal CH3 helix,
(d) an amino acid residue within the C-terminal CH3 beta-strand, and
(e) an amino acid residue corresponding to E345, E382 or Q386 in the Fc-region of a human IgG1 heavy chain, and (ii) a second mutation in the position corresponding to S440 in the Fc region of an IgG1 heavy chain, with the proviso that the mutation in S440 is not S440Y or S440W.

In one embodiment, the mutation in the position corresponding to K439 in the Fc-region of human IgG1 heavy chain is K439D/E, and/or the mutation in the position corresponding to S440 in the Fc-region of human IgG1 heavy chain is S440K/H/R.

In another aspect the present invention relates to a composition comprising a first variant of an parent polypeptide comprising an Fc-domain of an immunoglobulin and a binding region and a second variant of a parent polypeptide comprising an Fc-domain of an immunoglobulin and a binding region, wherein
the first variant comprises a first Fc-domain of an immunoglobulin and a first antigen-binding region, wherein the first variant comprises a first mutation in at least an amino acid residue selected from the group of (a) an amino acid residue within the CH2-CH3 region providing allosteric mutations,
(b) an amino acid residue within the hydrophobic knobs of the CH2-CH3 region,
(c) an amino acid residue within the N-terminal CH3 helix,
(d) an amino acid residue within the C-terminal CH3 beta-strand, with the proviso that in case of a mutation corresponding to S440 in the Fc-region of a human IgG1 heavy chain the mutation is S440Y or S440W, and
(e) an amino acid residue corresponding to E345, E382 or Q386 in the Fc-region of a human IgG1 heavy chain, and wherein
the second variant does not comprise a mutation in an amino acid residue selected from the group of (a) an amino acid residue within the CH2-CH3 region providing allosteric mutations,
(b) an amino acid residue within the hydrophobic knobs of the CH2-CH3 region,
(c) an amino acid residue within the N-terminal CH3 helix,
(d) an amino acid residue within the C-terminal CH3 beta-strand, with the proviso that in case of a mutation corresponding to S440 in the Fc-region of a human IgG1 heavy chain the mutation is S440Y or S440W, and
(e) an amino acid residue corresponding to E345, E382 or Q386 in the Fc-region of a human IgG1 heavy chain.

In one embodiment the first and/or second parent polypeptide may be an antibody.

The present invention also relates to an embodiment of the composition, wherein the first variant comprises (i) a first mutation in at least one amino acid residue other than a mutation in K439 selected from the group of (a) an amino acid residue within the CH2-CH3 region providing allosteric mutations,
(b) an amino acid residue within the hydrophobic knobs of the CH2-CH3 region,
(c) an amino acid residue within the N-terminal CH3 helix,
(d) an amino acid residue within the C-terminal CH3 beta-strand, with the proviso that in case of a mutation corresponding to S440 in the Fc-region of a human IgG1 heavy chain the mutation is S440Y or S440W, and
(e) an amino acid residue corresponding to E345, E382 or Q386 in the Fc-region of a human IgG1 heavy chain, and (ii) a second mutation in the position corresponding to K439 in the Fc-region of a human IgG1 heavy chain, and wherein the second variant comprises a mutation in the position corresponding to S440 in the Fc-region of a human IgG1 heavy chain, which is not is not S440Y or S440W.

The present invention also relates to an embodiment of the composition, wherein the first variant comprises a mutation in the position corresponding to K439 in the Fc-region of a human IgG1 heavy chain; and
wherein the second variant comprises a second Fc-domain of an immunoglobulin and an antigen-binding region, wherein said second variant comprises (i) a first mutation in at least one amino acid residue other than a mutation in S440 selected from the group of (a) an amino acid residue within the CH2-CH3 region providing allosteric mutations,
(b) an amino acid residue within the hydrophobic knobs of the CH2-CH3 region,
(c) an amino acid residue within the N-terminal CH3 helix,
(d) an amino acid residue within the C-terminal CH3 beta-strand, and
(e) an amino acid residue corresponding to E345, E382 or Q386 in the Fc-region of a human IgG1 heavy chain, and (ii) a second mutation in the position corresponding to S440 in the Fc region of an IgG1 heavy chain, with the proviso that the mutation in S440 is not S440Y or S440W.

In another aspect, the present invention relates to a composition comprising a first variant of an antibody and a second variant of a parent antibody, wherein the first variant comprises a first Fc-domain of an immunoglobulin and a first antigen-binding region, wherein the first variant comprises a first mutation in at least an amino acid residue selected from the group of
- (a) an amino acid residue within the CH2-CH3 region providing allosteric mutations,
- (b) an amino acid residue within the hydrophobic knobs of the CH2-CH3 region,
- (c) an amino acid residue within the N-terminal CH3 helix,
- (d) an amino acid residue within the C-terminal CH3 beta-strand, with the proviso that in case of a mutation corresponding to S440 in the Fc-region of a human IgG1 heavy chain the mutation is S440Y or S440W, and
- (e) an amino acid residue corresponding to E345, E382 or Q386 in the Fc-region of a human IgG1 heavy chain, and wherein the second variant comprises a second Fc-domain of an immunoglobulin and a second antigen-binding region, wherein said second variant does not comprise a mutation in an amino acid residue selected from the group of
- (a) an amino acid residue within the CH2-CH3 region providing allosteric mutations,
- (b) an amino acid residue within the hydrophobic knobs of the CH2-CH3 region,
- (c) an amino acid residue within the N-terminal CH3 helix,
- (d) an amino acid residue within the C-terminal CH3 beta-strand, with the proviso that in case of a mutation corresponding to S440 in the Fc-region of a human IgG1 heavy chain the mutation is S440Y or S440W, and
- (e) an amino acid residue corresponding to E345, E382 or Q386 in the Fc-region of a human IgG1 heavy chain.

In the embodiments, wherein the second variant does not comprise any of the listed mutations herein described, such second variant may include any of the suitable second antibody examples listed above in relation to the methods of effector functions.

In one embodiment, the first and second variant comprise a first mutation in at least one amino acid residue selected from those corresponding to E345, E430, Q386, P247, I253, S254, Q311, D/E356, T359, E382, Y436, and K447 in the Fc-region of a human IgG1 heavy chain.

In one embodiment, the first variant comprises a mutation in at least one amino acid residue selected from those corresponding to E345, E430, S440, Q386, P247, I253, S254, Q311, D/E356, T359, E382, Y436, and K447 in the Fc-region of a human IgG1 heavy chain, with the proviso that the mutation in S440 is S440Y or S440W.

In one particular embodiment, the first variant comprises a mutation in the amino acid residues corresponding to E345R and Q386K in the Fc-region of a human IgG1 heavy chain, and the second variant does not comprise such mutations.

In one particular embodiment, the first variant comprises a mutation in the amino acid residues corresponding to E345R, Q386K and E430G in the Fc-region of a human IgG1 heavy chain, and the second variant does not comprise such mutations.

In one embodiment, the at least one first mutation in the first and second variants are different.

In one embodiment, the first variant and second variant is each a human IgG1, IgG2, IgG3, IgG4, IgA1, IgA2, IgD or IgE antibody, optionally each a human full-length antibody, such as each a human full-length IgG1 antibody.

In one embodiment, the first variant and second variant is selected from a monospecific antibody, bispecific antibody or multispecific antibody.

In a further embodiment, the first and the second variant bind different epitopes on the same antigen or on different antigens. Thus, in the embodiment, wherein the first and second antibody are bispecific antibodies may be binding each two different epitopes. The at least two bispecific antibodies may be the same or different. If the bispecific antibodies are different, the composition, thus, comprises targeting up to four different epitopes on either the same or different targets.

In a further embodiment, one or both of the first variant and second variant is conjugated to a drug, toxin or radio-label, such as wherein one or both of the first variant and second variant is conjugated to a toxin via a linker.

In a further embodiment, one or both of the first variant and second variant is part of a fusion protein.

In another aspect, the invention relates to a composition comprising any variant, any bispecific antibody or any composition described here and a pharmaceutically acceptable carrier.

It is contemplated that any of the embodiments according to the "mixed-mutant" aspect also may be comprised in any of the composition embodiments.

In one embodiment, the variants of the first and second parent antibodies bind to antigens expressed on the same cell.

In another embodiment, the variant of the first parent antibody comprises an amino acid substitution of K439 into an amino acid selected from E and D.

In another embodiment, the amino acid substitution in the variant of the first parent antibody is K439E.

In another embodiment, the variant of the second parent antibody comprises an amino acid substitution of S440 into an amino acid selected from K, R and H.

In another embodiment, the amino acid substitution in the variant of the second parent antibody variant is S440K.

In an alternative embodiment, the variant of the first and/or second antibody further comprises a mutation in a residue selected from the group consisting of H310, G385, H433, N434, and Q438.

In a further alternative embodiment, the variant of the first and/or second parent antibody further comprise a mutation selected from E345 to D, K, N, Q, R, or W; E382 to D, Q, K, or R; and H433 to R.

In a further embodiment, the variants of the first and second parent antibodies further comprise a mutation selected from E345R, E382R and H433R, such as E345R.

In another aspect, the invention relates to a pharmaceutical composition comprising the variant of the first parent antibody and the variant of the second parent antibody of any one of embodiments listed above.

The pharmaceutical compositions may be formulated in accordance with conventional techniques such as those disclosed in Remington: The Science and Practice of Pharmacy, 19th Edition, Gennaro, Ed., Mack Publishing Co., Easton, PA, 1995. A pharmaceutical composition of the present invention may e.g. include diluents, fillers, salts, buffers, detergents (e.g., a nonionic detergent, such as Tween-20 or Tween-80), stabilizers (e.g., sugars or protein-free amino acids), preservatives, isotonicity agents, antioxidants, tissue fixatives, solubilizers, and/or other materials suitable for inclusion in a pharmaceutical composition. Examples of suitable aqueous and nonaqueous carriers which may be employed in the pharmaceutical compositions of the present invention include water, saline, phosphate buffered saline, ethanol, dextrose, polyols (such as glycerol, propylene glycol, polyethylene glycol).

The pharmaceutical composition may be administered by any suitable route and mode. In one embodiment, a pharmaceutical composition of the present invention is administered parenterally. The term "administered parenterally" as used herein means modes of administration other than enteral and topical administration, usually by injection, and include epidermal, intravenous, intramuscular, intraarterial, intrathecal, intracapsular, intraorbital, intracardiac, intradermal, intraperitoneal, intratendinous, transtracheal, subcutaneous, subcuticular, intraarticular, subcapsular, subarachnoid, intraspinal, intracranial, intrathoracic, epidural and intrasternal injection and infusion.

Kit-of-Parts

It is to be understood that all embodiments described herein with reference to a parent antibody, first parent antibody or second parent antibody are also to be understood as embodiments relating to a parent, first parent or second parent polypeptide comprising an Fc-domain of an immunoglobulin and a binding region.

The invention also relates to kit-of-parts for simultaneous, separate or sequential use in therapy comprising variants and parent antibodies, wherein any variant and parent antibody may be as described herein. Specific aspects and embodiments will be described below. Furthermore, such variants may be obtained according to any method described herein.

The invention also relates to kit-of-parts for simultaneous, separate or sequential use in therapy comprising variants and parent antibodies may be any variant and parent antibody as described herein. Specific aspects and embodiments will be described below. Furthermore, such variants may be obtained according to any method described herein.

In one aspect the present invention relates to a kit-of-parts for simultaneous, separate or sequential use in therapy comprising a first variant of a parent polypeptide and a second variant of a parent polypeptide, wherein the first variant comprises a first Fc-domain of an immunoglobulin and a binding region, wherein the second variant comprises a second Fc-domain of an immunoglobulin and a binding region, and wherein (i) said first variant comprises a mutation in the position corresponding to K439 in the Fc-region of a human IgG1 heavy chain, and said second variant comprises a mutation in the position corresponding to S440 in the Fc-region of a human IgG1 heavy chain, with the proviso that the mutation in S440 is not S440Y or S440W, (ii) said first variant comprises a mutation in the position corresponding to K447D/E in the Fc region of a human IgG1 heavy chain; and said second variant comprises a mutation in the position corresponding to K447K/R/H and 448P in the Fc-region of a human IgG1 heavy chain, or (iii) said first variant comprises a mutation in the position corresponding to K447D/E in the Fc region of a human IgG1 heavy chain; and said second variant comprises a mutation in the position corresponding to K447K/R/H, 448K/R/H and 449P in the Fc-region of a human IgG1 heavy chain.

In one embodiment the first one or both of the variant of a parent polypeptide and the second variant of a parent polypeptide may be an antibody.

Thus in one an aspect, the invention relates to a kit-of-parts for simultaneous, separate or sequential use in therapy, comprising a first variant of a parent antibody and a second variant of a parent antibody, wherein the first variant comprises a first Fc-domain of an immunoglobulin and an antigen-binding region, wherein the second variant comprises a second Fc-domain of an immunoglobulin and an antigen-binding region, and wherein (i) said first variant comprises a mutation in the position corresponding to K439 in the Fc-region of a human IgG1 heavy chain, and said second variant comprises a mutation in the position corresponding to S440 in the Fc-region of a human IgG1 heavy chain, with the proviso that the mutation in S440 is not S440Y or S440W, (ii) said first variant comprises a mutation in the position corresponding to K447D/E in the Fc region of a human IgG1 heavy chain; and said second variant comprises a mutation in the position corresponding to K447K/R/H and 448P in the Fc-region of a human IgG1 heavy chain, or (iii) said first variant comprises a mutation in the position corresponding to K447D/E in the Fc region of a human IgG1 heavy chain; and said second variant comprises a mutation in the position corresponding to K447K/R/H, 448K/R/H and 449P in the Fc-region of a human IgG1 heavy chain.

In one embodiment the kit-of-parts for simultaneous, separate or sequential use in therapy, comprising a first variant of a parent antibody and a second variant of a parent antibody, wherein the first variant comprises a first Fc-domain of an immunoglobulin and an antigen-binding region, wherein the second variant comprises a second Fc-domain of an immunoglobulin and an antigen-binding region, and wherein said first variant comprises a mutation in the position corresponding to K439 in the Fc-region of a human IgG1 heavy chain, and wherein the second variant comprises a mutation in the position corresponding to S440, with the proviso that the mutation in S440 is not S440Y or S440W.

In one embodiment, the kit-of-parts for simultaneous, separate or sequential use in therapy, comprising the first variant of a parent antibody and the second variant of a parent antibody, wherein the first variant comprises a first Fc-domain of an immunoglobulin and an antigen-binding region, wherein said first variant comprises (i) a first mutation in at least one amino acid residue other than a mutation in K439 selected from the group of (a) an amino acid residue within the CH2-CH3 region providing allosteric mutations,
(b) an amino acid residue within the hydrophobic knobs of the CH2-CH3 region,
(c) an amino acid residue within the N-terminal CH3 helix,
(d) an amino acid residue within the C-terminal CH3 beta-strand, with the proviso that in case of a mutation corresponding to S440 in the Fc-region of a human IgG1 heavy chain the mutation is S440Y or S440W, and
(e) an amino acid residue corresponding to E345, E382 or Q386 in the Fc-region of a human IgG1 heavy chain, and (ii) a second mutation in the position corresponding to K439 in the Fc-region of a human IgG1 heavy chain; and wherein the second variant comprises a second Fc-domain of an immunoglobulin and an antigen-binding region, wherein said second variant comprises (i) a first mutation in at least one amino acid residue other than a mutation in S440 selected from the group of (a) an amino acid residue within the CH2-CH3 region providing allosteric mutations,
(b) an amino acid residue within the hydrophobic knobs of the CH2-CH3 region,
(c) an amino acid residue within the N-terminal CH3 helix, (d) an amino acid residue within the C-terminal CH3 beta-strand, and
(e) an amino acid residue corresponding to E345, E382 or Q386 in the Fc-region of a human IgG1 heavy chain, and
(ii) a second mutation in the position corresponding to S440 in the Fc region of an IgG1 heavy chain, with the proviso that the mutation in S440 is not S440Y or S440W.

In another embodiment, the kit-of-parts for simultaneous, separate or sequential use in therapy, comprising the first variant of an antibody and the second variant of a parent antibody, wherein the first variant comprises (i) a first mutation in at least one amino acid residue other than a mutation in K439 selected from the group of
(a) an amino acid residue within the CH2-CH3 region providing allosteric mutations,
(b) an amino acid residue within the hydrophobic knobs of the CH2-CH3 region,
(c) an amino acid residue within the N-terminal CH3 helix,
(d) an amino acid residue within the C-terminal CH3 beta-strand, with the proviso that in case of a mutation corresponding to S440 in the Fc-region of a human IgG1 heavy chain the mutation is S440Y or S440W, and
(e) an amino acid residue corresponding to E345, E382 or Q386 in the Fc-region of a human IgG1 heavy chain, and
(ii) a second mutation in the position corresponding to K439 in the Fc-region of a human IgG1 heavy chain, and
wherein the second variant comprises a mutation in the position corresponding to S440 in the Fc-region of a human IgG1 heavy chain, which is not is not S440Y or S440W.

In another embodiment, the kit-of-parts for simultaneous, separate or sequential use in therapy, comprising the first variant of a parent antibody and the second variant of a parent antibody,
wherein the first variant comprises a mutation in the position corresponding to K439 in the Fc-region of a human IgG1 heavy chain; and
wherein the second variant comprises a second Fc-domain of an immunoglobulin and an antigen-binding region, wherein said second variant comprises (i) a first mutation in at least one amino acid residue other than a mutation in S440 selected from the group of
(a) an amino acid residue within the CH2-CH3 region providing allosteric mutations,
(b) an amino acid residue within the hydrophobic knobs of the CH2-CH3 region,
(c) an amino acid residue within the N-terminal CH3 helix,
(d) an amino acid residue within the C-terminal CH3 beta-strand, and
(e) an amino acid residue corresponding to E345, E382 or Q386 in the Fc-region of a human IgG1 heavy chain, and (ii) a second mutation in the position corresponding to S440 in the Fc region of an IgG1 heavy chain, with the proviso that the mutation in S440 is not S440Y or S440W.

In one embodiment, the mutation in the position corresponding to K439 in the Fc-region of human IgG1 heavy chain is K439D/E, and/or the mutation in the position corresponding to S440 in the Fc-region of human IgG1 heavy chain is S440K/H/R.

In another aspect the present invention relates to a kit-of-parts for simultaneous, separate or sequential use in therapy, comprising a first variant of an parent polypeptide comprising an Fc-domain of an immunoglobulin and a binding region and a second variant of a parent polypeptide comprising an Fc-domain of an immunoglobulin and a binding region, wherein
the first variant comprises a first Fc-domain of an immunoglobulin and a first antigen-binding region, wherein the first variant comprises a first mutation in at least an amino acid residue selected from the group of
(a) an amino acid residue within the CH2-CH3 region providing allosteric mutations,
(b) an amino acid residue within the hydrophobic knobs of the CH2-CH3 region,
(c) an amino acid residue within the N-terminal CH3 helix,
(d) an amino acid residue within the C-terminal CH3 beta-strand, with the proviso that in case of a mutation corresponding to S440 in the Fc-region of a human IgG1 heavy chain the mutation is S440Y or S440W, and
(e) an amino acid residue corresponding to E345, E382 or Q386 in the Fc-region of a human IgG1 heavy chain, and wherein the second variant does not comprise a mutation in an amino acid residue selected from the group of
(a) an amino acid residue within the CH2-CH3 region providing allosteric mutations,
(b) an amino acid residue within the hydrophobic knobs of the CH2-CH3 region,
(c) an amino acid residue within the N-terminal CH3 helix,
(d) an amino acid residue within the C-terminal CH3 beta-strand, with the proviso that in case of a mutation corresponding to S440 in the Fc-region of a human IgG1 heavy chain the mutation is S440Y or S440W, and
(e) an amino acid residue corresponding to E345, E382 or Q386 in the Fc-region of a human IgG1 heavy chain.

In one embodiment the first and/or second parent polypeptide may be an antibody.

The present invention also relates to an embodiment of the kit-of-parts for simultaneous, separate or sequential use in therapy, wherein the first variant comprises (i) a first mutation in at least one amino acid residue other than a mutation in K439 selected from the group of
(a) an amino acid residue within the CH2-CH3 region providing allosteric mutations,
(b) an amino acid residue within the hydrophobic knobs of the CH2-CH3 region,
(c) an amino acid residue within the N-terminal CH3 helix,
(d) an amino acid residue within the C-terminal CH3 beta-strand, with the proviso that in case of a mutation corresponding to S440 in the Fc-region of a human IgG1 heavy chain the mutation is S440Y or S440W, and
(e) an amino acid residue corresponding to E345, E382 or Q386 in the Fc-region of a human IgG1 heavy chain, and
(ii) a second mutation in the position corresponding to K439 in the Fc-region of a human IgG1 heavy chain, and
wherein the second variant comprises a mutation in the position corresponding to S440 in the Fc-region of a human IgG1 heavy chain, which is not is not S440Y or S440W.

The present invention also relates to an embodiment of the kit-of-parts for simultaneous, separate or sequential use in therapy, wherein the first variant comprises a mutation in the position corresponding to K439 in the Fc-region of a human IgG1 heavy chain; and
wherein the second variant comprises a second Fc-domain of an immunoglobulin and an antigen-binding region, wherein said second variant comprises (i) a first mutation in at least one amino acid residue other than a mutation in S440 selected from the group of
  (a) an amino acid residue within the CH2-CH3 region providing allosteric mutations,
  (b) an amino acid residue within the hydrophobic knobs of the CH2-CH3 region,
  (c) an amino acid residue within the N-terminal CH3 helix,
  (d) an amino acid residue within the C-terminal CH3 beta-strand, and
  (e) an amino acid residue corresponding to E345, E382 or Q386 in the Fc-region of a human IgG1 heavy chain, and (ii) a second mutation in the position corresponding to S440 in the Fc region of an IgG1 heavy chain, with the proviso that the mutation in S440 is not S440Y or S440W.

In another aspect, the present invention relates to a kit-of-parts for simultaneous, separate or sequential use in therapy, comprising a first variant of an antibody and a second variant of a parent antibody, wherein
the first variant comprises a first Fc-domain of an immunoglobulin and a first antigen-binding region, wherein the first variant comprises a first mutation in at least an amino acid residue selected from the group of
  (a) an amino acid residue within the CH2-CH3 region providing allosteric mutations,
  (b) an amino acid residue within the hydrophobic knobs of the CH2-CH3 region,
  (c) an amino acid residue within the N-terminal CH3 helix,
  (d) an amino acid residue within the C-terminal CH3 beta-strand, with the proviso that in case of a mutation corresponding to S440 in the Fc-region of a human IgG1 heavy chain the mutation is S440Y or S440W, and
  (e) an amino acid residue corresponding to E345, E382 or Q386 in the Fc-region of a human IgG1 heavy chain, and
wherein the second variant comprises a second Fc-domain of an immunoglobulin and a second antigen-binding region, wherein said second variant does not comprise a mutation in an amino acid residue selected from the group of
  (a) an amino acid residue within the CH2-CH3 region providing allosteric mutations,
  (b) an amino acid residue within the hydrophobic knobs of the CH2-CH3 region,
  (c) an amino acid residue within the N-terminal CH3 helix,
  (d) an amino acid residue within the C-terminal CH3 beta-strand, with the proviso that in case of a mutation corresponding to S440 in the Fc-region of a human IgG1 heavy chain the mutation is S440Y or S440W, and
  (e) an amino acid residue corresponding to E345, E382 or Q386 in the Fc-region of a human IgG1 heavy chain.

In the embodiments, wherein the second variant does not comprise any of the listed mutations herein described, such second variant may include any of the suitable second antibody examples listed above in relation to the methods of effector functions.

In one embodiment, the first and second variant comprise a first mutation in at least one amino acid residue selected from those corresponding to E345, E430, Q386, P247, I253, S254, Q311, D/E356, T359, E382, Y436, and K447 in the Fc-region of a human IgG1 heavy chain.

In one embodiment, the first variant comprises a mutation in at least one amino acid residue selected from those corresponding to E345, E430, S440, Q386, P247, I253, S254, Q311, D/E356, T359, E382, Y436, and K447 in the Fc-region of a human IgG1 heavy chain, with the proviso that the mutation in S440 is S440Y or S440W.

In one particular embodiment, the first variant comprises a mutation in the amino acid residues corresponding to E345R and Q386K in the Fc-region of a human IgG1 heavy chain, and the second variant does not comprise such mutations.

In one particular embodiment, the first variant comprises a mutation in the amino acid residues corresponding to E345R, Q386K and E430G in the Fc-region of a human IgG1 heavy chain, and the second variant does not comprise such mutations.

In one embodiment, the at least one first mutation in the first and second variants are different.

In one embodiment, the first variant and second variant is each a human IgG1, IgG2, IgG3, IgG4, IgA1, IgA2, IgD or IgE antibody, optionally each a human full-length antibody, such as each a human full-length IgG1 antibody.

In one embodiment, the first variant and second variant is selected from a monospecific antibody, bispecific antibody or multispecific antibody.

In a further embodiment, the first and the second variant bind different epitopes on the same antigen or on different antigens. Thus, in the embodiment, wherein the first and second antibody are bispecific antibodies may be binding each two different epitopes. The at least two bispecific antibodies may be the same or different. If the bispecific antibodies are different, the kit-of-parts for simultaneous, separate or sequential use in therapy, thus, comprises targeting up to four different epitopes on either the same or different targets.

In a further embodiment, one or both of the first variant and second variant is conjugated to a drug, toxin or radiolabel, such as wherein one or both of the first variant and second variant is conjugated to a toxin via a linker.

In a further embodiment, one or both of the first variant and second variant is part of a fusion protein.

It is contemplated that any of the embodiments according to the "mixed-mutant" aspect also may be comprised in any of the kit-of-parts for simultaneous, separate or sequential use in therapy, embodiments.

In one embodiment, the variants of the first and second parent antibodies bind to antigens expressed on the same cell.

In another embodiment, the variant of the first parent antibody comprises an amino acid substitution of K439 into an amino acid selected from E and D.

In another embodiment, the amino acid substitution in the variant of the first parent antibody is K439E.

In another embodiment, the variant of the second parent antibody comprises an amino acid substitution of S440 into an amino acid selected from K, R and H.

In another embodiment, the amino acid substitution in the variant of the second parent antibody variant is S440K.

In an alternative embodiment, the variant of the first and/or second antibody further comprises a mutation in a residue selected from the group consisting of H310, G385, H433, N434, and Q438.

In a further alternative embodiment, the variant of the first and/or second parent antibody further comprise a mutation selected from E345 to D, K, N, Q, R, or W; E382 to D, Q, K, or R; and H433 to R.

In a further embodiment, the variants of the first and second parent antibodies further comprise a mutation selected from E345R, E382R and H433R, such as E345R.

In another aspect, the invention relates to a pharmaceutical kit-of-parts for simultaneous, separate or sequential use in therapy, comprising the variant of the first parent antibody and the variant of the second parent antibody of any one of embodiments listed above.

The pharmaceutical kit-of-parts for simultaneous, separate or sequential use in therapy, may be administered by any suitable route and mode. In one embodiment, a pharmaceutical kit-of-parts for simultaneous, separate or sequential use in therapy, of the present invention is administered parenterally. The term "administered parenterally" as used herein means modes of administration other than enteral and topical administration, usually by injection, and include epidermal, intravenous, intramuscular, intraarterial, intrathecal, intracapsular, intraorbital, intracardiac, intradermal, intraperitoneal, intratendinous, transtracheal, subcutaneous, subcuticular, intraarticular, subcapsular, subarachnoid, intraspinal, intracranial, intrathoracic, epidural and intrasternal injection and infusion.

Combinations

It is to be understood that all embodiments described herein with reference to a parent antibody, first parent antibody or second parent antibody are also to be understood as embodiments relating to a parent, first parent or second parent polypeptide comprising an Fc-domain of an immunoglobulin and a binding region.

Additionally, the invention provides for a preparation of a variant of any "single mutant" aspect or embodiment described above, i.e., preparations comprising multiple copies of the variant. The invention also provides for a composition comprising a variant of any "single-mutant" aspect and embodiment described above, e.g., a pharmaceutical composition. The invention also provides for the use of any such "single-mutant" variant, preparation, or composition as a medicament.

The invention also provides for combinations of variants, wherein one variant comprises at least one mutation independently selected from those in Table 1 and one variant comprises at least one other mutation independently selected from those in Table 1, as well as preparations and pharmaceutical compositions of such variant combinations and their use as a medicament. Preferably, the two variants bind the same antigen or to different antigens typically expressed on the surface of the same cell, cell membrane, virion and/or other particle.

Conjugates

It is to be understood that all embodiments described herein with reference to a parent antibody, first parent antibody or second parent antibody are also to be understood as embodiments relating to a parent, first parent or second parent polypeptide comprising an Fc-domain of an immunoglobulin and a binding region.

In one aspect, the present invention relates to a variant, wherein said variant is conjugated to a drug, toxin or radiolabel, such as wherein the variant is conjugated to a toxin via a linker.

In one embodiment said variant is part of a fusion protein.

In another aspect, the variant of the invention is not conjugated at the C-terminus to another molecule, such as a toxin or label. In one embodiment, the variant is conjugated to another molecule at another site, typically at a site which does not interfere with oligomer formation. For example, the antibody variant may, at the other site, be linked to a compound selected from the group consisting of a toxin (including a radioisotope) a prodrug or a drug. Such a compound may make killing of target cells more effective, e.g. in cancer therapy. The resulting variant is thus an immunoconjugate.

Thus, in a further aspect, the present invention provides an antibody linked or conjugated to one or more therapeutic moieties, such as a cytotoxin, a chemotherapeutic drug, a cytokine, an immunosuppressant, and/or a radioisotope. Such conjugates are referred to herein as "immunoconjugates" or "drug conjugates". Immunoconjugates which include one or more cytotoxins are referred to as "immunotoxins".

A cytotoxin or cytotoxic agent includes any agent that is detrimental to (e.g., kills) cells. Suitable therapeutic agents for forming immunoconjugates of the present invention include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, maytansine or an analog or derivative thereof, enediyene antitumor antibiotics including neocarzinostatin, calicheamycins, esperamicins, dynemicins, lidamycin, kedarcidin or analogs or derivatives thereof, anthracyclins, mitoxantrone, mithramycin, actinomycin D, 1-dehydrotestosterone, glucocorticoids, procaine, tetracaine, lidocaine, propranolol, and puromycin, antimetabolites (such as methotrexate, 6-mercaptopurine, 6-thioguanine, cytarabine, fludarabin, 5-fluorouracil, decarbazine, hydroxyurea, asparaginase, gemcitabine, cladribine), alkylating agents (such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin; as well as duocarmycin A, duocarmycin SA, CC-1065 (a.k.a. rachelmycin), or analogs or derivatives of CC-1065), dolastatin, pyrrolo[2,1-c][1,4] benzodiazepins (PDBs) or analogues thereof, antibiotics (such as dactinomycin (formerly actinomycin), bleomycin, daunorubicin (formerly daunomycin), doxorubicin, idarubicin, mithramycin, mitomycin, mitoxantrone, plicamycin, anthramycin (AMC)), anti-mitotic agents (e.g., tubulin-inhibitors) such as monomethyl auristatin E, monomethyl auristatin F, or other analogs or derivatives of dolastatin 10; Histone deacetylase inhibitors such as the hydroxamic acids trichostatin A, vorinostat (SAHA), belinostat, LAQ824, and panobinostat as well as the benzamides, entinostat, CI994, mocetinostat and aliphatic acid compounds such as phenylbutyrate and valproic acid, proteasome inhibitors such as Danoprevir, bortezomib, amatoxins such as α-amantin, diphtheria toxin and related molecules (such as diphtheria A chain and active fragments thereof and hybrid molecules); ricin toxin (such as ricin A or a deglycosylated ricin A chain toxin), cholera toxin, a Shiga-like toxin (SLT-I, SLT-II, SLT-IIV), LT toxin, C3 toxin, Shiga toxin, pertussis toxin, tetanus toxin, soybean Bowman-Birk protease inhibitor, *Pseudomonas* exotoxin, alorin, saporin, modeccin, gelanin, abrin A chain, modeccin A chain, alpha-sarcin, *Aleurites fordii* proteins, dianthin proteins, *Phytolacca americana* proteins (PAPI, PAPII, and PAP-S), *Momordica charantia* inhibitor, curcin, crotin,

*Sapaonaria officinalis* inhibitor, gelonin, mitogellin, restrictocin, phenomycin, and enomycin toxins. Other suitable conjugated molecules include antimicrobial/lytic peptides such as CLIP, Magainin 2, mellitin, Cecropin, and P18; ribonuclease (RNase), DNase I, Staphylococcal enterotoxin-A, pokeweed antiviral protein, diphtherin toxin, and *Pseudomonas* endotoxin. See, for example, Pastan et al., Cell 47, 641 (1986) and Goldenberg, Calif. A Cancer Journal for Clinicians 44, 43 (1994). Therapeutic agents that may be administered in combination with an antibody of the present invention as described elsewhere herein, such as, e.g., anticancer cytokines or chemokines, are also candidates for therapeutic moieties useful for conjugation to an antibody of the present invention.

In one embodiment, the drug conjugates of the present invention comprise an antibody as disclosed herein conjugated to auristatins or auristatin peptide analogs and derivates (U.S. Pat. Nos. 5,635,483; 5,780,588). Auristatins have been shown to interfere with microtubule dynamics, GTP hydrolysis and nuclear and cellular division (Woyke et al (2001) Antimicrob. Agents and Chemother. 45(12): 3580-3584) and have anti-cancer (U.S. Pat. No. 5,663,149) and anti-fungal activity (Pettit et al., (1998) Antimicrob. Agents and Chemother. 42:2961-2965. The auristatin drug moiety may be attached to the antibody via a linker, through the N (amino) terminus or the C (terminus) of the peptidic drug moiety.

Exemplary auristatin embodiments include the N-terminus-linked monomethyl auristatin drug moieties DE and DF, disclosed in Senter et al., Proceedings of the American Association for Cancer Research. Volume 45, abstract number 623, presented Mar. 28, 2004 and described in US 2005/0238649).

An exemplary auristatin embodiment is MMAE (monomethyl auristatin E). Another exemplary auristatin embodiment is MMAF (monomethyl auristatin F).

In one embodiment, an antibody of the present invention comprises a conjugated nucleic acid or nucleic acid-associated molecule. In one such embodiment, the conjugated nucleic acid is a cytotoxic ribonuclease, an antisense nucleic acid, an inhibitory RNA molecule (e.g., a siRNA molecule) or an immunostimulatory nucleic acid (e.g., an immunostimulatory CpG motif-containing DNA molecule). In another embodiment, an antibody of the present invention is conjugated to an aptamer or a ribozyme.

In one embodiment, antibodies comprising one or more radiolabeled amino acids are provided. A radiolabeled variant may be used for both diagnostic and therapeutic purposes (conjugation to radiolabeled molecules is another possible feature). Non-limiting examples of labels for polypeptides include 3H, 14C, 15N, 35S, 90Y, 99Tc, and 125I, 131I, and 186Re. Methods for preparing radiolabeled amino acids and related peptide derivatives are known in the art, (see, for instance Junghans et al., in Cancer Chemotherapy and Biotherapy 655-686 ($2^{nd}$ Ed., Chafner and Longo, eds., Lippincott Raven (1996)) and U.S. Pat. Nos. 4,681,581, 4,735,210, 5,101,827, 5,102,990 (U.S. RE35,500), U.S. Pat. Nos. 5,648,471 and 5,697,902. For example, a radioisotope may be conjugated by the chloramine-T method.

In one embodiment, the variant of the present invention is conjugated to a radioisotope or to a radioisotope-containing chelate. For example, the variant can be conjugated to a chelator linker, e.g. DOTA, DTPA or tiuxetan, which allows for the antibody to be complexed with a radioisotope. The variant may also or alternatively comprise or be conjugated to one or more radiolabeled amino acids or other radiolabeled molecule. A radiolabeled variant may be used for both diagnostic and therapeutic purposes. In one embodiment the variant of the present invention is conjugated to an alpha-emitter. Non-limiting examples of radioisotopes include $^{3}H$, $^{14}C$, $^{15}N$, $^{35}S$, $^{90}Y$, $^{99}Tc$, $^{125}I$, $^{111}In$, $^{131}I$, $^{186}Re$, $^{213}Bs$, $^{225}Ac$ and $^{227}Th$.

In one embodiment the variant of the present invention may be conjugated to a cytokine selected from the group consisting of IL-2, IL-4, IL-6, IL-7, IL-10, IL-12, IL-13, IL-15, IL-18, IL-23, IL-24, IL-27, IL-28a, IL-28b, IL-29, KGF, IFNα, IFNβ, IFNγ, GM-CSF, CD40L, Flt3 ligand, stem cell factor, ancestim, and TNFα.

Variants of the present invention may also be chemically modified by covalent conjugation to a polymer to for instance increase their circulating half-life. Exemplary polymers, and methods to attach them to peptides, are illustrated in for instance U.S. Pat. Nos. 4,766,106, 4,179,337, 4,495,285 and 4,609,546. Additional polymers include polyoxyethylated polyols and polyethylene glycol (PEG) (e.g., a PEG with a molecular weight of between about 1,000 and about 40,000, such as between about 2,000 and about 20,000).

Any method known in the art for conjugating the variant of the present invention to the conjugated molecule(s), such as those described above, may be employed, including the methods described by Hunter et al., Nature 144, 945 (1962), David et al., Biochemistry 13, 1014 (1974), Pain et al., J. Immunol. Meth. 40, 219 (1981) and Nygren, J. Histochem. and Cytochem. 30, 407 (1982). Such variants may be produced by chemically conjugating the other moiety to the N-terminal side or C-terminal side of the variant or fragment thereof (e.g., an antibody H or L chain) (see, e.g., Antibody Engineering Handbook, edited by Osamu Kanemitsu, published by Chijin Shokan (1994)). Such conjugated variant derivatives may also be generated by conjugation at internal residues or sugars, where appropriate.

The agents may be coupled either directly or indirectly to a variant of the present invention. One example of indirect coupling of a second agent is coupling via a spacer or linker moiety to cysteine or lysine residues in the bispecific antibody. In one embodiment, an variant is conjugated to a prodrug molecule that can be activated in vivo to a therapeutic drug via a spacer or linker. In some embodiments, the linker is cleavable under intracellular conditions, such that the cleavage of the linker releases the drug unit from the antibody in the intracellular environment. In some embodiments, the linker is cleavable by a cleavable agent that is present in the intracellular environment (e. g. within a lysosome or endosome or caveola). For example, the spacers or linkers may be cleaveable by tumor-cell associated enzymes or other tumor-specific conditions, by which the active drug is formed. Examples of such prodrug techologies and linkers are described in WO02083180, WO2004043493, WO2007018431, WO2007089149, WO2009017394 and WO201062171 by Syntarga B V, et al. Suitable antibody-prodrug technology and duocarmycin analogs can also be found in U.S. Pat. No. 6,989,452 (Medarex), incorporated herein by reference. The linker can also or alternatively be, e.g. a peptidyl linker that is cleaved by an intracellular peptidase or protease enzyme, including but not limited to, a lysosomal or endosomal protease. In some embodiments, the peptidyl linker is at least two amino acids long or at least three amino acids long. Cleaving agents can include cathepsins B and D and plasmin, all of which are known to hydrolyze dipeptide drug derivatives resulting in the release of active drug inside the target cells (see e. g. Dubowchik and Walker, 1999, Pharm. Therapeutics 83:67-123). In a specific embodiment, the peptidyl linker cleavable by an intracellular protease is a Val-Cit (valine-citrulline) linker or a Phe-Lys (phenylalanine-lysine) linker (see e.g. U.S. Pat. No. 6,214,345, which describes the synthesis of doxorubicin with the Val-Cit linker and different examples of Phe-Lys linkers). Examples of the structures of a Val-Cit and a Phe-Lys linker include but are not limited to MC-vc-PAB described below, MC-vc-GABA, MC-Phe-Lys-PAB or MC-Phe-Lys-GABA, wherein MC is an abbreviation for maleimido caproyl, vc is an abbreviation for Val-Cit, PAB is an abbreviation for p-aminobenzylcarbamate and GABA is an abbreviation for γ-aminobutyric acid. An advantage of using intracellular proteolytic release of the therapeutic agent is that the agent is typically attenuated when conjugated and the serum stabilities of the conjugates are typically high.

In yet another embodiment, the linker unit is not cleavable and the drug is released by antibody degradation (see US 2005/0238649). Typically, such a linker is not substantially sensitive to the extracellular environment. As used herein, "not substantially sensitive to the extracellular environment" in the context of a linker means that no more than 20%, typically no more than about 15%, more typically no more than about 10%, and even more typically no more than about 5%, no more than about 3%, or no more than about 1% of the linkers, in a sample of variant antibody drug conjugate compound, are cleaved when the variant antibody drug conjugate compound presents in an extracellular environment (e.g. plasma). Whether a linker is not substantially sensitive to the extracellular environment can be determined for example by incubating the variant antibody drug conjugate compound with plasma for a predetermined time period (e.g. 2, 4, 8, 16 or 24 hours) and then quantitating the amount of free drug present in the plasma. Exemplary embodiments comprising MMAE or MMAF and various linker components have the following structures (wherein Ab means antibody and p, representing the drug-loading (or average number of cytostatic or cytotoxic drugs per antibody molecule), is 1 to about 8, e.g. p may be from 4-6, such as from 3-5, or p may be 1, 2, 3, 4, 5, 6, 7 or 8).

Examples where a cleavable linker is combined with an auristatin include MC-vc-PAB-MMAF (also designated as vcMMAF) and MC-vc-PAB-MMAF (also designated as vcMMAE), wherein MC is an abbreviation for maleimido caproyl, vc is an abbreviation for the Val-Cit (valine-citrulline) based linker, and PAB is an abbreviation for p-aminobenzylcarbamate.

Other examples include auristatins combined with a non-cleavable linker, such as mcMMAF (mc (MC is the same as mc in this context) is an abbreviation of maleimido caproyl).

In one embodiment, the drug linker moiety is vcMMAE. The vcMMAE drug linker moiety and conjugation methods are disclosed in WO2004010957, U.S. Pat. Nos. 7,659,241, 7,829,531, 7,851,437 and U.S. Ser. No. 11/833,028 (Seattle Genetics, Inc.), (which are incorporated herein by reference), and the vcMMAE drug linker moiety is bound to the antibodies at the cysteines using a method similar to those disclosed in therein.

In one embodiment, the drug linker moiety is mcMMAF. The mcMMAF drug linker moiety and conjugation methods are disclosed in U.S. Pat. No. 7,498,298, U.S. Ser. No. 11/833,954, and WO2005081711 (Seattle Genetics, Inc.), (which are incorporated herein by reference), and the mcMMAF drug linker moiety is bound to the variants at the cysteines using a method similar to those disclosed in therein.

In one embodiment, the variant of the present invention is attached to a chelator linker, e.g. tiuxetan, which allows for the bispecific antibody to be conjugated to a radioisotope.

In one embodiment, each arm (or Fab-arm) of the variant is coupled directly or indirectly to the same one or more therapeutic moieties.

In one embodiment, only one arm of the variant is coupled directly or indirectly to one or more therapeutic moieties.

In one embodiment, each arm of the variant is coupled directly or indirectly to different therapeutic moieties. For example, in embodiments where the variant is a bispecific antibody and is prepared by controlled Fab-arm exchange of two different monospecific antibodies, e.g. a first and second antibody, as described herein, such bispecific antibodies can be obtained by using monospecific antibodies which are conjugated or associated with different therapeutic moieties.

Further Uses

It is to be understood that all embodiments described herein with reference to a parent antibody, first parent antibody or second parent antibody are also to be understood as embodiments relating to a parent, first parent or second parent polypeptide comprising an Fc-domain of an immunoglobulin and a binding region.

In a further aspect, the invention relates to a variant of the invention as described above for use as a medicament, in particular for use as a medicament for the treatment of diseases or disorders, wherein CDC-mediated killing of a target cell (e.g., a tumor, bacterial or fungal cell) or target organism (e.g., a virus) is desired or a bacterial or virus infected cell. Examples of such diseases and disorders include, without limitation, cancer and bacterial, viral or fungal infections.

In another aspect, the present invention relates to the variants, bispecific antibodies, compositions and kit-of-parts described herein, for treatment of a disease, such as cancer.

In another aspect, the present invention relates to a method for treatment of a human comprising administration of a variant, a composition or a kit-of-parts described herein.

In another aspect, the present invention relates to a method for treatment of cancer in a human comprising administration of a variant, a composition or a kit-of-parts "Treatment" refers to the administration of an effective amount of a therapeutically active compound of the present invention with the purpose of easing, ameliorating, arresting or eradicating (curing) symptoms or disease states.

An "effective amount" or "therapeutically effective amount" refers to an amount effective, at dosages and for periods of time necessary, to achieve a desired therapeutic result. A therapeutically effective amount of an antibody may vary according to factors such as the disease state, age, sex, and weight of the individual, and the ability of the antibody to elicit a desired response in the individual. A therapeutically effective amount is also one in which any toxic or detrimental effects of the antibody or antibody portion are outweighed by the therapeutically beneficial effects.

Without being bound by theory, the effective amount of a therapeutically active compound may be decreased when any "single-mutant" aspect or embodiment according to the present invention is introduced to such a therapeutically active compound.

Suitable antigens for cancer antibodies may be the same as described herein. Examples 15 to 18 describe specific applications for providing an enhanced and/or more specific complement activation or CDC of tumor cells. For example, an anti-tumor antibody according to the "single-mutant" aspect, comprising, e.g., a E345R mutation, can provide for an enhanced CDC or ADCC, ADCP response of tumor cells. Further, in a variant of this method, a mutation according to the "single-mutant" aspect, such as, e.g., E345R, E430, S440, or Q386, alternatively E382 or H433R, or any other mutation as listed in Table 1, can be added to each antibody, thus providing for an enhanced CDC and/or ADCC response specifically directed to tumor cells expressing at least two antigens.

Suitable antibodies for bacterial infections include, without limitation, those targeting *S. aureus*, such as the chimeric monoclonal IgG1 pagibaximab (BSYX-A110; Biosynexus), targeting Lipoteichoic acid (LTA) that is embedded in the cell wall of staphylococci, and described in Baker (Nat Biotechnol. 2006 December; 24(12):1491-3) and Weisman et al. (Int Immunopharmacol. 2009 May; 9(5):639-44), both of which are incorporated by reference in their entirety. Example 14 describes a specific embodiment using *S. aureus* antibody variants comprising an E345R mutation. However, other mutations in Table 1, including but not limited to E430G and S440W, alternatively E382R and H433R, can be applied in a similar manner to enhance the CDC-mediating capability of an antibody against a bacterial antigen.

Suitable antigens for viral or fungal infections may be any of the herein described.

In one embodiment, the antigen to which the variant binds is not human EphA2. In another embodiment, the variant is not derived from human EphA2 mAb 12G3H11 (described in Dall'Acqua et al., supra, which is hereby incorporated by reference in its entirety). In another embodiment, the antigen to which the variant binds is not IL-9. In another embodiment, the variant is not derived from Fa-hG1 or Fa-hG4 antibody described in WO2007005612, hereby incorporated by reference in its entirety, or any variant thereof. In one embodiment, the antigen to which the variant binds is not HIV-1 gp120. In another embodiment, the variant is not derived from b12 human IgG1κ antibody directed against gp120.

In a particular embodiment, the variant derives from a bispecific parent antibody. The bispecific antibody can be of any isotype, such as, e.g., IgG1, IgG2, IgG3, or IgG4, and may be a full-length antibody or an Fc-containing fragment thereof. An exemplary method for preparing a bispecific antibody is described in WO 2008/119353 (Genmab).

Dosages

It is to be understood that all embodiments described herein with reference to a parent antibody, first parent antibody or second parent antibody are also to be understood as embodiments relating to a parent, first parent or second parent polypeptide comprising an Fc-domain of an immunoglobulin and a binding region.

Efficient dosages and the dosage regimens for the antibody depend on the disease or condition to be treated and may be determined by the persons skilled in the art. An exemplary, non-limiting range for a therapeutically effective amount of an antibody of the present invention is about 0.1 to 100 mg/kg, such as about 0.1 to 50 mg/kg, for example about 0.1 to 20 mg/kg, such as about 0.1 to 10 mg/kg, for instance about 0.5, about such as 0.3, about 1, about 3, about 5, or about 8 mg/kg.

Antibody variants of the present invention may also be administered in combination with one or more complement factors or related components to enhance the therapeutic efficacy of the variant and/or to compensate for complement consumption. Such complement factors and related components include, but are not limited to, C1q, C4, C2, C3, C5, C6, C7, C8, C9, MBL, and factor B. The combined administration may be simultaneous, separate or sequential. In a particular embodiment, the invention provides for a kit comprising a pharmaceutical composition comprising a variant of the invention, and at least one complement factor or related component in the same or different pharmaceutical composition, together with instructions for use.

Antibody variants of the present invention may also be administered in combination therapy, i.e., combined with other therapeutic agents relevant for the disease or condition to be treated. Accordingly, in one embodiment, the antibody-containing medicament is for combination with one or more further therapeutic agents, such as a cytotoxic, chemotherapeutic or anti-angiogenic agents. Such combined administration may be simultaneous, separate or sequential.

In a further embodiment, the present invention provides a method for treating or preventing disease, such as cancer, which method comprises administration to a subject in need thereof of a therapeutically effective amount of an variant or pharmaceutical composition of the present invention, in combination with radiotherapy and/or surgery.

Method of Preparation

It is to be understood that all embodiments described herein with reference to a parent antibody, first parent antibody or second parent antibody are also to be understood as embodiments relating to a parent, first parent or second parent polypeptide comprising an Fc-domain of an immunoglobulin and a binding region.

The invention also provides isolated nucleic acids and vectors encoding a variant according to any one of the aspects described above, as well as vectors and expression systems encoding the variants. Suitable nucleic acid constructs, vectors and expression systems for antibodies and variants thereof are known in the art, and described in the Examples. In embodiments where the variant comprises not only a heavy chain (or Fc-containing fragment thereof) but also a light chain, the nucleotide sequences encoding the heavy and light chain portions may be present on the same or different nucleic acids or vectors.

The invention also provides a method for producing, in a host cell, an antibody variant according to any one of the aspects described above, wherein said variant comprises at least the Fc region of a heavy chain, said method comprising the following steps:

a) providing a nucleotide construct encoding said Fc region of said variant, b) expressing said nucleotide construct in a host cell, and c) recovering said antibody variant from a cell culture of said host cell.

In some embodiments, the antibody is a heavy-chain antibody. In most embodiments, however, the antibody will also contain a light chain and thus said host cell further expresses a light-chain-encoding construct, either on the same or a different vector.

Host cells suitable for the recombinant expression of antibodies are well-known in the art, and include CHO, HEK-293, PER-C6, NS/0 and Sp2/0 cells. In one embodiment, said host cell is a cell which is capable of Asn-linked glycosylation of proteins, e.g. a eukaryotic cell, such as a mammalian cell, e.g. a human cell. In a further embodiment, said host cell is a non-human cell which is genetically engineered to produce glycoproteins having human-like or human glycosylation. Examples of such cells are genetically-modified *Pichia pastoris* (Hamilton et al., Science 301 (2003) 1244-1246; Potgieter et al., J. Biotechnology 139 (2009) 318-325) and genetically-modified *Lemna minor* (Cox et al., Nature Biotechnology 12 (2006) 1591-1597).

In one embodiment, said host cell is a host cell which is not capable of efficiently removing C-terminal lysine K447 residues from antibody heavy chains. For example, Table 2 in Liu et al. (2008) J Pharm Sci 97: 2426 (incorporated herein by reference) lists a number of such antibody production systems, e.g. Sp2/0, NS/0 or transgenic mammary gland (goat), wherein only partial removal of C-terminal lysines is obtained. In one embodiment, the host cell is a host cell with altered glycosylation machinery. Such cells have been described in the art and can be used as host cells in which to express variants of the invention to thereby produce an antibody with altered glycosylation. See, for example, Shields, R. L. et al. (2002) J. Biol. Chem. 277: 26733-26740; Umana et al. (1999) Nat. Biotech. 17:176-1, as well as EP1176195; WO03/035835; and WO99/54342. Additional methods for generating engineered glycoforms are known in the art, and include but are not limited to those described in Davies et al., 2001, Biotechnol Bioeng 74:288-294; Shields et al, 2002, J Biol Chem 277:26733-26740; Shinkawa et al., 2003, J Biol Chem 278:3466-3473), U.S. Pat. No. 6,602,684, WO00/61739A1; WO01/292246A1; WO02/311140A1; WO 02/30954A1; Potelligent™ technology (Biowa, Inc. Princeton, N.J.); GlycoMAb™ glycosylation engineering technology (GLYCART biotechnology AG, Zurich, Switzerland); US 20030115614; Okazaki et al., 2004, JMB, 336: 1239-49.

The invention also relates to an antibody obtained or obtainable by the method of the invention described above.

In a further aspect, the invention relates to a host cell capable of producing an antibody variant of the invention. In one embodiment, the host cell has been transformed or transfected with a nucleotide construct of the invention.

The present invention is further illustrated by the following examples which should not be construed as further limiting.

EXAMPLES

Example 1

Design and Generation of 7D8 Mutants

The human monoclonal antibody HuMab-7D8 (described in WO 2004/035607) was used as a model antibody. It belongs to a group of human anti-CD20 IgG1 antibodies, including ofatumumab (HuMax-CD20, 2F2). These antibodies target a unique membrane-proximal epitope on the CD20 molecule and show strong CDC.

To test the functional relevance of oligomeric Fc-Fc interactions in complement activation and CDC, amino acids in the hydrophobic patch at the Fc:Fc interface were mutated to potentially disrupt the Fc-Fc side-on interaction and CDC efficacy of 7D8. In a first set of mutants (Table 3), mutations were introduced to change the charge at positions that were chosen based on the 1HZH crystal structure and described to be exposed in hydrophobic patches in the CH2-CH3 domain (Burton Mol Immunol 1985 March; 22(3):161-206)).

From the first set of mutations, I253D and H433A were found to induce the strongest effect on loss of CDC by 7D8 (e.g., Example 5). The 1HZH crystal structure shows that I253 and H433 bind two different pockets on the opposing Fc positions of the partnering antibody. Based on these data, a second set of mutations was synthesized, around the I253 and H433 positions in the crystal structure to further study the importance of residues at the Fc:Fc side-on interface for CDC. The second set of mutations around the I253 and H433 positions that potentially destabilize the Fc:Fc interface and consequently CDC are listed in Table 4.

To exclude the possibility that disruption of direct binding sites for C1q were the cause of the observed effects on CDC, a double mutant was generated based on two single mutants that showed loss of CDC, to test its ability to restore the loss of CDC by the single mutants. This principle is schematically represented in FIG. 1D The double mutant is listed in Table 5 and a structural representation is shown in FIG. 4 and FIG. 5.

Mutants were prepared using the Quikchange site-directed mutagenesis kit (Stratagene, US). Briefly, a forward and a reverse primer encoding the desired mutation were used to replicate full length plasmid DNA template encoding the 7D8 heavy chain with IgG1m(f) allotype. The resulting DNA mixture was digested using DpnI to remove source plasmid DNA and used to transform *E. coli*. Mutant plasmid DNA isolated from resulting colonies was checked by DNA sequencing (Agowa, Germany). Plasmid DNA mixtures encoding both heavy and light chain of antibodies were transiently transfected to Freestyle HEK293F cells (Invitrogen, US) using 293fectin (Invitrogen, US) essentially as described by the manufacturer.

TABLE 3

Set 1 mutations introduced in the CH2-CH3 domain of 7D8.

| Mutation | Charge WT aa | Charge mutant aa |
|---|---|---|
| I253D | = | − |
| I253Y | = | = |
| I253A | = | = |
| Q311A | = | = |
| H433A | δ+ | = |
| N434A | = | = |
| H435A | Δ+ | = |
| H435R | δ+ | + |

(=) no charge (−) negative charge (+) positive charge (δ+) partial positive charge

TABLE 4

Set 2 mutations introduced in the CH2-CH3 domain of 7D8.

| Mutation(s) | Charge WT aa | Charge mutant aa |
|---|---|---|
| I253K | = | + |
| I253R | = | + |
| I253D/H433A | =/δ+ | −/= |
| H310E | δ+ | − |
| H310R | δ+ | + |
| H310K | δ+ | + |
| Q311K | = | + |
| K322A | + | = |
| E345R | − | + |
| E382R | − | + |
| G385D | = | − |
| H433D | δ+ | − |
| H433R | δ+ | + |
| Y436C | = | = |
| Y436D | = | − |
| Q438D | = | − |
| K439E | + | − |
| S440K | = | + |

(=) no charge
(−) negative charge
(+) positive charge
(δ+) partial positive charge

TABLE 5

Double mutations introduced in the CH2-CH3 domain of 7D8 to combine two single mutations that each show loss of CDC.

| Mutations | Charge WT aa | Charge mutant aa |
|---|---|---|
| K439E/S440K | +/= | −/+ |

(=) no charge
(−) negative charge
(+) positive charge

Example 2

CD20 Binding on Cells by 7D8 Mutants

Binding of purified antibody samples to CD20-positive cells was analyzed by FACS analysis. The 1st set of mutations (Table 3) was tested on Daudi cells and the second set of mutations (Table 4) was tested on Raji cells. $10^5$ cells were incubated in 50 μL in polystyrene 96-well round-bottom plates (Greiner bio-one 650101) with serial dilutions of antibody preparations (range 0.04 to 10 μg/mL in 3-fold dilutions for 1st set on Daudi and range 0.003 to 10 μg/mL in 3-fold dilutions for 2n° set on Raji) in RPMI1640/0.1% BSA at 4° C. for 30 min. After washing twice in RPMI1640/0.1% BSA, cells were incubated in 100 μL with secondary antibody at 4° C. for 30 min. As a secondary antibody, fluorescein isothiocyanate (FITC)-conjugated rabbit-anti-human IgG (F0056, Dako, Glostrup, Denmark; 1/100) was used for all experiments on Daudi cells and for experiments with 7D8 antibodies on Raji cells. For the experiments with purified 7D8 antibodies on Raji cells, R-phycoerythrin (R-PE)-conjugated goat F(ab')2 anti-human kappa light chain (2062-09, SouthernBiotech; 1/500) was used as a secondary antibody. Next, cells were washed twice in PBS/0.1% BSA/0.02% azide, resuspended in 100 μL PBS/0.1% BSA/0.02% azide and analyzed on a FACS Cantoll (BD Biosciences). Binding curves were analyzed using non-linear regression (sigmoidal dose-response with variable slope) using GraphPad Prism V5.01 software (GraphPad Software, San Diego, CA, USA).

Binding of 7D8 antibody to Daudi cells was not affected by the introduction of the point mutations in the CH2-CH3 domain and was identical for all tested mutants and wild type 7D8. Further, binding of 7D8 antibody to Raji cells was not significantly affected by the introduction of the point mutations in the CH2-CH3 domain compared to wild type 7D8, except for E345R. Diminished binding of IgG1-7D8-E345R was detected on CD20-positive Raji cells at test concentrations above 0.3 μg/mL. Also for H433D and H433R diminished binding was detected at the highest antibody concentration tested (10 μg/mL). The dimished binding by IgG1-7D8-E345R, H433D and H433R could be explained by shielding of the epitope of the secondary antibody since direct labeling of E345R and H433R resulted in similar or even increased binding to Daudi cells. The increased avidity can be explained by the increased Fc-Fc side-on binding by E345R and H433R in comparison to wild-type IgG1-7D8.

Combining the K439E and S440K mutations did not affect binding of the 7D8 antibody to Raji cells and was identical to that of the single mutants and wild type 7D8.

Example 3

C1q Binding ELISA by 7D8 Mutants

C1q binding by the 7D8 mutants was tested in an ELISA, in which the purified antibodies were coated on the plastic surface, bringing about random antibody multimerization. Pooled human serum was used as a source of C1q.

96-well Microlon ELISA plates (Greiner, Germany) were coated overnight at 4° C. with a dilution series of the antibodies in PBS (range 0.58-10.0 μg/mL in 1.5-fold dilutions). Plates were washed and blocked with 200 μL/well 0.5×PBS supplemented with 0.025% Tween 20 and 0.1% gelatine. With washings in between incubations, plates were sequentially incubated with 3% pooled human serum (Sanquin, product #M0008) for 1 h at 37° C., with 100 μL/well rabbit anti-human C1q (DAKO, product #A0136, 1/4.000) for 1 h at RT, and with 100 μL/well swine anti-rabbit IgG-HRP (DAKO, P0399, 1:10.000) as detecting antibody for 1 h at RT. Development was performed for circa 30 min with 1 mg/mL 2,2'-azino-bis (3-ethylbenzothiazoline-6-sulfonic acid) (ABTS; Roche, Mannheim, Germany). The reaction was stopped by the addition of 100 μL 2% oxalic acid. Absorbance was measured at 405 nm in a microplate reader (Biotek, Winooski, VT). Log transformed data were analyzed by fitting sigmoidal dose-response curves with variable slope using GraphPad Prism software. $EC_{50}$ values of the mutants were normalized per plate against wild type IgG1-7D8 and multiplied by the average of all wild type IgG1-7D8 data.

As shown in FIG. 6 and Table 6, the tested point mutations had minimal effect on C1q binding as measured by ELISA. For the IgG1-7D8-I253D mutant, a slightly less efficient C1q binding was measured in the ELISA (higher $EC_{50}$ value). Coating efficacy was tested for all antibodies and was found to be similar for all antibodies.

TABLE 6

| $EC_{50}$ for C1q binding in ELISA | | | |
|---|---|---|---|
| Antibody | Mean $EC_{50}$ (μg/mL) [1] | SD [1] | Significance [2] |
| IgG1-7D8-WT | 2.048 | 0 | Na |
| IgG1-7D8-I253D | 3.838 | 1.341 | * |
| IgG1-7D8-I253Y | 2.209 | 0.385 | Ns |
| IgG1-7D8-I253A | 2.556 | 0.187 | Ns |
| IgG1-7D8-Q311A | 2.182 | 0.062 | ns |
| IgG1-7D8-H433A | 3.327 | 1.719 | ns |
| IgG1-7D8-N434A | 2.120 | 0.492 | ns |
| IgG1-7D8-H435A | 2.267 | 0.317 | ns |
| IgG1-7D8-H435R | 1.242 | 0.492 | ns |

[1] Mean and SD were calculated from at least 3 experiments.
[2] Statistics: 1 way ANOVA on log transformed data using Dunnett's Multiple Comparison Test (GraphPad Prism 5.01). Significance was calculated in comparison to wild type IgG1-7D8: (na) not applicable (ns) not significant (*) p = 0.01 to 0.05 () p = 0.001 to 0.01 (*) $p < 0.001$.

Example 4

C1q Binding on Cells by 7D8 Mutants

Coating of antibodies on a plastic surface results in an artificial static system of antibody binding and Fc-tail presentation. Therefore, complement binding was also tested in a cell-based assay, in which C1q binding to antibody-opsonized CD20-positive B cells was measured by FACS analysis. In experiments with set 1 mutants, Daudi or Raji cells were suspended on ice in 90 μL RPMI 1640 media with 10% FBS ($2\times10^6$ cells/mL). 10 μL of a concentration series of C1q (Complement Technologies, Tyler, TX) was added (final concentration range varies between 0-60 μg/mL and 0-140 μg/mL depending on the maximal binding). Then, 10 μL of purified antibody (10 μg/mL final concentration, i.e. saturating conditions) was added and the reaction mixtures were immediately transferred to a 37° C. water bath and incubated for one hour. In experiments with set 2 mutants, test mAb was added to Daudi cells in bulk, then varying concentrations of C1q were added to aliquots and the mixtures incubated as above. Cells were washed three times with PBS/1% BSA and incubated for 30 minutes at room temperature with rabbit FITC-labeled anti-C1q antibody (DakoCytomation, 10 ug/mL). Cells were washed with PBS/1% BSA and resuspended in PBS or fixed in 2% formaldehyde in PBS. Flow cytometry was performed on a FACSCalibur flow cytometer (BD Biosciences) and mean fluorescence intensities were converted to molecules of equivalent soluble fluorescence (MESF) using calibrated beads (Spherotech). The dissociation constants ($K_D$ values) for binding of C1q to CD20-positive cells opsonised with the indicated 7D8 antibodies were calculated using Sigma-Plot® software (Systat Software Inc., Washington). Average $K_D$ values were calculated from repeated binding experiments (4 times on Daudi cells, 3 times on Raji cells) and compared to the $K_D$ value for C1q binding on cells opsonized with wild type 7D8 (Table 7 and Table 8).

Set 1 mutants were tested on both Daudi and Raji cells and gave the same results. In contrast to the C1q ELISA results, most tested mutants showed decreased C1q binding avidity (increased $K_D$) on both antibody-opsonized Daudi (Table 7A) and Raji cells (Table 8). Compared to wild type 7D8, IgG1-7D8-Q311A and H435A showed little to no decrease, I253A, I253Y and N434A a more pronounced decrease, and I253D and H433A a very drastic decrease in C1q binding avidity on opsonized Daudi or Raji cells. IgG1-7D8-H435R showed a slightly higher avidity (lower $K_D$) for C1q binding than wild type 7D8 on both cell types, which, however, was not significant.

Set 2 mutants were tested on Daudi cells. Compared to wild type 7D8, IgG1-7D8-E345R, E382R and H433R showed increased binding avidity on opsonized Daudi cells, reflected by the lower $K_D$ values (Table 7B). All other Set 2 mutants showed decreased binding avidity compared to wild type 7D8, with G385D, Y436D, Q438D, K439E and S440K showing drastically increased $K_D$ values (Table 7B) and H433D and Y436C showing such a drastically reduced binding that no reliable $K_D$ value could be measured.

The double mutant IgG1-7D8-K439E/S440K showed restored C1q binding on antibody-opsonized Daudi cells, while both single mutants showed decreased C1q binding compared to wild type 7D8. The binding avidity of the K439E/S440K double mutant was even slightly increased compared to wild type 7D8 (Table 7C). Mixtures of single mutants IgG1-7D8-K439E and IgG1-7D8-K440E were able to completely restore C1q binding which was comparable to C1q binding of wild type 7D8 (Table 7C).

The discrepancy between the unchanged C1q binding in the ELISA (Example 3) and the affected C1q binding in the cell-based assay by the IgG1-7D8 mutants, shows that the tested CH3 positions that are involved in the Fc:Fc interaction between antibody molecules, do not influence C1q binding directly, but are important determinants that affect the dynamic positioning of antibody Fc-tails when bound on cells, and thereby also the strength of the C1q binding.

TABLE 7A $K_D$ values for C1q binding to antibody-opsonized Daudi cells (mutants set 1)

| mAb | $K_D$ (nM) Exp. 1 | $K_D$ (nM) Exp. 2 | $K_D$ (nM) Exp. 3 | $K_D$ (nM) Exp. 4 | $K_D$ (nM) Exp. 10 | $K_D$ (nM) Exp. 11 | Average $K_D$ (nM) | sd | P-value* |
|---|---|---|---|---|---|---|---|---|---|
| 7D8 | 7.7 | 9.3 | 4.2 | 4.3 | 11.8 | 13.3 | 8.4 | 3.7 | na** |
| 7D8-I253A | 33.0 | 20.4 | 16.7 | 15.7 | | | 21.5 | 8.0 | 0.007 |
| 7D8-I253Y | 58.5 | 37.0 | 21.1 | 48.7 | | | 41.3 | 16.1 | 0.001 |
| 7D8-I253D | 146.5 | 176.1 | 101.7 | 205.2 | | | 157.4 | 44.2 | <0.001 |
| 7D8-Q311A | 14.3 | 13.0 | 9.6 | 5.9 | | | 10.7 | 3.8 | 0.379 |
| 7D8-H433A | 168.0 | 76.1 | 45.2 | 180.7 | | | 117.5 | 67.0 | 0.003 |
| 7D8-N434A | 36.7 | 47.8 | 28.3 | 48.7 | | | 42.6 | 9.7 | <0.001 |
| 7D8-H435A | 7.8 | 10.9 | 5.0 | 10.9 | | | 8.6 | 2.8 | 0.925 |
| 7D8-H435R | 5.2 | 8.7 | 2.6 | 3.0 | | | 4.9 | 2.8 | 0.147 |

*Compared to wild type 7D8 (t-test)
**(na) not applicable

TABLE 7B $K_D$ values for C1q binding to antibody-opsonized Daudi cells (mutants set 2)

| mAb | $K_D$ (nM) Exp. 5 | $K_D$ (nM) Exp. 6 | $K_D$ (nM) Exp. 7 | $K_D$ (nM) Exp. 8 | $K_D$ (nM) Exp. 9 | $K_D$ (nM) Exp. 10 | $K_D$ (nM) Exp. 11 | Average $K_D$ (nM) | sd | P-value* |
|---|---|---|---|---|---|---|---|---|---|---|
| Ofatumumab | 6 | 5.4 | 4 | 2.7 | 12.47 | 12.8 | | 7.2 | 4.3 | 0.6192 |
| 7D8 | | | | | | 11.8 | 13.3 | 8.4*** | 3.7 | na** |
| 7D8-H310K | 32.4 | | | | | | 216 | 124 | 130 | 0.0371 |
| 7D8-E345R | 3.5 | | 0.17 | 0.35 | | 2.7 | | 1.7 | 1.7 | 0.0106 |
| 7D8-E382R | | 3.5 | 1.18 | 1.13 | | 3.3 | | 2.3 | 1.3 | 0.0150 |
| 7D8-G385D | | 77 | | | | | 71 | 74 | 4 | <0.0001 |
| *7D8-H433D**** | | *(1227)* | | | | | *(2694)* | *(1961)* | *1037* | *0.0013* |
| 7D8-H433R | | 5.2 | 0.72 | 1.78 | 5.69 | 1.6 | | 3 | 2.3 | 0.0205 |
| *7D8-Y436C**** | *(2420)* | | | | | *(128)* | *(1274)* | *1621* | | *0.0576* |
| 7D8-Y436D | | 431 | | | | 504 | 468 | 52 | | <0.0001 |
| 7D8-Q438D | 767 | | | | | 667 | 717 | 70 | | <0.0001 |
| 7D8-K439E | | 418 | | | | 304 | 361 | 81 | | <0.0001 |

TABLE 7B-continued

K$_D$ values for C1q binding to antibody-opsonized Daudi cells (mutants set 2)

| mAb | K$_D$ (nM) Exp. 5 | K$_D$ (nM) Exp. 6 | K$_D$ (nM) Exp. 7 | K$_D$ (nM) Exp. 8 | K$_D$ (nM) Exp. 9 | K$_D$ (nM) Exp. 10 | K$_D$ (nM) Exp. 11 | Average K$_D$ (nM) | sd | P-value* |
|---|---|---|---|---|---|---|---|---|---|---|
| 7D8-S440K | | 170 | | | | | 48 | 109 | 87 | 0.0131 |
| 7D8-I253D/H433A | | 10316[1] | | | | | 246 | 5291 | 7106 | 0.0681 |

*Compared to wild type 7D8 (t-test)
**(na) not applicable
***Average K$_D$ of 7D8 was calculated from experiments 1, 2, 3, 4, 10 and 11.
****No reliable fitting curve and K$_D$ value could be measured due to too weak binding of these mutants.

TABLE 7C

K$_D$ values for C1q binding to antibody-opsonized Daudi cells (double mutant)

| mAb | K$_D$ (nM) Exp. 5 | K$_D$ (nM) Exp. 6 | K$_D$ (nM) Exp. 7 | K$_D$ (nM) Exp. 8 | K$_D$ (nM) Exp. 9 | K$_D$ (nM) Exp. 10 | K$_D$ (nM) Exp. 11 | Average K$_D$ (nM) | sd | P-value* |
|---|---|---|---|---|---|---|---|---|---|---|
| 7D8 | | | | | | 11.8 | 13.3 | 8.4*** | 3.7 | na** |
| 7D8-K439E | | 418 | | | | | 304 | 361 | 81 | <0.0001 |
| 7D8-S440K | | 170 | | | | | 48 | 109 | 87 | 0.0131 |
| 7D8-K439E/S440K | | 4.6 | 1.63 | 1.01 | | 2.9 | | 2.6 | 1.6 | 0.0196 |
| 7D8-K439E + 7D8-S440K mix | | 3.6 | 3.05 | | | 3.1 | | 3.3 | 0.3 | 0.0555 |

*Compared to wild type 7D8 (t-test)
**(na) not applicable
***Average K$_D$ of 7D8 was calculated from experiments 1, 2, 3, 4, 10, and 11.

TABLE 8

K$_D$ values for C1q binding to antibody-opsonized Raji cells (mutant set 1)

| mAb | K$_D$ (nM) Exp. 1 | K$_D$ (nM) Exp. 2 | K$_D$ (nM) Exp. 3 | Average K$_D$ (nM) | sd | P-value* |
|---|---|---|---|---|---|---|
| 7D8 | 4.8 | 7.0 | 10.9 | 6.5 | 3.1 | na** |
| 7D8-I253A | 10.0 | 25.7 | 20.1 | 18.6 | 7.9 | 0.020 |
| 7D8-I253Y | 24.3 | 45.6 | 46.2 | 38.7 | 12.4 | 0.001 |
| 7D8-I253D | 70.0 | 172.0 | 85.2 | 109.1 | 55.0 | 0.005 |
| 7D8-Q311A | 4.1 | 10.1 | 12.2 | 9.1 | 3.5 | 0.280 |
| 7D8-H433A | 124.8 | 85.0 | 84.0 | 97.9 | 23.3 | <0.001 |
| 7D8-N434A | 35.9 | 46.7 | 35.2 | 44.9 | 12.5 | <0.001 |
| 7D8-H435A | 5.4 | 9.9 | 6.6 | 7.3 | 2.3 | 0.721 |
| 7D8-H435R | 3.5 | 6.2 | 4.5 | 4.7 | 1.4 | 0.721 |

*Compared to wild type 7D8 (t-test)
**(na) not applicable

Example 5

C1q Efficacy by 7D8 Mutants in a CDC Assay on CD20-Positive Raji Cells

C1q efficacy using cells opsonized with IgG1-7D8 mutants was tested in a CDC assay to investigate the impact of the observed changes in C1q binding avidity on CDC activity. Therefore, a CDC assay was performed using C1q-depleted normal human serum that was supplemented with a defined concentration series of C1q. 0.1×10$^6$ Raji cells were pre-incubated in round-bottom 96-well plates (Nunc, Rochester, NY) with 10 μg/mL purified antibody and a concentration series human C1q (0.005, 0.025, 0.1, 0.3, 1.0, 5.0, 30.0 μg/mL) at RT for 15 min in a total volume of 100 μL RPMI1640 medium, supplemented with 0.1% BSA. Next, 25 μL C1q-depleted serum (Quidel, San Diego, CA) was added and incubated at 37° C. in a water bath for 30 min or in an incubator for 45 min. After incubation, the reaction was stopped by placing the samples on ice. Cell lysis was determined on FACS by using propidium iodide (PI, Sigma Aldrich, Zwijndrecht, the Netherlands) viable cell exclusion assay. % lysis was determined as follows: % lysis=(number of PI pos cells/total number of cells)×100%.

The lysis by wild type 7D8 in the presence of 30 μg/mL C1q minus the lysis when no C1q was added, was set to 100%. CH$_{50}$ values (the C1q concentration resulting in 50% lysis) were calculated from fitting sigmoidal dose-response curves on log-transformed data using GraphPad Prism software. CH$_{50}$ values of the mutants were normalized to wild type 7D8 (Table 9).

The data in Table 9 show that, in accordance with the C1q binding avidity measurements, IgG1-7D8-Q311A, E382R and H435A showed no decrease in C1q efficacy; I253A, I253Y, G385D, N434A and Y436C a significant decrease in C1q-efficacy; and I253D, H310K, K322A, H433A, H433D, Y436D, Q438D, K439E and S440K almost completely lost the capacity to induce CDC with all C1q concentrations tested.

IgG1-7D8-H435R and H433R used C1q slightly more efficient which resulted in more efficient CDC than wild type 7D8. IgG1-7D8-E345R showed a drastic increase in C1q efficacy, which resulted in significantly higher CDC lysis compared to wild type 7D8 (Table 9).

Figure 7:
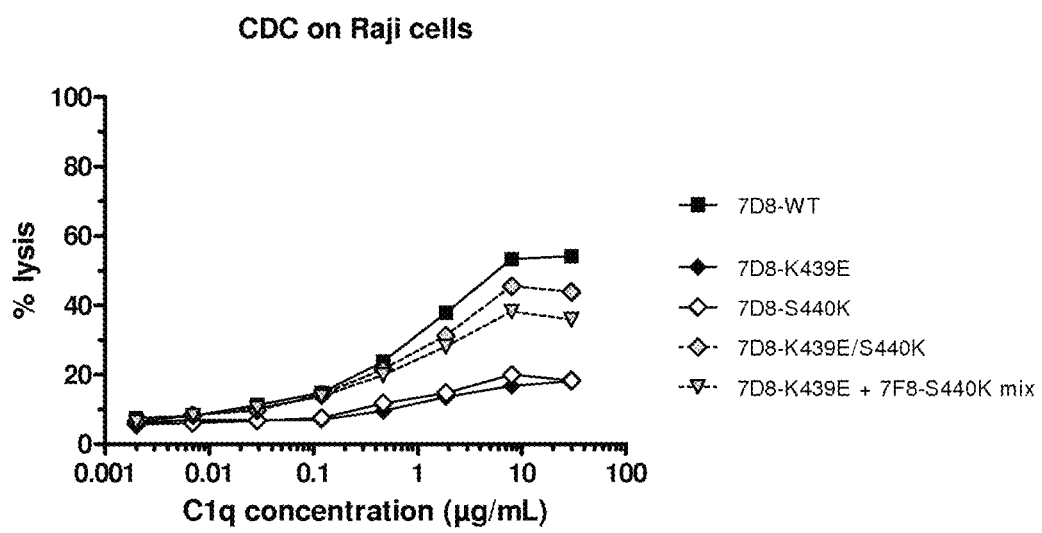
FIG. 7: CDC mediated by 7D8 variants on CD20-positive Raji cells. Raji cells were incubated with the 7D8 mutants (K439E, S440K, K439E/S440K Double mutant, K439E+ S440K mix) and a concentration series of C1q to test the CDC efficacy by measuring cell lysis. A representative graph of repeated experiments is shown.

FIG. 7 shows that combining the K439E and S440K mutation, which both result in loss of CDC as a single mutant, restored CDC in the C1q efficacy assay when both mutations were combined in one molecule (K439E/S440K double mutant) or when both single mutants were combined (K439E+S440K mix).

TABLE 9

CH$_{50}$ for C1q efficacy in a CDC assay on Raji cells

| Antibody | n[1] | Mean CH$_{50}$ (μg/mL) [2] | SD [2] | Significance [3] |
|---|---|---|---|---|
| IgG1-7D8-WT | 8 | 0.49 | 0.26 | na |
| IgG1-7D8-I253A | 3 | 11.16 | 16.31 | *** |
| IgG1-7D8-I253D | 3 | >30 [4] | 0.00 | nd |
| IgG1-7D8-I253Y | 3 | 16.07 | 12.50 | *** |
| IgG1-7D8-H310K | 3 | >30 | 0.00 | na |
| IgG1-7D8-Q311A | 3 | 0.63 | 0.58 | ns |
| IgG1-7D8-K322A | 6 | >30 | 0.00 | nd |
| IgG1-7D8-E345R | 3 | 0.03 | 0.01 | *** |
| IgG1-7D8-E382R | 3 | 0.77 | 0.476 | ns |
| IgG1-7D8-G385D | 3 | 22.51 | 12.97 | *** |
| IgG1-7D8-H433A | 3 | >30 | 0.00 | nd |
| IgG1-7D8-H433D | 3 | >30 | 0.00 | nd |
| IgG1-7D8-H433R | 3 | 0.16 | 0.09 | ns |
| IgG1-7D8-N434A | 3 | 21.16 | 15.32 | *** |
| IgG1-7D8-H435A | 3 | 0.96 | 0.20 | ns |
| IgG1-7D8-H435R | 3 | 0.24 | 0.15 | ns |
| IgG1-7D8-Y436C | 3 | 23.03 | 12.07 | *** |
| IgG1-7D8-Y436D | 3 | >30 | 0.00 | nd |
| IgG1-7D8-Q438D | 3 | >30 | 0.00 | nd |
| IgG1-7D8-K439E | 3 | >30 | 0.00 | nd |
| IgG1-7D8-S440K | 3 | >30 | 0.00 | nd |
| IgG1-7D8-I253D/H433A | 3 | >30 | 0.00 | nd |
| IgG1-7D8-K439E/S440K | 3 | 0.09 | 0.71 | ns |
| IgG1-7D8-K439E + IgG1-7D8-S440K mix | 3 | 1.33 | 1.48 | ns |

[1] (n) Number of experiments
[2] Mean and SD were calculated from all performed experiments.
[3] Statistics: 1 way ANOVA on log transformed data using Dunnett's Multiple Comparison Test (GraphPad Prism 5.01). Significance was calculated in comparison to wild type IgG1-7D8: (na) not applicable (nd) not determined (ns) not significant (*) p = 0.01 to 0.05 () p = 0.001 to 0.01 (*) p < 0.001.
[4] When lysis did not reach 50%, the CH$_{50}$ was set to >30 μg/mL.
[5] No P-value could be determined for mutants that did not reach 50% lysis. However, these are assumed to be significantly different from IgG1-7D8-WT.

Example 6

CDC by 7D8 Mutants in a CDC Assay on CD20-Positive Cells 0.1×10$^6$ cells were pre-incubated in round-bottom 96-well plates (Nunc, Rochester, NY) with antibody concentration series (0.01, 0.03, 0.1, 0.3, 1.0, 3.0, 10.0, 30.0 μg/mL) in a total volume of 80 μL for 15 min on a shaker at RT. Next, 20 μL normal human serum was added as a source of C1q (20% final concentration) and incubated in a 37° C. incubator for 45 min. The reaction was stopped by adding 30 μL ice cold RPMI medium, supplemented with 0.1% BSA. Cell lysis was determined on FACS by using propidium iodide.

For the CDC assays on Daudi cells, EC$_{50}$ values (the antibody concentration resulting in 50% lysis) were calculated from fitting sigmoidal dose-response curves on log-transformed data using GraphPad Prism software. EC$_{50}$ values of the mutants were normalized to wild type 7D8 (Table 10 and Table 11).

Figure 8:
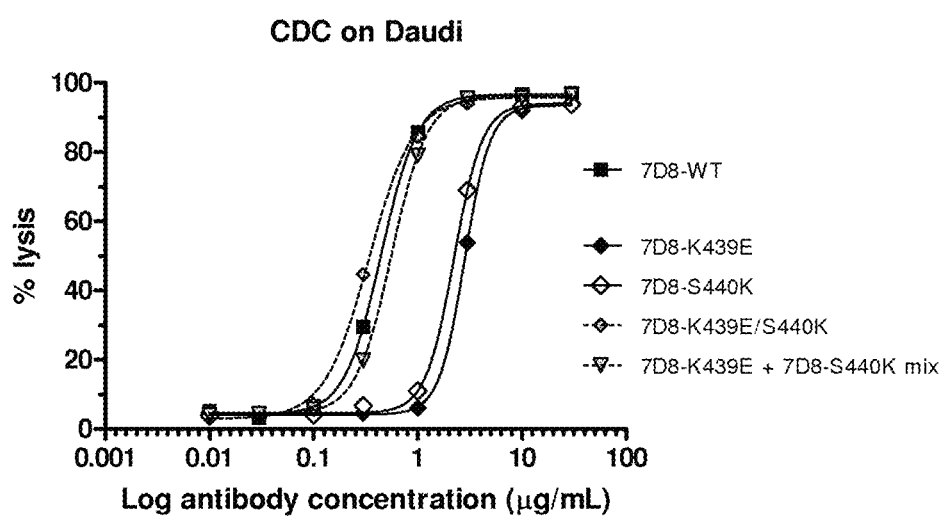
FIG. 8: CDC mediated by 7D8 mutants (7D8-WT, K439E, S440K, K439E/S440K double mutant, K439E+

Table 10 shows that on Daudi cells, IgG1-7D8-I253A, Q311A, E382R, H433R and H435A showed no difference in CDC compared to wild type 7D8; a significant worse CDC (higher EC$_{50}$) than wild type 7D8 was found for IgG1-7D8-I253D, I253Y, H310K, G385D, H433A, H433D, N434A, Y436C, Y436D, Q438D, K439E, S440K and I253D/H433A, which only induced CDC at higher antibody concentrations; The C1q binding deficient mutant IgG1-7D8-K322A, which was included as control, almost completely lost the capacity to induce CDC and did not reach EC$_{50}$ at the tested concentrations; IgG1-7D8-H435R showed more efficient CDC than wild type 7D8 on Daudi cells. Importantly, in accordance with the C1q efficacy CDC assay, E345R showed drastically better CDC than wild type 7D8 with a 10-fold lower EC$_{50}$ value on Daudi cells (Table 10). FIG. 8 shows that combining the K439E and S440K mutation, which both result in loss of CDC as a single mutant, restored CDC when both mutations were combined in one molecule (K439E/S440K double mutant) or when both single mutants were combined (K439E+S440K mix).

Table 11 shows that similar data were found for the IgG1-7D8 mutants on Raji cells.

TABLE 10

EC$_{50}$ calculated from the CDC assay on Daudi cells

| Antibody | n[1] | Mean EC$_{50}$ (μg/mL) [2] | SD [2] | Significance [3] |
|---|---|---|---|---|
| IgG1-7D8 | 12 | 0.48 | 0.11 | na |
| IgG1-7D8-I253A | 4 | 0.79 | 0.15 | ns |
| IgG1-7D8-I253D | 5 | 3.33 | 1.05 | *** |
| IgG1-7D8-I253Y | 4 | 1.77 | 0.43 | *** |
| IgG1-7D8-H310K | 3 | 3.03 | 0.30 | *** |
| IgG1-7D8-Q311A | 4 | 0.42 | 0.12 | ns |
| IgG1-7D8-K322A |  | >30 [4] | Nd | ***[5] |
| IgG1-7D8-E345R | 4 | 0.04 | 0.01 | *** |
| IgG1-7D8-E382R | 4 | 0.76 | 0.25 | ns |
| IgG1-7D8-G385D | 3 | 2.12 | 0.45 | *** |
| IgG1-7D8-H433A | 5 | 3.44 | 1.17 | *** |
| IgG1-7D8-H433D | 4 | 4.73 | 2.57 | *** |
| IgG1-7D8-H433R | 4 | 0.33 | 0.14 | ns |
| IgG1-7D8-N434A | 4 | 1.77 | 0.46 | *** |
| IgG1-7D8-H435A | 4 | 0.81 | 0.27 | ns |
| IgG1-7D8-H435R | 5 | 0.28 | 0.06 | ** |
| IgG1-7D8-Y436C | 4 | 1.90 | 1.21 | *** |
| IgG1-7D8-Y436D | 3 | 1.88 | 0.45 | *** |
| IgG1-7D8-Q438D | 3 | 2.61 | 0.38 | *** |
| IgG1-7D8-K439E | 4 | 2.34 | 0.38 | *** |
| IgG1-7D8-S440K | 4 | 1.78 | 0.46 | *** |
| IgG1-7D8-I253D/H433A | 4 | 4.77 | 1.36 | *** |
| IgG1-7D8-K439E/S440K | 4 | 0.33 | 0.08 | ns |
| IgG1-7D8-K439E + IgG1S440K | 4 | 0.48 | 0.17 | ns |

[1] (n) Number of experiments
[2] Mean and SD were calculated from all performed experiments.
[3] Statistics: 1 way ANOVA on log transformed data using Dunnett's Multiple Comparison Test (GraphPad Prism 5.01). Significance was calculated in comparison to wild type 7D8: (na) not applicable (nd) not determined (ns) not significant (*) p = 0.01 to 0.05 () p = 0.001 to 0.01 (*) p < 0.001.
[4] When lysis did not reach 50%, the EC$_{50}$ was set to >30 μg/mL.
[5] No P-value could be determined for mutants that did not reach EC$_{50}$. However, these are assumed to be significantly different from wild 7D8-WT.

TABLE 11

EC$_{50}$ calculated from the CDC assay on Raji cells

| Antibody | n[1] | Mean EC$_{50}$ (μg/mL) [2] | SD [2] | Significance [3] |
|---|---|---|---|---|
| IgG1-7D8 | 13 | 1.54 | 0.77 | Na |
| IgG1-7D8-I253A | 4 | 5.55 | 3.19 | * |
| IgG1-7D8-I253D | 6 | >30 [4] | 0.00 | ***[5] |
| IgG1-7D8-I253Y | 4 | 28.95 | 2.09 | *** |
| IgG1-7D8-H310K | 2 | 19.29 | 15.15 | *** |
| IgG1-7D8-Q311A | 4 | 1.72 | 0.42 | Ns |
| IgG1-7D8-K322A |  | >30 |  | *** |
| IgG1-7D8-E345R | 4 | 0.16 | 0.09 | *** |
| IgG1-7D8-E382R | 4 | 2.96 | 1.27 | Ns |
| IgG1-7D8-G385D | 2 | 17.40 | 17.82 | *** |
| IgG1-7D8-H433A | 6 | 22.60 | 9.30 | *** |
| IgG1-7D8-H433D | 4 | >30 | 0.00 | *** |
| IgG1-7D8-H433R | 4 | 1.42 | 0.67 | Ns |
| IgG1-7D8-N434A | 4 | 23.02 | 6.16 | *** |
| IgG1-7D8-H435A | 4 | 2.22 | 1.47 | Ns |
| IgG1-7D8-H435R | 6 | 0.61 | 0.21 | ** |
| IgG1-7D8-Y436C | 2 | 11.93 | 10.13 | ** |
| IgG1-7D8-Y436D | 2 | 16.58 | 3.93 | *** |
| IgG1-7D8-Q438D | 2 | 19.49 | 14.87 | *** |

TABLE 11-continued

EC$_{50}$ calculated from the CDC assay on Raji cells

| Antibody | n[1] | Mean EC$_{50}$ (μg/mL) [2] | SD [2] | Significance [3] |
|---|---|---|---|---|
| IgG1-7D8-K439E | 4 | 21.51 | 9.96 | *** |
| IgG1-7D8-S440K | 4 | 19.53 | 12.71 | *** |
| IgG1-7D8-I253D/H433A | 4 | >30 | 0.00 | *** |
| IgG1-7D8-K439E/S440K | 4 | 1.34 | 0.45 | Ns |
| IgG1-7D8-K439E + IgG1S440K | 4 | 1.58 | 0.64 | Ns |

[1](n) Number of experiments
[2] Mean and SD were calculated from all performed experiments.
[3] Statistics: 1 way ANOVA on log transformed data using Dunnett's Multiple Comparison Test (GraphPad Prism 5.01). Significance was calculated in comparison to wild type 7D8: (na) not applicable (nd) not determined (ns) not significant (*) p = 0.01 to 0.05 () p = 0.001 to 0.01 (*) p < 0.001.
[4] when lysis did not reach CH$_{50}$, the CH$_{50}$ was set to >30 μg/mL.
[5] No P-value could be determined for mutants that did not reach EC$_{50}$. However, these are assumed to be significantly different from wild 7D8-WT.

Example 7

Ranking of 7D8 Mutants According to their Capacity to Induce CDC

For the tested 7D8 mutants, a correlation was found between C1q binding on Daudi cells (described in Example 4) and C1q efficacy assays on Raji cells (described in Example 5), and between C1q binding on Daudi cells and CDC assays on Daudi and Raji cells (described in Example 6) (correlation data Table 13). Therefore, the K$_D$ values of the C1q binding assays on Daudi cells were used to rank all tested 7D8 mutants according to their capacity to induce CDC, as shown in Table 12.

TABLE 12

Ranking of all tested 7D8 mutants according to descending K$_D$ values for C1q binding on Daudi cells, which serve as a representative for their capacity to induce CDC.

| | | C1q binding on Daudi cells | |
|---|---|---|---|
| Antibody | n[1] | K$_D$ (nM)[2] | SD |
| IgG1-7D8-E345R | 4 | 1.7 | 1.7 |
| IgG1-7D8-E382R | 4 | 2.3 | 1.3 |
| IgG1-7D8-K439E/S440K | 4 | 2.6 | 1.6 |
| IgG1-7D8-H433R | 5 | 3.0 | 2.3 |
| IgG1-7D8-K439E + IgG1S440K | 3 | 3.3 | 0.3 |
| IgG1-7D8-H435R | 3 | 4.9 | 2.8 |
| IgG1-7D8-H435A | 3 | 8.6 | 2.8 |
| IgG1-7D8 | 7 | 8.7 | 3.5 |
| IgG1-7D8-Q311A | 3 | 10.7 | 3.8 |
| IgG1-7D8-I253A* | 3 | 21.5 | 8.0 |
| IgG1-7D8-I253Y* | 3 | 41.3 | 16.1 |
| IgG1-7D8-N434A* | 3 | 42.6 | 9.7 |
| IgG1-7D8-G385D* | 2 | 74.0 | 4.0 |
| IgG1-7D8-S440K* | 2 | 109.0 | 87.0 |
| IgG1-7D8-H433A* | 3 | 117.5 | 16.1 |
| IgG1-7D8-H310K* | 2 | 124.0 | 130.0 |
| IgG1-7D8-I253D* | 3 | 157.4 | 44.2 |
| IgG1-7D8-K439E* | 2 | 361.0 | 81.0 |
| IgG1-7D8-Y436D* | 2 | 468.0 | 52.0 |
| IgG1-7D8-Q438D* | 2 | 717.0 | 70.0 |
| IgG1-7D8-Y436C* | 2 | (1274.0) | 1621.0 |
| IgG1-7D8-H433D* | 2 | (1961.0) | 1037.0 |
| IgG1-7D8-I253D/H433A* | 2 | (5291.0) | 7106.0 |

*No reliable fitting curve. Italicized K$_D$ values could not be measured due to too weak binding of these mutants.

TABLE 13 correlation between C1q binding on Daudi cells (Example 4) and C1q efficacy assays on Raji cells (Example 5), and between C1q binding on Daudi cells and CDC assays on Daudi and Raji cells (Example 06). Data were log transformed before the correlation was analyzed.

| Parameter | C1q efficacy Raji | CDC Raji | CDC Daudi |
|---|---|---|---|
| Number of XY Pairs | 21 | 21 | 21 |
| Pearson r | 0.8600 | 0.8668 | 0.8959 |
| 95% confidence interval | 0.6812 to 0.9420 | 0.6952 to 0.9449 | 0.7569 to 0.9573 |
| P value (two-tailed) | <0.0001 | <0.0001 | <0.0001 |
| P value summary | *** | *** | *** |
| Is the correlation significant? (alpha = 0.05) | Yes | Yes | Yes |
| R squared | 0.7396 | 0.7513 | 0.8026 |

Example 8

Design and Generation of CD38 Antibody 005 Mutants

The human monoclonal antibody HuMab 005 is a fully human IgG1, K antibody described in WO/2006/099875. Here, it was used as a model antibody for validation of the identified Fc mutations to enhance CDC activity. The tested mutations are listed in Table 14.

DNA constructs for the different mutants were prepared and transiently transfected as described in Example 1, using the heavy chain of HuMab 005 with IgG1m(f) allotype as a template for mutagenesis reactions.

TABLE 14 set of mutations that were introduced in the CH2-CH3 domain of 005 (HuMax-CD38).

| Mutation | Charge WT aa | Charge mutant aa |
|---|---|---|
| I253D | = | – |
| E345R | – | + |
| H433A | δ+ | = |
| K439E | + | – |
| S440K | = | + |

(=) no charge
(–) negative charge
(+) positive charge
(δ+) partial positive charge

Example 9

CD38 Binding on Cells by HuMab-005 Mutants

Binding of unpurified antibody samples to CD38-positive Daudi and Raji cells was analyzed by FACS analysis. $10^5$ cells were incubated in 100 μL in polystyrene 96-well round-bottom plates with serial dilutions of antibody preparations (0.01, 0.03, 0.1, 0.3, 1.0, 3.0, 10.0, 30.0 μg/mL) in RPMI1640/0.1% BSA at 4° C. for 30 min. After washing twice in RPMI1640/0.1% BSA, cells were incubated in 50 μL with FITC-conjugated rabbit F(ab')$_2$ anti-human IgG (cat. no. F0056; DAKO; 1:150) at 4° C. for 30 min. Next, cells were washed twice in PBS/0.1% BSA/0.02% azide, resuspended in 100 μL PBS/0.1% BSA/0.02% azide and analyzed on a FACS Cantoll (BD Biosciences). Binding curves were analyzed using GraphPad Prism V5.01 software. As a negative control, supernatant of mock-transfected cells was used.

Binding of HuMab 005 to Daudi cells was not much affected by the introduction of point mutations in the CH2-CH3 domain. All tested antibodies bound Daudi cells in a dose-dependent manner. Binding was similar to wild type HuMab-005 for all tested mutants, with the exception of 005-E345R, which showed slightly decreased binding. However, without being bound by any theory, the lower binding might be a result of decreased binding by the secondary antibody, analogous to IgG1-7D8-E345 in Example 2. The actual binding avidity by 005-E345R might be similar or even increased compared 005-WT, however we could not confirm this because of lack of directly labeled antibodies.

Binding of HuMab-005 to Raji cells was also not much affected by the introduction of point mutations in the CH2-CH3 domain. All tested antibodies bound Raji cells in a dose-dependent manner. Maximal binding was similar to that of wild type 005 for the 005-I253D and H433A mutants and lower for the 005-E435R, K439E, S440K mutants and the combination of 005-K439E+005-S440K. However, without being bound by any theory, the lower binding might be a result of decreased binding by the secondary antibody, analogous to IgG1-7D8-E345R in example 2 (shielding of the epitope).

Example 10

CDC Assay on CD38-Positive Cells by Mutants of the CD38 Antibody 005

$0.1 \times 10^6$ Daudi or Raji cells were pre-incubated in round-bottom 96-well plates with a concentration series of unpurified antibodies (0.01, 0.03, 0.1, 0.3, 1.0, 3.0, 10.0, 30.0 µg/mL) in a total volume of 100 µL for 15 min on a shaker at RT. Next, 25 µL normal human serum was added as a source of C1q (20% final concentration) and incubated in a 37° C. incubator for 45 min. The reaction was stopped by putting the plates on ice. 10 µL propidium iodide was added and cell lysis was determined by FACS.

The CDC enhancing capacity of the E435R mutation, which was shown to enhance CDC activity of both 7D8 and 005 antibodies on Daudi and Raji cells, was further analyzed on Wien133 cells with different concentration normal human serum (NHS). $0.1 \times 10^6$ Wien133 cells were pre-incubated for 15 min on a shaker at RT in round-bottom 96-well plates with a concentration series of unpurified antibodies (0.001, 0.003, 0.01, 0.03, 0.1, 0.3, 1.0, 3.0, 10.0, 30.0 µg/mL) in a total volume of 50 µL. Next, NHS was added as a source of C1q to reach a final concentration of either 20% or 50% NHS in a total volume of 100 µL. The reaction mixture was incubated in a 37° C. incubator for 45 min. The reaction was stopped by putting the plates on ice. 10 µL propidium iodide was added and cell lysis was determined by FACS.

Figure 9A:
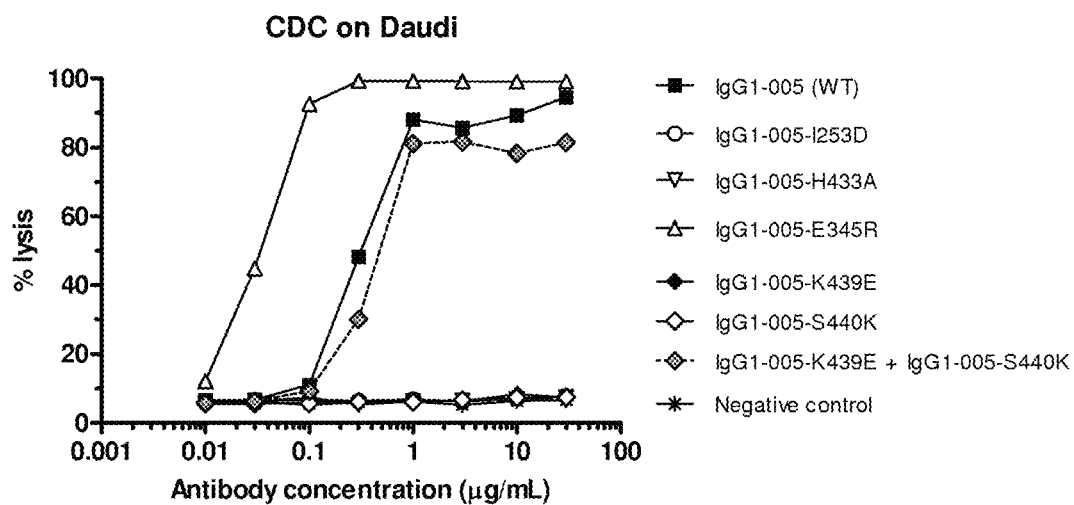
Figure 9B:
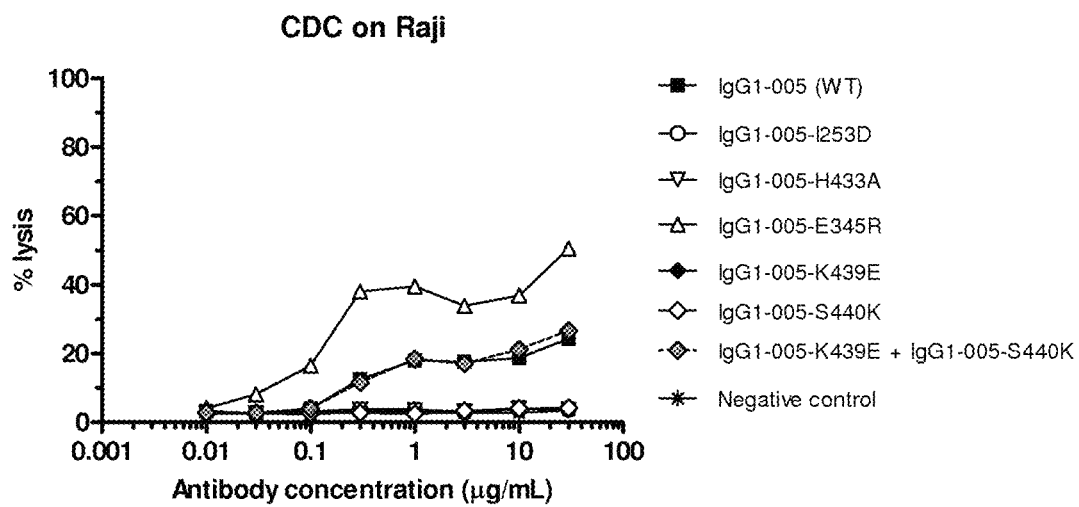
Figure 9C:
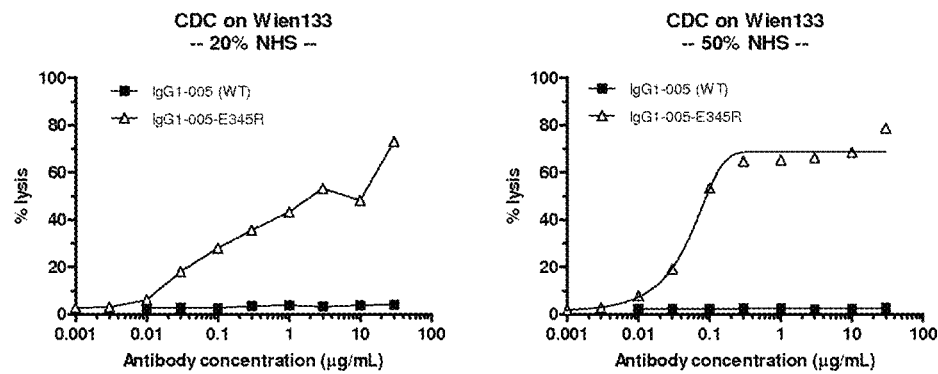
Figure 9D:
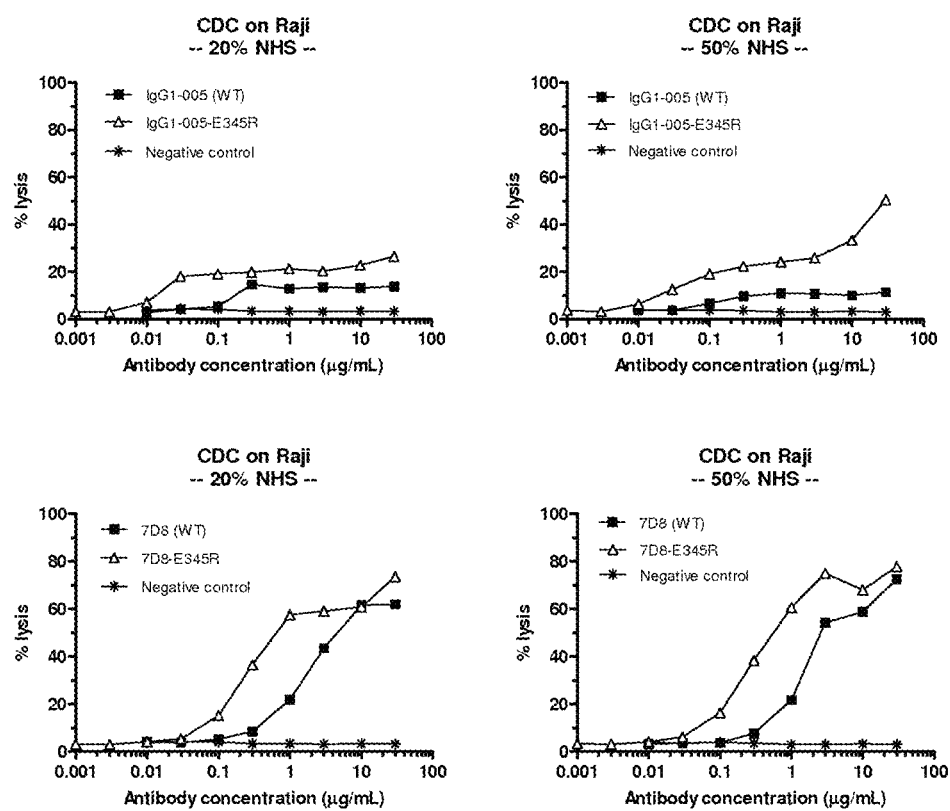

Identified mutations in the CH2-CH3 region that resulted in either loss or increased CDC activity for the CD20 antibody 7D8, were found to have the same effect on the 005 antibody recognizing CD38. FIG. 9 shows that 005-I253D, H443A, K439E and S440K showed complete loss of CDC activity on both Daudi (FIG. 9A) and Raji (FIG. 9B) cells, whereas the 005-E345R mutant showed strongly enhanced CDC activity on both cell lines. Comparable to 7D8 data, a combination of 005-K439E+005-S440K, which both result in loss of CDC as a single mutant, resulted in restored CDC. Surprisingly, 005-E435R even strongly induced CDC on Wien133 cells, for which wild type 005 is not capable to induce killing by CDC (FIG. 9C). CDC killing by 005-E345R on Wien133 cells was observed with both 20% and 50% serum concentrations (FIG. 9C). Also on Raji cells, both 7D8-E345R and 005-E345R showed enhanced CDC in vitro in 50% serum, with similar efficacy as in 20% serum (FIG. 9D).

As the E345R mutation in the CH2-CH3 region resulted in enhanced CDC activity in both the tested CD20 antibody 7D8 and CD38 antibody 005, the E345R mutation is considered to be a general antibody modification that can be applied to induce or enhance CDC.

Example 11

IgG1 Antibodies Containing the CDC-Enhancing Mutation E345R are Less Sensitive to Inhibition of CDC by Fc Binding Peptide DCAWHLGELVWCT than Wild Type Antibodies By mutating amino acid positions in the hydrophobic patch at the Fc:Fc interface of IgG, CDC efficacy was found to be either disturbed or enhanced. The involvement of the interactions at the Fc-Fc interface, and thus possibly the formation of an oligomeric (e.g., hexameric ring) structure as observed in the b12 crystal structure, in CDC efficacy was further explored. Therefore, a 13-residue peptide (DCAWHLGELVWCT (SEQ ID NO:7)) was used that targets a consensus binding site in the hydrophobic patch region on the surface of wild type IgG Fc (Delano et al., Science 2000 Feb. 18; 287(5456):1279-83). Indeed, the identification of the consensus binding site on the surface of IgG Fc as an adaptive region that is primed for interaction with a variety of distinct molecules (Delano et al., Science 2000 Feb. 18; 287(5456):1279-83), is consistent with the identification of the core amino acids in the hydrophobic patch that are involved in the Fc-Fc interaction in the IgG1 b12 crystal structure (Saphire et al., Science 2001 Aug. 10; 293(5532):1155-9). Interactions that are present in all of the binding interfaces are mediated by a shared set of six amino acids (Met-252, Ile-253, Ser-254, Asn-434, His-435, and Tyr-436), as well as shared backbone contacts (Delano et al., Science 2000 Feb. 18; 287(5456):1279-83). Accordingly, the Fc binding peptide is expected to affect the Fc-Fc interaction and consequently CDC efficacy.

$0.1 \times 10^6$ Daudi cells were pre-incubated in 75 µL with 1.0 µg/mL unpurified antibody in round-bottom 96-well plates for 10 min at room temperature on a shaker. 25 µL of a concentration series (range 0.06-60 µg/mL final concentration) of the Fc binding peptide DCAWHLGELVWCT was added to the opsonized cells and incubated for 10 min on a shaker at RT. Next, 25 µL NHS was added as a source of complement (20% final concentration) and incubated in a 37° C. incubator for 45 min. The reaction was stopped by adding 25 µL ice cold RPMI medium, supplemented with 0.1% BSA. 15 µL propidium iodide was added and cell lysis was determined by FACS analysis.

CDC mediated by wild type 005 (FIG. 10A) or 7D8 (FIG. 10B) was found to be inhibited by the Fc-binding peptide DCAWHLGELVWCT in a dose-dependent manner. These competition data suggest again the involvement of the Fc-Fc interactions at the hydrophobic patch of IgG in CDC efficacy. The CDC-enhanced IgG1-005-E345R and IgG1-7D8-E345R mutants were both less sensitive for competition by the Fc-binding peptide compared to their corresponding wild type antibodies, suggesting that the E345R mutation results in increased stability of the Fc-Fc interaction, and consequently increased CDC.

Example 12

Antibody-Dependent Cell-Mediated Cytotoxicity (ADCC) of CD38 Expressing Cells by Variants of CD38 Antibody HuMAb 005

Daudi cells were harvested ($5 \times 10^6$ cells/ml), washed (twice in PBS, 1200 rpm, 5 min) and collected in 1 mL RPMI 1640 medium supplemented with 10% cosmic calf serum (CCS) (HyClone, Logan, UT, USA), to which 200 μCi $^{51}$Cr (Chromium-51; Amersham Biosciences Europe GmbH, Roosendaal, The Netherlands) was added. The mixture was incubated in a shaking water bath for 1 hour at 37° C. After washing of the cells (twice in PBS, 1200 rpm, 5 min), the cells were resuspended in RPMI 1640 medium supplemented with 10% CCS, counted by trypan blue exclusion and diluted to a concentration of $1 \times 10^5$ cells/mL.

Meanwhile, peripheral blood mononuclear cells (PBMCs) were isolated from fresh buffy coats (Sanquin, Amsterdam, The Netherlands) using standard Ficoll density centrifugation according to the manufacturer's instructions (lymphocyte separation medium; Lonza, Verviers, France). After resuspension of cells in RPMI 1640 medium supplemented with 10% CCS, cells were counted by trypan blue exclusion and concentrated to $1 \times 10^7$ cells/mL.

For the ADCC experiment, 50 μL $^{51}$Cr-labeled Daudi cells (5.000 cells) were pre-incubated with 15 μg/mL CD38 antibody IgG1-005 or mutant IgG1-005-E345R in a total volume of 100 μL RPMI medium supplemented with 10% CCS in a 96-well microtiter plate. After 10 min at RT, 50 μL PBMCs (500.000 cells) were added, resulting in an effector to target ratio of 100:1. The maximum amount of cell lysis was determined by incubating 50 μL $^{51}$Cr-labeled Daudi cells (5,000 cells) with 100 μL 5% Triton-X100. The amount of spontaneous lysis was determined by incubating 5,000 $^{51}$Cr-labeled Daudi cells in 150 μL medium, without any antibody or effector cells. The level of antibody-independent cell lysis was determined by incubating 5,000 Daudi cells with 500,000 PBMCs without antibody. Subsequently, the cells were incubated 4 hr at 37° C., 5% $CO_2$. To determine the amount of cell lysis, the cells were centrifuged (1200 rpm, 3 min) and 75 μL of supernatant was transferred to micronic tubes, after which the released $^{51}$Cr was counted using a gamma counter. The measured counts per minute (cpm) were used to calculate the percentage of antibody-mediated lysis as follows:

(cpm sample−cpm Ab-independent lysis)/(cpm max. lysis−cpm spontaneous lysis)×100%

Table 15 shows the calculated EC50 values of IgG1-005-wt and IgG1-005-E345R in the performed ADCC assay. Four samples were tested. IgG1-005-E345R shows a significant lower $EC_{50}$ value than IgG1-005-wt of all four tested samples.

TABLE 15

Calculated $EC_{50}$ values of the four performed experiments.

| ADCC | | IgG1-005-wt EC50 | IgG1-005-E345R EC50 | |
|---|---|---|---|---|
| A | | 5.7 | 1.2 | |
| B | | 8.3 | 4.0 | |
| C | | 14.1 | 4.1 | |
| D | | 5.0 | 0.6 | |
| | average | 8.3 | 2.5 | ng/ml |
| | SEM | 4.1 | 1.9 | |
| TTEST | 2-tail | P= | 0.04 | |
| Factor enhanced | | | 3.3 | times |

FIG. 11 shows that compared to wild type antibody HuMab-005, mutant IgG1-005-E345R demonstrated enhanced efficacy of ADCC capacity, being able to induce ADCC at lower concentrations.

Example 13

FcRn Binding and Pharmacokinetic Analysis of 7D8 Mutants Compared to Wild Type 7D8

The neonatal Fc receptor (FcRn) is responsible for the long plasma half-life of IgG by protecting IgG from degradation. After internalization of the antibody, FcRn binds to antibody Fc regions in endosomes, where the interaction is stable in the mildly acidic environment (pH 6.0). Upon recycling to the plasma membrane, where the environment is neutral (pH7.4), the interaction is lost and the antibody is released back into the circulation. This influences the plasma half-life of IgG.

The capability of the 7D8 mutant IgG1-7D8-E354R to interact with FcRn from mouse, cynomolgus monkey and human was tested in an ELISA. All incubations were done at room temperature. 96 well plates were coated with 5 μg/mL (100 μL/well) recombinantly produced biotinylated extracellular domain of FcRn (mouse, human or cynomolgus) (FcRnECDHis-B2M-BIO), diluted in PBST plus 0.2% BSA; 1 hour. Plates were washed 3 times with PBST, and 3-fold serially diluted (in PBST/0.2% BSA, pH 6.0) wild type IgG1-7D8 or IgG1-7D8-E354R was added, and plates were incubated for 1 hour. Plates were washed with PBST/ 0.2% BSA, pH 6.0. Goat-anti-human IgG(Fab'2)-HRP (Jackson Immuno Research, cat no:109-035-097) diluted in PBST/0.2% BSA, pH 6.0 was added, and plates were incubated for 1 hour. After washing, ABTS was added as substrate and plates were incubated in the dark for 30 minutes. Absorbance was read at 405, using an EL808 ELISA reader.

The mice in this study were housed in a barrier unit of the Central Laboratory Animal Facility (Utrecht, The Netherlands) and kept in filter-top cages with water and food provided ad libitum. All experiments were approved by the Utrecht University animal ethics committee.

To analyse pharmacokinetics of the 7D8 mutants in vivo, SCID mice (C.B-17/IcrCrl-scid-BR, Charles-River) were injected intravenously with 100 μg (5 mg/kg) wild type 7D8, IgG1-7D8-E354R, -S440K or K322A; 3 mice per group.

50 μL blood samples were collected from the saphenous vein at 10 minutes, 4 hours, 24 hours, 2 days, 7 days, 14 days and 21 days after antibody administration. Blood was collected into heparin containing vials and centrifuged for 5 minutes at 10,000 g. Plasma was stored at −20° C. until determination of mAb concentrations.

Human IgG concentrations were determined using a sandwich ELISA. Mouse mAb anti-human IgG-kappa clone MH16 (#M1268, CLB Sanquin, The Netherlands), coated to 96-well Microlon ELISA plates (Greiner, Germany) at a concentration of 2 μg/mL was used as capturing antibody. After blocking plates with PBS supplemented with 2% chicken serum, samples were added, serially diluted in ELISA buffer (PBS supplemented with 0.05% Tween 20 and 2% chicken serum), and incubated on a plate shaker for 1 h at room temperature (RT). Plates were subsequently incubated with goat anti-human IgG immunoglobulin (#109-035-098, Jackson, West Grace, PA) and developed with 2,2'-azino-bis (3-ethylbenzthiazoline-6-sulfonic acid) (ABTS; Roche, Mannheim, Germany). Absorbance was measured in a microplate reader (Biotek, Winooski, VT) at 405 nm.

SCID mice were chosen because they have low plasma IgG concentrations and therefore relatively slow clearance of IgG. This provides a PK model that is very sensitive for detecting changes in clearance due to diminished binding of the Fcγ-part to the neonatal Fc receptor (FcRn).

Statistical testing was performed using GraphPad PRISM version 4 (Graphpad Software).

FIG. 12 shows that both wild HuMab-7D8 and IgG1-7D8-E345R bound well to mouse, human and cynomolgus FcRn. Binding of IgG1-7D8-E345R was slightly better than that of wild type 7D8.

FIG. 13 shows the plasma concentrations in time. There was no difference in the change of plasma concentrations (clearance) over time of wild type HuMab-7D8 versus either one of IgG1-7D8-E345R, -S440K or K322A.

Example 14

Use of the Fc-Fc Stabilizing Mutation E345R for Increased Bactericidal Activity of IgG Antibodies Against Bacteria that Express Fc-Binding Surface Proteins The complement cascade system is an important host defense mechanism against pathogens and can be divided in three different activation routes to recognize pathogens: i) the antibody-mediated classical pathway, which is activated upon C1q binding to the pathogen-bound antibody, ii) the lectin and iii) the alternative pathway, in which the complement system directly recognizes and is triggered by the pathogen in the absence of antibody. The three pathways converge at the step of C3 cleavage and C3b deposition. Microorganisms have developed multiple mechanisms of complement evasion, one of which is mediated by Protein A (Joiner Ann. Rev. Microbiol. (1988) 42:201-30; Foster Nat Rev Microbiol (2005) December; 3(12):948-58). Protein A was first identified in the cell wall of *Staphylococcus aureus* and is well known for its binding to the Fc region of IgG (Deisenhofer et al., Biochem (1981) 20, 2361-70; Uhlen et al., J. Biol. Chem (1984) 259, 1695-1702). So far, the antiphagocytotic effect of Protein A and its role in the pathogenesis of *S. aureus* was explained by the interaction between Protein A and IgG, which results in an incorrect antibody orientation to be recognized by the neutrophil Fc receptor (Foster Nat Rev Microbiol (2005) December; 3(12):948-58).

Example 11 shows that CDC mediated by B cell-specific IgG1 antibodies was inhibited by the competing Fc-binding peptide DCAWHLGELVWCT. The peptide targets the consensus binding site on IgG Fc that coincides with the binding site for Protein A, Protein G and rheumatoid factor (Delano et al., Science 2000 Feb. 18; 287(5456):1279-83). Based on these data, it is believed that the Protein A-mediated bacterial complement evasion mechanism could work by competing for Fc binding, resulting in destabilization of the Fc-Fc interaction of a microbe-specific antibody, and consequently inhibition of antibody-mediated complement activation. Moreover, Example 11 also shows that B cell-specific IgG1 antibodies containing the CDC-enhancing E345R mutation were less sensitive to inhibition of CDC by the competing Fc-binding peptide DCAWHLGELVWCT than the parent wild type antibodies. By extrapolating these results to Fc binding proteins expressed on microbes, increased stabilization of the IgG1 Fc-Fc interactions by the E345R mutation would make microbe-specific antibodies less prone to complement inhibition by an escape strategy of the pathogen via Fc binding competition by microbial surface proteins, such as Protein A. Consequently, introduction of the E345R mutation in IgG antibodies directed against a bacterium would result in increased C3b deposition on bacteria and increased bactericidal activity compared to the parent wild type antibodies.

As an in vitro measure for complement-mediated bacterial killing, both phagocytosis by neutrophils and the generation of C3a in the plasma, which coincides with C3b deposition on the bacteria, can be determined as described below. Indeed, it has been described that C3b deposition on *S. aureus* results in enhanced phagocytosis and correlates with bacterial killing (Rooijakkers et. al., Nature Immunology 2005: 6, 920-927).

*S. aureus* will be labelled with FITC by incubating an exponentially growing bacterial culture with 100 μg/mL FITC for 1h at 37° C. in 0.1 M carbonate buffer (pH 9.6). Human polymorph nuclear cells (PMN) will be isolated using a Ficoll gradient. FITC-labelled bacteria will be opsonized with a concentration series of specific antibodies with or without the mutation E345R. Phagocytosis will be performed in vitro by incubating $1 \times 10^8$ opsonized FITC-labelled bacteria with human PMN in the presence of 25% IgG-depleted serum as complement source for 25 min at 37° C. in a total volume of 200 μL under vigorous shaking. The cells will be fixed and erythrocytes lyzed by incubation with BD FACS lysing solution for 15 min at room temperature. After washing, phagocytosis will be measured by FACS. The neutrophil population will be selected through forward and side scatter gating and phagocytosis will be expressed as the mean fluorescence in the neutrophil population. Alternatively, C3a generation will be measured in the samples by ELISA as a measure for complement activation and C3b deposition.

It is expected that the *S. aureus*-specific antibodies containing the E345R mutation will induce more complement activation and phagocytosis by neutrophils than the parent wild type antibodies. An example of an antibody that could be used in such experiments is the chimeric monoclonal IgG1 pagibaximab (BSYX-A110; Biosynexus), targeting Lipoteichoic acid (LTA) that is embedded in the cell wall of staphylococci (Baker, Nat Biotechnol. 2006 December; 24(12):1491-3; Weisman et al., Int Immunopharmacol. 2009 May; 9(5):639-44).

Example 15

Use of CDC-Inhibiting Mutations that Restrict CDC Activation to Target Cells Simultaneously Bound by a Mixture of Two Different Therapeutic Monoclonal Antibodies As described in Example 6, CD20 antibody 7D8 mutations K439E and S440K decreased the CDC efficacy as monoclonal antibodies. Mixing 7D8 antibodies containing these mutations restored CDC. Efficient CDC was thus restricted to cells bound by both mutant antibodies simultaneously. As described in Example 10, CD38 antibody 005 mutations K439E and S440K decreased the CDC efficacy as monoclonal antibodies. Mixing 005 antibodies containing these mutations restored CDC. Efficient CDC was thus restricted to cells bound by both mutant antibodies simultaneously.

It can be advantageous to restrict the induction of efficient CDC to target cells that express two specific antigens simultaneously, exploiting their combined expression to improve selectivity of CDC induction. To restrict CDC induction to cells bound by both CD20 and CD38 antibodies simultaneously, the pair of 7D8-K439E and 005-S440K or the pair of 7D8-S440K and 005-K439E will be added separately or mixed 1:1 in CDC experiments as follows. $0.1 \times 10^6$ Daudi or Raji cells will be pre-incubated in round-bottom 96-well plates with a concentration series of unpurified antibodies or antibody mixture (0.01, 0.03, 0.1, 0.3, 1.0, 3.0, 10.0, 30.0 µg/mL) in a total volume of 100 µL for 15 min on a shaker at RT. Next, 25 µL normal human serum will be added as a source of complement (20% final concentration) and incubated in a 37° C. incubator for 45 min. The reaction will be stopped by putting the plates on ice. 10 µL propidium iodide will be added and cell lysis will be determined by FACS. It is expected, that 7D8-K439E, 005-S440K, 7D8-S440K and 005-K439E will display limited CDC efficacy. It is expected, that the simultaneous addition of 7D8-K439E and 005-S440K will restore efficient CDC specifically on cells expressing both CD20 and CD38. Likewise, it is expected that the mixture of 7D8-S440K and 005-K439E will restore efficient CDC specifically on cells expressing both CD20 and CD38.

Example 16

Increased Specificity of Enhanced CDC by Combining E345R with Complementary Inhibiting Mutations K439E and S440K in a Mixture of Two Different Monoclonal Antibodies As described in Example 6, CD20 antibody 7D8 mutations K439E and S440K decreased the CDC efficacy as monoclonal antibodies. Mixing 7D8 antibodies containing these mutations restored CDC. Efficient CDC was thus restricted to cells bound by both mutant antibodies simultaneously. As described in Example 10, CD38 antibody 005 mutations K439E and S440K decreased the CDC efficacy as monoclonal antibodies. Mixing 005 antibodies containing these mutations restored CDC. Efficient CDC was thus restricted to cells bound by both mutant antibodies simultaneously.

It can be advantageous to restrict the enhancement of CDC induction to target cells that express two specific antigens simultaneously, exploiting their combined expression to improve selectivity of enhanced CDC induction. It can also be advantageous to restrict the enhancement of CDC induction to target cells that are bound by mixtures of at least two different antibodies simultaneously, said antibodies binding an identical cell surface antigen at two different epitopes simultaneously, or at two cross-competing, similar, or identical epitopes.

Therefore, to restrict enhanced CDC induction to cells bound by both CD20 and CD38 antibodies simultaneously, the CDC enhancing mutation E345R was combined with CDC inhibiting mutations in the antibodies 7D8-E345R/K439E, 7D8-E345R/S440K, 005-E345R/S440K and 005-E345R/K439E. These antibodies were added separately or mixed 1:1 in CDC experiments as follows. $0.1\times10^6$ Wien133 cells (other cell types such as Daudi or Raji cells may also be used) were pre-incubated in round-bottom 96-well plates with a concentration series of unpurified antibodies (final concentration 0.056-10,000 ng/mL in 3-fold dilutions for 7D8-E345R/K439E, 7D8-E345R/S440K, 005-E345R/S440K or 005-E345R/K439E) or antibody mixtures (final concentrations 0.01 μg/mL CD20 antibody mixed with 0-333 ng/mL in 3-fold dilutions CD38 antibody; or 3.3 μg/mL CD38 antibody mixed with 0.0056-1,000 ng/mL in 3-fold dilutions CD20 antibody) in a total volume of 100 μL for 15 min on a shaker at RT. Next, 25 μL normal human serum was added as a source of complement (20% final concentration) and incubated in a 37° C. incubator for 45 min. The reaction was stopped by putting the plates on ice. 10 μL propidium iodide was added and cell lysis was determined by FACS.

A concentration series of 005-E345R/K439E or 005-E345R/S440K antibody was mixed with a fixed concentration of 0.01 μg/mL 7D8 double mutant antibody (maximal concentration with minimal CDC on Wien133 cells as a single agent as determined from FIG. 14A) to make the complementary combinations 005-E345R/K439E+7D8-E345R/S440K or 005-E345R/S440K+7D8-E345R/K439E. FIG. 14C shows that the 005 double mutant CD38 antibodies induced CDC dose-dependently in the presence of fixed concentration of the complementary 7D8-E345R/K439E or 7D8-E345R/S440K CD20 antibody, respectively. The CDC efficacy by these complementary combinations (FIG. 14C) was comparable to the 005-E345R single mutant (enhancer) antibody as a single agent (FIG. 14B). In contrast, in the presence of irrelevant antibody b12, both 005-E345R/K439E and 005-E345R/S440K showed hardly any CDC in the concentration series tested (comparable to 005-E345R/K439E or 005-E345R/S440K as single agents shown in FIG. 14B).

A concentration series of 7D8-E345R/K439E or 7D8-E345R/S440K antibody was mixed with a fixed concentration of 3.3 μg/mL 005 double mutant antibody (showing a little but limited CDC on Wien133 cells as a single agent as determined from FIG. 14B) to make the complementary combinations 7D8-E345R/K439E+005-E345R/S440K or 7D8-E345R/S440K+005-E345R/K439E. FIG. 14D shows that the 7D8 double mutant CD20 antibodies induced CDC very efficiently in the presence of the complementary 005-E345R/K439E or 005-E345R/S440K CD38 antibody respectively, even at the lowest concentrations tested, resembling not more than a few 7D8 double mutant antibody molecules per cell. To eliminate the contribution of increased Fc-tail density on the cell membrane to the observed enhanced CDC by the mixture of 7D8 and 005 antibodies with complementary K439E and S440K mutations, also antibody combinations with non-complementary mutations were tested. FIG. 14D shows that non-complementary combinations showed much lower CDC efficacy than complementary combinations, as a result of less efficient Fc-Fc interaction than the complementary combinations.

These data suggest that the induction of (enhanced) CDC by therapeutic antibodies can be limited to cells that bind simultaneous a mixture of two complementary antibodies, in this case with different antigen specificities, thereby increasing target cell specificity by requiring co-expression of both antigens.

As can be seen in FIGS. 14A and 14B, 7D8-E345R/K439E, 005-E345R/S440K, 7D8-E345R/S440K and 005-E345R/K439E displayed limited CDC efficiency in comparison to 7D8-E345R alone. It is further seen, that the mixture of 7D8-E345R/K439E and 7D8-E345R/S440K enabled CDC with enhanced efficiency compared to wildtype 7D8 antibody as single agent. Likewise, it was observed that the mixture of 005-E345R/K439E and 005-E345R/S440K enabled CDC with enhanced efficiency compared to wildtype 005 antibody as single agent (data not shown).

Example 17

Use of CDC-Inhibiting Mutations that Restrict Efficient CDC Activation to Antibody Complexes Exclusively Consisting of Therapeutically Administered Antibodies As described in Example 6, the CD20 antibody 7D8 double mutant K439E/S440K restored the CDC efficiency diminished by K439E or S440K single point mutants. As described in Example 10, the CD38 antibody 005 double mutant K439E/S440K restored the CDC efficiency inhibited by K439E or S440K single point mutants. As observed, the single point mutations disrupt the Fc:Fc interaction with the unmutated amino acid on the facing side of the Fc:Fc interface. Introduction of the compensatory mutation on the facing side of the Fc:Fc interface restored CDC efficiency. Efficient CDC was thus apparently restricted to antibody complexes exclusively consisting of antibodies containing both mutations.

In another example, the induction of CDC is restricted to antibody complexes exclusively consisting of therapeutically administered antibodies. To restrict CDC induction to cells bound by therapeutically CD20 or by CD38 antibodies exclusively, the CDC inhibiting mutations K439E and S440K will be combined in the antibodies 7D8-K439E/S440K or 005-K439E/S440K. These antibodies will be added separately in CDC experiments in the absence or presence of non-target specific IgG as follows. $0.1 \times 10^6$ Daudi or Raji cells will be pre-incubated in round-bottom 96-well plates with a concentration series of unpurified antibodies or antibody mixture (0.01, 0.03, 0.1, 0.3, 1.0, 3.0, 10.0, 30.0 µg/mL) in a total volume of 100 µL for 15 min on a shaker at RT. Next, 25 µL normal human serum will be added as a source of complement (20% final concentration) and incubated in a 37° C. incubator for 45 min. The reaction will be stopped by putting the plates on ice. 10 µl propidium iodide will be added and cell lysis will be determined by FACS.

It is expected, that 7D8-K439E/S440K will induce CDC with efficiency similar to wildtype 7D8 antibody. Addition of non-specific IgG to 7D8-K439E/S440K is expected not to affect the efficiency of CDC induction for this antibody. Likewise, it is expected that 005-K439E/S440K will enable CDC with efficiency similar to wildtype HuMAb 005. Addition of non-specific IgG to 005-K439E/S440K is expected not to affect the efficiency of CDC induction for this antibody.

Example 18

Use of CDC-Inhibiting Mutations that Restrict Enhanced CDC Activation to Antibody Complexes Exclusively Consisting of Therapeutically Administered Antibodies As described in Example 6, the CD20 antibody 7D8 double mutant K439E/S440K restored the CDC efficiency diminished by K439E or S440K single point mutants. As described in Example 10, the CD38 antibody HuMAb 005 double mutant K439E/S440K restored the CDC efficiency inhibited by K439E or S440K single point mutants. As observed, the single point mutations disrupt the Fc:Fc interaction with the unmutated amino acid on the facing side of the Fc:Fc interface. Introduction of the compensatory mutation on the facing side of the Fc:Fc interface restored CDC efficiency. Efficient CDC was thus apparently restricted to antibody complexes exclusively consisting of antibodies containing both mutations.

In another example, the enhancement of CDC induction is restricted to antibody complexes exclusively consisting of therapeutically administered antibodies. By screening and selection of mutations that stimulate the Fc:Fc interaction exploited for CDC stimulation, one could identify mutations that can form CDC-inducing antibody complexes with serum antibodies not specific for the antigen target of interest. To restrict enhanced CDC induction to cells bound by complexes of CD20 or by CD38 antibodies exclusively, the CDC enhancing mutation E345R will be combined with CDC inhibiting mutations in the antibodies 7D8-E345R/K439E/S440K or 005-E345R/K439E/S440K. These antibodies will be added separately in CDC experiments in the absence or presence of non-target specific IgG as follows. $0.1\times10^6$ Daudi or Raji cells will be pre-incubated in round-bottom 96-well plates with a concentration series of unpurified antibodies or antibody mixture (0.01, 0.03, 0.1, 0.3, 1.0, 3.0, 10.0, 30.0 μg/mL) in a total volume of 100 μL for 15 min on a shaker at RT. Next, 25 μL normal human serum will be added as a source of complement (20% final concentration) and incubated in a 37° C. incubator for 45 min. The reaction will be stopped by putting the plates on ice. 10 μl propidium iodide will be added and cell lysis will be determined by FACS.

It is expected that 7D8-E345R/K439E/S440K will induce CDC with enhanced efficiency compared to wildtype HuMAb 7D8. Addition of non-specific IgG to 7D8-E345R/K439E/S440K is expected not to affect the efficiency of CDC induction compared to wildtype 7D8 antibody. Likewise, it is expected that the 005-E345R/K439E/S440K will enable CDC with enhanced efficiency compared to wildtype 005 antibody. Addition of non-specific IgG to 005-E345R/K439E/S440K is expected not to affect the efficiency of CDC induction relative to wildtype 005 antibody.

Example 19

Use of a Mutant Screening Approach to Identify Mutations Stimulating Fc:Fc Interaction Mediated Antibody Oligomerization Detected by a CDC Assay As described in Examples 6 and 10, amino acid mutations were identified that stimulated CDC for antibodies recognizing two different target antigens, CD20 and CD38, on multiple cell lines expressing variable levels of said antigens. Surprisingly, the single point mutation E345R proved sufficient to endow CDC-dependent cell lysis of Wien133 cells to the anti-CD38 antibody 005, which failed to lyse these cells by CDC in wild type IgG1 format.

Other mutations on or at the periphery of the Fc:Fc interface could stimulate oligomerization and CDC in an analogous fashion. Alternatively, mutations could indirectly stimulate oligomerization, for example by allosterically inducing Fc:Fc interactions.

To determine if other amino acid mutations could stimulate Fc-mediated antibody oligomerization, a library of anti-CD38 IgG1-005 mutants was screened using CDC assays, both individually and mixed in a pairwise fashion to select for example amino acid pairs interacting across the Fc:Fc interface. However, the same strategy can be applied to other antibodies, such as another IgG1 or an IgG3 antibody.

A focused library of mutations at the positions indicated in Table 15 was generated. Mutations were introduced into the IgG1-005 Fc region using the Quikchange site-directed mutagenesis kit (Stratagene, US). Briefly, for each desired mutation position, a forward and a reverse primer encoding a degenerate codon at the desired location were used to replicate full length plasmid DNA template of the 005 heavy chain with IgG1m(f) allotype. The resulting DNA mixtures were digested using DpnI to remove source plasmid DNA and used to transform *E. coli*. Resulting colonies were pooled and cultured and plasmid DNA was isolated from these pools and retransformed into *E. coli* to obtain clonal colonies. Mutant plasmid DNA isolated from resulting colonies was checked by DNA sequencing (LGC genomics, Berlin, Germany). Expression cassettes were amplified from plasmid DNA by PCR and DNA mixes containing both a mutant heavy and a wildtype light chain of IgG1-005 were transiently transfected to Freestyle HEK293F cells (Invitrogen, US) using 293fectin (Invitrogen, US) essentially as described by the manufacturer. Supernatants of transfected cells containing antibody mutants were collected. Mutant antibody supernatants were screened in CDC assays both individually and in pairwise mixtures as follows.

$0.1 \times 10^6$ Daudi or Wien-133 cells (other cells types such as Raji cells may be used) were pre-incubated in round-bottom 96-well plates with 1.0 ug/ml of unpurified antibodies in a total volume of 100 μL for 15 min on a shaker at RT. Next, 30 μL normal human serum was added as a source of complement (30% final concentration) and incubated in a 37° C. incubator for 45 min. The reaction was stopped by putting the plates on ice. 10 μl propidium iodide was added and cell lysis was determined by FACS.

Mutations described in Table 16, Table 17 and Table 18 were selected for their ability to enhance oligomerization as detected by CDC efficiency, either as a single mutant or when mixed with other mutants for example facing the mutation across the Fc:Fc interface. Mutations can optionally be further screened for their ability to not compromise FcRn, Protein-A or Protein-G binding, ADCC, ADCP or other effector functions mediated by the Fc domain. Combining such stimulating point mutations into one Fc domain can stimulate oligomerization and CDC efficiency even further.

Mutations in the CH2-CH3 region incorporated in the CD38 antibody 005 were tested for their ability to inhibit oligomerization as determined by CDC on Daudi cells. Lysis of the mutant antibody was compared to wild type 005, for which lysis was set to 100%. The cut-off for inhibition was set to 66% lysis. Measured in this way, most of the tested mutations inhibited CDC (see Table 16).

Mutations in the CH2-CH3 region incorporated in the CD38 antibody 005 were tested for their ability to enhance oligomerization as determined by CDC on Wien133 cells (Table 17). Wild type CD38 antibody 005 is not able to induce CDC on Wien133 cells. Mutants displaying ≥39% cell lysis were scored as enhancing. Completely unexpectedly, virtually all obtained substitutions of amino acids E345 and E430 stimulated cell lysis by CDC. To verify this result, amino acids E345, E430 and S440 were substituted with each possible mutation by site directed mutagenesis and tested for their ability to enhance oligomerization as determined by CDC of Wien133 cells using a new human serum batch, yielding slightly more efficient lysis (Table 18). Again, all substitutions of E345 and E430 induced efficient CDC of Wien133 cells.

The following preferred mutations caused ≥39% cell lysis of Wien133 cells: P247G, I253V, S254L, Q311L, Q311W, E345A, E345C, E345D, E345F, E345G, E345H, E345I, E345K, E345L, E345M, E345N, E345P, E345Q, E345R, E345S, E345T, E345V, E345W, E345Y, D/E356G, D/E356R, T359R, E382L, E382V, Q386K, E430A, E430C, E430D, E430F, E430G, E430H, E430I, E430L, E430M, E430N, E430P, E430Q, E430R, E430S, E430T, E430V, E430W, E430Y, Y436I, S440Y and S440W.

TABLE 16

Percentage lysis of daudi cells in the presence of 1.0 μg/ml IgG1-005 antibody point mutations. IgG1-005 wildtype lysed 66% of cells under these conditions. For each of the individual positions which have been substituted by another amino acid are given in the outer left column. The substituted amino acid for each particular position is given followed by the measured percentage lysis indicated in parantheses ( ) in the horizontal rows of the individual positions.

| Position | | | | | | | | | |
|---|---|---|---|---|---|---|---|---|---|
| P247 | A (42) | C (67) | D (91) | F (93) | G (95) | H (80) | I (89) | K (96) | L (13) |
| I253 | A (17) | 0 (12) | K (13) | M (6) | N (5) | R (7) | S (6) | V (94) | |
| S254 | E (14) | F (75) | G (100) | H (46) | I (93) | K (86) | L (99) | P (4) | T (8) |
| H310 | K (6) | W (87) | | | | | | | |
| Q311 | A (53) | C (72) | E (5) | F (90) | G (68) | H (72) | I (92) | K (93) | L (96) |
| E345 | A (85) | C (91) | F (95) | G (86) | H (83) | I (96) | K (94) | L (98) | M (94) |
| D/E356 | G (88) | I (95) | L (94) | R (97) | T (97) | V (98) | | | |
| T359 | G (88) | N (93) | P (87) | R (96) | | | | | |
| E382 | F (3) | K (3) | L (99) | M (90) | P (3) | V (96) | W (3) | | |
| G385 | D (28) | H (9) | Q (24) | R (27) | S (14) | T (10) | | | |
| Q386 | A (56) | C (18) | D (6) | E (9) | F (11) | G (10) | H (26) | I (42) | K (98) |
| E430 | A (97) | F (97) | G (99) | H (98) | L (95) | P (95) | Q (90) | R (96) | S (94) |
| N434 | D (5) | E (5) | K (5) | R (5) | S (6) | W (98) | | | |
| Y436 | I (98) | K (7) | L (10) | R (35) | S (8) | T (7) | W (6) | | |
| Q438 | E (5) | K (6) | S (5) | T (8) | W (10) | Y (31) | | | |
| K439 | A (6) | D (5) | H (5) | L (5) | P (8) | T (4) | Y (7) | | |
| S440 | A (61) | C (10) | D (95) | E (24) | F (13) | G (40) | I (8) | N (33) | R (11) |
| K447 | E(20) | *del(90) | | | | | | | |

| Position | | | | | | | | |
|---|---|---|---|---|---|---|---|---|
| P247 | M (83) | N (78) | R (93) | S (93) | T (10) | V (9) | W (82) | |
| I253 | | | | | | | | |
| S254 | W (7) | | | | | | | |
| H310 | | | | | | | | |
| Q311 | N (53) | P (97) | R (87) | S (66) | T (54) | W (93) | Y (85) | |
| E345 | N (97) | P (74) | R (98) | S (93) | T (82) | V (92) | W (95) | Y (95) |
| D/E356 | | | | | | | | |
| T359 | | | | | | | | |
| E382 | | | | | | | | |
| G385 | | | | | | | | |

TABLE 16-continued

Percentage lysis of daudi cells in the presence of 1.0 μg/ml IgG1-005 antibody point mutations. IgG1-005 wildtype lysed 66% of cells under these conditions. For each of the individual positions which have been substituted by another amino acid are given in the outer left column. The substituted amino acid for each particular position is given followed by the measured percentage lysis indicated in paranteses ( ) in the horizontal rows of the individual positions.

| | | | | | | | | | |
|---|---|---|---|---|---|---|---|---|---|
| Q386 | L (15) | N (25) | P (6) | R (10) | S (43) | T (12) | V (53) | W (13) | Y (42) |
| E430 | V (98) | | | | | | | | |
| N434 | | | | | | | | | |
| Y436 | | | | | | | | | |
| Q438 | | | | | | | | | |
| K439 | | | | | | | | | |
| S440 | T (28) | Y (98) | | | | | | | |
| K447 | | | | | | | | | |

*where "del" means that there was a deletion of the amino acid residue at the indicated position.

TABLE 17

Percentage lysis of Wien-133 cells in the presence on 1.0 μg/ml IgG1-005 antibody point mutants. IgG1-005 wildtype lysed 3% of cells under these conditions. For each of the individual positions which have been substituted by another amino acid are given in the outer left column. The substituted amino acid for each particular position is given followed by the measured percentage lysis indicated in paranteses ( ) in the horizontal rows of the individual positions.

| Position | | | | | | | | | |
|---|---|---|---|---|---|---|---|---|---|
| P247 | A (5) | C (5) | D (12) | F (16) | G (50) | H (11) | I (10) | K (14) | L (4) |
| I253 | A (11) | D (9) | K (3) | M (3) | N (3) | R (4) | S (3) | V (51) | |
| S254 | E (14) | F (10) | G (32) | H (2) | I (15) | K (12) | L (65) | P (2) | T (9) |
| H310 | K (3) | W (13) | | | | | | | |
| Q311 | A (9) | C (4) | E (3) | F (19) | G (4) | H (6) | I (28) | K (16) | L (55) |
| E345 | A (57) | C (22) | F (48) | G (47) | H (49) | I (59) | K (42) | L (72) | M (67) |
| D/E356 | G (39) | I (31) | L (30) | R (64) | T (32) | V (13) | | | |
| T359 | G (2) | N (3) | P (4) | R (40) | | | | | |
| E382 | F (2) | K (2) | L (44) | M (21) | P (3) | V (53) | W (2) | | |
| G385 | D (5) | H (4) | N (18) | Q (4) | R (14) | S (4) | T (4) | | |
| Q386 | A (3) | C (4) | D (4) | E (4) | F (3) | G (3) | H (3) | I (4) | K (60) |
| E430 | A (54) | F (68) | G (55) | H (57) | L (58) | P (56) | Q (31) | R (39) | S (20) |
| N434 | D (2) | E (2) | K (2) | R (2) | S (3) | W (18) | | | |
| Y436 | I (49) | K (3) | L (4) | R (3) | S (3) | T (2) | W (3) | | |
| Q438 | E (3) | K (3) | S (2) | T (2) | W (2) | Y (2) | | | |
| K439 | A (3) | D (2) | H (2) | L (2) | P (2) | T (2) | Y (4) | | |
| S440 | A (3) | C (3) | D (6) | E (2) | F (2) | G (3) | I (2) | N (2) | R (2) |

| Position | | | | | | | | |
|---|---|---|---|---|---|---|---|---|
| P247 | M (13) | N (7) | R (10) | S (7) | T (4) | V (3) | W (9) | |
| I253 | | | | | | | | |
| S254 | W (9) | | | | | | | |
| H310 | | | | | | | | |
| Q311 | N (6) | P (12) | R (18) | S (9) | T (3) | W (41) | Y (12) | |
| E345 | P (51) | R (64) | S (60) | T (53) | V (67) | W (52) | Y (70) | |
| D/E356 | | | | | | | | |
| T359 | | | | | | | | |
| E382 | | | | | | | | |
| G385 | | | | | | | | |
| Q386 | L (3) | N (4) | P (2) | R (4) | S (3) | T (3) | V (3) | W (3) Y (4) |
| E430 | V (53) | | | | | | | |
| N434 | | | | | | | | |
| Y436 | | | | | | | | |
| Q438 | | | | | | | | |
| K439 | | | | | | | | |
| S440 | T (3) | Y (64) | | | | | | |

TABLE 18

Percentage lysis of Wien-133 cells in the presence on 1.0 µg/ml IgG1-005 antibody point mutants.
IgG1-005 wildtype lysed 12% of cells under these conditions. Each of the individual positions
which have been substituted by another amino acid are given in the outer left column. The substituted
amino acid for each particular position is given followed by the measured percentage lysis
indicated in paranteses ( ) in the horizontal rows of the individual positions.

| Position | | | | | | | | | | |
|---|---|---|---|---|---|---|---|---|---|---|
| E345 | A (94) | C (87) | D (76) | F (95) | G (95) | H (94) | I (93) | K (97) | L (94) | M (96) |
| E430 | A (95) | C (79) | D (91) | F (96) | G (96) | H (95) | I (96) | K (83) | L (94) | M (75) |
| S440 | A (12) | C (8) | D (41) | E (9) | F (7) | G (8) | H (26) | I (7) | K (6) | L (7) |

| Position | | | | | | | | | |
|---|---|---|---|---|---|---|---|---|---|
| E345 | N (93) | P (97) | Q (98) | R (94) | S (93) | T (92) | V (96) | W (93) | Y (94) |
| E430 | N (95) | P (97) | Q (86) | R (92) | S (96) | T (97) | V (96) | W (98) | Y (97) |
| S440 | M (8) | N (12) | P (10) | Q (21) | R (9) | T (10) | V (7) | W (86) | Y (90) |

Example 20

In Vivo Efficacy of IgG1-7D8-E345R in a Subcutaneous B Cell Lymphoma Xenograft Model The in vivo anti-tumor efficacy of the IgG1-7D8-E345R antibody was evaluated in a subcutaneous model with Raji-luc #2D1 cells. These cells show ~300,000 CD20 molecules per cell (determined by QIFIKIT analysis, data not shown) and high complement defense receptor expression. Cells were cultured in RPMI with 10% cosmic calf serum (Hy-Clone, Logan, UT), penicillin and streptomycin, 1% (v/v) sodium Pyruvate and 1 µg/mL puromycin (P-8833, Sigma, Zwijndrecht). Cells were harvested in log-phase (approximately 70% confluency). Six to eleven weeks old female SCID mice (C.B-17/IcrPrkdc-scid/CRL) were used (Charles-River). At day 0, $5 \times 10^6$ Raji-luc #2D1 cells in 200 µL PBS were subcutaneously injected in the right flank of each mouse. The tumor development was monitored by caliper measurement. When average tumor volume was 100 mm$^3$ (around day 7), the mice were sorted into groups (n=9) and treated by intraperitoneal (i.p.) injection of a single dose of 50 µg antibody per mouse (2.5 mg/kg). All antibody samples were supplemented with irrelevant antibody b12 to obtain a total antibody concentration of 0.5 mg/mL. Treatment groups are shown in Table 18. Seven days after treatment, blood samples were obtained to determine human IgG serum levels to check correct antibody administration. Tumors were measured at least twice per week using caliper (PLEXX) until an endpoint tumor volume of 1500 mm$^3$, tumors showed ulcerations or until serious clinical signs were observed.

TABLE 18

Treatment groups and dosing.

| Group | Antibody | Dose |
|---|---|---|
| 1. wild type | IgG1-7D8-WT | 50 µg (=2.5 mg/kg) |
| 2. CDC-enhancing mutant | IgG1-7D8-E345R | 50 µg (=2.5 mg/kg) |
| 3. Irrelevant Ab control | IgG1-b12 | 50 µg (=2.5 mg/kg) |

FIG. 15A shows mean tumor growth on day 22, when all groups were still complete. Wild type antibody IgG1-7D8 slightly inhibited tumor growth compared to negative control antibody IgG1-b12, although this was not statistically significant. Only IgG1-7D8-E345R inhibited tumor growth significantly compared to the negative control antibody IgG1-b12 (one-way ANOVA analysis p<0.01).

FIG. 15B shows a Kaplan-Meier plot of the percentage mice with tumor sizes smaller then 700 mm$^3$. Compared to mice treated with negative control antibody IgG1-b12, tumor formation was significantly delayed in mice treated with IgG1-7D8-E345R antibody (Mantel-Cox analysis p<0.01), but not in mice treated with wild type IgG1-7D8.

These data show that the E345R mutation enhanced the in vivo anti-tumor efficacy of the CD20 antibody 7D8.

Example 21

In Vivo Efficacy of IgG1-005-E345R in a Subcutaneous B Cell Lymphoma Xenograft Model The in vivo anti-tumor efficacy of the IgG1-005-E345R antibody was evaluated in a subcutaneous model with Raji-luc #2D1 cells. These cells show ~150,000 CD38 molecules per cell (determined by QIFIKIT analysis, data not shown) and high complement defense receptor expression. The protocol for tumor inoculation and measurement is basically the same as described in Example 20. At day 0, $5 \times 10^6$ Raji-luc #2D1 cells in 200 µL PBS were s.c. injected in the right flank of SCID mice. When average tumor volume was 100 mm$^3$ (around day 7), the mice were sorted into groups (n=7) and treated by i.p. injection of a single dose of 500 µg antibody per mouse (25 mg/kg). Treatment groups are shown in Table 19. Tumors were measured until an endpoint tumor volume of 1500 mm$^3$ or until tumors showed ulcerations or serious clinical signs were observed to avoid major discomfort.

FIG. 16A shows mean tumor growth on day 21, when all groups were still complete. Wild type antibody IgG1-005 slightly inhibited tumor growth, although this was not statistically significant. Only IgG1-005-E345R significantly inhibited tumor growth compared to the irrelevant antibody control at day 21 (One-way ANOVA p<0.05).

FIG. 16B shows a Kaplan-Meier plot of the percentage mice with tumor sizes smaller then 500 mm$^3$. Tumor formation was significantly delayed in mice treated with IgG1-005-E345R antibody compared to mice treated with negative control antibody IgG1-b12 (Mantel-Cox analysis p<0.001) or wild type IgG1-005 (p<0.05).

These data show that introduction of the E345R mutation in the CD38 antibody 005 resulted in enhanced in vivo anti-tumor activity.

TABLE 19

Treatment groups and dosing.

| Group | Antibody | Dose |
|---|---|---|
| 1. wild type | IgG1-005-WT | 500 µg (=25 mg/kg) |
| 2. CDC-enhancing mutant | IgG1-005-E345R | 500 µg (=25 mg/kg) |
| 3. Irrelevant Ab control | IgG1-b12 | 500 µg (=25 mg/kg) |

Example 22

Monovalent Target Binding Further Enhances the CDC Efficacy of E345R Antibodies

A molecular surface of the IgG1 hexameric ring observed in the b12 crystal structure demonstrates that for each IgG in the hexameric ring, one of the two C1q binding sites is facing upwards and the other site is facing downwards of the ring structure, and also one Fab-arm of each antibody is oriented up and one is oriented down, resulting in only one Fab-arm per antibody to take part in antigen binding, suggesting monovalent binding per antibody molecule in the hexameric antibody ring. Monovalency might bring antibodies upon antigen binding in a hexamerization compatible orientation. To test this hypothesis, the CDC efficacy of a bispecific CD38/EGFR antibody with the E345R mutation was tested on CD38-positive, EGFR-negative Wien133 cells, to which this bispecific antibody can only bind monovalently via CD38, and compared to the CDC efficacy of the bivalent binding CD38 antibody, also with the E345R mutation. The human monoclonal antibody HuMax-EGFr (2F8, described in WO 2004/056847) was used as a basis for the EGFR antibodies described in this example.

Bispecific antibodies were generated in vitro according to the DuoBody™ platform, i.e. 2-MEA-induced Fab-arm exchange as described in WO 2011/147986. The basis for this method is the use of complementary CH3 domains, which promote the formation of heterodimers under specific assay conditions. To enable the production of bispecific antibodies by this method, IgG1 molecules carrying certain mutations in the CH3 domain were generated: in one of the parental IgG1 antibody the F405L mutation, in the other parental IgG1 antibody the K409R mutation. To generate bispecific antibodies, these two parental antibodies, each antibody at a final concentration of 0.5 mg/mL, were incubated with 25 mM 2-mercaptoethylamine-HCl (2-MEA) in a total volume of 100 µL TE at 37° C. for 90 min. The reduction reaction is stopped when the reducing agent 2-MEA is removed by using spin columns (Microcon centrifugal filters, 30 k, Millipore) according to the manufacturer's protocol.

For the CDC assay, 0.1×10$^6$ Wien133 cells were pre-incubated in round-bottom 96-well plates with a concentration series of antibodies (0.01 to 10.0 µg/mL) in a total volume of 100 µL for 15 min on a shaker at RT. Next, 25 µL normal human serum was added as a source of complement (20% final concentration) and incubated in a 37° C. incubator for 45 min. The reaction was stopped by putting the plates on ice. 10 µL propidium iodide was added and cell lysis was determined by FACS.

FIG. 17 shows that, as expected, CD38 antibodies without the E345R mutation (wild type IgG1-005 and IgG-b12-K409R×IgG1-005-F405Q did not induce killing of Wien133 cells. Also the EGFR antibody IgG1-2F8-E345R/F405L, that did not bind the EGFR-negative Wien133 cells (data not shown), did not induce CDC, as expected. The introduction of the K409R mutation did not influence the capacity of the IgG1-005-E345R antibody to induce ~60% killing on Wien133 cells (described in Example 10). Interestingly, the bispecific CD38/EGFR antibody IgG1-005-E345R/K409R× IgG1-2F8-E345R/F405L, which can only bind monovalently to the CD38-positive, EGFR-negative Wien133 cells, showed increased maximal CDC killing (from ~60% to ~100% killing).

These data show that monovalent targeting can further enhance the maximal killing capacity of antibodies containing the CDC enhancing E345R mutation. Furthermore, these data show that the E345R oligomerization enhancing mutation, as measured by enhancing CDC activity, can be applied to other antibody formats, such as DuoBody.

Example 23

The Oligomerization Enhancing E345R Mutation can be Applied to Other Antibody Formats Such as DuoBody™

The effect of the E345R mutation was tested in a bispecific antibody of the DuoBody format. CDC assays were performed with CD20/CD38 bispecific antibodies on CD20-positive, CD38-positive Wien133 and Raji cells.

Bispecific antibodies were generated as described in Example 22. For the CDC assay, 0.1×10$^6$ Wien133 or Raji cells were pre-incubated in round-bottom 96-well plates with a concentration series of antibodies (0.01 to 30.0 µg/mL) in a total volume of 100 µL for 15 min on a shaker at RT. Next, 25 µL normal human serum was added as a source of complement (20% final concentration) and incubated in a 37° C. incubator for 45 min. The reaction was stopped by putting the plates on ice. 10 µL propidium iodide was added and cell lysis was determined by FACS.

FIG. 18 shows that introduction of the E345R mutation enhanced CDC of the bispecific IgG1-005-F405L×IgG1-7D8-K409R antibody on Wien 133 (FIG. 18A) and Raji (FIG. 18B) cells. These data show that the E345R oligomerization enhancing mutation can be applied to other antibody formats to enhance CDC activity.

Example 24

E345R Rescues CDC by EGFR Antibody 2F8, which can be Further Enhanced by Monovalent Target Binding As described in Examples 6, 10 and 26, E345R enhanced or rescued CDC for antibodies recognizing different hematological tumor targets (CD20 and CD38). To extend the analysis to a solid tumor antigen, the effect of E345R on the CDC capacity of the EGFR antibody 2F8 was tested on A431 epidermoid carcinoma cells.

Furthermore, the effect of monovalent EGFR targeting on E345R-mediated CDC induction was tested using a bispecific EGFRxCD20 antibody (IgG1-2F8-E345R/F405L× IgG1-7D8-E345R/K409R) on EGFR-positive, CD20-negative A431 cells.

Bispecific antibodies were generated as described in Example 22. For the CDC assay, 5×10$^6$ A431 cells/mL were labeled with 100 µCi $^{51}$Cr for 1h at 37° C. Cells were washed three times with PBS and resuspended in medium at a concentration of 1×10$^5$ cells/mL. 25,000 labeled cells were incubated in round-bottom 96-well plates with a concentration series of unpurified antibodies (0-30 µg/mL in 3-fold dilutions) in a total volume of 100 µL for 15 min at RT. Next, 50 µL normal human serum dilution was added as a source of complement (25% final concentration) and incubated in a 37° C. incubator for 1h. Cells were spun down (3 min at 300×g) and 25 µL supernatant was added to 100 µL microscint in a white 96 well optiplate (PerkinElmer) for incubation on a shaker (750 rpm) for 15 min. $^{51}$Cr release was determined as counts per minute (cpm) on a scintillation counter. Maximum lysis (100%) was determined by the $^{51}$Cr level measured in the supernatant of Triton X-100-treated cells. Spontaneous lysis was determined by the $^{51}$Cr level measured in the supernatant of cells incubated without antibody. Specific cell lysis was calculated according to the formula: Specific lysis=100×(cpm sample−cpm spont)/(cpm max−cpm spont).

FIG. 19 shows that IgG1-2F8-E345R/F405L is able to lyse A431 cells by CDC, whereas wild type 2F8 is not capable of killing A431 cells. These data show that CDC activity can be rescued in the EGFR antibody 2F8 by introduction of the E345R mutation. This potentially extends the applicability of the CDC enhancing E345R mutation to antibodies targeting solid tumor antigens.

Bispecific EGFRxCD20 antibody IgG-2F8-E345R/F405L×IgG1-7D8-E345R/K409R, showed further enhancement of CDC on the EGFR-positive, CD20-negative A431 cells.

These data further support the hypothesis that monovalency facilitates the formation of Fc-Fc interactions and subsequent CDC induction as postulated for a CD38 binding antibody described in Example 22.

Example 25

E345R Enhances or Rescues CDC by CD38 Antibody 003 and CD20 Antibodies 1188 and Rituximab As described in Examples 6, 10 and 24, E345R enhances or induces CDC activity of several antibodies with different target specificities (CD20, CD38 and EGFR), as was tested on multiple cell lines expressing variable levels of said antigens. Therefore, introduction of the E345R mutation was considered to be a general mechanism to enhance or rescues CDC for existing antibodies. To further support this, the effect of the E345R mutation on CDC was tested for more antibodies with variable intrinsic CDC efficacy on Daudi and Wien133 cells: CD38 antibody 003, described in WO 2006/099875 and CD20 antibodies rituximab (type I) and 1168 (type II), described in WO 2005/103081. CD20 antibodies can be divided in two subgroups (Beers et al. Seminars in Hematology 47, (2) 2010, 107-114). Type I CD20 antibodies display a remarkable ability to activate complement and elicit CDC by redistributing the CD20 molecules in the plasma membrane into lipid rafts, which cluster the antibody Fc regions and enabling improved C1q binding. Type II CD20 antibodies do not appreciably change CD20 distribution and without concomitant clustering, they are relatively ineffective in CDC.

0.1×10$^6$ Daudi or Raji cells were pre-incubated in round-bottom 96-well plates with a concentration series of unpurified antibodies (0.001, 0.003, 0.01, 0.03, 0.1, 0.3, 1.0, 3.0, 10.0 µg/mL) in a total volume of 70 µL for 15 min on a shaker at RT. Next, 30 µL normal human serum was added as a source of C1q (30% final concentration) and incubated in a 37° C. incubator for 45 min. The reaction was stopped by putting the plates on ice. 10 µL propidium iodide was added and cell lysis was determined by FACS.

FIG. 20 shows that the E345R mutation enhanced CDC for all tested antibodies on both (A) Daudi and (B) Wien133 cells. Interestingly, at the used concentrations all antibodies that did not induce CDC in the wild type format, induced CDC efficiently after introduction of the E345R mutation: CD38 mAb 003 and CD20 type II mAb 11B8 on Daudi cells, and CD38 mAbs 005 and 003 and CD20 type II mAb 11B8 on Wien133 cells. These data suggest that enhancement of antibody oligomerization, more specifically by introduction of an E345R mutation, is a general mechanism to enhance or rescue CDC by existing antibodies.

Example 26

E345R Enhances Internalization of Tissue Factor Antibodies

To test if enhanced oligomerization can induce increased antibody internalization, colocalization studies of wild type and E345R mutated Tissue Factor (TF) antibodies with the lysosomal marker LAMP1 were performed by confocal microscopy.

SK-OV-3 cells were grown on glass coverslips (thickness 1.5 micron, Thermo Fisher Scientific, Braunschweig, Germany) in standard tissue culture medium at 37° C. for 1 day. Cells were pre-incubated for 1 hour with 50 µg/mL leupeptin (Sigma) to block lysosomal activity, after which 10 µg/mL Tissue Factor (TF) antibody (WO 2010/066803) was added. The cells were incubated for an additional 1, 3 or 16 hours at 37° C. Hereafter, cells were washed with PBS and incubated for 30 minutes at room temperature (RT) with 4% formaldehyde (Klinipath). Slides were washed with blocking buffer (PBS supplemented with 0.1% saponin [Roche] and 2% BSA [Roche]) and incubated for 20 minutes with blocking buffer containing 20 mM NH4Cl to quench formaldehyde. Slides were washed again with blocking buffer and incubated for 45 minutes at RT with a cocktail of mouse-anti-human CD107a-APC (BD Pharmingen) to identify lysosomal LAMP1 and goat-anti-human IgG-FITC (Jackson) to identify TF antibodies. Slides were washed again with blocking buffer and mounted overnight on microscope slides using 20 µL mounting medium (6 gram Glycerol [Sigma] and 2.4 gram Mowiol 4-88 [Omnilabo] was dissolved in 6 mL distilled water to which 12 mL 0.2M Tris [Sigma] pH8.5 was added followed by incubation for 10 min at 50-60° C.; mounting medium was aliquoted and stored at −20° C.). Slides were imaged with a Leica SPE-II confocal microscope (Leica Microsystems) equipped with a 63×1.32-0.6 oil immersion objective lens and LAS-AF software.

12-bit grayscale TIFF images were analyzed for colocalization using MetaMorph® software (version Meta Series 6.1, Molecular Devices Inc, Sunnyvale California, USA). Images were imported as stacks and background was subtracted. Identical thresholds settings were used (manually set) for all FITC images and all APC images. Colocalization was depicted as the pixel intensity of FITC in the region of interest (ROI), were the ROI is composed of all APC positive regions. To compare different slides stained with different TF antibodies, the images were normalized using the pixel intensity of APC. Mouse-anti-human CD107a-APC was used to stain the lysosomal marker LAMP1 (CD107a). The pixel intensity of LAMP1 should not differ between various TF antibodies imaged.

Normalized values for colocalization of FITC and APC are expressed as arbitrary units according to the formula[(TPI FITC×percentage colocalization)/100]×[1/TPI APC]

Percentage colocalization=TPI FITC that colocalizes with an APC pixel/TPI APC

TPI, total pixel Intensity

FIG. 21 depicts the amount of FITC pixel intensity of wild type and E345R mutated TF antibodies that overlap with APC-labeled lysosomal marker. For each antibody or condition tested, three different images were analyzed from one slide containing ~1, 3 or >5 cells. Variation was observed between the different images within each slide. Still, it was evident that the E345R mutation for antibodies 011 and 098 resulted in increased lysosomal colocalization after 1 hour incubation, when compared with wild type 011 and 098. These results indicate that mutation E345R induces more rapid internalization and lysosomal colocalization and could therefore potentiate antibody drug conjugates.

Example 27

Enhanced CDC by E345R Mutation in Rituximab in Different B Cell Lines with Similar CD20 Expression but Different Levels of Membrane-Bound Complement Regulatory Proteins Examples 25 and 28 show that the CDC efficacy of wild type rituximab on Daudi and Wien133 cells was enhanced by introducing the E345R mutation. This enhanced CDC efficacy results from the E345R-mediated stabilization of Fc-Fc interactions. The concomitantly formed hexameric antibody ring structure on the target cell membrane can then promote efficient generation of the membrane attack complex by facilitating the capture and concentration of activated complement components close to the cell membrane. As a result of this efficient complement activation, the inhibiting effects of membrane-bound complement regulatory proteins (mCRP) could be partly overcome. Overexpression of mCRPs, such as CD55, CD46 and CD59, is considered as a barrier for successful immunotherapy with monoclonal anti-tumor antibodies (Jurianz et al., Mol Immunol 1999 36:929-39; Fishelson et al. Mol Immunol 2003 40:109-23, Gorter et al., Immunol Today 1999 20:576-82, Zell et al., Clin Exp Immunol. 2007 December 150(3):576-84). Therefore, the efficacy of rituximab-E345R was compared to that of wild type rituximab on a series of B cell lines with different levels of the mCRPs CD46, CD55 and CD59, but comparable levels of the CD20 target expression.

The B cell lines Daudi, WIL2-S, WSU-NHL, MEC-2 and ARH-77 express comparable amounts of CD20 molecules (~250.000 specific antibody-binding capacity—sABC) as determined by QIFIKIT analysis (data not shown). To compare the expression levels of complement regulatory proteins between these cell lines, QIFIKIT analysis was performed to determine the levels of CD46 (mouse anti-human CD46, CBL488, clone 34.48 Chemicon), CD55 (mouse anti-human CD55, CBL511, Clone BRIC216, Chemicon), and CD59 (mouse anti-human CD59, MCA1054x, clone MEM-43, Serotec).

For the CDC assay, $0.1 \times 10^6$ of cells were pre-incubated in round-bottom 96-well plates with a saturating antibody concentration series (0.002-40.0 µg/mL in 4-fold dilutions) in a total volume of 100 µL for 15 min on a shaker at RT. Next, 25 µL normal human serum was added as a source of complement (20% final concentration) and incubated in a 37° C. incubator for 45 min. The reaction was stopped by putting the plates on ice. 10 µL propidium iodide was added and cell lysis was determined by FACS. The maximal CDC-mediated killing was calculated from two independent experiments using the top of best-fit values of a non-linear fit in GraphPad PRISM 5.

FIG. 22A-D shows that introduction of E345R in wild type rituximab resulted in enhanced CDC efficacy as observed by an increased maximal lysis and decreased $EC_{50}$ for all tested B cell lines.

FIG. 22E shows that the maximal CDC-mediated killing induced by the rituximab-E345R mutant was always higher than by wild type rituximab, independent of the expression levels of the membrane-bound complement regulatory proteins. These data indicate that introduction of E345R enhances the therapeutic potential of monoclonal antibodies as the tumor cells are less effective in evading antibody-mediated complement attack by the E345R containing antibodies.

Example 28

Comparison of CDC Kinetics for Wild Type and E345R Antibodies

Introduction of the Fc: Fc interaction stabilizing E345R mutation has been shown to enhance or rescue CDC as observed by decreased $EC_{50}$ values and increased maximal lysis for different antibodies on different cell lines described in Example 6 (CD20 antibody 7D8 on Daudi and Raji), Example 10 (CD38 antibody 005 on Daudi, Raji and Wien133) and Example 25 (CD38 antibody 003 and CD20 antibodies rituximab and 11B8 on Daudi and Wien133). Next, the kinetics of the CDC reactions were analyzed to further unravel the difference in CDC efficacy between wild type and E345R antibodies.

$0.1 \times 10^6$ Raji cells were pre-incubated in round-bottom 96-well plates with antibody at a saturating concentration (10.0 µg/mL) in a total volume of 100 µL for 15 min on a shaker at RT. Next, 25 µL normal human serum was added as a source of complement (20% final concentration) and incubated in a 37° C. incubator for different periods of time, varying between 0 and 60 min. The reaction was stopped by putting the plates on ice. 10 µL propidium iodide was added and cell lysis was determined by FACS.

Figure 23A:
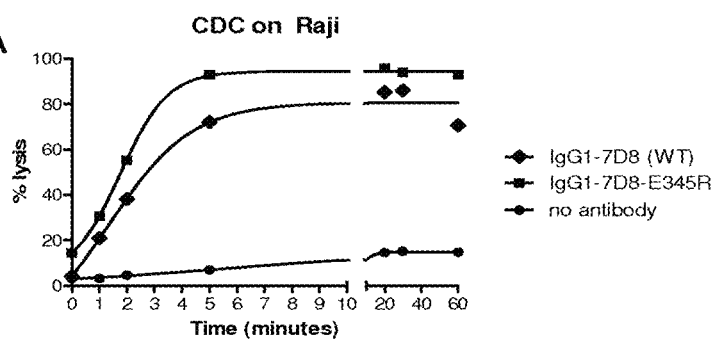

FIG. 23A shows that wild type CD20 antibody IgG1-7D8 showed a maximal CDC-mediated killing of 80% of the Raji cells, which was already reached after 5 min under the tested conditions. However, for IgG-7D8-E345R, 80% killing of Raji cells was observed even faster, after 3 min. Maximal lysis by IgG-7D8-E345R (95%) was also reached after 5 minutes.

Figure 23B:
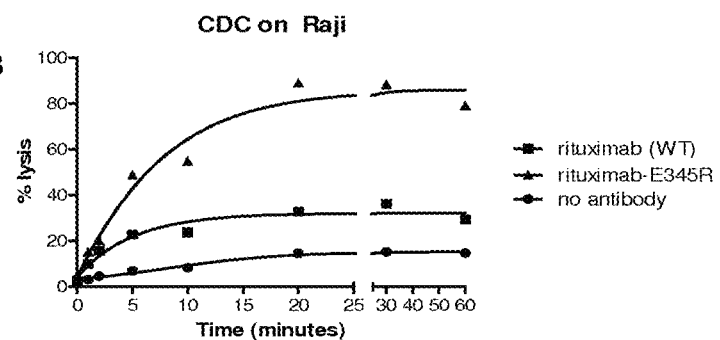

FIG. 23B shows that also for wild type CD20 antibody rituximab, which is less potent than 7D8 to induce CDC on the used Raji cells, introduction of the E345R mutation resulted in faster killing of the target cells. Wild type rituximab showed a maximal CDC-mediated killing of 32%, which was reached after 20 minutes. Rituximab-E345R reached 32% killing already after approximately 3 minutes and remarkably, maximal lysis by rituximab-E345R (85%) was also reached after 20 minutes.

Figure 23C:
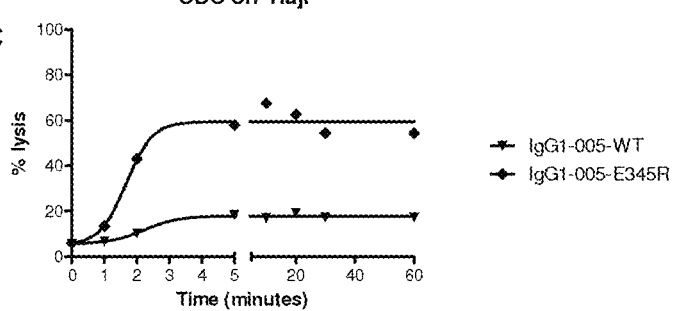
Figure 23D:
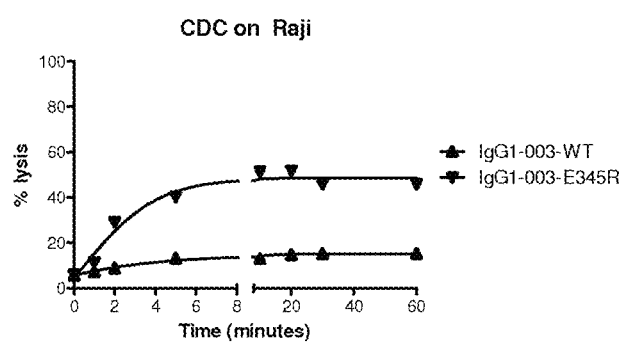

FIG. 23C+D shows that the used Raji cells, which are resistant for CDC-mediated killing by wild type CD38 antibodies IgG1-003 and IgG1-005, could be killed fast by introducing the E345R mutation. IgG1-003-E345R and IgG1-005-E345R showed maximal CDC (50% and 60%, respectively) already after 5 min.

In summary, E345R antibodies are more potent than their wild type counterparts, which results from a combination of higher efficacy (lower $EC_{50}$), increased maximal lysis and a faster kinetics of the CDC reaction.

Example 29

Comparison of CDC Kinetics for Bispecific Antibodies with or without the E345R Mutation In example 23 it is described that the E345R mutation can be applied to the CD38×CD20 bispecific antibody IgG1-005-F405L×IgG1-7D8-K409R that was generated by the DuoBody platform, resulting in an enhanced killing capacity as observed by a decreased $EC_{50}$ in CDC assays on Raji and Wien133 cells. Next, the kinetics of the CDC reaction was analyzed to further unravel the difference in CDC efficacy between the CD38×CD20 bispecific antibodies with and without E345R.

$0.1 \times 10^6$ Raji cells were pre-incubated in round-bottom 96-well plates with antibody at a saturating concentration (10.0 μg/mL) in a total volume of 100 μL for 15 min on a shaker at RT. Next, 25 μL normal human serum was added as a source of complement (20% final concentration) and incubated in a 37° C. incubator for different periods of time, varying between 0 and 60 min. The reaction was stopped by putting the plates on ice. 10 μL propidium iodide was added and cell lysis was determined by FACS.

FIG. 24 shows that the bispecific antibody IgG1-005-F405L×IgG1-7D8-K409R induced a maximal CDC-mediated killing of 83%, which was reached after 10 minutes. Introduction of E345R resulted in an increased maximal killing by IgG1-005-E345R-F405L×IgG1-7D8-E345R-K409R (98%), which was already reached after 2 minutes. These data indicate that introducing the Fc-Fc stabilizing E345R mutation in the bispecific antibody results in an accelerated CDC-mediated killing of the target cells.

Example 30

Comparison of CDC Kinetics for Monovalent Binding Antibodies with and without E345R Example 22 shows that monovalent target binding further enhanced the CDC efficacy of E345R antibodies as observed by increased maximal lysis with a CD38×EGFR bispecific antibody on the CD38-positive, EGFR-negative Wien133 cells. Next, the kinetics of the CDC reaction was analyzed to further unravel the difference in CDC-mediated killing capacity between monovalently binding antibodies with and without E345R.

Bispecific CD38×EGFR and CD20×EGFR antibodies, with or without the E345R mutation, were generated in vitro according to the DuoBody platform as described in Example 22. CDC efficacy of the CD38×EGFR bispecific antibodies was tested on the CD38-positive, EGFR-negative Raji cells, to which the bispecific antibodies can only bind monovalently via CD38. $0.1 \times 10^6$ Raji cells were pre-incubated in round-bottom 96-well plates with antibody at a saturating concentration (10.0 μg/mL) in a total volume of 100 μL for 15 min on a shaker at RT. Next, 25 μL normal human serum was added as a source of complement (20% final concentration) and incubated in a 37° C. incubator for different periods of time, varying between 0 and 60 min. The reaction was stopped by putting the plates on ice. 10 μL propidium iodide was added and cell lysis was determined by FACS.

FIG. 25 shows that bispecific antibody CD38×EGFR (IgG1-005-K409R×IgG1-2F8-F405L) induced a maximal CDC-mediated killing of 55%, which was reached after approximately 10 minutes. Introduction of E345R resulted in an increased maximal killing (96%), which was already reached within 5 minutes.

Bispecific antibody CD20×EGFR (IgG1-7D8-K409R×IgG1-2F8-F405L) was also tested and induced a maximal CDC-mediated killing of 85%, which was reached after approximately 5 minutes. However, with the CD20×EGFR antibody with introduced E345R, 85% lysis was observed faster, after 2 minutes. Maximal lysis by the E345R CD20×EGFR antibody (97%) was also reached after 5 minutes (data not shown).

In summary, introduction of the E345R mutation in these monovalent binding antibodies resulted in more potent antibodies, which results from a combination of increased maximal lysis and a faster kinetics of the CDC reaction.

Example 31

CDC by a Combination of Therapeutic and E345R/Q386K Antibodies

As described in Example 19, mutant CD38 antibodies derived from IgG1-005 could induce efficient CDC on Wien133 cells when the E345 position of the wild type antibody was substituted to any amino acid other than Glutamate (E). This suggests that oligomerization, as a prerequisite of CDC, is hindered by the presence of the Glutamate side chain at position 345 of the antibody. Since E345 on one Fc is in close proximity to Q386 on the facing second Fc moiety in the hexameric antibody ring structure, the E345-mediated hindrance of oligomerization in a first antibody could possibly be removed by substitutions at the Q386 position of a second antibody. This would then enable E345 in the first antibody to interact better with the mutated 386 position in the second antibody in case both antibodies are combined. To test this hypothesis, CDC assays were performed on Wien133, in which wild type antibodies (IgG1-003, IgG1-005 or IgG1-11B8) were mixed with IgG1-005-E345R/Q386K or IgG1-005-E345R/Q386K/E430G as an example.

$0.1 \times 10^6$ Wien133 cells were pre-incubated in round-bottom 96-well plates with a concentration series of unpurified IgG1-005-E345R/Q386K, IgG1-005-E345R/Q386K/E430G or control antibody (0.0001-20.0 μg/mL in 3.33-fold dilutions) in the presence or absence of 1.0 or 10.0 μg/mL wild type IgG1-003, IgG1-005 or IgG1-11B8 antibody in a total volume of 100 μL for 15 min on a shaker at RT. Next, 25 μL normal human serum was added as a source of complement (20% final concentration) and incubated in a 37° C. incubator for 45 min. The reaction was stopped by putting the plates on ice. 10 μL propidium iodide was added and cell lysis was determined by FACS.

FIG. 26A/B/C shows that CD38 antibody IgG1-005-E345R/Q386K induced CDC-mediated lysis of Wien133 cells in a dose-dependent fashion (dashed line). Combining IgG1-005-E345R/Q386K with 1 or 10 μg/mL wild type CD38 antibody IgG1-003 (FIG. 26A) or wild type CD20 antibody IgG1-11B8 (FIG. 26B) resulted in an increased maximal cell lysis. Combining IgG1-005-E345R/Q386K with wild type IgG1-005 inhibited CDC in a dose-dependent fashion, possibly by competing for the binding site (FIG. 26C).

Figure 26D:
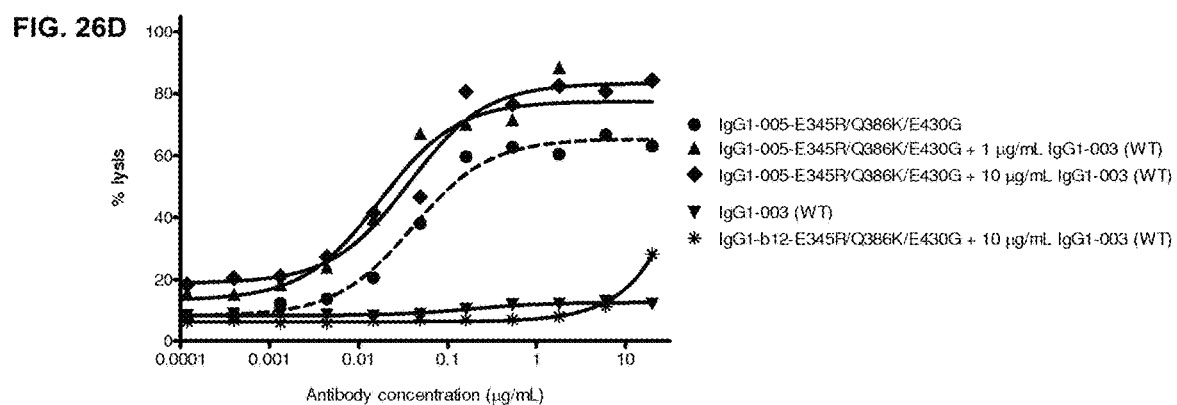
Figure 26E:
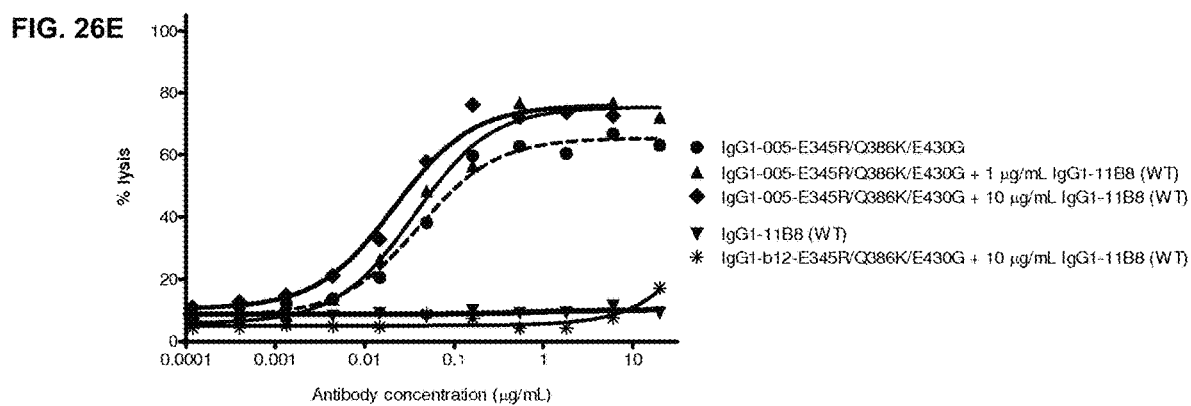
Figure 26F:
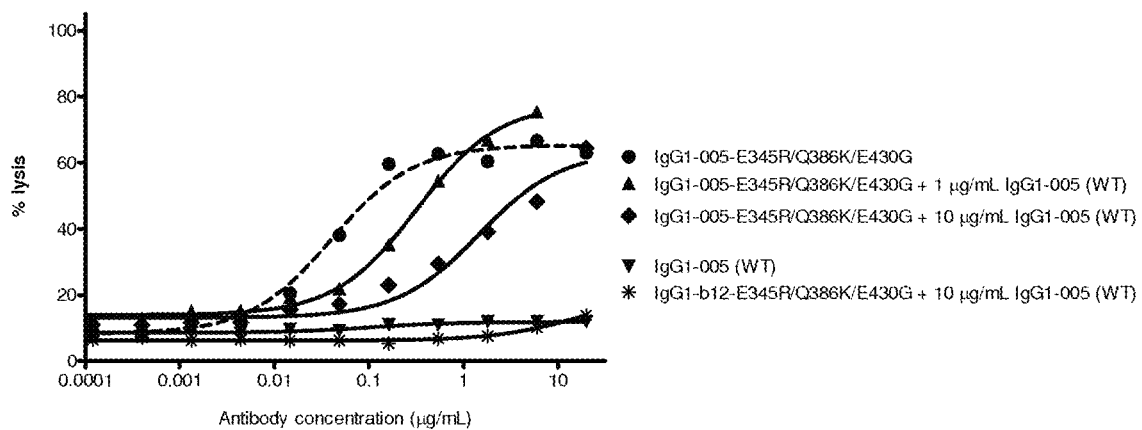

FIG. 26D/E/F shows similar results for CD38 antibody IgG1-005-E345R/Q386K/E430G.

These data indicate that wild type antibodies IgG1-003 and IgG1-11B8 participated in antibody oligomerization and CDC activation when combined with IgG1-005-E345R/Q386K or IgG1-005-E345R/Q386K/E430G. In such combinations, the hindrance of oligomerization by the E345-position that is present in the wild type antibody could be, at least partly, removed by the Q386K substitution in the mutant antibody. This application is in particular interesting to improve therapies with antibodies that are wild type in the E345 position, such as rituximab, ofatumumab, daratumumab or trastuzumab. Also, such oligomerization-inducing antibodies might promote formation of cell-bound complexes with patient-own antibodies directed against target cells like tumor cells or bacteria.

Example 19 describes multiple amino acids in addition to E345 that enhance CDC upon mutation, for example E430 and S440, of which specific mutations induced efficient CDC on Wien133 cells when incorporated in CD38 antibody IgG1-005. With the exception of I253 and Y436 mutants, the identified oligomerization-enhancing mutations contact unmutated amino acids on the facing second Fc moiety in the hexameric ring structure. Therefore, the identified oligomerization-enhancing mutations, both alone or combined, can be expected to also promote oligomerization with unmutated antibodies, and further optimization of such mutants could be achieved by a selection strategy similar to that applied in example 19.

Example 32

E345R Induced CDC in IgG2, IgG3 and IgG4 Antibody Isotypes

To test if the introduction of oligomerization-promoting mutations can stimulate the CDC activity of non-IgG1 antibody isotypes, isotypic variants of the CD38 antibody IgG1-005 were generated with constant domains of human IgG2, IgG3 or IgG4 yielding IgG2-005, IgG3-005 and IgG4-005 by methods known in the art. Furthermore, the oligomerization enhancing E345R mutation was introduced in all these antibodies, yielding IgG2-005-E345R, IgG3-005-E345R and IgG4-005-E345R. In a similar way, also IgG2-003 and IgG2-003-E345R were generated from CD38 antibody IgG1-003. CDC efficacy of the different isotypes was compared in an in vitro CDC assay.

$0.1 \times 10^6$ Wien133 cells were pre-incubated in round-bottom 96-well plates with 10 µg/mL unpurified antibodies in a total volume of 100 µL for 15 min on a shaker at RT. IgG1-005-E345R was added at 3.0 µg/mL. Next, 25 µL normal human serum was added as a source of complement (20% final concentration) and incubated in a 37° C. incubator for 45 min. The reaction was stopped by putting the plates on ice. 10 µL propidium iodide was added and cell lysis was determined by FACS.

FIG. 27 shows that IgG2-005, IgG2-003, IgG3-005 and IgG4-005 were unable to lyse either (A) Daudi or (B) Wien133 cells efficiently under the tested conditions (the observed ~20% lysis was considered as background). Introduction of the E345R mutation enabled potent CDC on Daudi cells by all IgG isotypes tested. These results were confirmed using CDC on Wien133 cells, albeit that IgG3-005-E345R displayed limited CDC activity relative to the other isotypic variants. These data indicate that besides IgG1, an oligomerization enhancing mutation such as E345R can also be applied to promote CDC activity of IgG2, IgG3 and IgG4 antibodies.

Example 33

CDC by IgG1-005 and IgG1-005-E345R in an Ex Vivo CDC Assay on Patient-Derived CD38-Positive B Cell Chronic Lymphocytic Leukemia (CLL) Cells.

Cryopreserved primary cells from CLL patient samples were obtained from the hematopathology biobank from CDB-IDIBAPS-Hospital Clinic (Dr. Elias Campo, Hematopathology Unit, Department of Pathology, Hospital Clinic, Institut d'Investigacions Biomediques August Pi i Sunyer (IDIBAPS), University of Barcelona, Barcelona, Spain), or from clinical studies by the National Heart, Lung, and Blood Institute (NHLBI) (Dr. Adrian Wiestner, NHLBI, Hematology Branch of the National Institutes of Health (NIH), Bethesda). Informed consent was obtained from all patients in accordance with the Institutional Ethics Committee of the Hospital Clinic (Barcelona, Spain) or the Institutional Review Board of the NIH and the Declaration of Helsinki. All samples were genetically and immunophenotypically characterized.

The CLL samples were categorized into two groups according to their CD38 expression as determined by FACS: five samples were included in the CD38 high group (between 50% and 98% of the CD38 expression on Daudi cells) and four samples were included in the CD38 low group (between 0.5% and 3% of the CD38 expression on Daudi cells).

Fluorescently labeled CLL cells (labeling with 5 µM Calcein AM) were incubated with a concentration series of antibody (0.01-10 µg/mL in 10-fold dilutions). Next, normal human serum was added to the antibody-opsonized cells (100,000 cells/well) as a source of complement (10% final concentration) and incubated for 45 min at 37° C. Supernatans were recovered and fluorescence was read in a Synergy™ HT fluorometer as a measure for cell lysis. Cell killing was calculated as follows: Specific lysis=100× (sample-spontaneous lysis)/(max lysis-spontaneous lysis) where max lysis is determined by a sample of cells treated with 1% Triton, and spontaneous lysis is determined from a sample where cells were incubated in the presence of 10% NHS without antibody.

FIG. 28 shows that IgG1-005-E345R strongly enhanced CDC efficacy compared to wild type IgG1-005 on both CLL primary cells with high CD38 expression and CLL primary cells with low CD38 expression.

EQUIVALENTS

Those skilled in the art will recognize, or be able to ascertain using no more than routine experimentation, many equivalents of the specific embodiments of the invention described herein. Such equivalents are intended to be encompassed by the following claims. Any and all combination of embodiments disclosed in dependent claims is also contemplated to be within the scope of the invention.

The invention claimed is:

1. A variant of a parent antibody comprising an Fc domain of an IgG immunoglobulin and an antigen-binding region, wherein the variant comprises (i) an E345R mutation and (ii) a K439E mutation or an S440K mutation, wherein the numbering of positions is according to the EU Index.

2. A kit-of-parts comprising the variant of claim 1 and instructions for use.

3. The variant of claim 1, wherein the variant comprises an E345R mutation and a K439E mutation.

4. The variant of claim 1, wherein the variant comprises an E345R mutation and an S440K mutation.

5. The variant of claim 1, wherein the antigen-binding region binds to an antigen expressed on a cell membrane.

6. The variant of claim 1, wherein the antigen-binding region binds to a tumor cell antigen.

7. The variant of claim 1, wherein the variant is an IgG1 antibody.

8. The variant of claim 3, wherein the variant is an IgG1 antibody.

9. The variant of claim 4, wherein the variant is an IgG1 antibody.

10. A kit-of-parts comprising the variant of claim 3 and instructions for use.

11. A kit-of-parts comprising the variant of claim 4 and instructions for use.

12. A mixture of variant antibodies, wherein the mixture comprises (i) a first IgG antibody comprising an E345R mutation and a K439E mutation and (ii) a second IgG antibody comprising an E345R mutation and a S440K mutation, wherein the numbering of positions is according to the EU Index.

13. The mixture of variant antibodies of claim 12, wherein the first and second IgG antibodies bind to an antigen on a cell membrane.

14. The mixture of variant antibodies of claim 12, wherein the first and second IgG antibodies bind to a tumor cell antigen.

15. The mixture of variant antibodies of claim 12, wherein the first IgG antibody or second IgG antibody is an IgG1 antibody.

16. The mixture of variant antibodies of claim 12, wherein the first and second IgG antibodies are IgG1 antibodies.

17. A kit-of-parts comprising the mixture of variant antibodies of claim 12 and instructions for use.

* * * * *